(12) United States Patent
Basarab et al.

(10) Patent No.: US 8,071,605 B2
(45) Date of Patent: Dec. 6, 2011

(54) PIPERIDINE COMPOUNDS FOR USE IN THE TREATMENT OF BACTERIAL INFECTIONS

(75) Inventors: Gregory Basarab, Waltham, MA (US); Pamela Hill, Waltham, MA (US); Brian Sherer, Waltham, MA (US); Fei Zhou, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 12/634,809

(22) Filed: Dec. 10, 2009

(65) Prior Publication Data

US 2010/0173909 A1    Jul. 8, 2010

Related U.S. Application Data

(60) Provisional application No. 61/121,953, filed on Dec. 12, 2008.

(51) Int. Cl.
*A61K 31/4965* (2006.01)
*A61K 31/425* (2006.01)

(52) U.S. Cl. .............. 514/255.05; 514/370; 544/408; 546/244; 548/205; 548/562

(58) Field of Classification Search ............ 514/255.05, 514/370; 544/408; 546/244; 548/205, 562
See application file for complete search history.

(56) References Cited

FOREIGN PATENT DOCUMENTS

| WO | 2005026149 A1 | 3/2005 |
|---|---|---|
| WO | 2006087543 A1 | 8/2006 |
| WO | 2008020222 A1 | 2/2008 |
| WO | 2008152418 A1 | 12/2008 |

OTHER PUBLICATIONS

Eakin Novel DNA Gyrase Inhibitors: Fragment-Based NMR Screening to Antibacterial Agents. Presentation at 48th Interscience Conference on Antimicrobial Agents and Chemotherapy (Washington, DC, Oct. 25, 2008).
Green et al. "Novel DNA Gyrase Inhibitors: Structure Guided Discovery and Optimization of Pyrrolamides" Poster at 48th Interscience Conference on Antimicrobial Agents and Chemotherapy (Washington, DC, Oct. 25, 2008) F1-2025.
Hull et al. "Novel DNA Gyrase Inhibitors: The Effect of Pyrrolamide Variations at Site 1 and Site 2 Upon Potency" Poster at 48th Interscience Conference on Antimicrobial Agents and Chemotherapy (Washington, DC, Oct. 25, 2008) F1-2027.
Illingworth et al. "Novel DNA Gyrase Inhibitors: Microbiological Characterization and in Vivo Efficacy of Pyrrolamides" Poster at 48th Interscience Conference on Antimicrobial Agents and Chemotherapy (Washington, DC, Oct. 25, 2008) F1-2028.
Sherer et al. "Novel DNA Gyrase Inhibitors: The Effects of Pyrrolamide Linker Variations Upon Potency" Poster at 48th Interscience Conference on Antimicrobial Agents and Chemotherapy (Washington, DC, Oct. 25, 2008) F1-2026.
Sherer et al. "Novel DNA Gyrase Inhibitors: Improvement of Pyrrolamide Antibacterial Activity by 3-Fluoropiperidine Linkers" Poster at 49th Interscience Conference on Antimicrobial Agents and Chemotherapy (San Francisco, CA, Sep. 15, 2009) F1-1977.
Uria-Nickelsen et al. "Novel DNA Gyrase Inhibitors: Investigation of the Mechanism of Action of Pyrrolamides" Poster at 49th Interscience Conference on Antimicrobial Agents and Chemotherapy (San Francisco, CA, Sep. 15, 2009) F1-2029.
Uria-Nickelsen et al. "Novel DNA Gyrase Inhibitors: Microbiological Characterization and in Vivo Efficacy of 3-Fluoropiperidine Pyrrolamides" Poster at 49th Interscience Conference on Antimicrobial Agents and Chemotherapy (San Francisco, CA, Sep. 15, 2009) F1-1978.

*Primary Examiner* — James O Wilson
*Assistant Examiner* — Douglas M Willis

(57) ABSTRACT

Compounds of formula (I) and their pharmaceutically acceptable salts are described. Processes for their preparation, pharmaceutical compositions containing them, their use as medicaments and their use in the treatment of bacterial infections are also described.

(I)

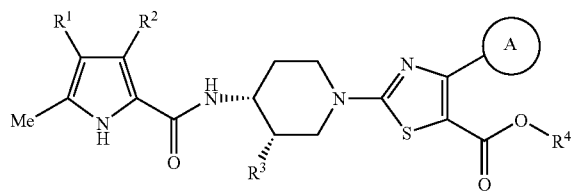

5 Claims, No Drawings

PIPERIDINE COMPOUNDS FOR USE IN THE TREATMENT OF BACTERIAL INFECTIONS

RELATED APPLICATIONS

This application claims priority to U.S. Provisional Application No. 61/121,953, filed on Dec. 12, 2008; the entire contents of which is hereby expressly incorporated by reference in its entirety.

FIELD OF THE INVENTION

The present invention relates to compounds that demonstrate antibacterial activity, processes for their preparation, pharmaceutical compositions containing them as the active ingredient, to their use as medicaments and to their use in the manufacture of medicaments for use in the treatment of bacterial infections in warm-blooded animals such as humans. In particular this invention relates to compounds useful for the treatment of bacterial infections in warm-blooded animals such as humans, more particularly to the use of these compounds in the manufacture of medicaments for use in the treatment of bacterial infections in warm-blooded animals such as humans.

BACKGROUND OF THE INVENTION

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant *staphylococcus aureus* (MRSA), methicillin resistant coagulase negative staphylococci (MRCNS), penicillin resistant *Streptococcus pneumoniae* and multiple resistant *Enterococcus faecium*.

The preferred clinically effective antibiotic for treatment of last resort of such resistant Gram-positive pathogens is vancomycin. Vancomycin is a glycopeptide and is associated with various toxicities, including nephrotoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Consequently, in order to overcome the threat of widespread multi-drug resistant organisms, there is an on-going need to develop new antibiotics, particularly those with either a novel mechanism of action and/or containing new pharmacophoric groups.

Deoxyribonucleic acid (DNA) gyrase is a member of the type II family of topoisomerases that control the topological state of DNA in cells (Champoux, J. J.; 2001. Ann. Rev. Biochem. 70: 369-413). Type II topoisomerases use the free energy from adenosine triphosphate (ATP) hydrolysis to alter the topology of DNA by introducing transient double-stranded breaks in the DNA, catalyzing strand passage through the break and resealing the DNA. DNA gyrase is an essential and conserved enzyme in bacteria and is unique among topoisomerases in its ability to introduce negative supercoils into DNA. The enzyme consists of two subunits, encoded by gyrA and gyrB, forming an $A_2B_2$ tetrameric complex. The A subunit of gyrase (GyrA) is involved in DNA breakage and resealing and contains a conserved tyrosine residue that forms the transient covalent link to DNA during strand passage. The B subunit (GyrB) catalyzes the hydrolysis of ATP and interacts with the A subunit to translate the free energy from hydrolysis to the conformational change in the enzyme that enables strand-passage and DNA resealing.

Another conserved and essential type II topoisomerase in bacteria, called topoisomerase IV, is primarily responsible for separating the linked closed circular bacterial chromosomes produced in replication. This enzyme is closely related to DNA gyrase and has a similar tetrameric structure formed from subunits homologous to Gyr A and to Gyr B. The overall sequence identity between gyrase and topoisomerase IV in different bacterial species is high. Therefore, compounds that target bacterial type II topoisomerases have the potential to inhibit two targets in cells, DNA gyrase and topoisomerase IV; as is the case for existing quinolone antibacterials (Maxwell, A. 1997, Trends Microbiol. 5: 102-109).

DNA gyrase is a well-validated target of antibacterials, including the quinolones and the coumarins. The quinolones (e.g. ciprofloxacin) are broad-spectrum antibacterials that inhibit the DNA breakage and reunion activity of the enzyme and trap the GyrA subunit covalently complexed with DNA (Drlica, K., and X. Zhao, 1997, Microbiol. Molec. Biol. Rev. 61: 377-392). Members of this class of antibacterials also inhibit topoisomerase IV and as a result, the primary target of these compounds varies among species. Although the quinolones are successful antibacterials, resistance generated by mutations in the target (DNA gyrase and topoisomerase IV) is becoming an increasing problem in several organisms, including *S. aureus* and *Streptococcus pneumoniae* (Hooper, D. C., 2002, The Lancet Infectious Diseases 2: 530-538). In addition, quinolones, as a chemical class, suffer from toxic side effects, including arthropathy that prevents their use in children (Lipsky, B. A. and Baker, C. A., 1999, Clin. Infect. Dis. 28: 352-364). Furthermore, the potential for cardiotoxicity, as predicted by prolongation of the $QT_c$ interval, has been cited as a toxicity concern for quinolones.

There are several known natural product inhibitors of DNA gyrase that compete with ATP for binding the GyrB subunit (Maxwell, A. and Lawson, D. M. 2003, Curr. Topics in Med. Chem. 3: 283-303). The coumarins are natural products isolated from *Streptomyces* spp., examples of which are novobiocin, chlorobiocin and coumermycin A1. Although these compounds are potent inhibitors of DNA gyrase, their therapeutic utility is limited due to toxicity in eukaryotes and poor penetration in Gram-negative bacteria (Maxwell, A. 1997, Trends Microbiol. 5: 102-109). Another natural product class of compounds that targets the GyrB subunit is the cyclothialidines, which are isolated from *Streptomyces filipensis* (Watanabe, J. et al 1994, J. *Antibiot.* 47: 32-36). Despite potent activity against DNA gyrase, cyclothialidine is a poor antibacterial agent showing activity only against some eubacterial species (Nakada, N, 1993, *Antimicrob. Agents Chemother.* 37: 2656-2661).

Synthetic inhibitors that target the B subunit of DNA gyrase and topoisomerase IV are known in the art. For example, coumarin-containing compounds are described in patent application number WO 99/35155, 5,6-bicyclic heteroaromatic compounds are described in patent application WO 02/060879, and pyrazole compounds are described in patent application WO 01/52845 (U.S. Pat. No. 6,608,087). AstraZeneca has also published certain applications describing anti-bacterial compounds: WO2005/026149, WO2006/087544, WO2006/087548, WO2006/087543, WO2006/092599 and WO2006/092608.

SUMMARY OF THE INVENTION

We have discovered a new class of compounds that are useful for inhibiting DNA gyrase and/or topoisomerase IV. The compounds of the present invention are regarded as effective against both Gram-positive and certain Gram-negative pathogens.

According to the present invention there is provided a compound of formula (I):

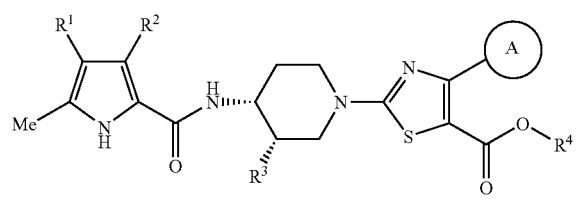

or a pharmaceutically acceptable salt thereof, wherein:
$R^1$ is chloro or cyano;
$R^2$ is hydrogen, chloro, or cyano;
$R^3$ is halo, $C_{1-4}$alkyl, $C_{1-4}$alkoxy, or allyloxy;
$R^4$ is hydrogen or $C_{1-4}$alkyl;
Ring A is selected from formula (a), (b) or (b'):

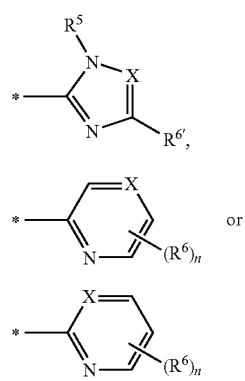

wherein:
"*" is the point of attachment to the thiazolyl ring;
X is CH, $CR^6$, or N;
$R^5$ is H, a $C_{1-4}$alkyl, or $C_{1-4}$alkoxy$C_{1-4}$alkyl;
$R^6$, for each occurrence is independently selected from halo, —$NR^7R^8$, —$OR^8$, and heterocycle wherein said heterocycle comprises at least one nitrogen ring member and is optionally substituted on one or more carbon atoms with one or more $R^9$ and is optionally substituted on one or more ring nitrogens with $R^{10}$;
$R^{6'}$ is hydrogen or $R^6$;
$R^7$ and $R^8$ are each, independently, selected from the group consisting of hydrogen and a $C_{1-6}$alkyl wherein said alkyl is optionally substituted with one or more independently selected from —OH, N,N-di($C_{1-4}$alkyl)amino, a $C_{1-6}$alkoxy, a $C_{1-6}$alkoxy$C_{1-6}$alkoxy, and heterocycle, wherein said heterocycle is optionally substituted on one or more carbon atoms with one or more independently selected halo, $C_{1-6}$alkyl, and $C_{1-6}$alkoxy, and wherein if said heterocyclyl contains an —NH— moiety that nitrogen may be optionally substituted by a $C_{1-4}$alkyl;
$R^9$ is, for each occurrence, is independently selected from a $C_{1-4}$alkyl, halo, hydroxy, $C_{1-4}$alkoxy, amino, N—($C_{1-4}$alkyl)amino, and N,N-di($C_{1-4}$alkyl)amino;
$R^{10}$, for each occurrence, is independently selected from a $C_{1-4}$alkyl optionally substituted with N,N-di($C_{1-4}$alkyl)amino, —OH, heterocycle, and $C_{3-6}$cycloalkyl, wherein the heterocycle may be optionally substituted with $C_{1-4}$alkyl; and
n is 0, 1, 2, or 3.

In another aspect, the present invention provides a compound of formula (I):

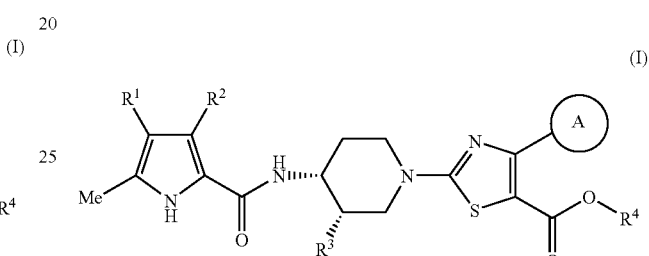

or a pharmaceutically acceptable salt thereof, wherein:
$R^1$ is chloro or cyano;
$R^2$ is hydrogen, chloro, or cyano;
$R^3$ is halo, $C_{1-4}$alkyl, $C_{1-4}$alkoxy, or allyloxy;
$R^4$ is hydrogen or $C_{1-4}$alkyl;
Ring A is selected from formula (a) or (b):

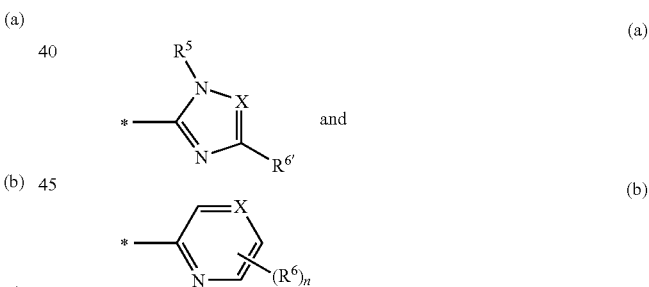

wherein:
"*" is the point of attachment to the thiazolyl ring;
X is CH, $CR^6$, or N;
$R^5$ is H, a $C_{1-4}$alkyl, or $C_{1-4}$alkoxy$C_{1-4}$alkyl;
$R^6$, for each occurrence, is independently selected from halo, —$NR^7R^8$, and heterocycle wherein said heterocycle comprises at least one nitrogen ring member and is optionally substituted on one or more carbon atoms with one or more $R^9$ and is optionally substituted on one or more ring nitrogens with $R^{10}$;
$R^{6'}$ is hydrogen or $R^6$;
$R^7$ and $R^8$ are each, independently, selected from the group consisting of hydrogen and a $C_{1-6}$alkyl wherein said alkyl is optionally substituted with one or more independently selected —OH, a $C_{1-6}$alkoxy, a $C_{1-6}$alkoxy$C_{1-6}$alkoxy, and heterocycle, wherein said heterocycle is optionally substituted on one or more carbon atoms with one or more independently selected halo, $C_{1-6}$alkyl, or $C_{1-6}$alkoxy, and wherein if said heterocyclyl contains an —NH— moiety that nitrogen may be optionally substituted by a $C_{1-4}$alkyl;

$R^9$ is, for each occurrence, is independently selected from a $C_{1-4}$alkyl, halo, hydroxy, $C_{1-4}$alkoxy, amino, N—($C_{1-4}$ alkyl)amino, and N,N-di($C_{1-4}$alkyl)amino;

$R^{10}$, for each occurrence, is independently selected from a $C_{1-4}$alkyl; and n is 0, 1, 2, or 3.

In certain embodiments of formula (I), n is 1, 2, or 3.

In certain embodiments of formula (I), $R^6$, for each occurrence, is independently selected from —$NR^7R^8$, and heterocycle wherein said heterocycle comprises at least one nitrogen ring member and is optionally substituted on one or more carbon atoms with one or more $R^9$ and is optionally substituted on one or more ring nitrogens with $R^{10}$; and $R^{6'}$ is $R^6$.

In certain embodiments of formula (I), —$OR^8$ is selected from the group consisting of hydrogen and a —$OC_{2-6}$alkyl wherein said alkyl moiety is optionally substituted with one or more independently selected from —OH, N,N-di($C_{1-4}$ alkyl)amino, a $C_{1-6}$alkoxy, a $C_{1-6}$alkoxy$C_{1-6}$alkoxy, and heterocycle, wherein said heterocycle is optionally substituted on one or more carbon atoms with one or more independently selected halo, $C_{1-6}$alkyl, and $C_{1-6}$alkoxy, and wherein if said heterocyclyl contains an —NH— moiety that nitrogen may be optionally substituted by a $C_{1-4}$alkyl. In particular embodiments, —$OR^8$ is ethoxy optionally substituted as described above.

In another embodiment, the invention provides pharmaceutical compositions comprising a compound represented by formula (I), or a pharmaceutically acceptable salt thereof, and a pharmaceutically acceptable excipient or carrier.

In another embodiment, the invention provides a method of inhibiting bacterial DNA gyrase and/or bacterial topoisomerase IV in a warm-blooded animal in need of such treatment, comprising administering to the animal an effective amount of a compound represented by formula (I), or a pharmaceutically acceptable salt thereof. In a particular embodiment, the warm-blooded animal is a human.

In another embodiment, the invention provides a method of producing an antibacterial effect in a warm-blooded animal in need of such treatment, comprising administering to the animal an effective amount of a compound represented by formula (I), or a pharmaceutically acceptable salt thereof. In a particular embodiment, the warm-blooded animal is a human.

In another embodiment, the invention provides a method of treating a bacterial infection in a warm-blooded animal in need thereof, comprising administering to the animal an effective amount of a compound represented by formula (I), or a pharmaceutically acceptable salt thereof. In a particular embodiment, the warm-blooded animal is a human. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections and infections caused by drug resistant bacteria such as Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides the use of a compound represented by formula (I), or a pharmaceutically acceptable salt thereof, for the manufacture of a medicament for use in the production of an antibacterial effect in a warm-blooded animal. In a particular embodiment, the warm-blooded animal is a human.

In another embodiment, the invention provides the use of a compound represented by formula (I), or a pharmaceutically acceptable salt thereof, for the manufacture of a medicament for use in inhibition of bacterial DNA gyrase and/or topoisomerase IV in a warm-blooded animal. In a particular embodiment, the warm-blooded animal is a human.

In another embodiment, the invention provides the use of a compound represented by formula (I), or a pharmaceutically acceptable salt thereof, for the manufacture of a medicament for use the treatment of a bacterial infection in a warm-blooded animal. In one embodiment, the bacterial infection is selected from the group consisting of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* and Vancomycin-Resistant Enterococci. In a particular embodiment, the warm-blooded animal is a human.

In another embodiment, the invention provides a compound represented by formula (I), or a pharmaceutically acceptable salt thereof, for use in production of an anti-bacterial effect in a warm-blooded animal.

In another embodiment, the invention provides a compound represented by formula (I), or a pharmaceutically acceptable salt thereof, for use in inhibition of bacterial DNA gyrase and/or topoisomerase IV in a warm-blooded animal.

In another embodiment, the invention provides a compound represented by formula (I), or a pharmaceutically acceptable salt thereof, for use in the treatment of a bacterial infection in a warm-blooded animal.

In another embodiment, the invention provides a compound represented by formula (I), or a pharmaceutically acceptable salt thereof, for use in the treatment of community-acquired pneumoniae, hospital-acquired pneumoniae, skin and skin structure infections, acute exacerbation of chronic bronchitis, acute sinusitis, acute otitis media, catheter-related sepsis, febrile neutropenia, osteomyelitis, endocarditis, urinary tract infections, Penicillin-resistant *Streptococcus pneumoniae*, methicillin-resistant *Staphylococcus aureus*, methicillin-resistant *Staphylococcus epidermidis* or Vancomycin-Resistant Enterococci.

DETAILED DESCRIPTION OF THE INVENTION

In this specification, the term "alkyl" includes both straight and branched chain hydrocarbon which are fully saturated. "$C_{1-6}$" or "$C_{1-4}$" before a group, such as an alkyl group or an alkoxy group, indicates the number of carbon atoms in the group. For example, a "$C_{1-6}$alkyl" is an alkyl groups that has from 1 to 6 carbon atoms. Likewise, a "$C_{1-4}$alkyl" is an alkyl group that has from 1 to 4 carbon atom. Examples of "$C_{1-4}$ alkyl" includes methyl, ethyl, propyl, isopropyl, n-butyl, 1-methylpropyl, isobutyl, and t-butyl. References to individual alkyl groups such as propyl are specific for the straight chain version only unless otherwise specified. An analogous convention applies to other generic terms.

Where optional substituents are chosen from one or more groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). In one aspect of the invention a "heterocyclyl" is a saturated, partially saturated or unsaturated, monocyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. In a further aspect of the invention a "heterocyclyl" is an unsaturated, carbon-linked, monocyclic ring containing 5 or 6 atoms of which at least one atom is chosen from nitrogen, sulphur or oxygen. Examples of suitable values of the term "heterocyclyl" are piperazinyl, piperidinyl, morpholinyl, 2-oxo-pyrrolidinyl, 1,3-dioxanyl, and 2-oxo-1,3-oxazolidinyl, 2-oxo-imidazolidinyl. Further examples of suitable values for the term "heterocyclyl" include pyridinyl, pyrazinyl, imidazolyl, and 1,2,4-triazolyl.

An "alkoxy" is an alkyl group that is linked to another moiety via —O—. Examples of "$C_{1-4}$alkoxy" include methoxy, ethoxy, n-propoxy, isopropoxy, n-butoxy, and t-butoxy.

An "alkoxyalkyl" is an alkyl group which is substituted with an alkoxy group.

An "alkoxyalkoxy" is an alkoxy group which is substituted with another alkoxy group, wherein the alkoxy groups may have the same or a different number of carbon atoms.

An "amino" group is —$NH_2$. An "N—($C_{1-4}$alkyl)amino" is an amino group in which on hydrogen is replaced with a $C_{1-4}$alkyl group. Examples of "N—($C_{1-4}$alkyl)amino" groups include methylamino and ethylamino. An "N,N-di($C_{1-4}$alkyl)amino" is an amino group in which both hydrogens are replaced with the same or a different $C_{1-4}$alkyl group. Examples of "N,N-di($C_{1-4}$alkyl)amino" include N,N-dimethylamino, N,N-diethylamino and N-ethyl-N-methylamino.

A compound of formula (I) may form stable acid or basic salts, and in such cases administration of a compound as a salt may be appropriate, and pharmaceutically acceptable salts may be made by conventional methods such as those described following.

Suitable pharmaceutically-acceptable salts include acid addition salts such as methanesulfonate, tosylate, α-glycerophosphate, fumarate, hydrochloride, citrate, maleate, tartrate and hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl)amine, N-methyl d-glucamine and amino acids such as lysine. There may be more than one cation or anion depending on the number of charged functions and the valency of the cations or anions. In one aspect of the invention the pharmaceutically-acceptable salt is the sodium salt.

However, to facilitate isolation of the salt during preparation, salts which are less soluble in the chosen solvent may be utilised whether pharmaceutically-acceptable or not.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which inhibits DNA gyrase and/or topoisomerase IV and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein. The same applies to compound names.

It will be appreciated by those skilled in the art that in addition to the two asymmetric carbons drawn in formula (I), compounds of formula (I) may contain additional asymmetrically substituted carbon(s) and sulphur atom(s), and accordingly may exist in, and be isolated in, as far as those additional asymmetrically substituted carbon(s) and sulphur atom(s) are concerned, optically-active and racemic forms at those positions. It is to be understood that the present invention encompasses any racemic, optically-active, polymorphic or stereoisomeric form, or mixtures thereof, at any additional asymmetrically substituted carbon(s) and sulphur atom(s), which possesses properties useful in the inhibition of DNA gyrase and/or topoisomerase IV.

Optically-active forms may be prepared by procedures known in the art for example, by resolution of the racemic form by recrystallization techniques, by synthesis from optically-active starting materials, by chiral synthesis, by enzymatic resolution, by biotransformation, or by chromatographic separation using a chiral stationary phase.

Some compounds may exhibit polymorphism. It is to be understood that the present invention encompasses any polymorphic form, or mixtures thereof, which form possesses properties useful in the inhibition of DNA gyrase and/or topoisomerase IV It is also to be understood that certain compounds of the formula (I) and salts thereof can exist in solvated as well as unsolvated forms such as, for example, hydrated forms. It is to be understood that the invention encompasses all such solvated forms which inhibit DNA gyrase and/or topoisomerase IV.

By way of clarity, compounds of the invention included all isotopes of the atoms present in formula (I) and any of the examples or embodiments disclosed herein. For example, H (or hydrogen) represents any isotopic form of hydrogen including $^{1}H$, $^{2}H$ (D), and $^{3}H$ (T); C represents any isotopic form of carbon including $^{12}C$, $^{13}C$, and $^{14}C$; O represents any isotopic form of oxygen including $^{16}O$, $^{17}O$ and $^{18}O$; N represents any isotopic form of nitrogen including $^{13}N$, $^{14}N$ and $^{15}N$; P represents any isotopic form of phosphorous including $^{31}P$ and $^{32}P$; S represents any isotopic form of sulfur including $^{32}S$ and $^{35}S$; F represents any isotopic form of fluorine including $^{19}F$ and $^{18}F$; Cl represents any isotopic form of chlorine including $^{35}Cl$, $^{37}Cl$ and $^{36}Cl$; and the like. In a preferred embodiment, compounds represented by formula (I) comprises isotopes of the atoms therein in their naturally occurring abundance. However, in certain instances, it is desirable to enrich one or more atom in a particular isotope which would normally be present in less abundance. For example, $^{1}H$ would normally be present in greater than 99.98% abundance; however, a compound of the invention can be enriched in $^{2}H$ or $^{3}H$ at one or more positions where H is present. In one embodiment, when a compound of the invention is enriched in a radioactive isotope, for example $^{3}H$ and $^{14}C$, they may be useful in drug and/or substrate tissue distribution assays. It is to be understood that the invention encompasses all such isotopic forms which inhibit DNA gyrase and/or topoisomerase IV.

Another embodiment of the invention provides a compound selected from the group consisting of any one or more of the compounds described in the Examples section, or a salt, e.g., a pharmaceutically acceptable salt, thereof. Moreover, if such compound is represented as a salt, the present invention is intended to include free bases, free acids, or alternative salts of these particular compounds. Additional embodiments comprise compositions and medicaments containing the same (including the aforementioned free bases, free acids, or alternative salts), as well as processes for the preparation and use of such compounds, compositions and medicaments. Moreover, it should be noted that each of these compounds, and salts thereof, are also intended to be separate embodiments, and in this regard, each species listed in the Examples, and salt thereof, should be considered to be an individual embodiment.

Moreover, it should be understood that the present invention is intended to include any novel compound or pharmaceutical composition described herein.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention. Unless otherwise stated, variables in the particular embodiments described below are defined as for formula (I).

$R^1$ is chloro.
$R^1$ is cyano.
$R^2$ is hydrogen.
$R^2$ is chloro.
$R^2$ is cyano.
$R^3$ is halo.
$R^3$ is fluoro.
$R^3$ is $C_{1-4}$alkyl.
$R^3$ is methyl.
$R^3$ is ethyl.
$R^3$ is $C_{1-4}$alkoxy.
$R^3$ is methoxy.
$R^3$ is ethoxy.
$R^3$ is allyloxy.
$R^3$ is methyl, ethoxy, or allyloxy.
$R^3$ is methyl, methoxy, ethoxy, or allyloxy.
$R^4$ is hydrogen.
$R^4$ is methyl.
$R^4$ is ethyl.
Ring A is represented by formula (a):

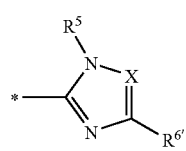

(a)

Ring A is represented by formula (a), and X is $CR^{6'}$.
Ring A is represented by formula (a), and X is N.
Ring A is 1-(2-methoxyethyl)-1H-imidazol-2-yl.
Ring A is 1-methyl-1H-1,2,4-triazol-5-yl.
Ring A is selected from the group consisting of 1-(2-methoxyethyl)-1H-imidazol-2-yl or 1-methyl-1H-1,2,4-triazol-5-yl.

Ring A is formula (c):

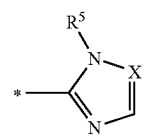

(c)

$R^5$ is hydrogen.
$R^5$ is $C_{1-4}$alkyl.
$R^5$ is methyl.
$R^5$ is $C_{1-4}$alkoxy$C_{1-4}$alkyl.
$R^5$ is methoxyethyl.
Ring A is represented by formula (b):

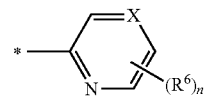

(b)

Ring A is represented by formula (b) and X is CH or $CR^6$.
Ring A is represented by formula (b) and X is N.
Ring A is 3-fluoropyridin-2-yl.
Ring A is pyrazin-2-yl
Ring A is selected from the group consisting of 3-fluoropyridin-2-yl or pyrazin-2-yl.
$R^6$ is piperidino.
$R^6$ is piperazinyl.
$R^6$ is N-methylpiperazino.
$R^6$ is morpholino.
$R^6$ is piperidino, piperazinyl, N-methylpiperazino or morpholino.
$R^6$ is 1-(1H-1,2,3-triazol-5-yl)methanamino.
$R^6$ is 2-(2-oxo-pyrrolidino)ethylamino.
$R^6$ is 2-methoxyethylamino
$R^6$ is 2-(4-fluoropiperidino)ethylamino.
$R^6$ is 1-(1,3-dioxan-4-yl)-N-methylmethanamino.
$R^6$ is N-(1-methoxymethyl-2-methoxyethyl)amino.
$R^6$ is 2-(2-oxo-1,3-oxazolidin-3-yl)-ethylamino.
$R^6$ is 2-(2-methoxyethoxy)-ethylamino.
$R^6$ is 2-morpholinoethylamino.
$R^6$ is 2-(2-oxo-imidazolidin-1-yl)ethylamino
$R^{6'}$ is hydrogen.
$R^{6'}$ is $R^6$.
Ring A is represented by formula (b), X is CH or $CR^6$, and $R^6$ is piperidino, piperazinyl, N-methylpiperazino or morpholino.
Ring A is represented by formula (b), X is N, and $R^6$ is piperidino, piperazinyl, N-methylpiperazino or morpholino.
Ring A is represented by formula (b), X is CH or $CR^6$, n is 1 and $R^6$ is selected from 1-(1H-1,2,3-triazol-5-yl)methanamino, 2-(2-oxo-pyrrolidino)ethylamino, 2-methoxyethylamino, 2-(4-fluoropiperidino)ethylamino, 1-(1,3-dioxan-4-yl)-N-methylmethanamino, N-(1-methoxymethyl-2-methoxyethyl)amino, 2-(2-oxo-1,3-oxazolidin-3-yl)-ethylamino, 2-(2-methoxyethoxy)-ethylamino, 2-morpholinoethylamino, or 2-(2-oxo-imidazolidin-1-yl)ethylamino.
Ring A is represented by formula (b), n is 1 and $R^6$ is selected from 1-(1H-1,2,3-triazol-5-yl)methanamino, 2-(2-oxo-pyrrolidino)ethylamino, 2-methoxyethylamino, 2-(4-fluoropiperidino)ethylamino, 1-(1,3-dioxan-4-yl)-N-methylmethanamino, N-(1-methoxymethyl-2-methoxyethyl)

amino, 2-(2-oxo-1,3-oxazolidin-3-yl)-ethylamino, 2-(2-methoxyethoxy)-ethylamino, 4-[2-(diethylamino)ethyl]piperazin-1-yl, 2-(4-methylpiperazin-1-yl)ethylamino, 2-(dimethylamino)ethoxy, 2-(4-methylpiperazin-1-yl)ethoxy, 2-morpholinoethylamino, or 2-(2-oxo-imidazolidin-1-yl)ethylamino.

Ring A is represented by formula (d):

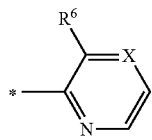
(d)

Ring A is represented by formula (e):

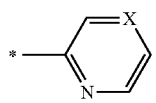
(e)

Ring A is selected from formula (d) or (e):

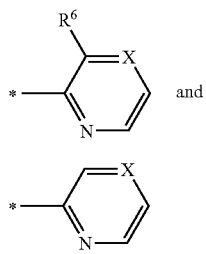
(d)

(e)

Therefore in a further aspect of the invention there is provided a compound of formula (I) (as depicted above) wherein:
R$^1$ is chloro;
R$^2$ is hydrogen, chloro or cyano;
R$^3$ is methyl, ethoxy, or allyloxy;
R$^4$ is hydrogen, methyl or ethyl;
Ring A is 1-(2-methoxyethyl)-1H-imidazol-2-yl, 1-methyl-1H-1,2,4-triazol-5-yl, 3-fluoropyridin-2-yl or pyrazin-2-yl.

Therefore in a further aspect of the invention there is provided a compound of formula (I) (as depicted above) wherein:
R$^1$ is chloro;
R$^2$ is hydrogen, chloro or cyano;
R$^3$ is methyl, ethoxy, or allyloxy;
R$^4$ is hydrogen, methyl or ethyl;
Ring A is formula (c):

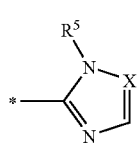
(c)

wherein:
X is CH or N; and
R$^5$ is H, a C$_{1-4}$alkyl, or C$_{1-4}$alkoxyC$_{1-4}$alkyl.

Therefore in a further aspect of the invention there is provided a compound of formula (I) (as depicted above) wherein:
R$^1$ is chloro;
R$^2$ is hydrogen, chloro or cyano;
R$^3$ is methyl, ethoxy, or allyloxy;
R$^4$ is hydrogen, methyl or ethyl;
Ring A is selected from formula (d) or (e):

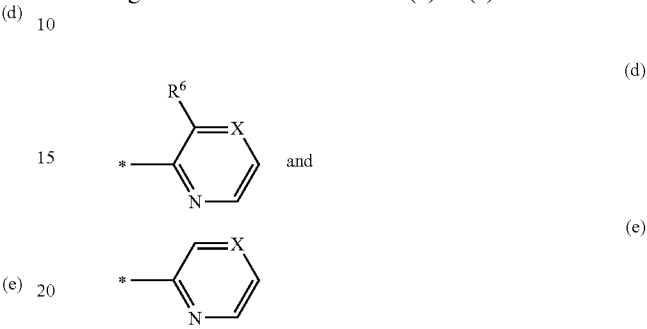

wherein:
X is CH or N; and
R$^6$ is a halo.

Therefore in a further aspect of the invention there is provided a compound of formula (I) (as depicted above) wherein:
R$^1$ is chloro;
R$^2$ is hydrogen, chloro or cyano;
R$^3$ is methyl, methoxy, ethoxy, or allyloxy;
R$^4$ is hydrogen, methyl or ethyl;
Ring A is selected from formula (d) or (e):

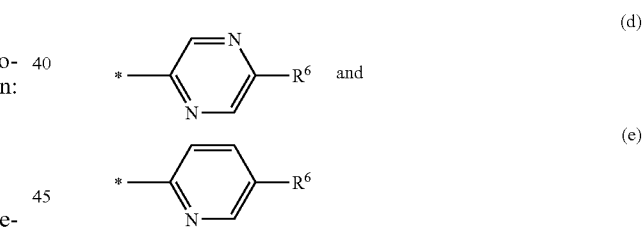

wherein:
R$^6$ is —OR$^8$ or —NR$^7$R$^8$;
R$^7$ is hydrogen or a C1-4alkyl; and
R$^8$ is selected from the group consisting of 1-(1H-1,2,3-triazol-5-yl)methyl, 2-(2-oxo-pyrrolidino)ethyl, 2-methoxyethyl, 2-(4-fluoropiperidino)ethyl, 1-(1,3-dioxan-4-yl)-N-methylmethyl, 1-methoxymethyl-2-methoxyethyl, 2-(4-methylpiperazin-1-yl)ethyl, 2-(dimethylamino)ethyl, 2-(4-methylpiperazin-1-yl)ethyl, 2-(2-oxo-1,3-oxazolidin-3-yl)-ethyl, 2-(2-methoxyethoxy)-ethyl, 2-morpholinoethyl, or 2-(2-oxo-imidazolidin-1-yl)ethyl.

Therefore in a further aspect of the invention there is provided a compound of formula (I) (as depicted above) wherein:
R$^1$ is chloro;
R$^2$ is hydrogen, chloro or cyano;
R$^3$ is methyl, methoxy, ethoxy, or allyloxy;
R$^4$ is hydrogen, methyl or ethyl;

Ring A is selected from formula (d) or (e):

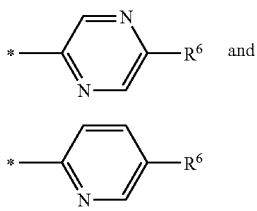

wherein:
R⁶ is —NR⁷R⁸;
R⁷ is hydrogen or a C1-4alkyl; and
R⁸ is selected from the group consisting of 1-(1H-1,2,3-triazol-5-yl)methyl, 2-(2-oxo-pyrrolidino)ethyl, 2-methoxyethyl, 2-(4-fluoropiperidino)ethyl, 1-(1,3-dioxan-4-yl)-N-methylmethyl, 1-methoxymethyl-2-methoxyethyl, 2-(2-oxo-1,3-oxazolidin-3-yl)-ethyl, 2-(2-methoxyethoxy)-ethyl, 2-morpholinoethyl, or 2-(2-oxo-imidazolidin-1-yl)ethyl.

Therefore in a further aspect of the invention there is provided a compound of formula (I) (as depicted above) wherein:
R¹ is chloro;
R² is hydrogen, chloro or cyano;
R³ is methyl, methoxy, ethoxy, or allyloxy;
R⁴ is hydrogen, methyl or ethyl;
Ring A is selected from formula (d) or (e):

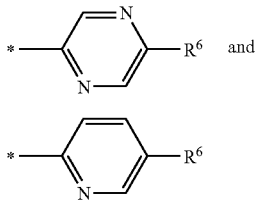

wherein:
R⁶ is piperidino, piperazinyl, N-methylpiperazino or morpholino.

Therefore in a further aspect of the invention there is provided a compound of formula (I) (as depicted above) wherein:
R¹ is chloro;
R² is hydrogen, chloro or cyano;
R³ is methoxy;
R⁴ is hydrogen, methyl or ethyl;
Ring A is selected from formula (d) or (e):

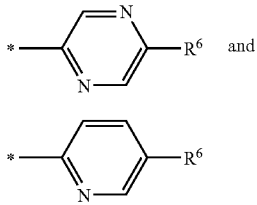

wherein:
R⁶ is —NR⁷R⁸;
R⁷ is hydrogen or a C1-4alkyl; and
R⁸ is selected from the group consisting of 1-(1H-1,2,3-triazol-5-yl)methyl, 2-(2-oxo-pyrrolidino)ethyl, 2-methoxyethyl, 2-(4-fluoropiperidino)ethyl, 1-(1,3-dioxan-4-yl)-N-methylmethyl, 1-methoxymethyl-2-methoxyethyl, 2-(2-oxo-1,3-oxazolidin-3-yl)-ethyl, 2-(2-methoxyethoxy)-ethyl, 2-morpholinoethyl, or 2-(2-oxo-imidazolidin-1-yl)ethyl.

Therefore in a further aspect of the invention there is provided a compound of formula (I) (as depicted above) wherein:
R¹ is chloro;
R² is hydrogen, chloro or cyano;
R³ is methoxy;
R⁴ is hydrogen, methyl or ethyl;
Ring A is selected from formula (d) or (e):

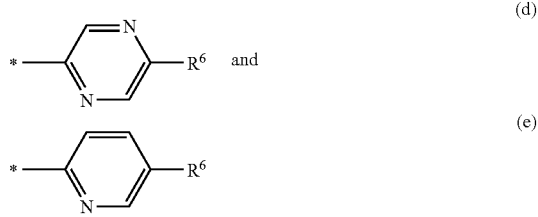

wherein:
R⁶ is piperidino, piperazinyl, N-methylpiperazino or morpholino.

Therefore in a further aspect of the invention there is provided a compound of formula (I) (as depicted above) wherein:
R¹ is chloro;
R² is chloro;
R³ is methoxy;
R⁴ is hydrogen, methyl or ethyl;
Ring A is selected from formula (d) or (e):

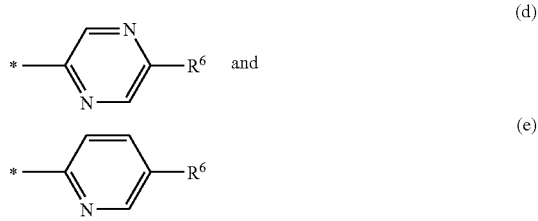

wherein:
R⁶ is —NR⁷R⁸;
R⁷ is hydrogen or a C1-4alkyl; and
R⁸ is selected from the group consisting of 1-(1H-1,2,3-triazol-5-yl)methyl, 2-(2-oxo-pyrrolidino)ethyl, 2-methoxyethyl, 2-(4-fluoropiperidino)ethyl, 1-(1,3-dioxan-4-yl)-N-methylmethyl, 1-methoxymethyl-2-methoxyethyl, 2-(2-oxo-1,3-oxazolidin-3-yl)-ethyl, 2-(2-methoxyethoxy)-ethyl, 2-morpholinoethyl, or 2-(2-oxo-imidazolidin-1-yl)ethyl.

Therefore in a further aspect of the invention there is provided a compound of formula (I) (as depicted above) wherein:
R¹ is chloro;
R² is chloro;
R³ is methoxy;
R⁴ is hydrogen, methyl or ethyl;

Ring A is selected from formula (d) or (e):

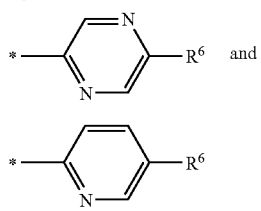

(d)

(e)

wherein:

$R^6$ is piperidino, piperazinyl, N-methylpiperazino or morpholino.

Particular compounds of the invention are the compounds of the Examples, each of which provides a further independent aspect of the invention. In further aspects, the present invention also comprises any two or more compounds of the Examples.

In one embodiment of the invention are provided compounds of formula (I). In an alternative embodiment are provided pharmaceutically-acceptable salts of compounds of formula (I).

In a further aspect the present invention provides a process for preparing a compound of formula (I), or a pharmaceutically-acceptable salt thereof.

Thus, the present invention also provides that the compounds of the formula (I) and pharmaceutically-acceptable salts thereof, can be prepared by a process as follows (wherein the variables are as defined above unless otherwise stated):

Process a) reacting a compound of formula (II) or:

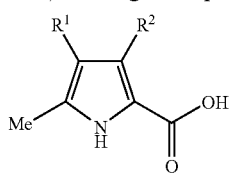

(II)

or an activated acid derivative thereof; with a compound of formula (III):

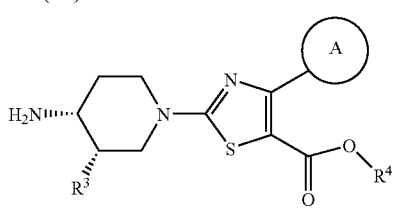

(III)

or

Process b) reacting a compound of formula (IV):

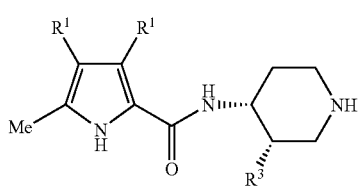

(IV)

with a compound of formula (V):

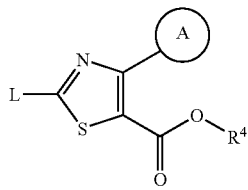

(V)

wherein L is a displaceable group; or

Process c) for compounds of formula (I) wherein $R^4$ is $C_{1-4}$alkyl; reacting a compound of formula (I) which is a compound of formula (VI) or (VI'):

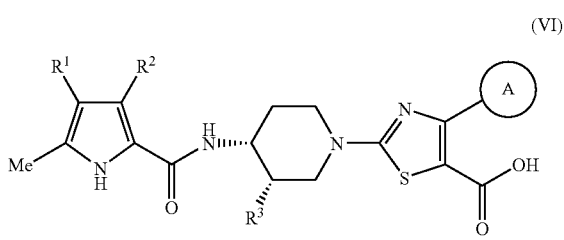

(VI)

with a compound of formula (VII):

$R^{4a}$—OH (VII)

wherein $R^{4a}$ is $C_{1-4}$alkyl;

or

Process d) for compounds of formula (I) or wherein $R^4$ is hydrogen; deprotecting a compound of formula (VIII):

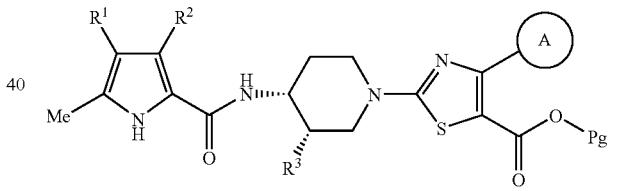

(VIII)

wherein Pg is a carboxylic acid protecting group, such as a $C_{1-4}$alkyl;

and thereafter if necessary:

i) converting a compound of the formula (I) into another compound of the formula (I);
ii) removing any protecting groups;
iii) forming a pharmaceutically acceptable salt; and/or
iv) chirally purifying the compound of formula (I).

L is a displaceable group. Suitable values for L include halo, for example chloro and bromo, pentafluorophenoxy and 2,5-oxopyrrolidin-1-yloxy.

Pg is a carboxylic acid protecting group. Suitable values for Pg are defined herein below.

Specific reaction conditions for the above reaction are as follows.

Process a) Compounds of formula (II) and (III) may be coupled together in the presence of a suitable coupling reagent. Standard peptide coupling reagents known in the art can be employed as suitable coupling reagents, or for example carbonyldiimidazole, 1-ethyl-3-(3-dimethylaminopropyl)carbodiimide, and dicyclohexyl-carbodiimide, optionally in the presence of a catalyst such as dimethylaminopyridine or 4-pyrrolidinopyridine, optionally in the presence of a base for example N-methyl-morpholine, triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (III) may be prepared according to Scheme 1:

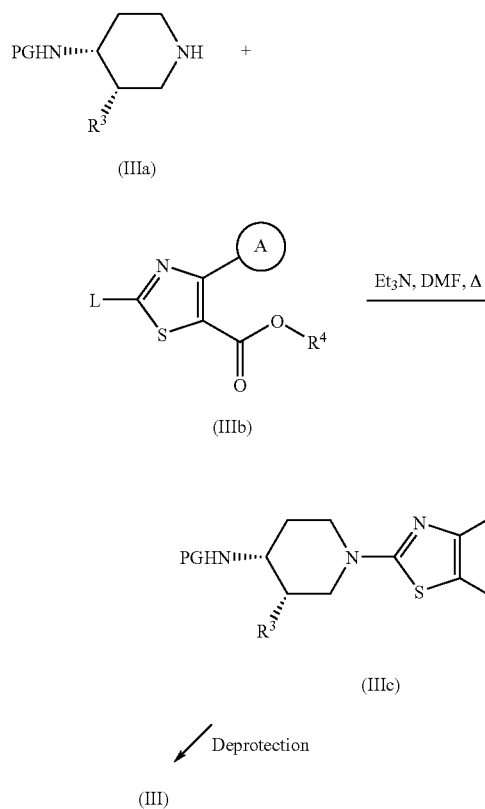

wherein PG is a nitrogen protecting group such as those defined herein below; and L is a displaceable group such as those defined herein above.

Compounds of formula (II) are commercially available compounds, or they are known in the literature, or they are prepared by standard processes known in the art.

Process b) Compounds of formula (IV) and (V) in a suitable solvent such as dimethylformamide, N-methylpyrrolidine, or N-methyl 2-pyrrolidinone and optionally in the presence of a base such as triethylamine or diisopropylethylamine are heated together at a temperature range between 50 to 100° C.

Compounds of formula (IV) may be prepared according to Scheme 2:

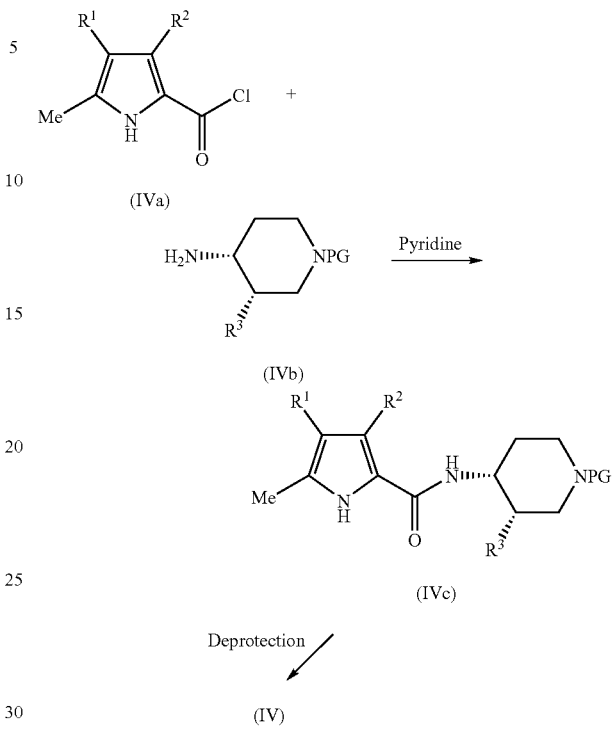

wherein PG is a nitrogen protecting group such as those defined herein below. Compounds of formula (IV) may also be prepared from a carboxylic acid derivative (IVd) and an amine derivative (IVb) using standard peptide coupling reagents as described hereinabove (see Scheme 3).

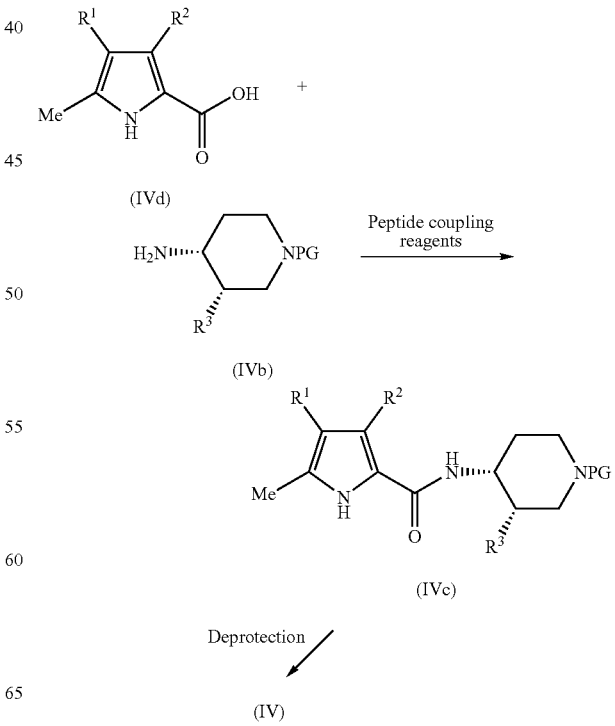

Compounds of formula (V) may be prepared according to Scheme 4:

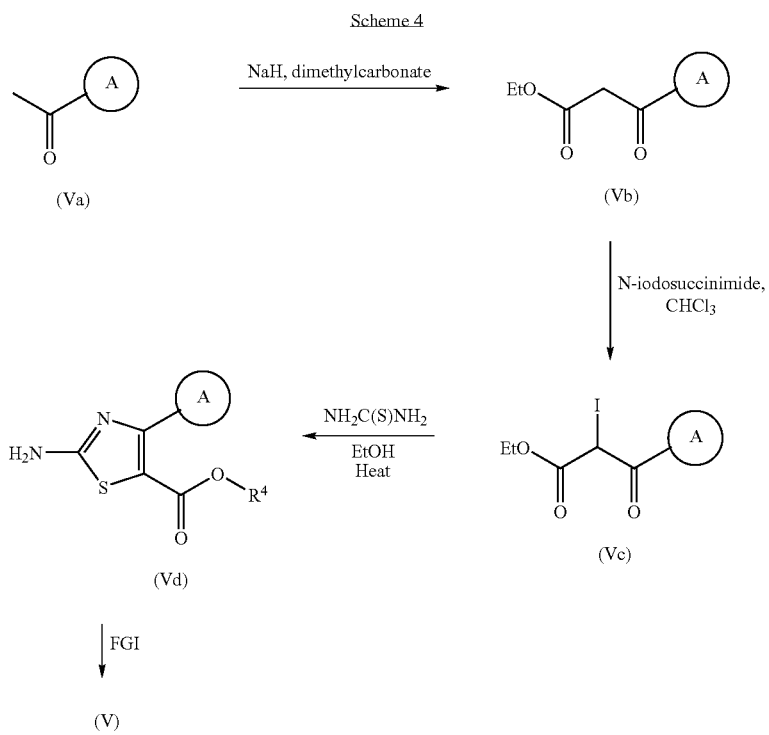

Scheme 4

Wherein FGI is functional group interconversion of the NH$_2$ group to the required "L". For example, a compound of formula (Vd) in glacial acetic acid and concentrated HCl can be treated with sodium nitrite to convert the amino group to a chloro group.

Process c) Compounds of formula (VI) and (VII) in a suitable solvent such as methanol, ethanol, or tetrahydrofuran in the presence of a base such as sodium hydroxide, lithium hydroxide, or barium hydroxide are reacted at a temperature range of 25 to 100° C.

Compounds of formula (VI) may be prepared by a suitable modification of the reactions described herein to make a compound of formula (I) wherein R$^4$ is hydrogen.

Compounds of formula (VII) are commercially available compounds, or they are known in the literature, or they are prepared by standard processes known in the art.

Process d) Suitable deprotection conditions are described hereinbelow.

Compounds of formula (VIII) may be prepared by a suitable modification of the reactions described herein to make a compound of formula (I).

The formation of a pharmaceutically-acceptable salt is within the skill of an ordinary organic chemist using standard techniques.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. The reagents used to introduce such ring substituents are either commercially available or are made by processes known in the art.

Introduction of substituents into a ring may convert one compound of the formula (I) into another compound of the formula (I). Such reactions and modifications include, for example, introduction of a substituent by means of an aromatic substitution reaction, reduction of substituents, alkylation of substituents, oxidation of substituents, esterification of substituents, amidation of substituents, formation of heteroaryl rings. The reagents and reaction conditions for such procedures are well known in the chemical art. Particular examples of aromatic substitution reactions include the introduction of alkoxides, diazotization reactions followed by introduction of thiol group, alcohol group, halogen group. Examples of modifications include; oxidation of alkylthio to alkylsulphinyl or alkylsulphonyl.

The skilled organic chemist will be able to use and adapt the information contained and referenced within the above references, and accompanying Examples therein and also the Examples herein, to obtain necessary starting materials, and products. If not commercially available, the necessary starting materials for the procedures such as those described above may be made by procedures which are selected from standard organic chemical techniques, techniques which are analogous to the synthesis of known, structurally similar compounds, or techniques which are analogous to the above described procedure or the procedures described in the examples. It is noted that many of the starting materials for synthetic methods as described above are commercially available and/or widely reported in the scientific literature, or could be made from commercially available compounds using adaptations of processes reported in the scientific literature. The reader is further referred to Advanced Organic Chemistry, 4$^{th}$ Edition, by Jerry March, published by John Wiley & Sons 1992, for general guidance on reaction conditions and reagents.

It will also be appreciated that in some of the reactions mentioned herein it may be necessary/desirable to protect any sensitive groups in compounds. The instances where protection is necessary or desirable are known to those skilled in the art, as are suitable methods for such protection. Conventional protecting groups may be used in accordance with standard practice (for illustration see T.W. Greene, Protective Groups in Organic Synthesis, John Wiley and Sons, 1991).

Examples of a suitable protecting group for a hydroxy group is, for example, an acyl group, for example an alkanoyl group such as acetyl, an aroyl group, for example benzoyl, a silyl group such as trimethylsilyl or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively a silyl group such as trimethylsilyl may be removed, for example, by fluoride or by aqueous acid; or an arylmethyl group such as a benzyl group may be removed, for example, by hydrogenation in the presence of a catalyst such as palladium-on-carbon.

A suitable protecting group for an amino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine or 2-hydroxyethylamine, or with hydrazine.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon, or for example, an allyl group which may be removed, for example, by use of a palladium catalyst such as palladium acetate.

The protecting groups may be removed at any convenient stage in the synthesis using conventional techniques well known in the chemical art, or they may be removed during a later reaction step or work-up.

Optically active forms of a compound of the invention may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

Enzyme Potency Testing Methods

E. coli GyrB ATPase Inhibition Activity: Compounds can be tested for inhibition of E. coli GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1 mM 1,4-Dithio-DL-threitol, 200 nM bovine serum albumin, 1.6 µg/ml sheared salmon sperm DNA, 400 pM E. coli GyrA, 400 pM E. coli GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid. Plates can be read in an absorbance plate reader at 650 nm and percent inhibition values are calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

E. coli Topoisomerase IV ATPase Inhibition Activity: Compounds can be tested for inhibition of E. coli topoisomerase IV ATPase activity as described above for E. coli GyrB except the 30 µl reactions contained the following: 20 mM TRIS buffer pH 8, 50 mM ammonium acetate, 8 mM magnesium chloride, 5% glycerol, 5 mM 1,4-Dithio-DL-threitol, 0.005% Brij-35, 5 µg/ml sheared salmon sperm DNA, 500 pM E. coli ParC, 500 pM E. coli ParE, 160 µM ATP, and compound in dimethylsulfoxide. An $IC_{50}$ measurement of compound potency for each compound can be determined from reactions performed in the presence of 10 different compound concentrations.

S. aureus GyrB ATPase Inhibition Activity: Compounds may be tested for inhibition of S. aureus GyrB ATPase activity using an ammonium molybdate/malachite green-based phosphate detection assay (Lanzetta, P. A., L. J. Alvarez, P. S. Reinach, and O. A. Candia, 1979, 100: 95-97). Assays can be performed in multiwell plates in 30 µl reactions containing: 50 mM Hepes buffer pH 7.5, 75 mM ammonium acetate, 8.0 mM magnesium chloride, 0.5 mM ethylenediaminetetraacetic acid, 5% glycerol, 1.0 mM 1,4-Dithio-DL-threitol, 200 nM bovine serum albumin, 1.0 µg/ml sheared salmon sperm DNA, 250 pM E. coli GyrA, 250 pM S. aureus GyrB, 250 µM ATP, and compound in dimethylsulfoxide. Reactions can be quenched with 30 µl of ammonium molybdate/malachite green detection reagent containing 1.2 mM malachite green hydrochloride, 8.5 mM ammonium molybdate tetrahydrate, and 1 M hydrochloric acid. Plates can be read in an absorbance plate reader at 650 nm and percent inhibition values can be calculated using dimethylsulfoxide (2%)-containing reactions as 0% inhibition and EDTA-containing (2.4 µM) reactions as 100% inhibition controls. An $IC_{50}$ measurement of compound potency for each compound can be determined from reactions performed in the presence of 10 different compound concentrations.

Compounds of the invention were tested in an assay substantially similar to the assay described above for measuring the inhibition of S. aureus GyrB ATPase. Percent inhibition of S. aureus GyrB ATPase at a compound concentration of 1 µM (unless otherwise noted) is disclosed in the following table:

| Example # | % Inhibition at 1 μM |
|---|---|
| 1 | 99 |
| 2 | 103 |
| 4 | 97 |
| 5 | 5 |
| 6 | 99 |
| 7 | 100 |
| 8 | 100 |
| 9 | 98 |
| 10 | 90 |
| 11 | 101 |
| 12 | 106 |
| 13 | 99 |
| 14 | 91 |
| 15 | 98 |
| 16 | 103 |
| 17 | 106 |
| 18 | 108 |
| 19 | 112 |
| 20 | 118 |
| 21 | 118 |
| 22 | 112 |
| 23 | 100 |
| 24 | 120 |
| 25 | 119 |
| 26 | 97 |
| 27 | 102 |
| 28 | 98 |
| 29 | 98 |
| 61 | 105 |
| 62 | 98 |
| 63 | 104 |
| 64 | 104 |
| 65 | 107 |
| 86 | 105 |
| 87 | 109 |
| 88 | 107 |
| 89 | 110 |
| 90 | 103 |
| 91 | 105 |
| 92 | 102 |
| 93 | 94 |
| 94 | 104 |
| 95 | 114 |
| 96 | 104 |
| 97 | 112 |
| 98 | 116 |
| 99 | 106 |
| 100 | 102 |
| 101 | 117 |
| 102 | 112 |
| 103 | 102 |
| 104 | 105 |
| 124 | 112 |
| 125 | 111 |
| 126 | 108 |
| 127 | 110 |
| 128 | 110 |
| 129 | 103 |
| 130 | 107 |
| 131 | 108 |
| 132 | 103 |
| 133 | 112 |
| 134 | 104 |
| 135 | 98 |
| 136 | 104 |
| 137 | 101 |
| 138 | 103 |
| 139 | 99 |
| 140 | 107 |
| 141 | 103 |
| 142 | 103 |
| 164 | 117 |
| 165 | 107 |
| 166 | 110 |
| 167 | 113 |
| 168 | 102 |
| 169 | 102 |
| 170 | 119 |
| 171 | 101 |
| 172 | 109 |
| 173 | 104 |
| 174 | 102 |
| 175 | 106 |
| 176 | 108 |
| 177 | 107 |
| 178 | 102 |
| 179 | 104 |
| 180 | 103 |
| 181 | 101 |
| 182 | 117 |
| 183 | 116 |
| 189 | 106 |
| 190 | 100 |
| 191 | 102 |
| 192 | 108 |
| 193 | 109 |
| 195 | 118 |
| 200 | 106 |
| 201 | 105 |
| 202 | 103 |
| 203 | 108 |
| 208 | 108 |
| 209 | 105 |
| 210 | 109 |
| 211 | 107 |
| 215 | 106 |
| 216 | 109 |
| 217 | 113 |

Bacterial Susceptibility Testing Methods

Compounds may be tested for antimicrobial activity by susceptibility testing in liquid media. Compounds may be dissolved in dimethylsulfoxide and tested in 10 doubling dilutions in the susceptibility assays. The organisms used in the assay may be grown overnight on suitable agar media and then suspended in a liquid medium appropriate for the growth of the organism. The suspension can be a 0.5 McFarland and a further 1 in 10 dilution can be made into the same liquid medium to prepare the final organism suspension in 100 μL. Plates can be incubated under appropriate conditions at 37° C. for 24 hrs prior to reading. The Minimum Inhibitory Concentration (MIC) may be determined as the lowest drug concentration able to reduce growth by 80% or more.

In an assay comparable to the above, Example 23 had an MIC of 0.78 μg/ml against *Streptococcus pneumoniae*.

According to a further feature of the invention there is provided a compound of the formula (I), or a pharmaceutically-acceptable salt thereof for use in a method of treatment of the human or animal body by therapy.

We have found that compounds of the present invention inhibit bacterial DNA gyrase and/or topoisomerase IV and are therefore of interest for their antibacterial effects. In one aspect of the invention the compounds of the invention inhibit bacterial DNA gyrase and are therefore of interest for their antibacterial effects. In one aspect of the invention, the compounds of the invention inhibit topoisomerase IV and are therefore of interest for their antibacterial effects. In one aspect of the invention, the compounds of the invention inhibit both DNA gyrase and topoisomerase IV and are therefore of interest for their antibacterial effects.

It is expected that the compounds of the present invention will be useful in treating bacterial infections. In one aspect of the invention "infection" or "bacterial infection" refers to a gynecological infection. In one aspect of the invention "infection" or "bacterial infection" refers to a respiratory tract infection (RTI). In one aspect of the invention "infection" or "bacterial infection" refers to a sexually transmitted disease. In one aspect of the invention "infection" or "bacterial infection" refers to a urinary tract infection. In one aspect of the invention "infection" or "bacterial infection" refers to acute exacerbation of chronic bronchitis (ACEB). In one aspect of the invention "infection" or "bacterial infection" refers to acute otitis media. In one aspect of the invention "infection" or "bacterial infection" refers to acute sinusitis. In one aspect of the invention "infection" or "bacterial infection" refers to an infection caused by drug resistant bacteria. In one aspect of the invention "infection" or "bacterial infection" refers to catheter-related sepsis. In one aspect of the invention "infection" or "bacterial infection" refers to chancroid. In one aspect of the invention "infection" or "bacterial infection" refers to chlamydia. In one aspect of the invention "infection" or "bacterial infection" refers to community-acquired pneumoniae (CAP). In one aspect of the invention "infection" or "bacterial infection" refers to complicated skin and skin structure infection. In one aspect of the invention "infection" or "bacterial infection" refers to uncomplicated skin and skin structure infection. In one aspect of the invention "infection" or "bacterial infection" refers to endocarditis. In one aspect of the invention "infection" or "bacterial infection" refers to febrile neutropenia. In one aspect of the invention "infection" or "bacterial infection" refers to gonococcal cervicitis. In one aspect of the invention "infection" or "bacterial infection" refers to gonococcal urethritis. In one aspect of the invention "infection" or "bacterial infection" refers to hospital-acquired pneumonia (HAP). In one aspect of the invention "infection" or "bacterial infection" refers to osteomyelitis. In one aspect of the invention "infection" or "bacterial infection" refers to sepsis. In one aspect of the invention "infection" or "bacterial infection" refers to syphilis.

In one aspect of the invention an "infection" or "bacterial infection" refers to an infection caused by *Acinetobacter baumanii*. In one aspect of the invention an "infection" or "bacterial infection" refers to an infection caused by *Acinetobacter haemolyticus*. In one aspect of the invention an "infection" or "bacterial infection" refers to an infection caused by *Acinetobacter junii*. In one aspect of the invention an "infection" or "bacterial infection" refers to an infection caused by *Acinetobacter johnsonii*. In one aspect of the invention an "infection" or "bacterial infection" refers to an infection caused by *Acinetobacter lwoffi*. In one aspect of the invention an "infection" or "bacterial infection" refers to an infection caused by *Bacteroides bivius*. In one aspect of the invention an "infection" or "bacterial infection" refers to an infection caused by *Bacteroides fragilis*. In one aspect of the invention an "infection" or "bacterial infection" refers to an infection caused by *Burkholderia cepacia*. In one aspect of the invention an "infection" or "bacterial infection" refers to an infection caused by *Campylobacter jejuni*. In one aspect of the invention an "infection" or "bacterial infection" refers to an infection caused by *Chlamydia pneumoniae*. In one aspect of the invention an "infection" or "bacterial infection" refers to an infection caused by *Chlamydia urealyticus*. In one aspect of the invention an "infection" or "bacterial infection" refers to an infection caused by *Chlamydophila pneumoniae*. In one aspect of the invention an "infection" or "bacterial infection" refers to an infection caused by *Clostridium difficili*. In one aspect of the invention an "infection" or "bacterial infection" refers to an infection caused by *Enterobacter aerogenes*. In one aspect of the invention an "infection" or "bacterial infection" refers to an infection caused by *Enterobacter cloacae*. In one aspect of the invention an "infection" or "bacterial infection" refers to an infection caused by *Enterococcus faecalis*. In one aspect of the invention an "infection" or "bacterial infection" refers to an infection caused by *Enterococcus faecium*. In one aspect of the invention an "infection" or "bacterial infection" refers to an infection caused by *Escherichia coli*. In one aspect of the invention an "infection" or "bacterial infection" refers to an infection caused by *Gardnerella vaginalis*. In one aspect of the invention an "infection" or "bacterial infection" refers to an infection caused by *Haemophilus parainfluenzae*. In one aspect of the invention an "infection" or "bacterial infection" refers to an infection caused by *Haemophilus influenzae*. In one aspect of the invention an "infection" or "bacterial infection" refers to an infection caused by *Helicobacter pylori*. In one aspect of the invention an "infection" or "bacterial infection" refers to an infection caused by *Klebsiella pneumoniae*. In one aspect of the invention an "infection" or "bacterial infection" refers to an infection caused by *Legionella pneumophila*. In one aspect of the invention an "infection" or "bacterial infection" refers to an infection caused by Methicillin-resistant *Staphylococcus aureus*. In one aspect of the invention an "infection" or "bacterial infection" refers to an infection caused by Methicillin-susceptible *Staphylococcus aureus*. In one aspect of the invention an "infection" or "bacterial infection" refers to an infection caused by *Moraxella catarrhalis*. In one aspect of the invention an "infection" or "bacterial infection" refers to an infection caused by *Morganella morganii*. In one aspect of the invention an "infection" or "bacterial infection" refers to an infection caused by *Mycoplasma pneumoniae*. In one aspect of the invention an "infection" or "bacterial infection" refers to an infection caused by *Neisseria gonorrhoeae*. In one aspect of the invention an "infection" or "bacterial infection" refers to an infection caused by Penicillin-resistant *Streptococcus pneumoniae*. In one aspect of the invention an "infection" or "bacterial infection" refers to an infection caused by Penicillin-susceptible *Streptococcus pneumoniae*. In one aspect of the invention an "infection" or "bacterial infection" refers to an infection caused by *Peptostreptococcus magnus*. In one aspect of the invention an "infection" or "bacterial infection" refers to an infection caused by *Peptostreptococcus micros*. In one aspect of the invention an "infection" or "bacterial infection" refers to an infection caused by *Peptostreptococcus anaerobius*. In one aspect of the invention an "infection" or "bacterial infection" refers to an infection caused by *Peptostreptococcus asaccharolyticus*. In one aspect of the invention an "infection" or "bacterial infection" refers to an infection caused by *Peptostreptococcus prevotii*. In one aspect of the invention an "infection" or "bacterial infection" refers to an infection caused by *Peptostreptococcus tetradius*. In one aspect of the invention an "infection" or "bacterial infection" refers to an infection caused by *Peptostreptococcus vaginalis*. In one aspect of the invention an "infection" or "bacterial infection" refers to an infection caused by *Proteus mirabilis*. In one aspect of the invention an "infection" or "bacterial infection" refers to an infection caused by *Pseudomonas aeruginosa*. In one aspect of the invention an "infection" or "bacterial infection" refers to an infection caused by Quinolone-Resistant *Staphylococcus aureus*. In one aspect of the invention an "infection" or "bacterial infection" refers to an infection caused by Quinolone-Resistant *Staphylococcus epidermis*. In one aspect of the invention an "infection" or "bacterial infection" refers to an infection caused by *Salmonella typhi*. In one aspect of the invention an "infection" or "bacterial infection" refers to an infection caused by *Salmonella paratyphi*. In one aspect of the invention an "infection" or "bacterial infection" refers to an infection caused by *Salmonella enteritidis*. In one aspect of the invention an "infection" or "bacterial infection" refers to an infection caused by *Salmonella typhimurium*. In one aspect of the invention an "infection" or "bacterial infection" refers to an infection caused by *Serratia marcescens*. In one aspect of the invention an "infection" or "bacterial infection" refers to an infection caused by *Staphylococcus aureus*. In one aspect of the invention an "infection" or "bacterial infection" refers to an infection caused by *Staphylococcus epidermidis*. In one aspect of the invention an "infection" or "bacterial infection" refers to an infection caused by *Staphylococcus saprophyticus*. In one aspect of the invention an "infection" or "bacterial infection" refers to an infection caused by *Streptoccocus agalactiae*. In one aspect of the invention an "infection" or "bacterial infection" refers to an infection caused by *Streptococcus agalactiae*. In one aspect of the invention an "infection" or "bacterial infection" refers to an infection caused by *Streptococcus pneumoniae*. In one aspect of the invention an "infection" or "bacterial infection" refers to an infection caused by *Streptococcus pyogenes*. In one aspect of the invention an "infection" or "bacterial infection" refers to an infection caused by *Stenotrophomonas maltophilia*. In one aspect of the invention an "infection" or "bacterial infection" refers to an infection caused by *Ureaplasma urealyticum*. In one aspect of the invention an "infection" or "bacterial infection" refers to an infection caused by Vancomycin-Resistant *Enterococcus faecium*. In one aspect of the invention an "infection" or "bacterial infection" refers to an infection caused by Vancomycin-Resistant *Enterococcus faecalis*. In one aspect of the invention an "infection" or "bacterial infection" refers to an infection caused by Vancomycin-Resistant *Staphylococcus aureus*. In one aspect of the invention an "infection" or "bacterial infection" refers to an infection caused by Vancomycin-Resistant *Staphylococcus epidermis*.

In one aspect of the invention an "infection" or "bacterial infection" refers to an infection caused by *Acinetobacter* spp. In one aspect of the invention an "infection" or "bacterial infection" refers to an infection caused by *Bacteroides* spp. In one aspect of the invention an "infection" or "bacterial infection" refers to an infection caused by *Burkholderia* spp. In one aspect of the invention an "infection" or "bacterial infection" refers to an infection caused by *Campylobacter* spp. In one aspect of the invention an "infection" or "bacterial infection" refers to an infection caused by *Chlamydia* spp. In one aspect of the invention an "infection" or "bacterial infection" refers to an infection caused by *Chlamydophila* spp. In one aspect of the invention an "infection" or "bacterial infection" refers to an infection caused by *Clostridium* spp. In one aspect of the invention an "infection" or "bacterial infection" refers to an infection caused by *Enterobacter* spp. In one aspect of the invention an "infection" or "bacterial infection" refers to an infection caused by *Enterococcus* spp. In one aspect of the invention an "infection" or "bacterial infection" refers to an infection caused by *Escherichia* spp. In one aspect of the invention an "infection" or "bacterial infection" refers to an infection caused by *Gardnerella* spp. In one aspect of the invention an "infection" or "bacterial infection" refers to an infection caused by *Haemophilus* spp. In one aspect of the invention an "infection" or "bacterial infection" refers to an infection caused by *Helicobacter* spp. In one aspect of the invention an "infection" or "bacterial infection" refers to an infection caused by *Klebsiella* spp. In one aspect of the invention an "infection" or "bacterial infection" refers to an infection caused by *Legionella* spp. In one aspect of the invention an "infection" or "bacterial infection" refers to an infection caused by *Moraxella* spp. In one aspect of the invention an "infection" or "bacterial infection" refers to an infection caused by *Morganella* spp. In one aspect of the invention an "infection" or "bacterial infection" refers to an infection caused by *Mycoplasma* spp. In one aspect of the invention an "infection" or "bacterial infection" refers to an infection caused by *Neisseria* spp. In one aspect of the invention an "infection" or "bacterial infection" refers to an infection caused by *Peptostreptococcus* spp. In one aspect of the invention an "infection" or "bacterial infection" refers to an infection caused by *Proteus* spp. In one aspect of the invention an "infection" or "bacterial infection" refers to an infection caused by *Pseudomonas* spp. In one aspect of the invention an "infection" or "bacterial infection" refers to an infection caused by *Salmonella* spp. In one aspect of the invention an "infection" or "bacterial infection" refers to an infection caused by *Serratia* spp. In one aspect of the invention an "infection" or "bacterial infection" refers to an infection caused by *Staphylococcus* spp. In one aspect of the invention an "infection" or "bacterial infection" refers to an infection caused by *Streptoccocus* spp. In one aspect of the invention an "infection" or "bacterial infection" refers to an infection caused by *Stenotrophomonas* spp. In one aspect of the invention an "infection" or "bacterial infection" refers to an infection caused by *Ureaplasma* spp. In one aspect of the invention an "infection" or "bacterial infection" refers to an infection caused by aerobes. In one aspect of the invention an "infection" or "bacterial infection" refers to an infection caused by obligate anaerobes. In one aspect of the invention an "infection" or "bacterial infection" refers to an infection caused by facultative anaerobes. In one aspect of the invention an "infection" or "bacterial infection" refers to an infection caused by gram-positive bacteria. In one aspect of the invention an "infection" or "bacterial infection" refers to an infection caused by gram-negative bacteria. In one aspect of the invention an "infection" or "bacterial infection" refers to an infection caused by gram-variable bacteria. In one aspect of the invention an "infection" or "bacterial infection" refers to an infection caused by atypical respiratory pathogens.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

According to a further feature of the invention there is provided a method for inhibition of bacterial DNA gyrase and/or topoisomerase IV in a warm-blooded animal, such as a human being, in need of such treatment which comprises administering to said animal an effective amount of a compound of formula (I), or a pharmaceutically acceptable salt thereof as defined hereinbefore.

According to a further feature of the invention there is provided a method of treating a bacterial infection in a warm-blooded animal, such as a human being, in need of such treatment which comprises administering to said animal an effective amount of a compound of formula (I), or a pharmaceutically acceptable salt thereof as defined hereinbefore.

According to a further feature of the invention there is provided a method of preventing a bacterial infection in a warm-blooded animal, such as a human being, in need of such treatment which comprises administering to said animal an effective amount of a compound of formula (I), or a pharmaceutically acceptable salt thereof as defined hereinbefore.

According to a further feature of the invention there is provided a method of treating a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal, such as a human being, in need of such treatment which comprises administering to said animal an effective amount of a compound of formula (I), or a pharmaceutically acceptable salt thereof as defined hereinbefore.

According to a further feature of the invention there is provided a method of preventing a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal, such as a human being, in need of such treatment which comprises administering to said animal an effective amount of a compound of formula (I), or a pharmaceutically acceptable salt thereof as defined hereinbefore.

A further feature of the present invention is a compound of formula (I), and pharmaceutically acceptable salts thereof for use as a medicament. Suitably the medicament is an antibacterial agent.

According to a further aspect of the invention there is provided the use of a compound of formula (I), or a pharmaceutically acceptable salt thereof in the manufacture of a medicament for the production of an anti-bacterial effect in a warm-blooded animal such as a human being.

According to a further aspect of the invention there is provided the use of a compound of formula (I), or a pharmaceutically acceptable salt thereof in the manufacture of a medicament for the inhibition of bacterial DNA gyrase and/or topoisomerase IV in a warm-blooded animal such as a human being.

Thus according to a further aspect of the invention there is provided the use of a compound of formula (I), or a pharmaceutically acceptable salt thereof in the manufacture of a medicament for the treatment of a bacterial infection in a warm-blooded animal such as a human being.

Thus according to a further aspect of the invention there is provided the use of a compound of formula (I), or a pharmaceutically acceptable salt thereof in the manufacture of a medicament for the prevention of a bacterial infection in a warm-blooded animal such as a human being.

Thus according to a further aspect of the invention there is provided the use of a compound of formula (I), or a pharmaceutically acceptable salt thereof in the manufacture of a medicament for the treatment of a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal such as a human being.

Thus according to a further aspect of the invention there is provided the use of a compound of formula (I), or a pharmaceutically acceptable salt thereof in the manufacture of a medicament for the prevention of a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal such as a human being.

According to a further aspect of the invention there is provided a compound of formula (I), or a pharmaceutically acceptable salt thereof for use in the production of an anti-bacterial effect in a warm-blooded animal such as a human being.

According to a further aspect of the invention there is provided a compound of formula (I), or a pharmaceutically acceptable salt thereof for use in inhibition of bacterial DNA gyrase and/or topoisomerase IV in a warm-blooded animal such as a human being.

Thus according to a further aspect of the invention there is provided a compound of formula (I), or a pharmaceutically acceptable salt thereof for use in the treatment of a bacterial infection in a warm-blooded animal such as a human being.

Thus according to a further aspect of the invention there is provided a compound of formula (I), or a pharmaceutically acceptable salt thereof for use in the prevention of a bacterial infection in a warm-blooded animal such as a human being.

Thus according to a further aspect of the invention there is provided a compound of formula (I), or a pharmaceutically acceptable salt thereof for use in the treatment of a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal such as a human being.

Thus according to a further aspect of the invention there is provided a compound of formula (I), or a pharmaceutically acceptable salt thereof for use in the prevention of a bacterial infection selected from a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal such as a human being.

In order to use a compound of the formula (I), or a pharmaceutically-acceptable salt thereof, for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I), or a pharmaceutically-acceptable salt thereof, and a pharmaceutically-acceptable diluent or carrier.

According to a further aspect of the invention there is provided a pharmaceutical composition which comprises a compound of formula (I), as defined hereinbefore or a pharmaceutically acceptable salt thereof, in association with a pharmaceutically acceptable excipient or carrier for use in producing an anti-bacterial effect in a warm-blooded animal, such as a human being.

According to a further aspect of the invention there is provided a pharmaceutical composition which comprises a compound of formula (I), as defined hereinbefore, or a pharmaceutically acceptable salt thereof, in association with a pharmaceutically acceptable excipient or carrier for use in inhibition of bacterial DNA gyrase and/or topoisomerase IV in a warm-blooded animal, such as a human being.

According to a further aspect of the invention there is provided a pharmaceutical composition which comprises a compound of formula (I), as defined hereinbefore, or a pharmaceutically acceptable salt thereof, in association with a pharmaceutically acceptable excipient or carrier for use in the treatment of a bacterial infection in a warm-blooded animal, such as a human being.

According to a further aspect of the invention there is provided a pharmaceutical composition which comprises a compound of formula (I), as defined hereinbefore, or a pharmaceutically acceptable salt thereof, in association with a pharmaceutically acceptable excipient or carrier for use in the treatment of a gynecological infection, a respiratory tract infection (RTI), a sexually transmitted disease, a urinary tract infection, acute exacerbation of chronic bronchitis (ACEB), acute otitis media, acute sinusitis, an infection caused by drug resistant bacteria, catheter-related sepsis, chancroid, chlamydia, community-acquired pneumoniae (CAP), complicated skin and skin structure infection, uncomplicated skin and skin structure infection, endocarditis, febrile neutropenia, gonococcal cervicitis, gonococcal urethritis, hospital-acquired pneumonia (HAP), osteomyelitis, sepsis and/or syphilis in a warm-blooded animal, such as a human being.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of the invention described herein may be applied as a sole therapy or may involve, in addition to a compound of the invention, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following:
  i) other antibacterial agents for example macrolides e.g. erythromycin, azithromycin or clarithromycin; quinolones e.g. ciprofloxacin or levofloxacin; β-lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or
  ii) anti-infective agents for example, an antifungal triazole e.g. or amphotericin; and/or
  iii) biological protein therapeutics for example antibodies, cytokines, bactericidal/permeability-increasing protein (BPI) products; and/or
  iv) efflux pump inhibitors.

Therefore, in a further aspect of the invention there is provided a compound of the formula (I), or a pharmaceutically acceptable salt thereof, and a chemotherapeutic agent selected from:
  i) one or more additional antibacterial agents; and/or
  ii) one or more anti-infective agents; and/or
  iii) biological protein therapeutics for example antibodies, cytokines, bactericidal/permeability-increasing protein (BPI) products; and/or
  iv) one or more efflux pump inhibitors.

In another embodiment, the invention relates to a method of treating a bacterial infection in an animal, such as a human, comprising administering to the animal an effective amount of a compound of formula (I), or a pharmaceutically acceptable salt thereof, and a chemotherapeutic agent selected from:
  i) one or more additional antibacterial agents; and/or
  ii) one or more anti-infective agents; and/or
  iii) biological protein therapeutics for example antibodies, cytokines, bactericidal/permeability-increasing protein (BPI) products; and/or
  iv) one or more efflux pump inhibitors.

As stated above the size of the dose required for the therapeutic or prophylactic treatment of a particular disease state will necessarily be varied depending on the host treated, the route of administration, the severity of the illness being treated, and whether or not an additional chemotherapeutic agent is administered in combination with a compound of the invention. Preferably a daily dose in the range of 1-50 mg/kg is employed. However the daily dose will necessarily be varied depending upon the host treated, the particular route of administration, the severity of the illness being treated, and whether or not an additional chemotherapeutic agent is administered in combination with a compound of the invention. Accordingly the optimum dosage may be determined by the practitioner who is treating any particular patient.

As noted above, one embodiment of the present invention is directed to treating or preventing diseases caused by bacterial infections, wherein the bacteria comprise a GyrB ATPase or topoisomerase IV ATPase enzyme. Treating a subject with a bacterial infection includes achieving, partially or substantially, one or more of the following: the reducing or amelioration of the progression, severity and/or duration of the infection, arresting the spread of an infection, ameliorating or improving a clinical symptom or indicator associated with a the infection (such as tissue or serum components), and preventing the reoccurrence of the infection.

As used herein, the terms "preventing a bacterial infection" refer to the reduction in the risk of acquiring the infection, or the reduction or inhibition of the recurrence of the infection. In a preferred embodiment, a compound of the invention is administered as a preventative measure to a patient, preferably a human, before a surgical procedure is preformed on the patient to prevent infection.

As used herein, the term "effective amount" refers to an amount of a compound of this invention for treating or preventing a bacterial infection is an amount which is sufficient to prevent the onset of an infection, reduce or ameliorate the severity, duration, or progression, of an infection, prevent the advancement of an infection, cause the regression of an infection, prevent the recurrence, development, onset or progression of a symptom associated with an infection, or enhance or improve the prophylactic or therapeutic effect(s) of another therapy.

In addition to its use in therapeutic medicine, compounds of formula (I), and their pharmaceutically acceptable salts are also useful as pharmacological tools in the development and standardisation of in-vitro and in-vivo test systems for the evaluation of the effects of inhibitors of DNA gyrase and/or topoisomerase IV in laboratory animals such as cats, dogs, rabbits, monkeys, rats and mice, as part of the search for new therapeutic agents.

In the above other, pharmaceutical composition, process, method, use and medicament manufacture features, the alternative and particular embodiments of the compounds of the invention described herein also apply.

Combinations

The compounds of the invention described herein may be applied as a sole therapy or may involve, in addition to a compound of the invention, one or more other substances and/or treatments. Such conjoint treatment may be achieved by way of the simultaneous, sequential or separate administration of the individual components of the treatment. Where the administration is sequential or separate, the delay in administering the second component should not be such as to lose the beneficial effect of the combination. Suitable classes and substances may be selected from one or more of the following:

i) other antibacterial agents for example macrolides e.g. erythromycin, azithromycin or clarithromycin; quinolones e.g. ciprofloxacin or levofloxacin; β-lactams e.g. penicillins e.g. amoxicillin or piperacillin; cephalosporins e.g. ceftriaxone or ceftazidime; carbapenems, e.g. meropenem or imipenem etc; aminoglycosides e.g. gentamicin or tobramycin; or oxazolidinones; and/or ii) anti-infective agents for example, an antifungal triazole e.g. or amphotericin; and/or iii) biological protein therapeutics for example antibodies, cytokines, bactericidal/permeability-increasing protein (BPI) products; and/or iv) efflux pump inhibitors.

Therefore, in a further aspect of the invention there is provided a compound of the formula (I), or a pharmaceutically acceptable salt thereof and a chemotherapeutic agent selected from:

i) one or more additional antibacterial agents; and/or
ii) one or more anti-infective agents; and/or
iii) biological protein therapeutics for example antibodies, cytokines, bactericidal/permeability-increasing protein (BPI) products; and/or
iv) one or more efflux pump inhibitors.

EXAMPLES

The invention is now illustrated but not limited by the following Examples in which unless otherwise stated:—

(i) evaporations were carried out by rotary evaporation in-vacuo and work-up procedures were carried out after removal of residual solids by filtration;

(ii) operations were generally carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques; proton magnetic resonance spectra is quoted and was generally determined in DMSO-$d_6$ unless otherwise stated using a Bruker DRX-300 spectrometer operating at a field strength of 300 MHz. Chemical shifts are reported in parts per million downfield from tetramethysilane as an internal standard (δ scale) and peak multiplicities are shown thus: s, singlet; d, doublet; AB or dd, doublet of doublets; dt, doublet of triplets; dm, doublet of multiplets; t, triplet, m, multiplet; br, broad;

(vi) fast-atom bombardment (FAB) mass spectral data were generally obtained using a Platform spectrometer (supplied by Micromass) run in electrospray and, where appropriate, either positive ion data or negative ion data were collected or using Agilent 1100 series LC/MSD equipped with Sedex 75ELSD, run in atmospheric pressure chemical ionisation mode and, where appropriate, either positive ion data or negative ion data were collected; mass spectra were run with an electron energy of 70 electron volts in the chemical ionization (CI) mode using a direct exposure probe; where indicated ionization was effected by electron impact (EI), fast atom bombardment (FAB) or electrospray (ES); values for m/z are given; generally, only ions which indicate the parent mass are reported;

(vii) each intermediate was generally purified to the standard required for the subsequent stage and was characterised in sufficient detail to confirm that the assigned structure was correct; purity was assessed by high pressure liquid chromatography, thin layer chromatography, or NMR and identity was determined by infra-red spectroscopy (IR), mass spectroscopy or NMR spectroscopy as appropriate;

(vii) the following abbreviations may be used:
CDCl₃ is deuterated chloroform;
DCM is dichloromethane;
DIEA is diisopropyl ethyl amine;
DMF is N,N-dimethylformamide;
DMSO is dimethylsulfoxide;
dppf is 1,1'-bis(diphenylphosphino)ferrocene;
EDC is 1-ethyl-3-(3-dimethylaminopropyl)carbodiimide;
EtOAc is ethyl acetate;
EtOH is ethanol;
HATU is N-[dimethylamino)-1H,2,3-triazolo[4,5-b-]pyridin-1-ylmethylene]-N-methylmethanaminium hexafluorophosphate N-oxide;
HOBt is 1-hydroxybenzotriazole;
MeOH is methanol;
MS is mass spectroscopy;
Pd₂(dba)₃ is tris(dibenzylideneacetone)dipalladium(0));
SM is starting material;
TFA is trifluoroacetic acid;
THF is tetrahydrofuran; and (viii) temperatures are quoted as ° C.

Example 1

2-[(3S,4R)-4-{[(3,4-dichloro-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylic acid

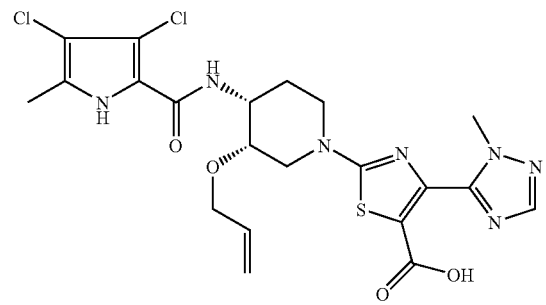

A solution of methyl 2-[(3S,4R)-4-{[(3,4-dichloro-5-methyl-1H-pyrrol-2-yl)carbonyl]amino}-3-(prop-2-en-1- yloxy)piperidin-1-yl]-4-(1-methyl-1H-1,2,4-triazol-5-yl)-1,3-thiazole-5-carboxylate (Example 30, 90 mg, 0.162 mmol) and 2N sodium hydroxide (4 mL) in methanol (30 mL) was stirred at room temperature for 4 h. The reaction mixture was concentrated under reduced pressure and the resulting residue was dissolved in water, which was acidified to pH 3 with 2 N hydrochloric acid (2 mL). The resulting solid was collected by filtration and dried to afford 2-[(3S,4R)-4-{[(3,4-dichloro-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylic acid (40 mg, 72%) as solid.

LCMS: m/z 540.1 (M+H).

$^{1}$H NMR (400 MHz, DMSO-d$_{6}$): δ 1.80 (m, 2H), 2.18 (s, 3H), 3.42 (m, 1H), 3.67 (s, 3H), 3.96 (m, 2H), 4.18 (m, 1H), 4.31 (m, 2H), 5.11 (d, 1H), 5.22 (d, 1H), 5.84 (m, 1H), 7.12 (d, 1H), 8.00 (s, 1H), 12.14 (s, 1H).

Examples 2-30

The following Examples were prepared by the procedure described in Example 1 from the starting materials (SM) indicated.

| Ex | Compound | Data | SM |
|---|---|---|---|
| 2 | 2-[(3S,4R)-4-{[(3,4-dichloro-5-methyl-1H-pyrrol-2-yl)carbonyl]amino}-3-(prop-2-en-1-yloxy)piperidin-1-yl]-4-[1-(2-methoxyethyl)-1H-imidazol-2-yl]-1,3-thiazole-5-carboxylic acid | $^{1}$H NMR (400 MHz, DMSO-d$_{6}$): δ 1.75(m, 2 H), 2.18(s, 3H), 2.87(m, 2H), 3.08(m, 2H), 3.93(m, 1H), 4.19(q, 2H), 5.19(d, 1H), 5.34(d, 1H), 5.89(m, 1H), 7.13(d, 1H), 12.12(s, 1H). | Example 31 |
| 3 | 2-[(3S,4R)-4-{[(3,4-dichloro-5-methyl-1H-pyrrol-2-yl)carbonyl]amino}-3-(prop-2-en-1-yloxy)piperidin-1-yl]-4-(3-fluoropyridin-2-yl)-1,3-thiazole-5-carboxylic acid | $^{1}$H NMR (400 MHz, DMSO-d$_{6}$): δ 1.80(m, 2H), 2.18(s, 3H), 3.71(m, 4H), 4.00(t, 2H), 4.18(m, 1H), 4.27(d, 1H), 5.16(d, 1H), 5.23(d, 1H), 5.82(m, 1H), 7.13(d, 1H), 7.56(m, 1H), 7.78(t, 1H), 8.45 (d, 1H), 12.15(s, 1H). | Example 32 |

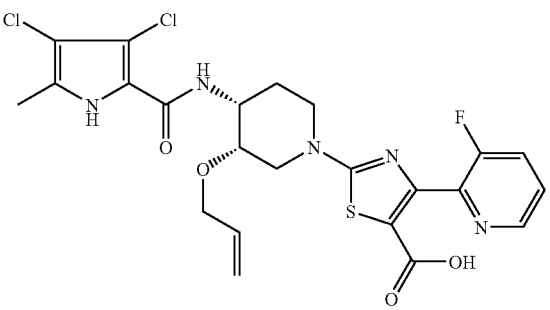

-continued

| Ex | Compound | Data | SM |
|---|---|---|---|
| 4 | 2-[(3S,4R)-4-{[(3,4-dichloro-5-methyl-1H-pyrrol-2-yl)carbonyl]amino}-3-(prop-2-en-1-yloxy)piperidin-1-yl]-4-(pyrazin-2-yl)-1,3-thiazole-5-carboxylic acid | $^1$H NMR (400 MHz, DMSO-$d_6$): δ 1.80(m, 2H), 2.18(s, 3H), 3.29(m, 1H), 3.65(s, 1H), 4.00(t, 2H), 4.22(m, 3H), 5.09(d, 1H), 5.21(d, 1H), 5.80(m, 1H), 7.16(d, 1H), 8.64(d, 2H), 8.81(s, 1H), 12.13(s, 1H). | Example 33 |
| 5 | 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylic acid | $^1$H NMR (400 MHz, DMSO-$d_6$): δ 1.73(m, 1H), 1.92(m, 1H), 2.21(s, 3H), 4.04(m, 5H), 4.26(m, 2H), 5.06(d, 1H), 5.17(d, 1H), 5.84(m, 1H), 7.79(d, 1H), 8.25(s, 1H), 12.80(s, 1H). | Example 34 |
| 6 | 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(3-fluoropyridin-2-yl)-1,3-thiazole-5-carboxylic acid | $^1$H NMR (400 MHz, DMSO-$d_6$): δ 1.70(m, 2H), 2.10(s, 3H), 3.65(br s, 2H), 3.97(m, 4H), 4.30(br s, 2H), 5.04(d, 1H), 5.17(d, 1H), 5.80(m, 1H), 7.41(d, 1H), 7.62(m, 2H), 8.38(d, 1H). | Example 35 |

| Ex | Compound | Data | SM |
|---|---|---|---|
| 7 | 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(pyrazin-2-yl)-1,3-thiazole-5-carboxylic acid | $^1$H NMR (400 MHz, DMSO-$d_6$): δ 1.73(m, 1H), 1.90(m, 1H), 2.20(s, 3H), 3.44(m, 2H), 4.02(m, 3H), 4.28(m, 2H), 5.04(d, 1H), 5.15(d, 1H), 5.81(m, 1H), 7.72(d, 1H), 8.83(d, 2H), 9.35(s, 1H), 12.71(s, 1H). $^1$H NMR (400 MHz, DMSO-$d_6$): δ 1.73(m, 1H), 1.90(m, 1H), 2.20(s, 3H), 3.44(m, 2H), 4.02(m, 3H), 4.28(m, 2H), 5.04(d, 1H), 5.15(d, 1H), 5.81(m, 1H), 7.72(d, 1H), 8.83(d, 2H), 9.35(s, 1H), 12.71(s, 1H). | Example 36 |
| 8 | 2-[(3S,4R)-4-{[(3,4-dichloro-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylic acid | LCMS: m/z 528 (M + H). $^1$H NMR (400 MHz, DMSO-$d_6$): δ 1.08(t, 3H), 1.78(m, 2H), 2.18(s, 3H), 3.32(m, 2H), 3.42(m, 3H), 3.65(s, 3H), 3.69(s, 3H), 4.00(m, 1H), 7.18(d, 1H), 8.00(s, 1H), 12.15(s, 1H). | Example 37 |
| 9 | 2-[(3S,4R)-4-{[(3,4-dicloro-5-methyl-1H-pyrrol-2-yl)carbonyl]amino}-3-ethoxypiperidin-1-yl]-4-[1-(2-methoxyethyl)-1H-imidazol-2-yl]-1,3-thiazole-5-carboxylic acid | LCMS: m/z 571 (M + H). $^1$H NMR (400 MHz, DMSO-$d_6$): δ 1.08(t, 3H), 1.81(m, 2H), 2.18(s, 3H), 3.17(s, 3H), 3.40(t, 2H), 3.45(m, 2H), 3.50(t, 4H), 4.28(m, 2H), 6.95(s, 1H), 7.15(d, 1H), 7.25(s, 1H), 12.18(s, 1H). | Example 38 |

| Ex | Compound | Data | SM |
|---|---|---|---|
| 10 | 2-[(3S,4R)-4-{[(3,4-dichloro-5-methyl-1H-pyrrol-2-yl)carbonyl]amino}-3-ethoxypiperidin-1-yl]-4-(3-fluoropyridin-2-yl)-1,3-thiazole-5-carboxylic acid | LCMS: m/z 542 (M + H). $^1$H NMR (400 MHz, DMSO-$d_6$): δ 1.07(m, 3H), 1.78(m, 2H), 2.18(s, 3H), 3.40(m, 3H), 3.71(m, 3H), 4.02(m, 3H), 4.31(m, 1H), 7.18(d, 1H), 7.56(d, 1H), 7.89(t, 1H), 8.45(d, 1H). | Example 39 |
| 11 | 2-[(3S,4R)-4-{[(3,4-dichloro-5-methyl-1H-pyrrol-2-yl)carbonyl]amino}-3-ethoxypiperidin-1-yl]-4-(pyrazin-2-yl)-1,3-thiazole-5-carboxylic acid | LCMS: m/z 525 (M + H). $^1$H NMR (400 MHz, DMSO-$d_6$): δ 1.09(t, 3H), 1.79(m, 2H), 2.18(s, 3H), 3.42(m, 3H), 3.66(m, 1H), 3.68(m, 2H), 4.09(m, 1H), 4.28(m, 2H), 7.14(d, 1H), 8.70(d, 2H), 8.82(s, 1H), 12.15(s, 1H). | Example 40 |
| 12 | 2-[(3S,4R)-4-{[(4-chloro-3-cyano-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylic acid | LCMS: m/z 519.1 (M + H). $^1$H NMR (400 MHz, DMSO-$d_6$): δ 1.04(t, 3H), 1.73(m, 1H), 1.83(m, 1H), 2.18(s, 3H), 3.42(m, 4H), 3.63(s, 3H), 4.00(m, 2H), 4.24(m, 2H), 7.57(d, 1H), 7.98(s, 1H), 12.66(s, 1H) | Example 41 |

-continued

| Ex | Compound | Data | SM |
|---|---|---|---|
| 13 | 2-[(3S,4R)-4-{[(4-chloro-3-cyano-5-methyl-1H-pyrrol-2-yl)carbonyl]amino}-3-ethoxypiperidin-1-yl]-4-[1-(2-methoxyethyl)-1H-imidazol-2-yl]-1,3-thiazole-5-carboxylic acid | $^1$H NMR (400 MHz, DMSO-$d_6$): δ 1.06(t, 3H), 1.81(m, 2H), 2.20(s, 3H), 3.17(s, 3H), 3.51(m, 4H), 3.61(s, 3H), 4.01(m, 2H), 4.45(m, 2H), 6.94(s, 1H), 7.25(s, 1H), 7.58 (d, 1H), 12.69(s, 1H). | Example 42 |
| 14 | Ethyl 2-[(3S,4R)-4-{[(4-chloro-3-cyano-5-methyl-1H-pyrrol-2-yl)carbonyl]amino}-3-ethoxypiperidin-1-yl]-4-(3-fluoropyridin-2-yl)-1,3-thiazole-5-carboxylate | $^1$H NMR (400 MHz, DMSO-$d_6$): δ 1.06(m, 3H), 1.74(m, 2H), 2.20(s, 3H), 3.39(m, 3H), 3.63(m, 2H), 4.01(m, 2H), 4.17(m, 1H), 7.56(m, 2H), 7.78(t, 1H), 8.45(d, 1H), 12.68(s, 1H). | Example 43 |
| 15 | 2-[(3S,4R)-4-{[(4-chloro-3-cyano-5-methyl-1H-pyrrol-2-yl)carbonyl]amino}-3-ethoxypiperidin-1-yl]-4-(pyrazin-2-yl)-1,3-thiazole-5-carboxylic acid | $^1$H NMR (400 MHz, DMSO-$d_6$): δ 1.05(m, 3H), 1.81(m, 2H), 2.20(s, 3H), 3.41(m, 3H), 3.75(m, 3H), 4.18(m, 2H), 4.25(m, 1H), 8.65(d, 2H), 8.81(s, 1H), 12.13(s, 1H). | Example 44 |

| Ex | Compound | Data | SM |
|---|---|---|---|
| 16 | 2-[(3S,4R)-4-{[(4-chloro-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylic acid | LCMS: m/z 494.2 (M + H); $^1$H NMR (400 MHz, DMSO-$d_6$): δ 1.03(t, 3H), 1.64(d, 1H), 1.97(m, 1H), 2.16(s, 3H), 3.42(m, 2H), 3.56(m, 1H), 3.65(m, 1H), 3.68(m, 1H), 3.73(s, 3H), 4.21(m, 3H), 6.88(s, 1H), 7.63(d, 1H), 8.00(s, 1H), 11.60(s, 1H). | Example 45 |
| 17 | 2-[(3S,4R)-4-{[(4-chloro-5-methyl-1H-pyrrol-2-yl)carbonyl]amino}-3-ethoxypiperidin-1-yl]-4-(3-fluoropyridin-2-yl)-1,3-thiazole-5-carboxylic acid | LCMS: m/z 508.1 (M + H); $^1$H NMR (400 MHz, DMSO-$d_6$): δ 1.05(m, 3H), 1.61(d, 1H), 1.89(m, 1H), 2.16(s, 3H), 3.41(m, 3H), 3.59(m, 1H), 3.68(s, 1H), 4.02(m, 2H), 4.20(m, 1H), 6.84(s, 1H), 7.56(m, 1H), 7.62(d, 1H), 7.80(t, 1H), 8.47(d, 1H), 11.60(s, 1H). | Example 46 |
| 18 | 2-[(3S,4R)-4-{[(4-chloro-5-methyl-1H-pyrrol-2-yl)carbonyl]amino}-3-ethoxypiperidin-1-yl]-4-(pyrazin-2-yl)-1,3-thiazole-5-carboxylic acid | LCMS: m/z 491.1 (M + H); $^1$H NMR (400 MHz, DMSO-$d_6$): δ 1.06(m, 3H), 1.61(d, 1H), 1.91(m, 1H), 2.16(s, 3H), 3.41(m, 2H), 3.58(m, 1H), 3.67(m, 1H), 4.08(m, 3H), 4.21(m, 1H), 6.86(s, 1H), 7.60(d, 1H), 8.68(d, 2H), 8.82(s, 1H), 11.60(s, 1H). | Example 47 |

| Ex | Compound | Data | SM |
|---|---|---|---|
| 19 | 2-[(3S,4R)-4-{[(4-chloro-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylic acid | LCMS: m/z 464.1 (M + H); $^1$H NMR (400 MHz, DMSO-$d_6$): δ 0.87(d, 3H), 1.84(m, 2H), 2.17(s, 3H), 3.65(m, 5H), 3.83(m, 2H), 4.08(s, 3H), 4.27(m, 1H), 6.91(s, 1H), 7.68(d, 1H), 8.24(s, 1H), 11.67(s, 1H). | Example 48 |
| 20 | 2-[(3S,4R)-4-{[(4-chloro-5-methyl-1H-pyrrol-2-yl)carbonyl]amino}-3-methylpiperidin-1-yl]-4-(3-fluoropyridin-2-yl)-1,3-thiazole-5-carboxylic acid | LCMS: m/z 478.1 (M + H); $^1$H NMR (400 MHz, DMSO-$d_6$): δ 0.87(d, 3H), 1.80(m, 2H), 2.14(s, 3H), 3.49(m, 3H), 3.77(br s, 1H), 4.24(s, 1H), 6.93(s, 1H), 7.55(d, 1H), 7.59(d, 1H), 7.79(m, 1H), 8.46(s, 1H), 11.60(s, 1H). | Example 49 |
| 21 | 2-[(3S,4R)-4-{[(4-chloro-5-methyl-1H-pyrrol-2-yl)carbonyl]amino}-3-methylpiperidin-1-yl]-4-(pyrazin-2-yl)-1,3-thiazole-5-carboxylic acid | LCMS: m/z 461.2 (M + H); $^1$H NMR (400 MHz, DMSO-$d_6$): δ 0.87(d, 3H), 1.78(m, 2H), 2.12(s, 3H), 3.58(m, 3H), 3.86(br s, 1H), 4.28(s, 1H), 6.91(s, 1H), 7.62(d, 1H), 8.76(d, 2H), 9.27(s, 1H), 11.62(s, 1H). | Example 50 |

-continued

| Ex | Compound | Data | SM |
|---|---|---|---|
| 22 | 2-[(3S,4R)-4-{[(3,4-dichloro-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylic acid | LCMS: m/z 498.1 (M + H); $^1$H NMR (400 MHz, DMSO-$d_6$): δ 0.93(d, 3H), 1.82(br s, 2H), 2.17(s, 3H), 3.63(m, 6H), 4.05(s, 3H), 4.25(br s, 1H), 7.21(d, 1H), 8.22(s, 1H), 12.05(s, 1H). | Example 51 |
| 23 | 2-[(3S,4R)-4-{[(3,4-dichloro-5-methyl-1H-pyrrol-2-yl)carbonyl]amino}-3-methylpiperidin-1-yl]-4-[1-(2-methoxyethyl)-1H-imidazol-2-yl]-1,3-thiazole-5-carboxylic acid | LCMS: m/z 541.3 (M + H); $^1$H NMR (400 MHz, DMSO-$d_6$): δ 0.95(d, 3H), 1.90(br s, 3H), 2.19(s, 3H), 3.24(s, 3H), 3.62(m, 4H), 3.71(t, 3H), 4.39(br s, 1H), 4.82(br s, 2H), 7.21(d, 1H), 7.34(s, 1H), 7.51(s, 1H), 12.02(s, 1H). | Example 52 |
| 24 | 2-[(3S,4R)-4-{[(3,4-dichloro-5-methyl-1H-pyrrol-2-yl)carbonyl]amino}-3-methylpiperidin-1-yl]-4-(3-fluoropyridin-2-yl)-1,3-thiazole-5-carboxylic acid | LCMS: m/z 512.26 (M + H); $^1$H NMR (400 MHz, DMSO-$d_6$): δ 0.93(d, 3H), 1.88(br s, 2H), 2.16(s, 3H), 3.57(m, 5H), 4.22(s, 1H), 7.47(s, 2H), 7.71(d, 1H), 8.40(s, 1H). | Example 53 |

-continued

| Ex | Compound | Data | SM |
|---|---|---|---|
| 25 | 2-[(3S,4R)-4-{[(3,4-dichloro-5-methyl-1H-pyrrol-2-yl)carbonyl]amino}-3-methylpiperidin-1-yl]-4-(pyrazin-2-yl)-1,3-thiazole-5-carboxylic acid | LCMS: m/z 495.1 (M + H); $^1$H NMR (400 MHz, DMSO-$d_6$): δ 0.94(d, 3H), 1.82(br s, 2H), 2.17(s, 3H), 3.78(m, 5H), 4.25(br s, 1H), 7.24(br s, 1H), 8.81(d, 2H), 9.32(s, 1H), 11.60(s, 1H). | Example 54 |
| 26 | 2-[(3S,4R)-4-{[(4-chloro-3-cyano-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylic acid | LCMS: m/z 489.3 (M + H); $^1$H NMR (DMSO-$d_6$, 400 MHz): δ 0.95(d, 3H), 1.84(br s, 2H), 2.21(s, 4H), 3.69(m, 5H), 4.06(s, 3H), 4.28(br s, 1H), 7.98(d, 1H), 8.23(s, 1H), 12.60(s, 1H). | Example 55 |
| 27 | 2-[(3S,4R)-4-{[(4-chloro-3-cyano-5-methyl-1H-pyrrol-2-yl)carbonyl]amino}-3-methylpiperidin-1-yl]-4-[1-(2-methoxyethyl)-1H-imidazol-2-yl]-1,3-thiazole-5-carboxylic acid | LCMS: m/z 532.21 (M + H); $^1$H NMR (DMSO-$d_6$, 400 MHz): δ 0.92(d, 3H), 1.80(br s, 2H), 1.88(s, 1H), 2.14(s, 3H), 3.23(s, 3H), 3.55(br s, 3H), 3.70(br s, 3H), 4.26(br s, 1H), 4.73(br s, 2H), 7.28(s, 1H), 7.47(s, 1H), 7.88(br s, 1H). | Example 56 |

| Ex | Compound | Data | SM |
|---|---|---|---|
| 28 | 2-[(3S,4R)-4-{[(4-chloro-3-cyano-5-methyl-1H-pyrrol-2-yl)carbonyl]amino}-3-methylpiperidin-1-yl]-4-(3-fluoropyridin-2-yl)-1,3-thiazole-5-carboxylic acid | LCMS: m/z 503.3 (M + H); $^1$H NMR (DMSO-d$_6$, 400 MHz): δ 0.92(d, 3H), 1.80(br s, 2H), 2.20(s, 4H), 3.46(m, 1H), 3.74(m, 4H), 4.24(s, 1H), 7.51(s, 1H), 7.73(br s, 1H), 7.98(br s, 1H), 8.44(s, 1H), 12.77(br s, 1H). | Example 57 |
| 29 | 2-[(3S,4R)-4-{[(4-chloro-3-cyano-5-methyl-1H-pyrrol-2-yl)carbonyl]amino}-3-methylpiperidin-1-yl]-4-(pyrazin-2-yl)-1,3-thiazole-5-carboxylic acid | LCMS: m/z 486.3 (M + H); $^1$H NMR (DMSO-d$_6$, 400 MHz): δ 0.92(d, 3H), 2.21(s, 4H), 3.64(m, 3H), 3.66(s, 1H), 4.25(br s, 1H), 7.94(d, 1H), 8.76(s, 1H), 8.81(s, 1H), 9.31(s, 1H), 12.61(s, 1H), 15.18(br s, 1H). | Example 58 |

Example 30

Methyl 2-[(3S,4R)-4-{[(3,4-dichloro-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylate

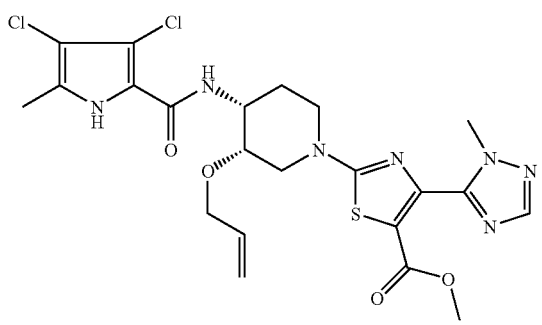

Methyl 2-chloro-4-(1-methyl-1H-1,2,4-triazol-5-yl)-1,3-thiazole-5-carboxylate (Intermediate 2, 77.91 mg, 3.02 mmol) was added to a solution of 3,4-dichloro-5-methyl-N-[(3S,4R)-3-(prop-2-en-1-yloxy)piperidin-4-yl]-1H-pyrrole-2-carboxamide (Intermediate 20, 100 mg, 3.02 mmol) and N,N-diisopropylethylamine (0.362 mL, 0.06 mM) in N-methyl 2-pyrrolidinone (1.5 mL) and the resulting reaction mixture was stirred overnight at 80° C. The reaction mixture was cooled to room temperature and poured into water (20 mL). The solid that formed was collected by filtration, washed with diethylether (25 mL) and dried to afford Methyl 2-[(3S,4R)-4-{[(3,4-dichloro-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylate (90 mg, 70%) as solid.

LCMS: m/z 553 (M+H).

$^1$H NMR (400 MHz, DMSO-d$_6$): δ 1.80 (m, 2H), 2.18 (s, 3H), 3.42 (m, 1H), 3.67 (s, 3H), 3.72 (s, 3H), 3.96 (m, 2H), 4.18 (m, 1H), 4.31 (m, 2H), 5.11 (d, 1H), 5.22 (d, 1H), 5.84 (m, 1H), 7.12 (d, 1H), 8.00 (s, 1H), 12.14 (s, 1H).

Examples 31-58

The following Examples were prepared by the procedure described in Example 30 from the starting materials (SM) indicated.

| Ex | Compound | Data | SM |
|---|---|---|---|
| 31 | Methyl 2-[(3S,4R)-4-{[(3,4-dichloro-5-methyl-1H-pyrrol-2-yl)carbonyl]amino}-3-(prop-2-en-1-yloxy)piperidin-1-yl]-4-[1-(2-methoxyethyl)-1H-imidazol-2-yl]-1,3-thiazole-5-carboxylate | LCMS: m/z 596 (M + H). $^1$H NMR (400 MHz, DMSO-d$_6$): δ 1.75(m, 2H), 2.18(s, 3H), 2.87(m, 2H), 3.08(d, 2H), 3.66(s, 3H), 3.93(m, 1H), 4.19(q, 2H), 5.19(d, 1H), 5.34(d, 1H), 5.89(m, 1H), 7.13(d, 1H), 12.12(s, 1H). | Intermediate 20 and Intermediate 1 |
| 32 | Ethyl 2-[(3S,4R)-4-{[(3,4-dichloro-5-methyl-1H-pyrrol-2-yl)carbonyl]amino}-3-(prop-2-en-1-yloxy)piperidin-1-yl]-4-(3-fluoropyridin-2-yl)-1,3-thiazole-5-carboxylate | LCMS: m/z 581 (M + H); NMR (400 MHz, DMSO-d$_6$): δ 1.02 (t, 3H), 1.80(m, 2H), 2.18(s, 3H), 3.71(m, 4H), 4.00(m, 2H), 4.02(q, 2H), 4.18(m, 1H), 4.27(d, 1H), 5.16(d, 1H), 5.23(d, 1H), 5.82(m, 1H), 7.13(d, 1H), 7.56(m, 1H), 7.78(t, 1H), 8.45(d, 1H), 12.15(s, 1H). | Intermediate 20 and Intermediate 4 |
| 33 | Ethyl 2-[(3S,4R)-4-{[(3,4-dichloro-5-methyl-1H-pyrrol-2-yl)carbonyl]amino}-3-(prop-2-en-1-yloxy)piperidin-1-yl]-4-(pyrazin-2-yl)-1,3-thiazole-5-carboxylate | $^1$H NMR (400 MHz, DMSO-d$_6$): δ 1.06(t, 3H), 1.80(m, 2H), 2.18(s, 3H), 3.29(m, 1H), 3.65(s, 1H), 4.00(m, 2H), 4.04(q, 2H), 4.22(m, 3H), 5.09(d, 1H), 5.21(d, 1H), 5.80(m, 1H), 7.16(d, 1H), 8.64(d, 2H), 8.81(s, 1H), 12.13(s, 1H). | Intermediate 20 and Intermediate 3 |

| Ex | Compound | Data | SM |
|---|---|---|---|
| 34 | Methyl 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(1-methyl-1H-1,2,4-triazol-5-yl)-1,3-thiazole-5-carboxylate | $^1$H NMR (400 MHz, DMSO-$d_6$): δ 1.74(m, 1H), 1.90(m, 1H), 2.19(s, 3H), 3.42(m, 2H), 3.74(s, 7H), 4.02(m, 3H), 4.26(br s, 2H), 5.08(d, 1H), 5.24(d, 1H), 5.85(m, 1H), 7.67(d, 1H), 8.01(s, 1H), 12.67(s, 1H). | Intermediate 22 and Intermediate 2 |
| 35 | Ethyl 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(3-fluoropyridin-2-yl)-1,3-thiazole-5-carboxylate | LCMS: m/z 573 (M + H). $^1$H NMR (400 MHz, DMSO-$d_6$): δ 1.04(t, 3H), 1.73(m, 1H), 1.90(m, 1H), 2.20(s, 3H), 3.41(m, 2H), 3.73(br s, 2H), 4.05(m, 5H), 4.25(m, 2H), 5.08(d, 1H), 5.23(d, 1H), 5.85(m, 1H), 7.55(m, 1H), 7.70(d, 1H), 7.71(t, 1H), 8.46 (d, 1H). | Intermediate 22 and Intermediate 4 |
| 36 | Ethyl 2-[(3S,4R)-4-{[(4-chloro-3-cyano-5-methyl-1H-pyrrol-2-yl)carbonyl]amino}-3-(prop-2-en-1-yloxy)piperidin-1-yl]-4-(pyrazin-2-yl)-1,3-thiazole-5-carboxylate | LCMS: m/z 556 (M + H). $^1$H NMR (400 MHz, DMSO-$d_6$): δ 1.07(t, 3H), 1.72(m, 1H), 1.88(m, 1H), 2.19(s, 3H), 3.41(m, 2H), 3.73(br s, 1H), 4.09(m, 5H), 4.26(m, 2H), 5.08(d, 1H), 5.22(d, 1H), 5.85(m, 1H), 7.68(d, 1H), 8.70(d, 2H), 8.83(s, 1H), 12.70(s, 1H). | Intermediate 22 and Intermediate 3 |

-continued

| Ex | Compound | Data | SM |
|---|---|---|---|
| 37 | Methyl 2-[(3S,4R)-4-{[(3,4-dichloro-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylate | $^1$H NMR (400 MHz, DMSO-$d_6$): δ 1.08(t, 3H), 1.78(m, 2H), 2.18(s, 3H), 3.32(m, 2H), 3.42(m, 3H), 3.65(s, 3H), 3.69(s, 3H), 4.00(m, 1H), 4.26(d, 2H), 7.18(d, 1H), 8.00(s, 1H), 12.15(s, 1H). | Intermediate 26 and Intermediate 2 |
| 38 | Methyl 2-[(3S,4R)-4-{[(3,4-dichloro-5-methyl-1H-pyrrol-2-yl)carbonyl]amino}-3-ethoxypiperidin-1-yl]-4-[1-(2-methoxyethyl)-1H-imidazol-2-yl]-1,3-thiazole-5-carboxylate | $^1$H NMR (400 MHz, DMSO-$d_6$): δ 1.08(t, 3H), 1.81(m, 2H), 2.18(s, 3H), 3.17(s, 3H), 3.40(m, 2H), 3.45(m, 2H), 3.50(m, 4H), 3.61(s, 3H), 3.68(m, 2H), 4.28(m, 2H), 6.95(s, 1H), 7.15(d, 1H), 7.25 (s, 1H), 12.18(s, 1H). | Intermediate 26 and Intermediate 1 |
| 39 | Ethyl 2-[(3S,4R)-4-{[(3,4-dichloro-5-methyl-1H-pyrrol-2-yl)carbonyl]amino}-3-ethoxypiperidin-1-yl]-4-(3-fluoropyridin-2-yl)-1,3-thiazole-5-carboxylate | $^1$H NMR (400 MHz, DMSO-$d_6$): δ 1.07(m, 6H), 1.78(m, 2H), 2.18(s, 3H), 3.40(m, 3H), 3.71(m, 3H), 4.02(m, 3H), 4.31(m, 2H), 7.18(d, 1H), 7.56(d, 1H), 7.89(m, 1H), 8.45(d, 1H). | Intermediate 26 and Intermediate 4 |

-continued

| Ex | Compound | Data | SM |
|---|---|---|---|
| 40 | Ethyl 2-[(3S,4R)-4-{[(3,4-dichloro-5-methyl-1H-pyrrol-2-yl)carbonyl]amino}-3-ethoxypiperidin-1-yl]-4-(pyrazin-2-yl)-1,3-thiazole-5-carboxylate | $^1$H NMR (400 MHz, DMSO-$d_6$): δ 0.95(t, 3H), 1.09(t, 3H), 1.79(m, 2H), 2.18(s, 3H), 3.42(m, 3H), 3.66(s, 1H), 3.68(m, 2H), 4.09(m, 2H), 4.28(m, 2H), 7.14(d, 1H), 8.70(d, 2H), 8.82(s, 1H), 12.15(s, 1H). | Intermediate 26 and Intermediate 3 |
| 41 | Methyl 2-[(3S,4R)-4-{[(4-chloro-3-cyano-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylate | $^1$H NMR (400 MHz, DMSO-$d_6$): δ 1.04(t, 3H), 1.73(m, 1H), 1.83(m, 1H), 2.18(s, 3H), 3.42(m, 4H), 3.63(s, 3H), 3.70(s, 3H), 4.00(m, 2H), 4.24(m, 2H), 7.57(d, 1H), 7.98(s, 1H), 12.66(s, 1H). | Intermediate 33 and Intermediate 2 |
| 42 | Methyl 2-[(3S,4R)-4-{[(4-chloro-3-cyano-5-methyl-1H-pyrrol-2-yl)carbonyl]amino}-3-ethoxypiperidin-1-yl]-4-[1-(2-methoxyethyl)-1H-imidazol-2-yl]-1,3-thiazole-5-carboxylate | $^1$H NMR (400 MHz, DMSO-$d_6$): δ 1.06(t, 3H), 1.81(m, 2H), 2.20(s, 3H), 3.17(s, 3H), 3.51(m, 4H), 3.61(s, 3H), 3.68(m, 3H), 4.01(m, 2H), 4.45(m, 2H), 6.94(s, 1H), 7.25(s, 1H), 7.58(d, 1H), 12.69(s, 1H). | Intermediate 33 and Intermediate 1 |

| Ex | Compound | Data | SM |
|---|---|---|---|
| 43 | Ethyl 2-[(3S,4R)-4-{[(4-chloro-3-cyano-5-methyl-1H-pyrrol-2-yl)carbonyl]amino}-3-ethoxypiperidin-1-yl]-4-(3-fluoropyridin-2-yl)-1,3-thiazole-5-carboxylate | $^1$H NMR (400 MHz, DMSO-$d_6$): δ 1.06(m, 6H), 1.74(m, 2H), 2.20(s, 3H), 3.39(m, 3H), 3.63(m, 2H), 4.01(m, 2H), 4.17(m, 3H), 7.56(m, 2H), 7.78(t, 1H), 8.45(d, 1H), 12.68(s, 1H). | Intermediate 33 and Intermediate 4 |
| 44 | Ethyl 2-[(3S,4R)-4-{[(4-chloro-3-cyano-5-methyl-1H-pyrrol-2-yl)carbonyl]amino}-3-ethoxypiperidin-1-yl]-4-(pyrazin-2-yl)-1,3-thiazole-5-carboxylate | $^1$H NMR (400 MHz, DMSO-$d_6$): δ 1.05(m, 6H), 1.81(m, 2H), 2.20(s, 3H), 3.41(m, 3H), 3.75(m, 3H), 4.18(m, 4H), 4.25(m, 1H), 8.65(d, 2H), 8.81(s, 1H), 12.13(s, 1H). | Intermediate 33 and Intermediate 3 |
| 45 | Methyl 2-[(3S,4R)-4-{[(4-chloro-5-methyl-1H-pyrrol-2-yl)carbonyl]amino}-3-ethoxypiperidin-1-yl]-4-(1-methyl-1H-1,2,4-triazol-5-yl)-1,3-thiazole-5-carboxylate | $^1$H NMR (400 MHz, DMSO-$d_6$): δ 1.03(t, 3H), 1.64(d, 1H), 1.97(m, 1H), 2.16(s, 3H), 3.42(m, 2H), 3.56(m, 1H), 3.65(m, 4H), 3.68(m, 1H), 3.73(s, 3H), 4.21(m, 3H), 6.88(s, 1H), 7.63(d, 1H), 8.00(s, 1H), 11.60(s, 1H). | Intermediate 35 and Intermediate 2 |

-continued

| Ex | Compound | Data | SM |
|---|---|---|---|
| 46 | Ethyl 2-[(3S,4R)-4-{[(4-chloro-5-methyl-1H-pyrrol-2-yl)carbonyl]amino}-3-ethoxypiperidin-1-yl]-4-(3-fluoropyridin-2-yl)-1,3-thiazole-5-carboxylate | $^1$H NMR (400 MHz, DMSO-$d_6$): δ 1.05(m, 6H), 1.61(d, 1H), 1.89(m, 1H), 2.16(s, 3H), 3.41(m, 3H), 3.59(m, 1H), 3.68(s, 1H), 4.02(m, 4H), 4.20(m, 1H), 6.84(s, 1H), 7.56(m, 1H), 7.62(d, 1H), 7.80(t, 1H), 8.47(d, 1H), 11.60(s, 1H). | Intermediate 35 and Intermediate 4 |
| 47 | Ethyl 2-[(3S,4R)-4-{[(4-chloro-5-methyl-1H-pyrrol-2-yl)carbonyl]amino}-3-ethoxypiperidin-1-yl]-4-(pyrazin-2-yl)-1,3-thiazole-5-carboxylate | $^1$H NMR (400 MHz, DMSO-$d_6$): δ 1.06(m, 6H), 1.61(d, 1H), 1.91(m, 1H), 2.16(s, 3H), 3.41(m, 2H), 3.58(m, 1H), 3.67(m, 1H), 4.08(m, 5H), 4.21(m, 1H), 6.86(s, 1H), 7.60(d, 1H), 8.68(d, 2H), 8.82(s, 1H), 11.60(s, 1H). | Intermediate 35 and Intermediate 3 |
| 48 | Methyl 2-[(3S,4R)-4-{[(4-chloro-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylate | $^1$H NMR (400 MHz, DMSO-$d_6$): δ 0.92(d, 3H), 1.80(m, 2H), 2.19(s, 3H), 2.69(s, 1H), 3.53(br s, 1H), 3.58(m, 3H), 3.65(s, 3H), 3.72(s, 3H), 3.78(m, 1H), 4.25(br s, 1H), 6.92(s, 1H), 7.59(d, 1H), 8.00(s, 1H). | Intermediate 39 and Intermediate 2 |

-continued

| Ex | Compound | Data | SM |
|---|---|---|---|
| 49 | Ethyl 2-[(3S,4R)-4-{[(4-chloro-5-methyl-1H-pyrrol-2-yl)carbonyl]amino}-3-methylpiperidin-1-yl]-4-(3-fluoropyridin-2-yl)-1,3-thiazole-5-carboxylate | $^1$H NMR (400 MHz, DMSO-$d_6$): δ 0.92(d, 3H), 1.05(t, 3H), 1.74(m, 2H), 2.14(s, 3H), 3.56(m, 4H), 3.57(br s, 1H), 4.02(q, 2H), 4.25(br s, 1H), 6.93(s, 1H), 7.58(m, 2H), 7.78(m, 1H), 8.46(d, 1H), 11.59(s, 1H). | Intermediate 39 and Intermediate 4 |
| 50 | Ethyl 2-[(3S,4R)-4-{[(4-chloro-5-methyl-1H-pyrrol-2-yl)carbonyl]amino}-3-methylpiperidin-1-yl]-4-(pyrazin-2-yl)-1,3-thiazole-5-carboxylate | $^1$H NMR (400 MHz, DMSO-$d_6$): δ 0.86(d, 3H), 1.16(d, 3H), 1.72(m, 2H), 2.17(s, 3H), 3.56(m, 3H), 3.82(br s, 1H), 4.18(q, 2H), 4.24(m, 1H), 6.91(s, 1H), 7.58(d, 1H), 8.64(d, 1H), 8.65(m, 1H), 8.81(s, 1H), 11.58(s, 1H). | Intermediate 39 and Intermediate 3 |
| 51 | Methyl 2-[(3S,4R)-4-{[(3,4-dichloro-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylate | $^1$H NMR (400 MHz, DMSO-$d_6$): δ 0.94(d, 3H), 1.83(br s, 2H), 2.19(s, 3H), 3.51(m, 1H), 3.58(m, 1H), 3.65(s, 3H), 3.67(s, 3H), 4.26(br s, 1H), 7.18(d, 1H), 8.00(s, 1H), 12.01(s, 1H). | Intermediate 41 and Intermediate 2 |

-continued

| Ex | Compound | Data | SM |
|---|---|---|---|
| 52 | Methyl 2-[(3S,4R)-4-{[(3,4-dichloro-5-methyl-1H-pyrrol-2-yl)carbonyl]amino}-3-methylpiperidin-1-yl]-4-[1-(2-methoxyethyl)-1H-imidazol-2-yl]-1,3-thiazole-5-carboxylate | $^1$H NMR (400 MHz, DMSO-$d_6$): δ 0.95(d, 3H), 1.85(br s, 2H), 2.21(s, 4H), 3.21(s, 3H), 3.54(d, 4H), 3.63(d, 4H), 3.63 (s, 4H), 3.71(m, 1H), 4.04(q, 2H), 4.28(br s, 1H), 6.92(s, 1H), 7.21(d, 1H), 7.28(s, 1H), 12.01(s, 1H). | Intermediate 41 and Intermediate 2 |
| 53 | Ethyl 2-[(3S,4R)-4-{[(3,4-dichloro-5-methyl-1H-pyrrol-2-yl)carbonyl]amino}-3-methylpiperidin-1-yl]-4-(3-fluoroyridin-2-yl)-1,3-thiazole-5-carboxylate | $^1$H NMR (400 MHz, DMSO-$d_6$): δ 0.93(d, 3H), 1.05(t, 3H), 1.82(br s, 2H), 2.19(s, 3H), 3.65(m, 4H), 4.06(q, 2H), 4.23(br s, 1H), 7.19(d, 1H), 7.57(m, 1H), 7.78(m, 1H), 8.46(s, 1H), 12.01(s, 1H). | Intermediate 41 and Intermediate 4 |
| 54 | Ethyl 2-[(3S,4R)-4-{[(3,4-dichloro-5-methyl-1H-pyrrol-2-yl)carbonyl]amino}-3-methylpiperidin-1-yl]-4-(pyrazin-2-yl)-1,3-thiazole-5-carboxylate | $^1$H NMR (400 MHz, DMSO-$d_6$): δ 0.93(d, 3H), 1.17(t, 3H), 1.85(br s, 2H), 2.20(s, 3H), 3.49(m, 5H), 4.25(br s, 1H), 8.67(d, 2H), 8.76(d, 1H), 8.82(s, 1H). | Intermediate 41 and Intermediate 3 |

-continued

| Ex | Compound | Data | SM |
|----|----------|------|-----|
| 55 | Methyl 2-[(3S,4R)-4-{[(4-chloro-3-cyano-5-methyl-1H-pyrrol-2-yl)carbonyl]amino}-3-methylpiperidin-1-yl]-4-(1-methyl-1H-1,2,4-triazol-5-yl)-1,3-thiazole-5-carboxylate | $^1$H NMR (DMSO-d$_6$, 400 MHz): δ 0.94(d, 3H), 1.83(br s, 2H), 2.21(s, 3H), 2.18(br s, 1H), 3.30(m, 3H), 3.65(s, 3H), 3.72(s, 3H), 4.51(br s, 1H), 7.94(d, 1H), 8.01(s, 1H), 12.61(s, 1H). | Intermediate 43 and Intermediate 2 |
| 56 | Methyl 2-[(3S,4R)-4-{[(4-chloro-3-cyano-5-methyl-1H-pyrrol-2-yl)carbonyl]amino}-3-methylpiperidin-1-yl]-4-[1-(2-methoxyethyl)-1H-imidazol-2-yl]-1,3-thiazole-5-carboxylate | $^1$H NMR (DMSO-d$_6$, 400 MHz): δ 0.94(d, 3H), 1.81(br s, 2H), 2.21(s, 4H), 3.21(s, 3H), 3.51(t, 3H), 3.62(s, 4H), 3.72(m, 1H), 4.03(q, 2H), 4.26(br s, 1H), 6.98(s, 1H), 7.23(s, 1H), 7.84(d, 1H), 12.61(s, 1H). | Intermediate 43 and Intermediate 1 |
| 57 | Ethyl 2-[(3S,4R)-4-{[(4-chloro-3-cyano-5-methyl-1H-pyrrol-2-yl)carbonyl]amino}-3-methylpiperidin-1-yl]-4-(3-fluoropyridin-2-yl)-1,3-thiazole-5-carboxylate | $^1$H NMR (DMSO-d$_6$, 400 MHz): δ 0.94(s, 3H), 1.03(t, 3H), 1.82(s, 2H), 2.17(s, 1H), 3.67(m, 4H), 4.06(q, 2H), 4.24(br s, 1H), 7.56(s, 1H), 7.78(m, 1H), 7.90(s, 1H), 8.47(s, 1H), 12.56(s, 1H). | Intermediate 43 and Intermediate 4 |

| Ex | Compound | Data | SM |
|---|---|---|---|
| 58 | Ethyl 2-[(3S,4R)-4-{[(4-chloro-3-cyano-5-methyl-1H-pyrrol-2-yl)carbonyl]amino}-3-methylpiperidin-1-yl]-4-(pyrazin-2-yl)-1,3-thiazole-5-carboxylate | $^1$H NMR (DMSO-d$_6$, 400 MHz): δ 0.94(d, 3H), 1.19(t, 3H), 1.84(s, 2H), 2.19(br s, 1H), 2.21(s, 3H), 3.63(m, 5H), 4.08(q, 2H), 4.24(s, 1H), 7.92(d, 1H), 8.66(d, 2H), 8.83 (s, 1H), 12.56(s, 1H). | Intermediate 43 and Intermediate 3 |

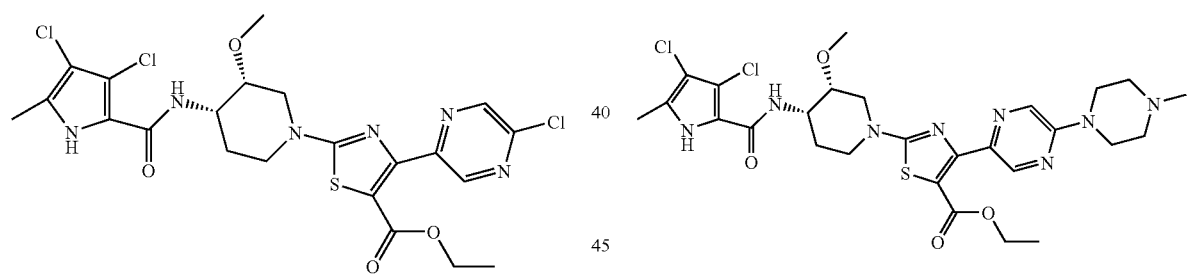

Example 59

Ethyl 4-(5-chloropyrazin-2-yl)-2-[(3R,4S)-4-{[(3,4-dichloro-5-methyl-1H-pyrrol-2-yl)carbonyl]amino}-3-methoxypiperidin-1-yl]-1,3-thiazole-5-carboxylate Ethyl 2-bromo-4-(5-chloropyrazin-2-yl)-1,3-thiazole-5-carboxylate (Intermediate 47, 120 mg, 0.3960 mM) was added to a solution of 3,4-dichloro-N-[(3R,4S)-3-methoxypiperidin-4-yl]-5-methyl-1H-pyrrole-2-carboxamide (WO2006087543, 127 mg, 0.4158 mM) and N,N-diisopropylethylamine (159.6 mg, 1.247 mM) in N-methyl 2-pyrrolidinone (1.0 mL) and the resulting reaction mixture was stirred at 50-55° C. for 1 h. The reaction mixture was cooled to room temperature and then poured into water (40 mL). The resulting solid was collected by filtration and dried to afford ethyl 4-(5-chloropyrazin-2-yl)-2-[(3R,4S)-4-{[(3,4-dichloro-5-methyl-1H-pyrrol-2-yl)carbonyl]amino}-3-methoxypiperidin-1-yl]-1,3-thiazole-5-carboxylate 140 mg (90%) of as an off-white solid.

$^1$H NMR (400 MHz, DMSO-d$_6$): δ 1.12 (t, 2H), 1.78 (m, 2H), 2.21 (s, 3H), 3.22-3.60 (m, 7H), 4.12 (q, 2H), 4.36 (d, 2H), 7.18 (d, 1H), 8.78 (s, 1H), 8.87 (s, 1H), 12.18 (s, 1H).

MASS (APCI) m/z 573.0 (M+H)

Example 60

Ethyl 2-[(3R,4S)-4-{[(3,4-dichloro-5-methyl-1H-pyrrol-2-yl)carbonyl]amino}-3-methoxypiperidin-1-yl]-4-[5-(4-methylpiperazin-1-yl)pyrazin-2-yl]-1,3-thiazole-5-carboxylate Ethyl 4-(5-chloropyrazin-2-yl)-2-[(3R,4S)-4-{[(3,4-dichloro-5-methyl-1H-pyrrol-2-yl)carbonyl]amino}-3-methoxypiperidin-1-yl]-1,3-thiazole-5-carboxylate (Example 59, 100 mg, 0.1748 mM) was added to a solution of 1-methylpiperazine (87.93 mg, 0.874 mM) and N,N-diisopropylethylamine (67.12 mg, 0.5244 mM) in N-methyl 2-pyrrolidinone (1.5 mL) and the resulting reaction mixture was stirred for over night at 80-90° C. After completion of the reaction, the reaction mixture was poured into water (40 mL), and the obtained solid was filtered and dried to afford ethyl 2-[(3R,4S)-4-{[(3,4-dichloro-5-methyl-1H-pyrrol-2-yl)carbonyl]amino}-3-methoxypiperidin-1-yl]-4-[5-(4-methylpiperazin-1-yl)pyrazin-2-yl]-1,3-thiazole-5-carboxylate 92 mg (82%) as off-white solid.

$^1$H NMR (400 MHz, DMSO-d$_6$): δ 1.12 (t, 2H), 1.78 (m, 2H), 2.20 (s, 3H), 2.21 (s, 3H), 2.41 (m, 4H), 3.22-3.60 (m, 7H), 3.64 (m, 4H), 4.12 (q, 2H), 4.36 (d, 2H), 7.18 (d, 1H), 8.37 (s, 2H), 12.18 (s, 1H).

MASS (APCI) m/z 637 (M+H)

Example 61

2-[(3R,4S)-4-{[(3,4-dichloro-5-methyl-1H-pyrrol-2-yl)carbonyl]amino}-3-methoxypiperidin-1-yl]-4-[5-(4-methylpiperazin-1-yl)pyrazin-2-yl]-1,3-thiazole-5-carboxylic acid

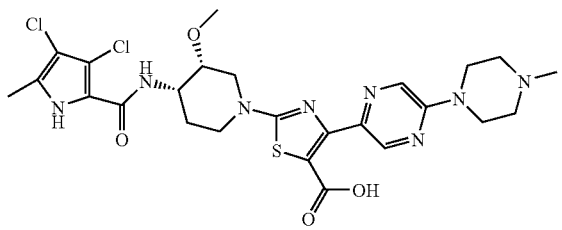

Ethyl 2-[(3R,4S)-4-{[(3,4-dichloro-5-methyl-1H-pyrrol-2-yl)carbonyl]amino}-3-methoxypiperidin-1-yl]-4-[5-(4-methylpiperazin-1-yl)pyrazin-2-yl]-1,3-thiazole-5-carboxylate (Example 60, 92 mg, 0.144 mM) was dissolved in methanol (15 mL). To this was added 2N sodium hydroxide (7 mL) and the reaction mixture was stirred at room temperature for 4 h. The methanol was completely evaporated and water (20 mL) was added. The aqueous layer was washed with diethyl ether (2×20 mL) and the aqueous layer was acidified to pH 6 with 2N hydrochloric acid (1.0 mL). The solid that precipitated out of solution was filtered and dried to afford 2-[(3R,4S)-4-{[(3,4-dichloro-5-methyl-1H-pyrrol-2-yl)carbonyl]amino}-3-methoxypiperidin-1-yl]-4-[5-(4-methylpiperazin-1-yl)pyrazin-2-yl]-1,3-thiazole-5-carboxylic acid 60 mg (82%) as an off-white solid.

$^1$H NMR (400 MHz, DMSO-$d_6$): δ 1.75 (s, 2H), 1.87 (m, 2H), 2.18 (s, 3H), 2.22 (s, 3H), 2.41 (m, 4H), 3.26-3.53 (m, 5H), 3.62 (m, 4H), 3.88 (br s, 1H), 4.24 (br s, 1H), 7.25 (d, 1H), 8.31 (s, 1H), 8.73 (s, 1H).

LC_MS: m/z 609.4 (M+H)

Example 62

2-[(3S,4R)-4-{[(3,4-dichloro-5-methyl-1H-pyrrol-2-yl)carbonyl]amino}-3-methoxypiperidin-1-yl]-4-{5-[2-(pyrrolidin-1-yl)ethoxy]pyrazin-2-yl}-1,3-thiazole-5-carboxylic acid

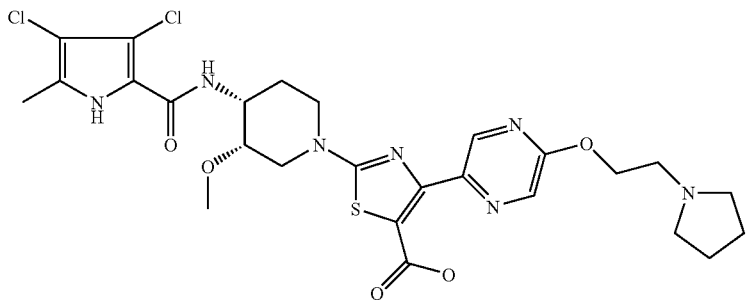

To a stirred solution of 2-(pyrrolidine-1-yl)ethanol (0.102 mL, 0.872 mmol) in dry tetrahydrofuran (20 mL) was added sodium hydride (70 mg, 1.771 mmol) at 0° C. The reaction mixture was heated to 80° C. After 10 min, ethyl 4-(5-chloropyrazin-2-yl)-2-[(3S,4R)-4-{[(3,4-dichloro-5-methyl-1H-pyrrol-2-yl)carbonyl]amino}-3-methoxypiperidin-1-yl]-1,3-thiazole-5-carboxylate (Example 59, 250 mg, 0.436 mmol) was added to the reaction mixture at 80° C. and further maintained at 80° C. for 10 min. After the completion of the reaction, the reaction mixture was cooled and carefully quenched by adding ice pieces. The aqueous layer was extracted with ethyl acetate (2×50 mL) to get rid of any organic impurities and discarded. The aqueous layer was acidified to pH=2 using 2N HCl solution and was extracted with 10% methanol/dichloromethane (2×100 mL). The organic layer was dried and concentrated under reduced pressure to yield the product. The obtained product was stirred in acetonitrile (10 mL). The solid was filtered and dried to obtain 120 mg (45%) of 2-[(3S,4R)-4-{[(3,4-dichloro-5-methyl-1H-pyrrol-2-yl)carbonyl]amino}-3-methoxypiperidin-1-yl]-4-{5-[2-(pyrrolidin-1-yl)ethoxy]pyrazin-2-yl}-1,3-thiazole-5-carboxylic acid as yellow solid.

$^1$H NMR (400 MHz, DMSO-$d_6$): δ 1.72-1.77 (m, 6H), 2.18 (s, 3H), 2.65 (m, 4H), 2.96 (m, 3H), 3.34-3.39 (m, 5H), 3.57 (t, 1H), 4.00 (m, 1H), 4.27-4.29 (m, 1H), 4.50-4.53 (m, 3H), 7.16-7.18 (d, 1H), 8.46 (s, 1H), 8.94 (s, 1H), 12.17 (s, 1H).

LC-MS: m/z 623 (M+H).

Examples 63-65

The following Examples were prepared according to the procedure described for Example 62 from the starting materials given in the Table.

| Ex | Compound | Data | SM |
|---|---|---|---|
| 63 | 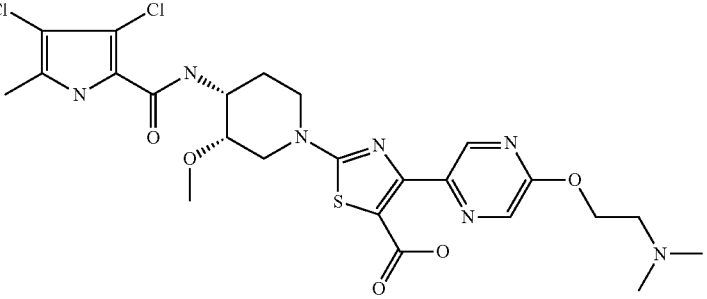<br>"2-[(3S,4R)-4-{[(3,4-dichloro-5-methyl-1H-pyrrol-2-yl)carbonyl]amino}-3-methoxypiperidin-1-yl]-4-{5-[2-(dimethylamino)ethoxy]pyrazin-2-yl}-1,3-thiazole-5-carboylic acid". | $^1$H NMR (400 MHz, DMSO-$d_6$): δ 1.78 (m, 2H), 2.18 (s, 3H), 2.24 (s, 6H), 2.71-2.82 (m, 2H), 3.27-3.31 (m, 2H), 3.38 (s, 4H), 3.57 (m, 1H), 3.98 (m, 1H), 4.27-4.60 (m, 4H), 7.16-7.18 (d, 1H), 8.46 (s, 1H), 8.95 (s, 1H), 12.17 (s, 1H).<br>LC-MS: m/z 598 (M + H) | Example 59 and N,N-dimethylamino-ethanol |
| 64 | 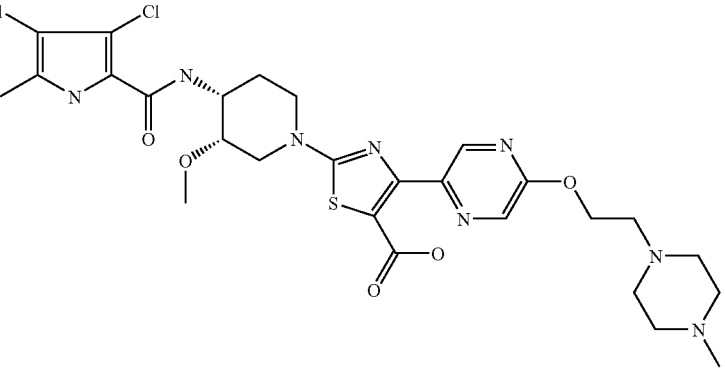<br>2-[(3S,4R)-4-{[(3,4-dichloro-5-methyl-1H-pyrrol-2-yl)carbonyl]amino}-3-methoxypiperidin-1-yl]-4-{5-[2-(4-methylpiperazin-1-yl)ethoxy]pyrazin-2-yl}-1,3-thiazole-5-carboylic acid | $^1$H NMR (400 MHz, DMSO-$d_6$): δ 1.78 (m, 2H), 2.16 (s, 3H), 2.18 (s, 3H), 2.33 (m, 4H), 2.71-2.82 (m, 2H), 3.31-3.36 (m, 5H), 3.34-3.38 (m, 2H), 3.388 (s, 3H), 3.57 (t, 1H), 3.98 (m, 1H), 4.27-4.29 (m, 1H), 4.49-4.51 (m, 3H), 7.15-7.17 (d, 1H), 8.45 (s, 1H), 8.95 (s, 1H), 12.14 (s, 1H).<br>LC-MS: m/z 652 (M +H). | Example 59 and N-methylpiperazine ethanol |
| 65 | 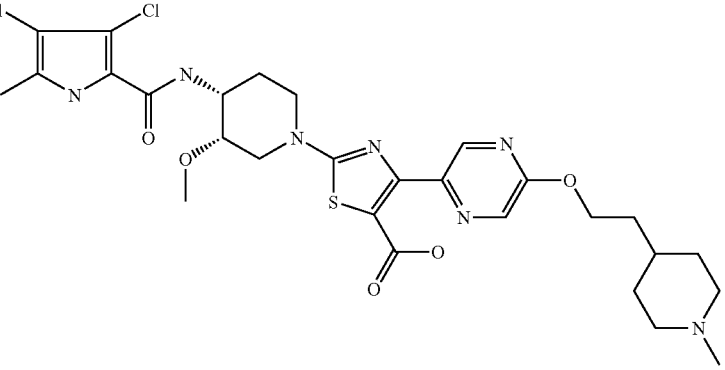<br>2-[(3S,4R)-4-{[(3,4-dichloro-5-methyl-1H-pyrrol-2-yl)carbonyl]amino}-3-methoxypiperidin-1-yl]-4-{5-[2-(1-methylpiperidin-4-yl)ethoxy]pyrazin-2-yl}-1,3-thiazole-5-carboylic acid | $^1$H NMR (400 MHz, DMSO-$d_6$): δ 1.23-1.25 (m, 3H), 1.35 (m, 2H), 1.62-1.77 (m, 6H), 2.18 (s, 3H), 2.53 (s, 3H), 2.71-2.82 (m, 2H), 3.13-3.16 (m, 1H), 3.34-3.38 (m, 2H), 3.388 (s, 3H), 3.57 (t, 1H), 3.98 (m, 1H), 4.27-4.29 (m, 1H), 4.43-4.46 (m, 3H), 7.17-7.19 (d, 1H), 8.44 (s, 1H), 8.94 (s, 1H), 12.18 (s, 1H).<br>LC-MS: m/z 651 (M +H). | Example 59 and N-methyl-piperidine4-ethanol |

Example 66

Ethyl 4-(5-chloropyrazin-2-yl)-2-[(3S,4R)-4-{[(3,4-dichloro-5-methyl-1H-pyrrol-2-yl)carbonyl]amino}-3-ethoxypiperidin-1-yl]-1,3-thiazole-5-carboxylate

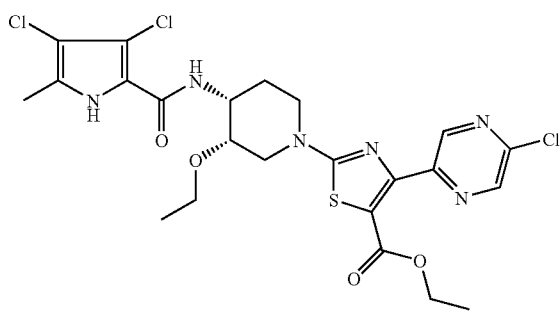

To the stirred the solution of 3,4-dichloro-N-[(3S,4R)-3-ethoxypiperidin-4-yl]-5-methyl-1H-pyrrole-2-carboxamide (Intermediate 26, 650 mg, 2.03 mmol) and ethyl 2-bromo-4-(5-chloropyrazin-2-yl)-1,3-thiazole-5-carboxylate (Intermediate 47, 636 mg, 1.828 mmol) in N-methylpyrrolidine was added N,N-diisopropyl ethylamine and stirred at stirred at 60° C. for 3 h. The reaction mixture was cooled to room temperature and poured on to ice water. The precipitate was collected by filtration and dried to afford 950 mg (79%) of ethyl 4-(5-chloropyrazin-2-yl)-2-[(3S,4R)-4-{[(3,4-dichloro-5-methyl-1H-pyrrol-2-yl)carbonyl]amino}-3-ethoxypiperidin-1-yl]-1,3-thiazole-5-carboxylate.

$^1$H NMR (400 MHz, CDCl$_3$): δ 1.21-1.31 (m, 6H), 1.95-2.11 (m, 2H), 2.31 (s, 3H), 3.21 (m, 2H), 3.41 (m, 4H), 3.80 (m, 1H), 4.20 (m, 2H), 4.31 (m, 1H), 4.41 (m, 1H), 8.65 (m, 2H), 9.01 (s, 1H).

LC-MS: m/z 587 (M+H).

Example 67

Ethyl 2-[(3S,4R)-4-{[(3,4-dichloro-5-methyl-1H-pyrrol-2-yl)carbonyl]amino}-3-ethoxypiperidin-1-yl]-4-[5-(piperidin-1-yl)pyrazin-2-yl]-1,3-thiazole-5-carboxylate

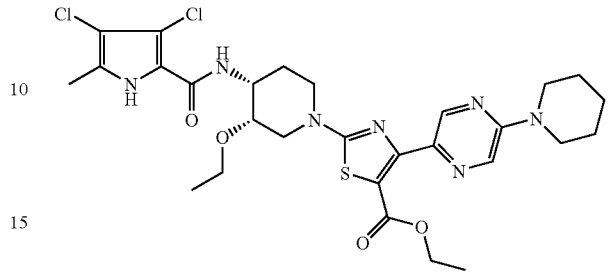

To a stirred solution of ethyl 4-(5-chloropyrazin-2-yl)-2-[(3S,4R)-4-{[(3,4-dichloro-5-methyl-1H-pyrrol-2-yl)carbonyl]amino}-3-ethoxypiperidin-1-yl]-1,3-thiazole-5-carboxylate (Example 66, 120 mg, 0.204 mmol) and piperidine (87 mg 1.023 mmol) in N-methyl pyrrolidine was added N,N-diisopropyl ethylamine; the reaction mixture was then stirred over night at 80° C. The reaction mixture was cooled to room temperature and poured on to ice cold water. The precipitated product was collected by filtration and dried to afford 120 mg (92%) of ethyl 2-[(3S,4R)-4-{[(3,4-dichloro-5-methyl-1H-pyrrol-2-yl)carbonyl]amino}-3-ethoxypiperidin-1-yl]-4-[5-(piperidin-1-yl)pyrazin-2-yl]-1,3-thiazole-5-carboxylate.

$^1$H NMR (400 MHz, CDCl$_3$): δ 1.18 (t, 3H), 1.23 (t, 3H), 1.75 (m, 6H), 2.02 (m, 2H), 2.32 (s, 3H), 3.21 (m, 2H), 3.42 (m, 2H), 3.61 (m, 5H), 4.21 (m, 5H), 4.42 (m, 1H), 8.17 (s, 1H), 8.45 (s, 1H), 9.29 (m, 1H).

LC-MS: m/z 636.47 (M+H).

Examples 68-85

The following Examples were prepared according to the procedure for Example 67 from the starting materials indicated in the table.

| Ex | Compound | Data | SM |
|----|----------|------|-----|
| 68 | Ethyl 2-[(3S,4R)-4-{[(3,4-dichloro-5-methyl-1H-pyrrol-2-yl)carbonyl]amino}-3-ethoxypiperidin-1-yl]-4-[5-(morpholin-4-yl)pyrazin-2-yl]-1,3-thiazole-5-carboxylate | $^1$H NMR (400 MHz, CDCl$_3$): δ 1.21 (t, 3H), 1.27 (t, 3H), 2.08 (m, 2H), 2.27 (s, 3H), 3.22 (m, 2H), 3.43 (m, 2H), 3.63 (m, 5H), 3.83 (m, 4H), 4.22 (m, 4H), 4.4 (m, 1H), 7.28 (d, 1H), 8.17 (s, 1H), 8.49 (s, 1H), 9.52 (m, 1H).<br>LC-MS: m/z 638.55 (M + H) | Example 66 and morpholine |

-continued

| Ex | Compound | Data | SM |
|---|---|---|---|
| 69 | Ethyl 2-[(3S,4R)-4-{[(3,4-dichloro-5-methyl-1H-pyrrol-2-yl)carbonyl]amino}-3-ethoxypiperidin-1-yl]-4-[5-(4-methylpiperazin-1-yl)pyrazin-2-yl]-1,3-thiazole-5-carboxylate | $^1$H NMR (400 MHz, CDCl$_3$): δ 1.18 (t, 3H), 1.23 (t, 3H), 2.05 (m, 2H), 2.35 (2s, 6H), 2.53 (m, 4H), 3.42 (m, 2H), 3.60 (m, 5H), 3.8 (m, 2H), 4.21 (m, 4H), 4.42 (m, 1H), 7.28 (d, 1H), 8.18 (s, 1H), 8.47 (s, 1H), 9.49 (m, 1H). LC-MS: m/z 651.59 (M + H) | Example 66 and N-methyl-piperazine |
| 70 | Ethyl 2-[(3S,4R)-4-{[(3,4-dichloro-5-methyl-1H-pyrrol-2-yl)carbonyl]amino}-3-ethoxypiperidin-1-yl]-4-[5-(piperazin-1-yl)pyrazin-2-yl]-1,3-thiazole-5-carboxylate | $^1$H NMR (400 MHz, CDCl$_3$): δ 0.89 (t, 3H), 1.18 (t, 3H), 2.03 (m, 2H), 2.27 (s, 3H), 3.02 (m, 4H), 3.22 (m, 2H), 3.41 (m, 2H), 3.62 (m, 5H), 4.21 (m, 4H), 4.42 (m, 1H), 8.18 (s, 1H), 8.47 (s, 1H), 9.18 (m, 1H) LC-MS: m/z 637.60 (M + H) | Example 66 and piperazine |
| 71 | Ethyl 2-[(3S,4R)-4-{[(3,4-dichloro-5-methyl-1H-pyrrol-2-yl)carbonyl]amino}-3-ethoxypiperidin-1-yl]-4-{5-[(2-methoxyethyl)amino]pyrazin-2-yl}-1,3-thiazole-5-carboxylate | $^1$H NMR (400 MHz, CDCl$_3$): δ 1.18 (t, 3H), 1.23 (t, 3H), 2.02 (m, 2H), 2.35 (s, 3H), 3.22 (m, 2H), 3.41 (s, 3H), 3.42 (m, 2H), 3.61 (m, 5H), 4.21 (m, 4H), 4.21 (m, 1H), 5.05 (m, 1H), 7.25 (d, 1H), 7.97 (s, 1H), 8.40 (s, 1H), 9.19 (m, 1H). LC-MS: m/z (M + H) | Example 66 and 2-methoxy-ethylamine |
| 72 | Ethyl 2-[(3S,4R)-4-{[(3,4-dichloro-5-methyl-1H-pyrrol-2-yl)carbonyl]amino}-3-ethoxypiperidin-1-yl]-4-(5-{[2-(morpholin-4-yl)ethyl]amino}pyrazin-2-yl)-1,3-thiazole-5-carboxylate | $^1$H NMR (400 MHz, CDCl$_3$): δ 0.88 (t, 3H), 1.15 (t, 3H), 2.02 (m, 2H), 2.29 (s, 3H), 2.55 (m, 4H), 2.62 (m, 2H), 3.21 (m, 2H), 3.42 (m, 4H), 3.62 (m, 1H), 3.75 (m, 6H), 4.20 (m, 2H), 4.31 (m, 1H), 5.39 (m, 1H), 7.98 (s, 1H), 8.41 (s, 1H), 9.34 (s, 1H). LC-MS: m/z 681 (M + H) | Example 66 and 4-morpholino-ethylamien |

| Ex | Compound | Data | SM |
|---|---|---|---|
| 73 | 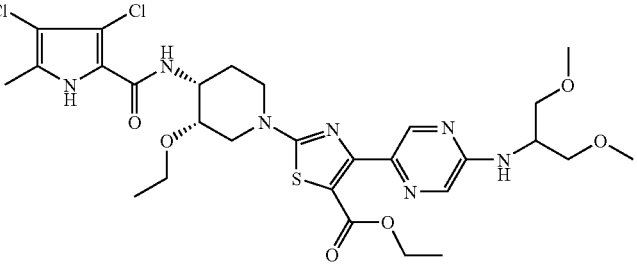<br>Ethyl 2-[(3S,4R)-4-{[(3,4-dichloro-5-methyl-1H-pyrrol-2-yl)carbonyl]amino}-3-ethoxypiperidin-1-yl]-4-{5-[(1,3-dimethoxypropan-2-yl)amino]pyrazin-2-yl}-1,3-thiazole-5-carboxylate | $^1$H NMR (400 MHz, CDCl$_3$): δ 0.88 (t, 3H), 1.16 (t, 3H), 2.05 (m, 2H), 2.31 (s, 3H), 3.42 (m, 13H), 4.31 (2s, 6H), 4.41 (m, 1H), 7.26 (d, 1H), 7.97 (s, 1H), 8.40 (s, 1H), 9.52 (m, 1H). LC-MS: m/z 670.67 (M + H). | Example 66 and 1,3-dimethoxy-prpane-2-yl-amine |
| 74 | 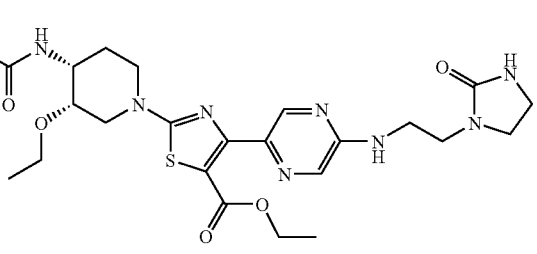<br>Ethyl 2-[(3S,4R)-4-{[(3,4-dichloro-5-methyl-1H-pyrrol-2-yl)carbonyl]amino}-3-ethoxypiperidin-1-yl]-4-(5-{[2-(2-oxoimidazolidin-1-yl)ethyl]amino}pyrazin-2-yl)-1,3-thiazole-5-carboxylate | $^1$H NMR (400 MHz, DMSO-d$_6$): δ 1.05 (t, 3H), 1.07 (t, 3H), 1.77 (m, 2H), 2.18 (s, 3H), 3.21 (m, 4H), 3.37 (m, 6H), 3.64 (m, 1H), 3.71 (m, 2H), 4.11 (m, 3H), 4.23 (m, 2H), 6.31 (s, 1H), 7.15 (d, 1H), 7.41 (m, 1H), 7.93 (s, 1H), 8.21 (s, 1H), 12.17 (s, 1H). LC-MS: m/z 680.43 (M + H) | Example 66 and 2-oxo-imidazolidin-1-yl)ethylamine |
| 75 | 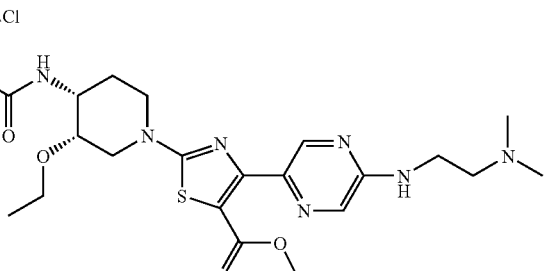<br>Ethyl 2-[(3S,4R)-4-{[(3,4-dichloro-5-methyl-1H-pyrrol-2-yl)carbonyl]amino}-3-ethoxypiperidin-1-yl]-4-(5-{[2-(dimethylamino)ethyl]amino}pyrazin-2-yl)-1,3-thiazole-5-carboxylate | $^1$H NMR (400 MHz, CDCl$_3$): δ 1.18 (t, 3H), 1.21 (t, 3H), 2.03 (m, 2H), 2.25 (m, 9H), 2.59 (m, 2H), 3.21 (m, 2H), 3.42 (m, 4H), 3.61 (m, 1H), 4.22 (m, 4H), 4.41 (m, 1H), 5.54 (m, 1H), 7.98 (s, 1H), 8.40 (s, 1H), 9.33 (s, 1H). LC-MS: m/z 639.43 (M + H) | Example 66 and dimethylamino-ethylamine |
| 76 | 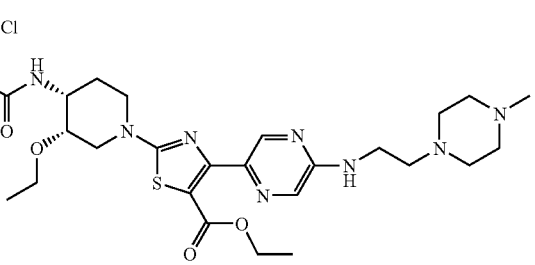<br>Ethyl 2-[(3S,4R)-4-{[(3,4-dichloro-5-methyl-1H-pyrrol-2-yl)carbonyl]amino}-3-ethoxypiperidin-1-yl]-4-(5-{[2-(4-methylpiperazin-1-yl)ethyl]amino}pyrazin-2-yl)-1,3-thiazole-5-carboxylate | $^1$H NMR (400 MHz, CDCl$_3$): δ 1.26 (t, 3H), 1.34 (m, 3H), 1.95 (m, 2H), 2.07 (m, 2H), 2.32 (s, 3H), 2.41 (s, 3H), 2.73 (m, 8H), 3.23 (m, 2H), 3.48 (m, 4H), 3.82 (m, 1H), 4.23 (m, 4H), 4.42 (m, 1H), 8.02 (s, 1H), 8.21 (s, 1H), 9.13 (s, 1H), LC-MS: m/z 694 (M + H) | Example 66 and 4-methyl-piperazin-1-yl-ethylamine |

| Ex | Compound | Data | SM |
|---|---|---|---|
| 77 | 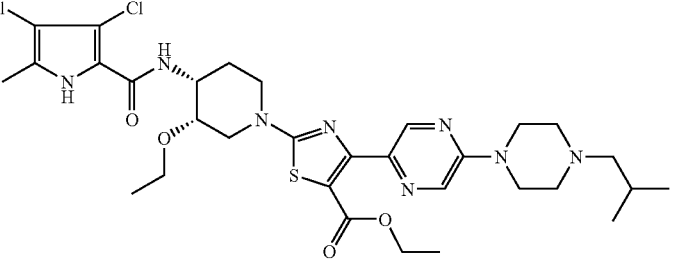<br>Ethyl 2-[(3S,4R)-4-{[(3,4-dichloro-5-methyl-1H-pyrrol-2-yl)carbonyl]amino}-3-ethoxypiperidin-1-yl]-4-{5-[4-(2-methylpropyl)piperazin-1-yl]pyrazin-2-yl}-1,3-thiazole-5-carboxylate | $^1$H NMR (400 MHz, CDCl$_3$): δ 0.95 (m, 6H), 1.23 (t, 3H), 1.34 (t, 3H), 1.35 (m, 1H), 2.01 (m, 2H), 2.22 (d, 2H), 2.35 (s, 3H), 2.53 (m, 4H), 3.24 (m, 2H), 3.46 (m, 2H), 3.63 (m, 4H), 4.21 (m, 2H), 4.43 (m, 2H), 4.56 (m, 1H), 7.22 (d, 1H), 8.23 (s, 1H), 8.44 (s, 1H), 9.4 (s, 1H).<br>LC-MS: m/z 693 (M + H) | Example 66 and 4-(2-methylpropyl)piperazine |
| 78 | 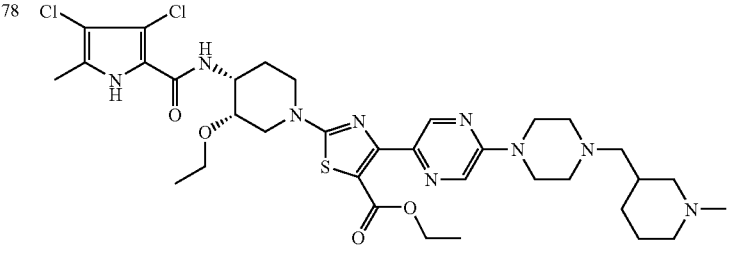<br>Ethyl 2-[(3S,4R)-4-{[(3,4-dichloro-5-methyl-1H-pyrrol-2-yl)carbonyl]amino}-3-ethoxypiperidin-1-yl]-4-(5-{4-[(1-methylpiperidin-3-yl)methyl]piperazin-1-yl}pyrazin-2-yl)-1,3-thiazole-5-carboxylate | $^1$H NMR (400 MHz, CDCl$_3$): δ 0.89 (t, 3H), 1.18 (t, 3H), 1.92 (m, 6H), 2.01 (m, 2H), 2.21 (m, 1H), 2.35 (m, 6H), 2.42 (m, 2H), 2.61 (m, 2H), 2.95 (m, 2H), 3.05 (m, 2H), 3.21 (m, 2H), 3.41 (m, 2H), 3.62 (m, 4H), 4.15 (m, 1H), 4.21 (m, 2H), 4.31 (m, 2H), 4.41 (m, 1H), 8.17 (s, 1H), 8.46 (s, 1H), 9.41 (s, 1H).<br>LC-MS: m/z 748.57 (M + H) | Example 66 and 4-(1-methyl-piperidin-3-yl)methyl-piperazine |
| 79 | 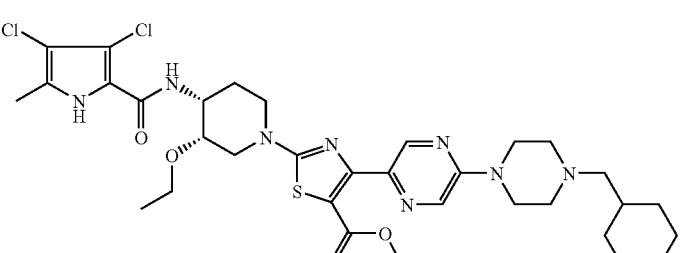<br>Ethyl 4-{5-[4-(cyclohexylmethyl)piperazin-1-yl]pyrazin-2-yl}-2-[(3S,4R)-4-{[(3,4-dichloro-5-methyl-1H-pyrrol-2-yl)carbonyl]amino}-3-ethoxypiperidin-1-yl]-1,3-thiazole-5-carboxylate | $^1$H NMR (400 MHz, CDCl$_3$): δ 1.22 (m, 3H), 1.33 (m, 3H), 1.35 (m, 2H), 1.82 (m, 12H), 2.03 (m, 1H), 2.25 (d, 2H), 2.36 (s, 3H), 2.54 (m, 4H), 3.21 (m, 2H), 3.45 (m, 1H), 3.62 (m, 4H), 4.22 (m, 4H), 4.41 (m, 1H), 8.25 (s, 1H), 8.44 (s, 1H), 9.42 (s, 1H).<br>LC-MS: m/z 734 (M + H) | Example 66 and cyclohexyl-methyl-piperazine |
| 80 | 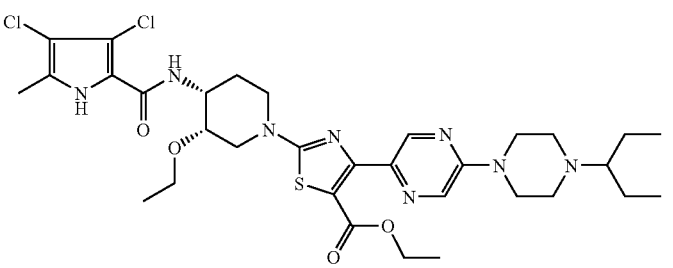<br>Ethyl 2-[(3S,4R)-4-{[(3,4-dichloro-5-methyl-1H-pyrrol-2-yl)carbonyl]amino}-3-ethoxypiperidin-1-yl]-4-{5-[4-(pentan-3-yl)piperazin-1-yl]pyrazin-2-yl}-1,3-thiazole-5-carboxylate | $^1$H NMR (400 MHz, CDCl$_3$): δ 0.91 (m, 6H), 1.22 (t, 3H), 1.31 (m, 4H), 1.51 (m, 3H), 2.02 (m, 2H), 2.22 (m, 1H), 2.25 (s, 3H), 2.64 (m, 4H), 3.23 (m, 2H), 3.46 (m, 2H), 3.61 (m, 4H), 4.10 (m, 1H), 4.22 (m, 2H), 4.31 (m, 2H), 4.45 (m, 1H), 8.22 (s, 1H), 8.45 (s, 1H), 9.42 (s, 1H).<br>LC-MS: m/z 708 (M + H) | Example 66 and 1-(1-ethylpropyl)piperazine |

| Ex | Compound | Data | SM |
|---|---|---|---|
| 81 | 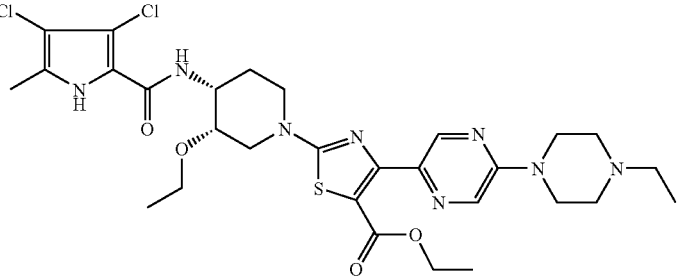<br>Ethyl 2-[(3S,4R)-4-{[(3,4-dichloro-5-methyl-1H-pyrrol-2-yl)carbonyl]amino}-3-ethoxypiperidin-1-yl]-4-[5-(4-ethylpiperazin-1-yl)pyrazin-2-yl]-1,3-thiazole-5-carboxylate | $^1$H NMR (400 MHz, CDCl$_3$): δ 1.22 (m, 5H), 1.35 (m, 6H), 2.01 (m, 2H), 2.32 (s, 3H), 2.65 (m, 4H), 3.25 (m, 2H), 3.41 (m, 1H), 3.85 (m, 6H), 4.24 (m, 4H), 4.42 (m, 1H), 8.26 (s, 1H), 8.45 (s, 1H), 9.25 (s, 1H).<br>LC-MS: m/z 665.4 (M + H) | Example 66 and ethylpiperazine |
| 82 | 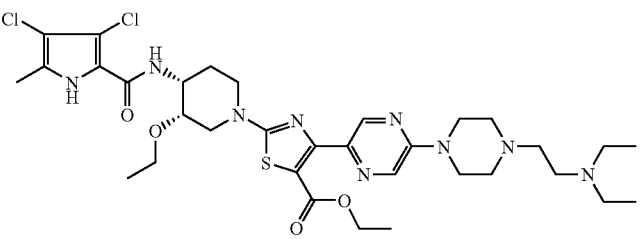<br>Ethyl 2-[(3S,4R)-4-{[(3,4-dichloro-5-methyl-1H-pyrrol-2-yl)carbonyl]amino}-3-ethoxypiperidin-1-yl]-4-(5-{4-[2-(diethylamino)ethyl]piperazin-1-yl}pyrazin-2-yl)-1,3-thiazole-5-carboxylate | $^1$H NMR (400 MHz, CDCl$_3$): δ 1.22 (m, 6H), 1.32 (m, 6H), 1.92 (m, 2H), 2.15 (m, 2H), 2.34 (s, 3H), 2.62 (m, 10H), 3.21 (m, 2H), 3.44 (m, 1H), 3.62 (m, 4H), 3.81 (m, 2H), 4.22 (m, 4H), 4.41 (m, 1H), 8.22 (s, 1H), 8.41 (s, 1H), 9.25 (s, 1H).<br>LC-MS: m/z 737 (M + H) | Example 66 and N,N-diethyl-2-piperazin-1-ylethanamine |
| 83 | 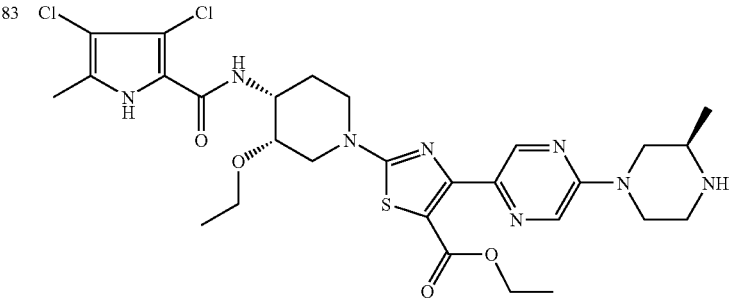<br>Ethyl 2-[(3S,4R)-4-{[(3,4-dichloro-5-methyl-1H-pyrrol-2-yl)carbonyl]amino}-3-ethoxypiperidin-1-yl]-4-{5-[(3R)-3-methylpiperazin-1-yl]pyrazin-2-yl}-1,3-thiazole-5-carboxylate | $^1$H NMR (400 MHz, CDCl$_3$): δ 1.24 (m, 6H), 1.99 (m, 2H), 2.03 (m, 2H), 2.37 (s, 3H), 2.63 (m, 1H), 3.04 (m, 4H), 3.22 (m, 3H), 3.61 (m, 1H), 3.85 (m, 2H), 4.22 (m, 6H), 4.42 (m, 1H), 7.22 (d, 1H), 8.18 (s, 1H), 8.47 (s, 1H), 8.47 (s, 1H), 9.50 (s, 1H).<br>LC-MS: m/z 649.82 (M + H) | Example 66 and (3R)-3-methyl-piperazine |
| 84 | 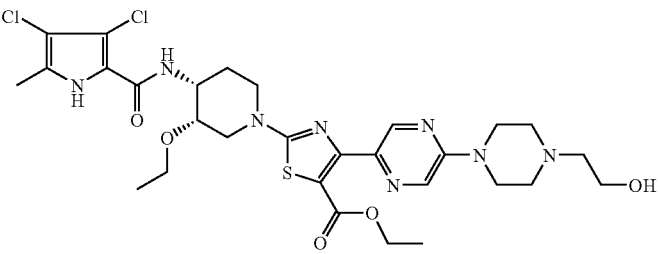<br>Ethyl 2-[(3S,4R)-4-{[(3,4-dichloro-5-methyl-1H-pyrrol-2-yl)carbonyl]amino}-3-ethoxypiperidin-1-yl]-4-{5-[4-(2-hydroxyethyl)piperazin-1-yl]pyrazin-2-yl}-1,3-thiazole-5-carboxylate | $^1$H NMR (400 MHz, CDCl$_3$): δ 1.18 (t, 3H), 1.24 (t, 3H), 2.03 (m, 2H), 2.27 (s, 3H), 2.64 (m, 6H), 3.22 (m, 2H), 3.41 (m, 2H), 3.61 (m, 1H), 3.71 (m, 6H), 4.25 (m, 4H), 8.19 (s, 1H), 8.48 (s, 1H), 9.36 (s, 1H).<br>LC-MS: m/z 681.50 (M + H) | Example 66 and 2-piperazin-1-ylethanol |

| Ex | Compound | Data | SM |
|---|---|---|---|
| 85 | Ethyl 2-[(3S,4R)-4-{[(3,4-dichloro-5-methyl-1H-pyrrol-2-yl)carbonyl]amino}-3-ethoxypiperidin-1-yl]-4-{5-[4-(tetrahydrofuran-2-ylmethyl)piperazin-1-yl]pyrazin-2-yl}-1,3-thiazole-5-carboxylate | $^1$H NMR (400 MHz, CDCl$_3$): δ 1.22 (t, 3H), 1.31 (m, 3H), 1.35 (m, 2H), 1.52 (m, 2H), 2.01 (m, 5H), 2.32 (s, 3H), 2.55 (m, 2H), 2.62 (m, 4H), 3.21 (m, 2H), 3.45 (m, 1H), 3.81 (m, 8H), 4.22 (m, 2H), 4.45 (m, 1H), 8.22 (s, 1H), 8.46 (s, 1H), 9.23 (s, 1H). LC-MS: m/z 721.5 (M + H) | Example 66 and 1-(tetrahydrofuran-2-ylmethyl)piperazine |

Example 86

2-[(3S,4R)-4-{[(3,4-dichloro-5-methyl-1H-pyrrol-2-yl)carbonyl]amino}-3-ethoxypiperidin-1-yl]-4-[5-(piperidin-1-yl)pyrazin-2-yl]-1,3-thiazole-5-carboxylic acid To the solution of ethyl 2-[(3S,4R)-4-{[(3,4-dichloro-5-methyl-1H-pyrrol-2-yl)carbonyl]amino}-3-ethoxypiperidin-1-yl]-4-[5-(piperidin-1-yl)pyrazin-2-yl]-1,3-thiazole-5-carboxylate (Example 67, 120 mg, 0.188 mmol) in methanol (20 mL) was added 2N sodium hydroxide (3 mL) in a dropwise fashion at 0° C. The reaction mixture was stirred overnight and then concentrated under reduced pressure to dryness. The resulting residue was diluted with water (20 mL) and extracted with ethyl acetate to remove any organic impurities. The aqueous layer was passed through celite bed and acidified with 2N hydrochloric acid. The precipitated product was collected by filtration and dried to afford 35 mg (31.8%) of 2-[(3S,4R)-4-{[(3,4-dichloro-5-methyl-1H-pyrrol-2-yl)carbonyl]amino}-3-ethoxy piperidin-1-yl]-4-[5-(piperidin-1-yl)pyrazin-2-yl]-1,3-thiazole-5-carboxylic acid as a yellow solid.

$^1$H NMR (400 MHz, DMSO-d$_6$): δ 1.04 (t, 3H), 1.58 (m, 8H), 2.18 (s, 3H), 3.44 (m, 2H), 3.46 (m, 1H), 3.75 (m, 8H), 4.27 (m, 1H), 7.14 (d, 1H), 8.40 (s, 1H), 8.95 (s, 1H), 12.18 (s, 1H), 16.86 (s, 1H).

LC-MS: m/z 608.45 (M+H)

Examples 87-104

The following Examples were prepared according to the procedure described for Example 86 from the starting material indicated in the table.

| Ex | Compound | Data | SM |
|---|---|---|---|
| 87 | 2-[(3S,4R)-4-{[(3,4-dichloro-5-methyl-1H-pyrrol-2-yl)carbonyl]amino}-3-ethoxypiperidin-1-yl]-4-[5-(morpholin-4-yl)pyrazin-2-yl]-1,3-thiazole-5-carboxylic acid | $^1$H NMR (400 MHz, DMSO-d$_6$): δ 1.04 (t, 3H), 1.78 (m, 2H), 2.18 (s, 3H), 8.33 (m, 2H), 3.48 (m, 1H), 3.68 (m, 10H), 4.02 (m, 1H), 4.27 (m, 2H), 7.13 (d, 1H), 8.41 (s, 1H), 8.98 (s, 1H), 12.15 (s, 1H), 16.67 (s, 1H). LC-MS: m/z 610.42 (M + H) | Example 68 |

-continued

| Ex | Compound | Data | SM |
|---|---|---|---|
| 88 | 2-[(3S,4R)-4-{[(3,4-dichloro-5-methyl-1H-pyrrol-2-yl)carbonyl]amino}-3-ethoxypiperidin-1-yl]-4-[5-(4-methylpiperazin-1-yl)pyrazin-2-yl]-1,3-thiazole-5-carboxylic acid | $^1$H NMR (400 MHz, DMSO-d$_6$): δ 1.03 (t, 3H), 1.78 (m, 2H), 2.18 (s, 3H), 2.23 (s, 3H), 2.50 (m, 4H), 3.44 (m, 4H), 3.66 (m, 6H), 4.02 (m, 1H), 4.26 (m, 1H), 7.13 (d, 1H), 8.43 (s, 1H), 9.00 (s, 1H), 12.16 (s, 1H). LC-MS: m/z 623.44 (M + H) | Example 69 |
| 89 | 2-[(3S,4R)-4-{[(3,4-dichloro-5-methyl-1H-pyrrol-2-yl)carbonyl]amino}-3-ethoxypiperidin-1-yl]-4-[5-(piperazin-1-yl)pyrazin-2-yl]-1,3-thiazole-5-carboxylic acid | $^1$H NMR (400 MHz, DMSO-d$_6$): δ 1.04 (t, 3H), 1.78 (m, 2H), 2.18 (s, 3H), 2.82 (m, 4H), 3.44 (m, 3H) 3.71 (m, 6H), 4.00 (m, 1H), 4.26 (m, 2H), 7.12 (d, 1H), 8.39 (s, 1H), 8.99 (s, 1H), 12.15 (s, 1H). LC-MS: m/z 609.39 (M + H) | Example 70 |
| 90 | 2-[(3S,4R)-4-{[(3,4-dichloro-5-methyl-1H-pyrrol-2-yl)carbonyl]amino}-3-ethoxypiperidin-1-yl]-4-{5-[(2-methoxyethyl)amino]pyrazin-2-yl}-1,3-thiazole-5-carboxylic acid | $^1$H NMR (400 MHz, DMSO-d$_6$): δ 1.05 (t, 3H), 1.88 (m, 2H), 2.18 (s, 3H), 3.45 (m, 6H), 3.48 (m, 5H), 3.64 (m, 1H), 3.96 (m, 1H), 4.24 (m, 2H), 7.16 (d, 1H), 7.76 (s, 1H), 7.97 (s, 1H), 8.77 (s, 1H), 12.22 (s, 1H). LC-MS: m/z 598.43 (M + H) | Example 71 |
| 91 | 2-[(3S,4R)-4-{[(3,4-dichloro-5-methyl-1H-pyrrol-2-yl)carbonyl]amino}-3-ethoxypiperidin-1-yl]-4-(5-{[2-(morpholin-4-yl)ethyl]amino}pyrazin-2-yl)-1,3-thiazole-5-carboxylic acid | $^1$H NMR (400 MHz, DMSO-d$_6$): δ 1.06 (t, 3H), 1.75 (m, 2H), 2.18 (s, 3H), 2.41 (m, 4H), 3.44 (m, 13H), 3.91 (m, 1H), 4.23 (m, 2H), 7.2 (d, 1H), 7.96 (s, 1H), 8.58 (s, 1H), 12.42 (s, 1H). LC-MS: m/z 653.60 (M + H) | Example 72 |

| Ex | Compound | Data | SM |
|---|---|---|---|
| 92 | 2-[(3S,4R)-4-{[(3,4-dichloro-5-methyl-1H-pyrrol-2-yl)carbonyl]amino}-3-ethoxypiperidin-1-yl]-4-{5-[(1,3-dimethoxypropan-2-yl)amino]pyrazin-2-yl}-1,3-thiazole-5-carboxylic acid | $^1$H NMR (400 MHz, DMSO-$d_6$): δ 0.95 (t, 3H), 1.79 (m, 2H), 2.21 (s, 3H), 3.41 (m, 6H), 3.45 (2s, 6H), 3.75 (m, 2H), 4.01 (m, 1H), 4.31 (m, 3H), 7.15 (d, 1H), 8.02 (m, 2H), 8.95 (s, 1H), 12.19 (s, 1H).<br>LC-MS: m/z 642.45 (M + H) | Example 73 |
| 93 | 2-[(3S,4R)-4-{[(3,4-dichloro-5-methyl-1H-pyrrol-2-yl)carbonyl]amino}-3-ethoxypiperidin-1-yl]-4-(5-{[2-(2-oxoimidazolidin-1-yl)ethyl]amino}pyrazin-2-yl)-1,3-thiazole-5-carboxylic acid | $^1$H NMR (400 MHz, DMSO-$d_6$): δ 1.04 (t, 3H), 1.76 (m, 2H), 2.18 (s, 3H), 3.30 (m, 4H), 3.41 (m, 6H), 3.65 (m, 3H), 3.90 (m, 1H), 4.22 (m, 2H), 6.27 (s, 1H), 7.22 (d, 1H), 7.90 (s, 1H), 8.60 (s, 1H), 12.42 (s, 1H).<br>LC-MS: m/z 652.47 (M + H) | Example 74 |
| 94 | 2-[(3S,4R)-4-{[(3,4-dichloro-5-methyl-1H-pyrrol-2-yl)carbonyl]amino}-3-ethoxypiperidin-1-yl]-4-(5-{[2-(dimethylamino)ethyl]amino}pyrazin-2-yl)-1,3-thiazole-5-carboxylic acid | $^1$H NMR (400 MHz, DMSO-$d_6$): δ 1.05 (t, 3H), 1.76 (m, 2H), 1.85 (s, 3H), 2.18 (s, 6H), 2.44 (m, 2H), 3.42 (m, 5H), 3.70 (m, 2H), 3.99 (m, 1H), 4.23 (m, 2H), 7.18 (d, 1H), 7.50 (m, 1H), 7.96 (s, 1H), 8.72 (s, 1H), 12.26 (s, 1H).<br>LC-MS: m/z 611.66 (M + H) | Example 75 |
| 95 | 2-[(3S,4R)-4-{[(3,4-dichloro-5-methyl-1H-pyrrol-2-yl)carbonyl]amino}-3-ethoxypiperidin-1-yl]-4-(5-{[2-(4-methylpiperazin-1-yl)ethyl]amino}pyrazin-2-yl)-1,3-thiazole-5-carboxylic acid | $^1$H NMR (400 MHz, DMSO-$d_6$): δ 1.03 (t, 3H), 1.77 (m, 2H), 2.18 (s, 3H), 2.41 (s, 3H), 2.56 (m, 8H), 3.41 (m, 8H), 3.71 (m, 2H), 4.27 (m, 2H), 7.17 (d, 1H), 7.79 (2s, 2H), 8.934 (s, 1H), 12.2 (s, 1H).<br>LC-MS: m/z 666.6 (M + H) | Example 76 |

| Ex | Compound | Data | SM |
|---|---|---|---|
| 96 | 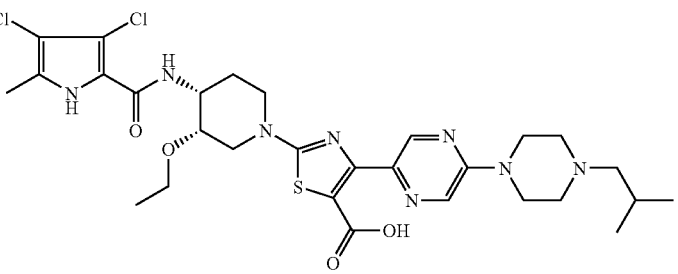<br>2-[(3S,4R)-4-{[(3,4-dichloro-5-methyl-1H-pyrrol-2-yl)carbonyl]amino}-3-ethoxypiperidin-1-yl]-4-{5-[4-(2-methylpropyl)piperazin-1-yl]pyrazin-2-yl}-1,3-thiazole-5-carboxylic acid | $^1$H NMR (400 MHz, DMSO-$d_6$): δ 0.86 (m, 6H), 1.04 (t, 3H), 1.77 (m, 3H), 2.05 (m, 2H), 2.16 (s, 3H), 2.42 (m, 4H), 3.30 (m, 2H), 3.63 (m, 6H), 3.89 (m, 2H), 4.22 (m, 2H), 7.24 (d, 1H), 8.25 (s, 1H), 8.64 (s, 1H), 12.38 (s, 1H). LC-MS: m/z 667.3 (M + H) | Example 77 |
| 97 | 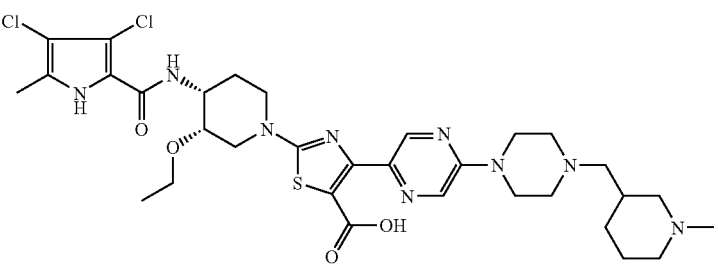<br>2-[(3S,4R)-4-{[(3,4-dichloro-5-methyl-1H-pyrrol-2-yl)carbonyl]amino}-3-ethoxypiperidin-1-yl]-4-(5-{4-[(1-methylpiperidin-3-yl)methyl]piperazin-1-yl}pyrazin-2-yl)-1,3-thiazole-5-carboxylic acid | $^1$H NMR (400 MHz, DMSO-$d_6$): δ 0.82 (m, 2H), 1.10 (t, 3H), 1.77 (m, 6H), 2.15 (2s, 6H), 2.51 (m, 9H), 2.79 (m, 2H), 3.21 (m, 2H), 3.61 (m, 7H), 3.85 (m, 1H), 4.21 (m, 2H), 7.30 (d, 1H), 8.19 (s, 1H), 8.52 (s, 1H). LC-MS: m/z 720.55 (M + H) | Example 78 |
| 98 | 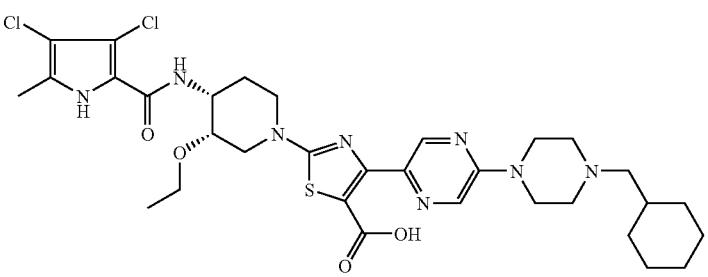<br>4-{5-[4-(cyclohexylmethyl)piperazin-1-yl]pyrazin-2-yl}-2-[(3S,4R)-4-{[3,4-dichloro-5-methyl-1H-pyrrol-2-yl)carbonyl]amino}-3-ethoxypiperidin-1-yl]-1,3-thiazole-5-carboxylic acid | $^1$H NMR (400 MHz, DMSO-$d_6$): δ 0.81 (m, 2H), 1.02 (t, 3H), 1.63 (m, 9H), 2.11 (m, 2H), 2.15 (s, 3H), 2.40 (m, 4H), 3.31 (m, 6H), 3.66 (m, 6H), 3.87 (m, 1H), 4.22 (s, 1H), 7.26 (d, 1H), 8.21 (s, 1H), 8.57 (s, 1H), 12.45 (s, 1H). LC-MS: m/z 705.68 (M + H) | Example 79 |
| 99 | 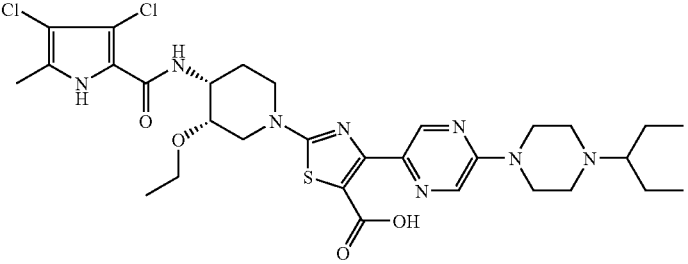<br>2-[(3S,4R)-4-{[(3,4-dichloro-5-methyl-1H-pyrrol-2-yl)carbonyl]amino}-3-ethoxypiperidin-1-yl]-4-{5-[4-(pentan-3-yl)piperazin-1-yl]pyrazin-2-yl}-1,3-thiazole-5-carboxylic acid | $^1$H NMR (400 MHz, DMSO-$d_6$): δ 0.84 (m, 6H), 1.01 (t, 3H), 1.24 (m, 4H), 1.44 (m, 1H), 1.76 (m, 2H), 2.16 (s, 3H), 2.55 (m, 4H), 3.44 (m, 4H), 3.71 (m, 6H), 4.26 (2m, 2H), 7.13 (d, 1H), 8.4 (s, 1H), 8.98 (s, 1H), 12.14 (s, 1H). LC-MS: m/z 681.44 (M + H) | Example 80 |

| Ex | Compound | Data | SM |
|---|---|---|---|
| 100 | 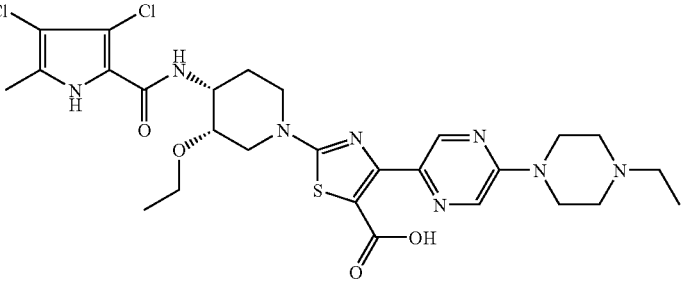<br>2-[(3S,4R)-4-{[(3,4-dichloro-5-methyl-1H-pyrrol-2-yl)carbonyl]amino}-3-ethoxypiperidin-1-yl]-4-[5-(4-ethylpiperazin-1-yl)pyrazin-2-yl]-1,3-thiazole-5-carboxylic acid | $^1$H NMR (400 MHz, DMSO-$d_6$): δ 1.03 (m, 6H), 2.16 (s, 3H), 2.36 (m, 2H), 2.47 (m, 4H), 3.25 (m, 4H), 3.41 (m, 2H), 3.68 (m, 6H), 3.85 (m, 1H), 4.21 (m, 1H), 7.30 (d, 1H), 8.20 (s, 1H), 8.53 (s, 1H). LC-MS: m/z 637.3 (M + H) | Example 81 |
| 101 | 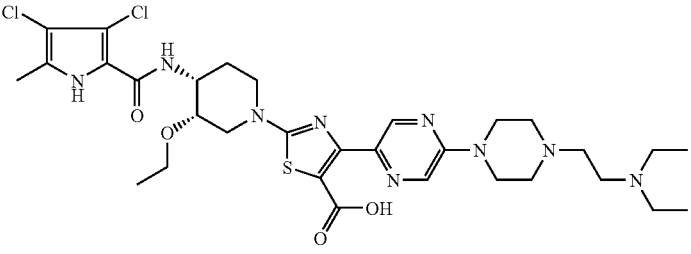<br>2-[(3S,4R)-4-{[(3,4-dichloro-5-methyl-1H-pyrrol-2-yl)carbonyl]amino}-3-ethoxypiperidin-1-yl]-4-(5-{4-[2-(diethylamino)ethyl]piperazin-1-yl}pyrazin-2-yl)-1,3-thiazole-5-carboxylic acid | $^1$H NMR (400 MHz, DMSO-$d_6$): δ 0.93 (m, 6H), 1.02 (t, 3H), 2.16 (s, 3H), 2.50 (m, 4H), 3.43 (m, 6H), 3.70 (m, 2H), 3.96 (m, 2H), 4.23 (s, 1H), 4.25 (m, 2H), 7.15 (d, 1H), 8.36 (s, 1H), 8.88 (s, 1H), 12.23 (s, 1H). LC-MS: m/z 708.7 (M + H) | Example 82 |
| 102 | 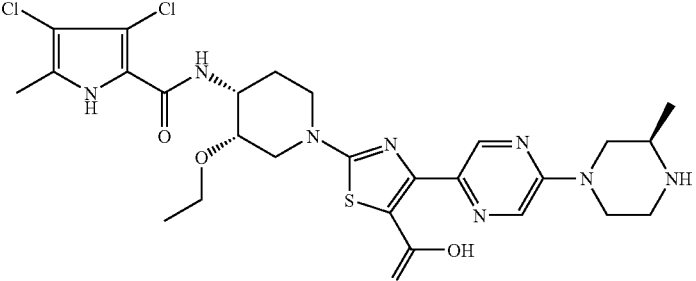<br>2-[(3S,4R)-4-{[(3,4-dichloro-5-methyl-1H-pyrrol-2-yl)carbonyl]amino}-3-ethoxypiperidin-1-yl]-4-{5-[(3R)-3-methylpiperazin-1-yl]pyrazin-2-yl}-1,3-thiazole-5-carboxylic acid | $^1$H NMR (400 MHz, DMSO-$d_6$): δ 1.04 (m, 6H), 1.90 (m, 2H), 2.18 (s., 3H), 2.55 (m, 1H), 2.68 (m, 2H), 3.35 (m, 4H), 3.42 (m, 1H), 3.79 (m, 2H), 4.02 (m, 1H), 4.29 (m, 4H) LC-MS: m/z 623.44 (M + H) | Example 83 |
| 103 | 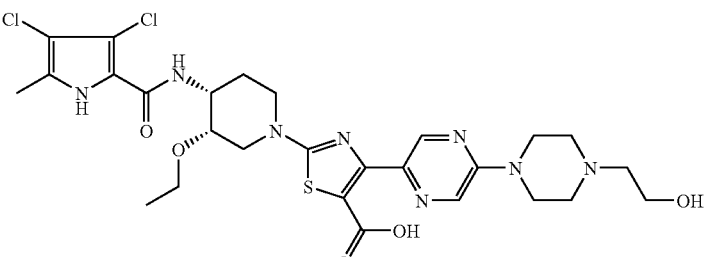<br>2-[(3S,4R)-4-{[(3,4-dichloro-5-methyl-1H-pyrrol-2-yl)carbonyl]amino}-3-ethoxypiperidin-1-yl]-4-{5-[4-(2-hydroxyethyl)piperazin-1-yl]pyrazin-2-yl}-1,3-thiazole-5-carboxylic acid | $^1$H NMR (400 MHz, DMSO-$d_6$): δ 1.06 (t, 3H), 1.76 (m, 2H), 2.18 (s, 3H), 2.52 (m, 4H), 3.42 (m, 5H), 3.91 (m, 1H), 4.23 (m, 2H), 7.22 (d, 1H), 8.29 (s, 1H), 8.71 (s, 1H), 12.12 (s, 1H). LC-MS: m/z 653.47 (M + H) | Example 84 |

| Ex | Compound | Data | SM |
|---|---|---|---|
| 104 | 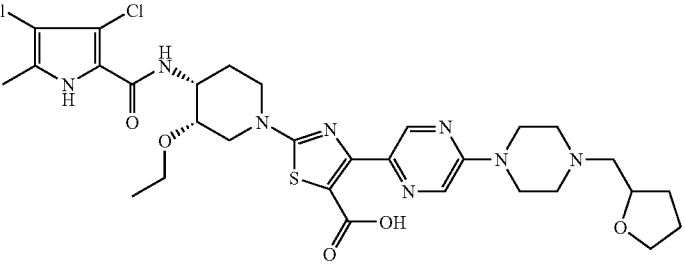<br>2-[(3S,4R)-4-{[(3,4-dichloro-5-methyl-1H-pyrrol-2-yl)carbonyl]amino}-3-ethoxypiperidin-1-yl]-4-{5-[4-(tetrahydrofuran-2-ylmethyl)piperazin-1-yl]pyrazin-2-yl}-1,3-thiazole-5-carboxylic acid | $^1$H NMR (400 MHz, DMSO-$d_6$): δ 1.02 (t, 3H), 1.44 (m, 1H), 1.74 (m, 4H), 1.93 (m, 2H), 2.16 (s, 3H), 2.39 (m, 2H), 2.41 (m, 4H), 2.61 (m, 2H), 3.32 (m, 4H), 3.47 (m, 2H), 3.73 (m, 4H), 3.93 (m, 1H), 4.24 (m, 1H), 7.19 (d, 1H), 8.32 (s, 1H), 8.81 (s, 1H), 12.28 (s, 1H).<br>LC-MS: m/z 693.3 (M + H) | Example 85 |

Examples 105-123

The following Examples were prepared according to the procedure described for Example 60 from the starting material listed in the table.

| Ex | Compound | Data | SM |
|---|---|---|---|
| 105 | Ethyl 2-[(3S,4R)-4-{[(3,4-dichloro-5-methyl-1H-pyrrol-2-yl)carbonyl]amino}-3-methoxypiperidin-1-yl]-4-[5-(piperidin-1-yl)pyrazin-2-yl]-1,3-thiazole-5-carboxylate | ¹H NMR (400 MHz, DMSO-d6): δ 0.93 (m, 4H), 1.14 (t, 3H), 1.55-1.76 (m, 8H), 2.19 (s, 3H), 3.28-3.33 (m, 4H), 3.55 (m, 1H), 3.64 (m, 2H), 4.10 (m, 2H), 4.27 (m, 2H), 7.16 (d, 1H), 8.30 (s, 2H), 12.12 (s, 1H). MASS (APCI − ve Scan) m/z 620 (M − H) | Example 60 and piperidine |
| 106 | Ethyl 2-[(3S,4R)-4-{[(3,4-dichloro-5-methyl-1H-pyrrol-2-yl)carbonyl]amino}-3-methoxypiperidin-1-yl]-4-[5-(morpholin-4-yl)pyrazin-2-yl]-1,3-thiazole-5-carboxylate | ¹H NMR (400 MHz, DMSO-d6): δ 1.14 (t, 3H), 1.77 (m, 2H), 2.18 (s, 3H), 3.36 (m, 5H), 3.60 (m, 6H), 3.72 (m, 4H), 4.10 (m, 2H), 4.27 (m, 2H), 7.15 (d, 1H), 8.34 (d, 2H), 12.13 (s, 1H). MASS (APCI + ve Scan) m/z 624 (M + H) | Example 60 and morpholine |

| Ex | Compound | Data | SM |
|---|---|---|---|
| 107 | Ethyl 2-[(3S,4R)-4-{[(3,4-dichloro-5-methyl-1H-pyrrol-2-yl)carbonyl]amino}-3-methoxypiperidin-1-yl]-4-[5-(piperazin-1-yl)pyrazin-2-yl]-1,3-thiazole-5-carboxylate[BOC OFF?] | ¹H NMR (400 MHz, CDCl₃): δ 1.27 (m, 6H), 1.41 (m, 9H), 1.90 (m, 1H), 2.06 (m, 1H), 2.27 (s, 3H), 3.22 (m, 3H), 3.56 (m, 9H), 4.03-4.32 (m, 4H), 4.50 (m, 1H), 7.23 (m, 1H), 8.18 (s, 1H), 8.49 (s, 1H). LC-MS: m/z 723.51 (M + H) | Example 60 and 4-boc-piperidine[PIPERAZINE??] |
| 108 | Ethyl 2-[(3S,4R)-4-{[(3,4-dichloro-5-methyl-1H-pyrrol-2-yl)carbonyl]amino}-3-methoxypiperidin-1-yl]-4-(5-{[2-(2-oxopyrrolidin-1-yl)ethyl]amino}pyrazin-2-yl)-1,3-thiazole-5-carboxylate | ¹H NMR (400 MHz, DMSO-d₆): δ 1.13 (t, 3H), 1.76 (m, 2H), 1.91 (t, 3H), 2.17 (m, 6H), 2.69 (m, 1H), 3.40-3.52 (m, 10H), 4.10 (m, 2H), 4.26 (m, 2H), 7.16 (d, 1H), 7.39 (s, 1H), 7.91 (s, 1H), 8.21 (s, 1H), 12.21 (brs, 1H). MASS (APCI – ve Scan) m/z 663 (M – H) | Example 60 and 1-(2-aminoethyl)pyrrolidin-2-one |

-continued

| Ex | Compound | Data | SM |
|---|---|---|---|
| 109 | Ethyl 2-[(3S,4R)-4-{[(3,4-dichloro-5-methyl-1H-pyrrol-2-yl)carbonyl]amino}-3-methoxypiperidin-1-yl]-4-{5-[(2-methoxyethyl)amino]pyrazin-2-yl}-1,3-thiazole-5-carboxylate 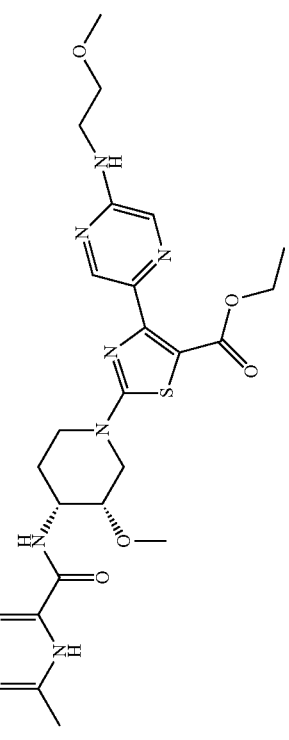 | $^1$H NMR (400 MHz, DMSO-d$_6$) δ 1.12 (t, 3H), 1.76 (m, 2H), 2.18 (s, 3H), 3.22 (m, 4H), 3.48 (s, 4H), 3.55 (s, 1H), 3.96 (br s, 1H), 4.09 (m, 2H), 4.26 (br s, 2H), 7.16 (d, 1H), 7.44 (s, 1H), 7.96 (s, 1H), 8.19 (s, 1H), 12.14 (br s, 2H). MASS (APCI – ve Scan) m/z 610 (M – H) | Example 60 and 2-methoxyethylamine |
| 110 | Ethyl 2-[(3S,4R)-4-{[(3,4-dichloro-5-methyl-1H-pyrrol-2-yl)carbonyl]amino}-3-methoxypiperidin-1-yl]-4-{5-[(1,3-dimethoxypropan-2-yl)amino]pyrazin-2-yl}-1,3-thiazole-5-carboxylate 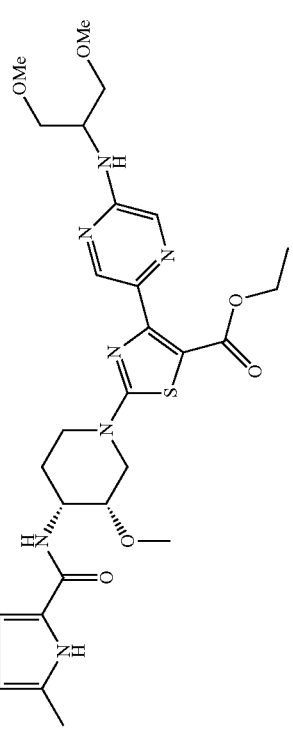 | $^1$H NMR (400 MHz, CDCl$_3$): δ 1.25 (m, 5H), 1.42 (m, 1H), 1.89 (m, 2H), 2.27 (s, 3H), 3.20 (m, 2H), 3.42 (m, 10H), 4.09 (m, 6H), 4.33 (m, 1H), 5.12 (m, 1H), 7.22 (m, 1H), 7.96 (s, 1H), 8.41 (s, 1H), 9.36 (br s, 1H) LC-MS: m/z 656 (M + H) | Example 60 and 1,3-dimethoxypropylamien |

-continued

| Ex | Compound | Data | SM |
|---|---|---|---|
| 111 | Ethyl 2-[(3S,4R)-4-{[(3,4-dichloro-5-methyl-1H-pyrrol-2-yl)carbonyl]amino}-3-methoxypiperidin-1-yl]-4-(5-{[2-(morpholin-4-yl)ethyl]amino}pyrazin-2-yl)-1,3-thiazole-5-carboxylate | $^1$H NMR (400 MHz, CDCl$_3$): δ 0.87 (m, 3H), 1.23 (m, 4H), 1.86 (m, 2H), 2.27 (s, 3H), 2.43 (m, 3H), 2.64 (m, 2H), 3.22 (m, 2H), 3.48 (m, 3H), 3.74 (m, 3H), 4.23 (m, 3H), 4.49 (d, 1H), 5.39 (brs, 1H), 7.23 (m, 1H), 7.98 (s, 1H), 8.41 (s, 1H), 8.41 (s, 1H), 9.5 (brs, 1H). LC-MS: m/z 667.4 (M + H) | Example 60 and morpholi-4-ethylamine |
| 112 | Ethyl 2-[(3S,4R)-4-{[(3,4-dichloro-5-methyl-1H-pyrrol-2-yl)carbonyl]amino}-3-methoxypiperidin-1-yl]-4-(5-{[2-(2-oxoimidazolidin-1-yl)ethyl]amino}pyrazin-2-yl)-1,3-thiazole-5-carboxylate | $^1$H NMR (400 MHz, CDCl$_3$): δ 1.25 (m, 6H), 1.92-2.04 (m, 3H), 2.27 (s, 3H), 3.18 (m, 2H), 3.43 (m, 8H), 4.09-4.49 (m, 6H), 5.49 (m, 1H), 7.22 (m, 1H), 7.96 (s, 1H), 8.40 (s, 1H), 9.45 (brs, 1H). LC-MS: m/z 666 (M + H) | Example 60 and 1-(2-aminoethyl)imido-2-one |

| Ex | Compound | Data | SM |
|---|---|---|---|
| 113 | Ethyl 2-[(3S,4R)-4-{[(3,4-dichloro-5-methyl-1H-pyrrol-2-yl)carbonyl]amino}-3-methoxypiperidin-1-yl]-4-(5-{[2-(dimethylamino)ethyl]amino}pyrazin-2-yl)-1,3-thiazole-5-carboxylate | $^1$H NMR (400 MHz, CDCl$_3$): 1.26 (m, 3H), 1.86 (m, 3H), 2.27 (m, 9H), 2.59 (m, 2H), 3.21 (m, 2H), 3.49 (m, 6H), 4.09 (m, 1H), 4.21 (m, 2H), 4.31 (m, 1H), 4.49 (m, 1H), 7.26 (m, 1H), 7.97 (s, 1H), 8.41 (s, 1H), 9.53 (brs, 1H). LC-MS: m/z 625.45 (M + H) | Example 60 and N,N-dimethyl-aminoethylamine |
| 114 | Ethyl 2-[(3S,4R)-4-{[(3,4-dichloro-5-methyl-1H-pyrrol-2-yl)carbonyl]amino}-3-methoxypiperidin-1-yl]-4-(5-{[2-(4-methylpiperazin-1-yl)ethyl]amino}pyrazin-2-yl)-1,3-thiazole-5-carboxylate | $^1$H NMR (400 MHz, DMSO-d$_6$): δ 1.21 (t, 3H), 1.28 (m, 3H), 1.81 (m, 2H), 2.22 (s, 3H), 3.04 (m, 4H), 3.21-3.56 (m, 14H), 3.98 (m, 1H), 4.12 (q, 2H), 4.34 (m, 2H), 7.18 (d, 1H), 7.25 (d, 1H), 7.96 (s, 1H), 8.22 (s, 1H), 12.18 (s, 1H) LC-MS: m/z 680 (M + H) | Example 60 and N-methylpiperdin-4-amine |

-continued

| Ex | Compound | Data | SM |
|---|---|---|---|
| 115 | Ethyl 2-[(3S,4R)-4-{[(3,4-dichloro-5-methyl-1H-pyrrol-2-yl)carbonyl]amino}-3-methoxypiperidin-1-yl]-4-{5-[4-(2-methylpropyl)piperazin-1-yl]pyrazin-2-yl}-1,3-thiazole-5-carboxylate | LC-MS: m/z 679 (M + H) | Example 60 and 2-methylpropyl4-piperidine |
| 116 | Ethyl 2-[(3S,4R)-4-{[(3,4-dichloro-5-methyl-1H-pyrrol-2-yl)carbonyl]amino}-3-methoxypiperidin-1-yl]-4-(5-{4-[(1-methylpiperidin-3-yl)methyl]piperazin-1-yl}pyrazin-2-yl)-1,3-thiazole-5-carboxylate | $^1$H NMR (400 MHz, DMSO-d$_6$): δ 1.16 (t, 3H), 1.3-1.82 (7H), 2.21 (s, 3H), 2.24 (m, 4H), 2.56 (s, 3H), 2.58 (m, 6H), 2.61-2.98 (m, 4H), 3.2-3.72 (m, 6H), 3.98 (d, 1H), 4.14 (q, 2H), 4.36 (d, 2H), 7.18 (d, 1H), 8.36 (s, 2H), 12.18 (s, 1H). LC-MS: m/z 734.34 (M + H) | Example 60 and 1-methylpiperidin-3-methylpiperazine |

| Ex | Compound | Data | SM |
|---|---|---|---|
| 117 | Ethyl 4-{5-[4-(cyclohexylmethyl)piperazin-1-yl]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylate 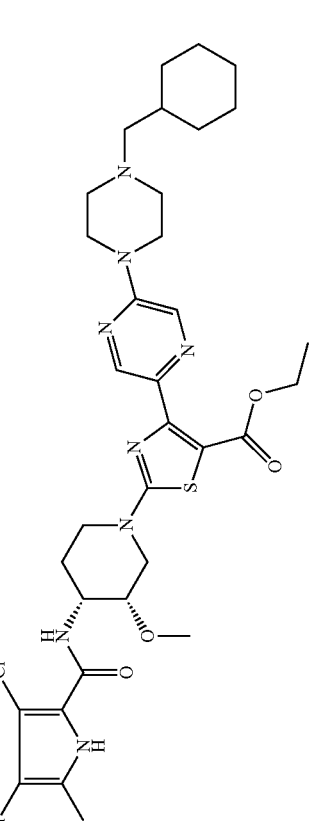 | $^1$H NMR (400 MHz, DMSO-d$_6$): δ 0.90 (m, 3H), 1.23 (m, 4H), 1.73 (m, 8H), 2.00 (m, 4H), 2.18 (s, 3H), 2.48 (m, 4H), 3.18 (m, 2H), 3.43 (m, 3H), 3.65 (m, 4H), 4.06 (m, 1H), 4.20 (m, 3H), 4.54 (m, 1H), 7.26 (m, 1H), 8.17 (s, 1H), 8.47 (s, 1H), 9.43 (brs, 1H). LC-MS: m/z (M + H) | Example 60 and cyclohexylmethyl-piperidine |
| 118 | Ethyl 2-[(3S,4R)-4-{[(3,4-dichloro-5-methyl-1H-pyrrol-2-yl)carbonyl]amino}-3-methoxypiperidin-1-yl]-4-{5-[4-(pentan-3-yl)piperazin-1-yl]pyrazin-2-yl}-1,3-thiazole-5-carboxylate 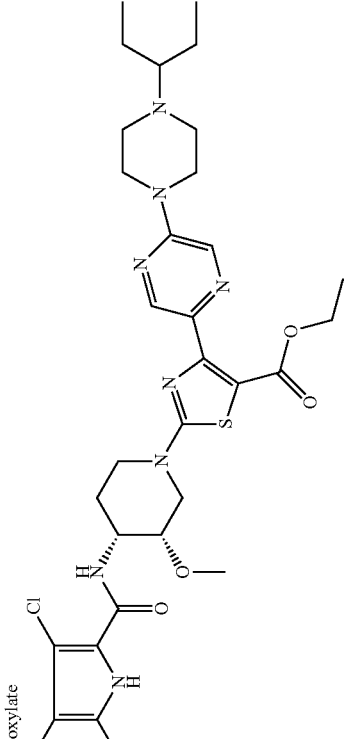 | $^1$H NMR (400 MHz, DMSO-d$_6$): δ 0.92 (t, 6H), 1.21 (t, 3H), 1.45 (m, 2H), 1.61-1.81 (m, 5H), 2.16-2.25 (m, 4H), 2.62 (m, 4H), 3.21-3.56 (m, 10H), 3.81 (m, 2H), 4.18 (m, 3H), 7.40 (brs, 1H), 8.20 (s, 1H), 8.45 (s, 1H). LC-MS: m/z 693 (M + H) | Example 60 and 1-(1-ethylpropyl)piperazine |

| Ex | Compound | Data | SM |
|---|---|---|---|
| 119 | Ethyl 2-[(3S,4R)-4-{[(3,4-dichloro-5-methyl-1H-pyrrol-2-yl)carbonyl]amino}-3-methoxypiperidin-1-yl]-4-[5-(4-ethylpiperazin-1-yl)pyrazin-2-yl]-1,3-thiazole-5-carboxylate | $^1$H NMR (400 MHz, CDCl$_3$): δ 1.00 (m, 3H), 1.13 (m, 3H), 1.86 (m, 2H), 2.27 (s, 3H), 2.46 (m, 4H), 3.22 (m, 2H), 3.46 (m, 6H), 3.69 (m, 4H), 4.23 (m, 4H), 4.50 (m, 1H), 7.26 (m, 1H), 8.18 (s, 1H), 8.48 (s, 1H), 9.33 (brs, 1H). LC-MS: m/z 651.40 (M + H) | Example 60 and ethylpiperazine |
| 120 | Ethyl 2-[(3S,4R)-4-{[(3,4-dichloro-5-methyl-1H-pyrrol-2-yl)carbonyl]amino}-3-methoxypiperidin-1-yl]-4-(5-{4-[2-(diethylamino)ethyl]piperazin-1-yl}pyrazin-2-yl)-1,3-thiazole-5-carboxylate | $^1$H NMR (400 MHz, DMSO-d$_6$): δ 0.99 (t, 6H), 1.22 (t, 3H), 1.81 (d, 2H), 2.18 (s, 3H), 2.51-3.82 (m, 8H), 3.21-3.42 (m, 9H), 3.42-3.78 (m, 5H), 3.98 (m, 1H), 4.18 (q, 2H), 4.34 (d, 2H), 7.19 (d, 1H), 8.37 (s, 2H), 12.19 (s, 1H). LC-MS: m/z 722. (M + H) | Example 60 and 2-diethylaminoethyl-piperazine |

-continued

| Ex | Compound | Data | SM |
|---|---|---|---|
| 121 | Ethyl 2-[(3S,4R)-4-{[(3,4-dichloro-5-methyl-1H-pyrrol-2-yl)carbonyl]amino}-3-methoxypiperidin-1-yl]-4-{5-[(3R)-3-methylpiperazin-1-yl]pyrazin-2-yl}-1,3-thiazole-5-carboxylate | ¹H NMR (400 MHz, CDCl₃): δ 1.21 (m, 6H), 1.89-2.05 (m, 3H), 2.27 (s, 3H), 2.70 (m, 1H), 2.95-3.33 (m, 6H), 3.51 (m, 4H), 4.02-4.32 (m, 6H), 4.50 (m, 1H), 7.26 (m, 1H), 8.18 (s, 1H), 8.48 (s, 1H), 9.44 (brs, 1H). LC-MS: m/z 637 (M + H) | Example 60 and (3R)-3-methylpiperazine |
| 122 | Ethyl 2-[(3S,4R)-4-{[(3,4-dichloro-5-methyl-1H-pyrrol-2-yl)carbonyl]amino}-3-methoxypiperidin-1-yl]-4-{5-[4-(2-hydroxyethyl)piperazin-1-yl]pyrazin-2-yl}-1,3-thiazole-5-carboxylate | ¹H NMR (400 MHz, CDCl₃): δ 1.25 (m, 2H), 1.86 (m, 2H), 1.90 (m, 2H), 2.09 (s, 3H), 2.65 (m, 6H), 3.18 (m, 2H), 3.46 (m, 4H), 3.74 (m, 6H), 4.06 (m, 1H), 4.23 (m, 2H), 4.32 (m, 1H), 4.50 (m, 1H), 7.26 (m, 1H), 8.19 (s, 1H), 8.49 (s, 1H), 9.44 (brs, 1H). LC-MS: m/z 667.62. (M + H) | Example 60 and 2-hydroxyethylpiperazine |

-continued

| Ex | Compound | Data | SM |
|---|---|---|---|
| 123 | Ethyl 2-[(3S,4R)-4-{[(3,4-dichloro-5-methyl-1H-pyrrol-2-yl)carbonyl]amino}-3-methoxypiperidin-1-yl]-4-{5-[4-(tetrahydrofuran-2-ylmethyl)piperazin-1-yl]pyrazin-2-yl}-1,3-thiazole-5-carboxylate | LC-MS: m/z 707 (M + H) | Example 60 and 1-(tetrahydrofuran-2-ylmethyl)piperazine |

Examples 124-142

The following Examples were prepared according to the procedure for Example 61 from the starting material indicated in the table.

| Ex | Compound | Data | SM |
|---|---|---|---|
| 124 | 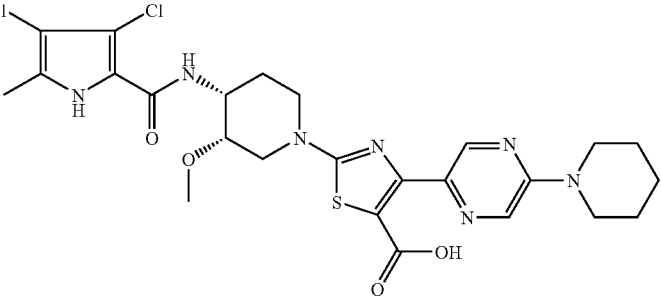  2-[(3S,4R)-4-{[(3,4-dichloro-5-methyl-1H-pyrrol-2-yl)carbonyl]amino}-3-methoxypiperidin-1-yl]-4-[5-(piperidin-1-yl)pyrazin-2-yl]-1,3-thiazole-5-carboxylic acid | $^1$H NMR (400 MHz, DMSO-$d_6$): δ 1.58 (m, 6H), 1.76 (s, 2H), 1.87 (s, 2H), 2.18 (s, 3H), 3.37 (m, 4H), 3.54 (s, 1H), 3.66 (s, 3H), 4.25 (d, 2H), 7.25 (d, 1H), 8.33 (d, 1H), 8.80 (br s, 1H), 12.32 (br s, 1H). LC-MS: m/z 594.3 (M + H) | Example 105 |
| 125 | 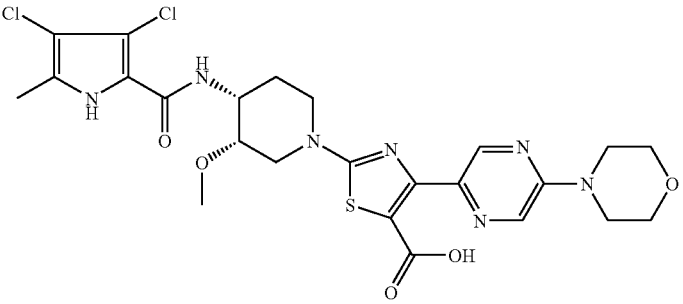  2-[(3S,4R)-4-{[(3,4-dichloro-5-methyl-1H-pyrrol-2-yl)carbonyl]amino}-3-methoxypiperidin-1-yl]-4-[5-(morpholin-4-yl)pyrazin-2-yl]-1,3-thiazole-5-carboxylic acid | $^1$H NMR (400 MHz, DMSO-$d_6$): δ 1.77 (m, 2H), 2.18 (s, 3H), 3.38 (m, 4H), 3.55 (m, 1H), 3.71 (m, 8H), 3.94 (br s, 2H), 4.77 (d, 1H), 7.20 (d, 1H), 8.40 (s, 1H), 8.95 (s, 1H), 12.21 (br s, 2H). LC-MS: m/z 596.3 (M + H) | Example 106 |
| 126 | 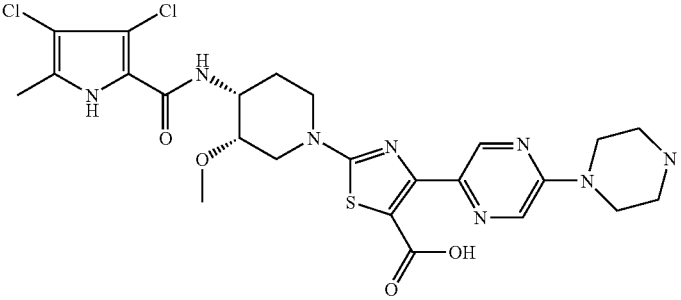  2-[(3S,4R)-4-{[(3,4-dichloro-5-methyl-1H-pyrrol-2-yl)carbonyl]amino}-3-methoxypiperidin-1-yl]-4-[5-(piperazin-1-yl)pyrazin-2-yl]-1,3-thiazole-5-carboxylic acid | $^1$H NMR (400 MHz, DMSO-$d_6$): δ 1.78 (m, 2H), 2.18 (s, 3H), 3.17 (m, 3H), 3.35 (m, 9H), 3.57 (m, 1H), 3.91 (m, 4H), 4.27 (m, 2H), 7.15 (d, 1H), 8.50 (s, 1H), 9.03 (s, 1H), 12.16 (br s, 1H). LC-MS: m/z 595.47 (M + H) | Example 107 |

-continued

| Ex | Compound | Data | SM |
|---|---|---|---|
| 127 | 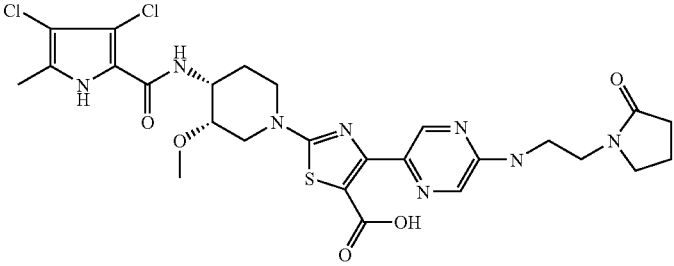<br>2-[(3S,4R)-4-{[(3,4-dichloro-5-methyl-1H-pyrrol-2-yl)carbonyl]amino}-3-methoxypiperidin-1-yl]-4-(5-{[2-(2-oxopyrrolidin-1-yl)ethyl]amino}pyrazin-2-yl)-1,3-thiazole-5-carboxylic acid | $^1$H NMR (400 MHz, DMSO-$d_6$): δ 1.78 (m, 2H), 1.88 (m, 2H), 2.61 (m, 5H), 3.30 (m, 9H), 3.52 (m, 3H), 4.02 (br s, 2H), 4.27 (m, 2H), 7.16 (d, 1H), 7.99 (d, 2H), 8.95 (s, 1H), 12.14 (s, 1H).<br>LC-MS: m/z 637.2 (M + H) | Example 108 |
| 128 | 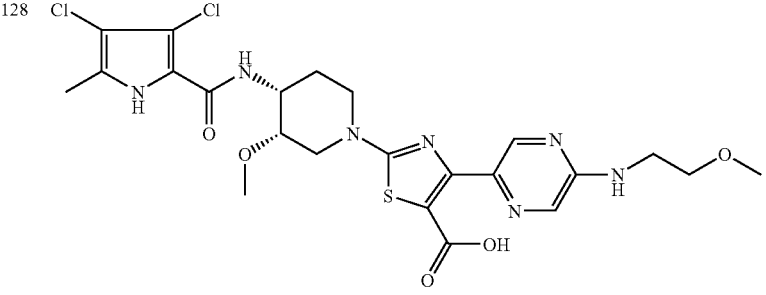<br>2-[(3S,4R)-4-{[(3,4-dichloro-5-methyl-1H-pyrrol-2-yl)carbonyl]amino}-3-methoxypiperidin-1-yl]-4-{5-[(2-methoxyethyl)amino]pyrazin-2-yl}-1,3-thiazole-5-carboxylic acid | $^1$H NMR (400 MHz, DMSO-$d_6$): δ 1.77 (s, 3H), 2.18 (s, 3H), 3.33 (m, 3H), 3.39 (m, 5H), 3.52 (m, 5H), 3.96 (br s, 2H), 4.27 (d, 1H), 4.49 (br s, 1H), 7.16 (d, 1H), 8.01 (d, 1H), 8.95 (s, 1H), 12.15 (s, 1H).<br>LC-MS: m/z 584.2 (M + H) | Example 109 |
| 129 | 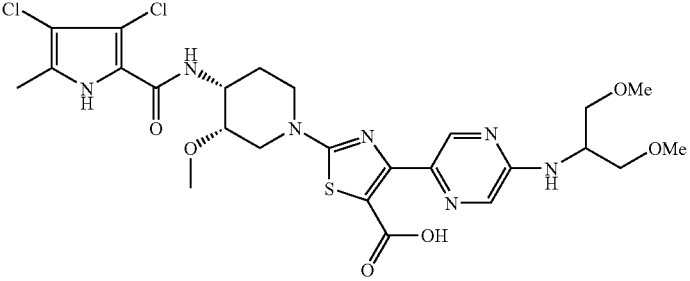<br>2-[(3S,4R)-4-{[(3,4-dichloro-5-methyl-1H-pyrrol-2-yl)carbonyl]amino}-3-methoxypiperidin-1-yl]-4-{5-[(1,3-dimethoxypropan-2-yl)amino]pyrazin-2-yl}-1,3-thiazole-5-carboxylic acid | $^1$H NMR (400 MHz, DMSO-$d_6$): δ 1.77 (m, 3H), 2.18 (s, 3H), 3.37 (m, 14H), 3.89 (m, 2H), 4.29 (m, 4H), 7.24 (d, 1H), 7.99 (s, 1H), 7.59 (brs, 1H), 8.75 (brs, 1H), 12.28 (brs, 1H).<br>LC-MS: m/z 628.43 (M + H) | Example 110 |
| 130 | 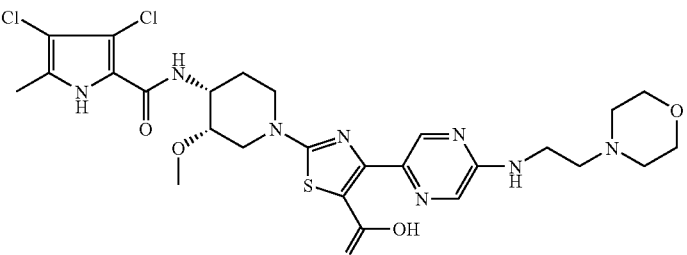<br>2-[(3S,4R)-4-{[(3,4-dichloro-5-methyl-1H-pyrrol-2-yl)carbonyl]amino}-3-methoxypiperidin-1-yl]-4-(5-{[2-(morpholin-4-yl)ethyl]amino}pyrazin-2-yl)-1,3-thiazole-5-carboxylic acid | $^1$H NMR (400 MHz, DMSO-$d_6$): δ 1.74 (m, 2H), 2.18 (s, 3H), 2.50 (m, 5H), 3.26 (m, 5H), 3.43 (m, 4H), 3.56 (m, 5H), 3.88 (brs, 1H), 4.25 (m, 2H), 7.28 (m, 1H), 8.64 (brs, 1H), 12.41 (brs, 1H)<br>LC-MS: m/z 639.37 (M + H) | Example 111 |

-continued

| Ex | Compound | Data | SM |
|---|---|---|---|
| 131 | 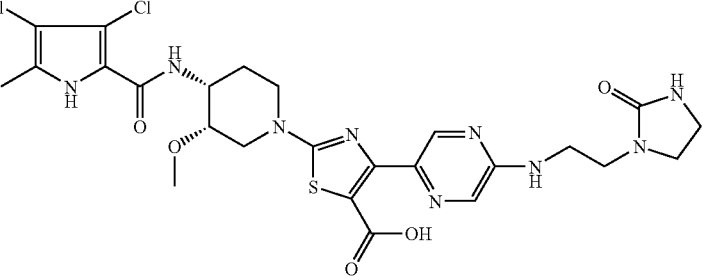<br>2-[(3S,4R)-4-{[(3,4-dichloro-5-methyl-1H-pyrrol-2-yl)carbonyl]amino}-3-methoxypiperidin-1-yl]-4-(5-{[2-(2-oxoimidazolidin-1-yl)ethyl]amino}pyrazin-2-yl)-1,3-thiazole-5-carboxylic acid | $^1$H NMR (400 MHz, DMSO-$d_6$): δ 1.76 (m, 3H), 2.18 (s, 3H), 3.18 (m, 15H), 3.91 (brs, 1H), 4.26 (m, 2H), 6.27 (m, 1H), 7.22 (d, 1H), 7.94 (s, 1H), 8.79 (brs, 1H), 12.28 (brs, 1H).<br>LC-MS: m/z 638.42 (M + H) | Example 112 |
| 132 | 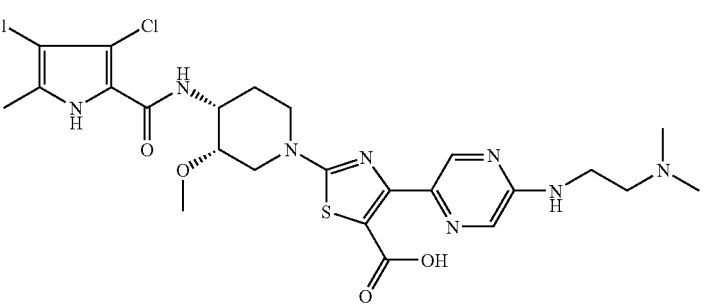<br>2-[(3S,4R)-4-{[(3,4-dichloro-5-methyl-1H-pyrrol-2-yl)carbonyl]amino}-3-methoxypiperidin-1-yl]-4-(5-{[2-(dimethylamino)ethyl]amino}pyrazin-2-yl)-1,3-thiazole-5-carboxylic acid | $^1$H NMR (400 MHz, DMSO-$d_6$): δ 1.78 (m, 2H), 2.18 (s, 3H), 2.81 (s, 6H), 3.21-3.41 (m, 8H), 3.57 (brs, 1H), 3.73 (m, 2H), 4.27 (m, 1H), 7.20 (m, 1H), 8.06 (s, 1H), 8.27 (brs, 1H), 8.97 (s, 1H), 10.12 (brs, 1H), 12.20 (s, 1H).<br>LC-MS: m/z 597.53 (M + H) | Example 113 |
| 133 | 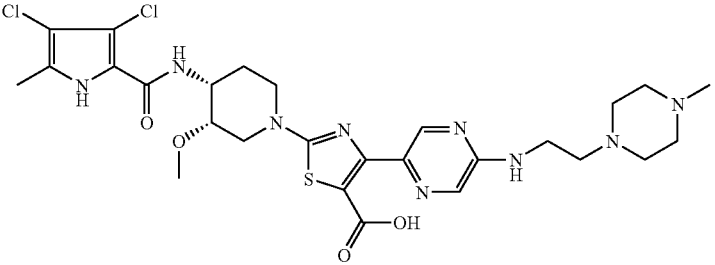<br>2-[(3S,4R)-4-{[(3,4-dichloro-5-methyl-1H-pyrrol-2-yl)carbonyl]amino}-3-methoxypiperidin-1-yl]-4-(5-{[2-(4-methylpiperazin-1-yl)ethyl]amino}pyrazin-2-yl)-1,3-thiazole-5-carboxylic acid | $^1$H NMR (400 MHz, DMSO-$d_6$): δ 1.76 (d, 2H), 2.16 (s, 3H) 2.65 (s, 9H), 3.21-3.62 (m, 12H), 3.97 (d, 1H), 4.24 (d, 1H), 4.45 (d, 1H), 4.45 (d, 1H), 7.13 (d, 1H), 7.85 (d, 1H), 7.99 (s, 1H), 7.93 (d, 1H), 12.13 (s, 1H).<br>LC-MS: m/z 652.6 (M + H) | Example 114 |
| 134 | 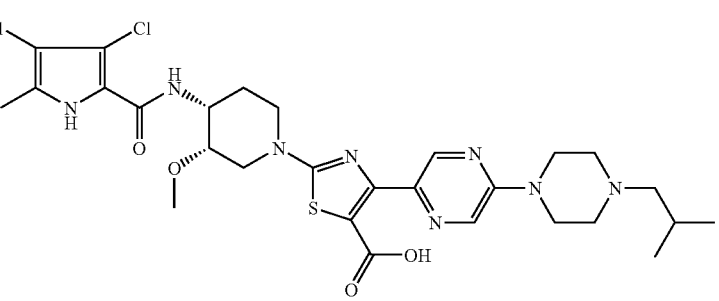<br>2-[(3S,4R)-4-{[(3,4-dichloro-5-methyl-1H-pyrrol-2-yl)carbonyl]amino}-3-methoxypiperidin-1-yl]-4-{5-[4-(2-methylpropyl)piperazin-1-yl]pyrazin-2-yl}-1,3-thiazole-5-carboxylic acid | $^1$H NMR (400 MHz, DMSO-$d_6$): δ 0.85 (d, 6H), 1.78 (m, 2H), 2.14 (m, 4H), 2.9 (m, 2H), 3.05-3.67 (m, 14H), 4.31 (m, 1H), 4.54 (m, 2H), 7.18 (d, 1H), 8.55 (s, 1H), 9.05 (s, 1H), 12.18 (s, 1H).<br>LC-MS: m/z 651 (M + H) | Example 115 |

| Ex | Compound | Data | SM |
|---|---|---|---|
| 135 | 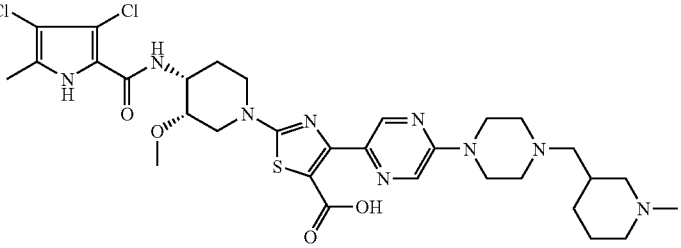<br>2-[(3S,4R)-4-{[(3,4-dichloro-5-methyl-1H-pyrrol-2-yl)carbonyl]amino}-3-methoxypiperidin-1-yl]-4-(5-{4-[(1-methylpiperidin-3-yl)methyl]piperazin-1-yl}pyrazin-2-yl)-1,3-thiazole-5-carboxylic acid | $^1$H NMR (400 MHz, DMSO-$d_6$): δ 1.3-1.82 (7H), 2.21 (s, 3H), 2.24 (m, 4H), 2.56 (s, 3H), 2.58 (m, 6H), 2.61-2.98 (m, 4H), 3.2-3.72 (m, 7H), 3.98 (d, 1H), 4.36 (d, 2H), 7.18 (d, 1H), 8.36 (s, 2H), 12.18 (s, 1H).<br>LC-MS: m/z 708 (M + H) | Example 116 |
| 136 | 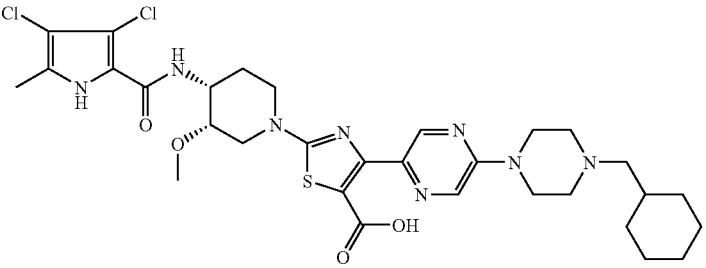<br>4-{5-[4-(cyclohexylmethyl)piperazin-1-yl]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylic acid | $^1$H NMR (400 MHz, DMSO-$d_6$): δ 0.95 (m, 2H), 1.19 (m, 4H), 1.61 (m, 8H), 2.18 (s, 3H), 3.11 (m, 3H), 3.39 (m, 8H), 3.61 (m, 4H), 4.27 (m, 1H), 4.51 (m, 2H), 7.20 (m, 1H), 8.54 (s, 1H), 9.05 (s, 1H), 10.41 (brs, 1H), 12.20 (s, 1H).<br>LC-MS: m/z 691.58 (M + H) | Example 117 |
| 137 | 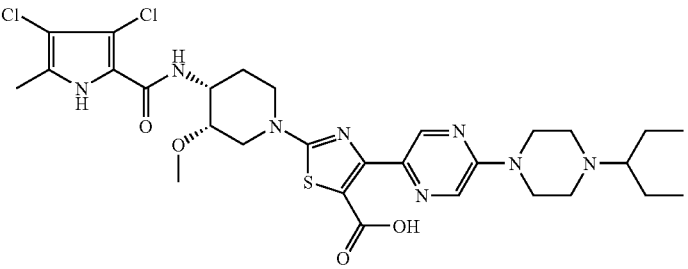<br>2-[(3S,4R)-4-{[(3,4-dichloro-5-methyl-1H-pyrrol-2-yl)carbonyl]amino}-3-methoxypiperidin-1-yl]-4-{5-[4-(pentan-3-yl)piperazin-1-yl]pyrazin-2-yl}-1,3-thiazole-5-carboxylic acid | $^1$H NMR (400 MHz, DMSO-$d_6$): δ 0.86 (t, 6H), 1.26 (t, 3H), 1.42 (m, 4H), 2.18 (s, 3H), 2.21 (s, 1H), 2.54 (s, 3H), 3.12-3.50 (m, 10H), 3.81 (d, 2H), 4.14 (d, 2H), 7.3 (d, 1H), 8.19 (s, 1H), 8.48 (s, 1H), 12.18 (s, 1H).<br>LC-MS: m/z 665 (M + H) | Example 118 |
| 138 | 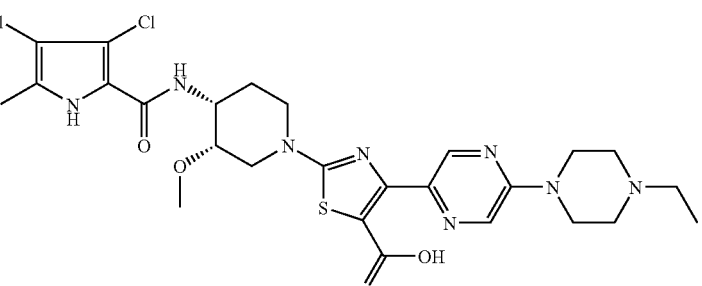<br>2-[(3S,4R)-4-{[(3,4-dichloro-5-methyl-1H-pyrrol-2-yl)carbonyl]amino}-3-methoxypiperidin-1-yl]-4-[5-(4-ethylpiperazin-1-yl)pyrazin-2-yl]-1,3-thiazole-5-carboxylic acid | $^1$H NMR (400 MHz, DMSO-$d_6$): δ 1.25 (m, 3H), 1.78 (m, 2H), 2.18 (s, 3H), 3.12 (m, 4H), 3.32 (m, 9H), 4.29 (m, 4H), 4.58 (m, 2H), 7.19 (m, 1H), 8.55 (s, 1H), 9.05 (s, 1H), 10.61 (brs, 1H), 12.18 (s, 1H).<br>LC-MS: m/z 623.37 (M + H) | Example 119 |

| Ex | Compound | Data | SM |
|---|---|---|---|
| 139 | 2-[(3S,4R)-4-{[(3,4-dichloro-5-methyl-1H-pyrrol-2-yl)carbonyl]amino}-3-methoxypiperidin-1-yl]-4-(5-{4-[2-(diethylamino)ethyl]piperazin-1-yl}pyrazin-2-yl)-1,3-thiazole-5-carboxylic acid | $^1$H NMR (400 MHz, DMSO-$d_6$): δ 0.99 (t, 6H), 1.81 (m, 2H), 2.18 (s, 3H), 2.41-2.60.81 (m, 12H), 3.21-3.78 (m, 13H), 4.22 (m, 1H), 7.18 (d, 1H), 8.42 (s, 1H), 9.02 (s, 1H), 12.19 (s, 1H). LC-MS: m/z 623 (M + H) | Example 120 |
| 140 | 2-[(3S,4R)-4-{[(3,4-dichloro-5-methyl-1H-pyrrol-2-yl)carbonyl]amino}-3-methoxypiperidin-1-yl]-4-{5-[(3R)-3-methylpiperazin-1-yl]pyrazin-2-yl}-1,3-thiazole-5-carboxylic acid | $^1$H NMR (400 MHz, DMSO-$d_6$): δ 1.02 (d, 3H), 1.76 (m, 7H), 2.18 (s, 3H), 2.40 (m, 1H), 2.71 (m, 3H), 2.93 (d, 1H), 3.22 (m, 2H), 3.50 (m, 2H), 3.80 (m, 1H), 4.15 (m, 4H), 7.46 (brs, 1H), 8.19 (s, 1H), 8.50 (s, 1H) LC-MS: m/z 609 43 (M + H) | Example 121 |
| 141 | 2-[(3S,4R)-4-{[(3,4-dichloro-5-methyl-1H-pyrrol-2-yl)carbonyl]amino}-3-methoxypiperidin-1-yl]-4-{5-[4-(2-hydroxyethyl)piperazin-1-yl]pyrazin-2-yl}-1,3-thiazole-5-carboxylic acid | $^1$H NMR (400 MHz, DMSO-$d_6$): δ 1.80 (m, 3H), 2.19 (m, 3H), 2.45 (m, 3H), 3.25 (m, 8H), 3.55 (m, 7H), 3.91 (brs, 1H), 4.21 (m, 2H), 4.24 (brs, 1H), 7.31 (brs, 1H), 8.27 (s, 1H), 8.72 (s, 1H), 12.59 (brs, 1H). LC-MS: m/z 639.49 (M + H) | Example 122 |
| 142 | 2-[(3S,4R)-4-{[(3,4-dichloro-5-methyl-1H-pyrrol-2-yl)carbonyl]amino}-3-methoxypiperidin-1-yl]-4-{5-[4-(tetrahydrofuran-2-ylmethyl)piperazin-1-yl]pyrazin-2-yl}-1,3-thiazole-5-carboxylic acid | $^1$H NMR (400 MHz, DMSO-$d_6$): δ 1.21 (d, 2H), 1.72 (s, 4H), 1.92 (s, 4H), 2.18 (s, 2H), 2.54 (d, 4H), 3.32 (m, 3H), 3.51-4.22 (m, 9H), 4.51 (m, 4H), 7.24 (d, 1H), 8.49 (s, 1H), 9.03 (s, 1H), 12.21 (s, 1H) LC-MS: m/z 679.63 (M + H) | Example 123 |

Example 143

Ethyl 4-(5-chloropyrazin-2-yl)-2-[(3S,4R)-4-{[(3,4-dichloro-5-methyl-1H-pyrrol-2-yl)carbonyl]amino}-3-methylpiperidin-1-yl]-1,3-thiazole-5-carboxylate

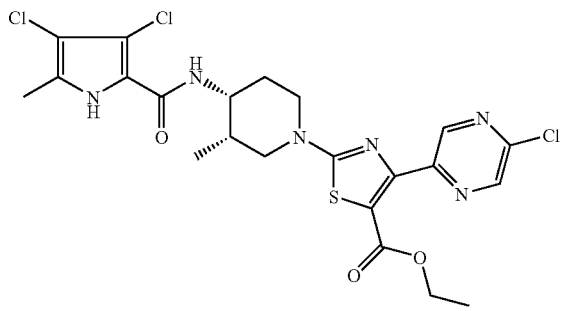

To a stirred solution of ethyl 2-bromo-4-(5-chloropyrazin-2-yl)-1,3-thiazole-5-carboxylate (Intermediate 47, 1.8 g, 5.142 mmol), and 3,4-dichloro-5-methyl-N-[(3S,4R)-3-methylpiperidin-4-yl]-1H-pyrrole-2-carboxamide (Intermediate 39, 1.47 g, 5.142 mmol) in N-methyl 2-pyrrolidinone (1 mL) was added N,N-Diisopropylethylamine (1.7 mL, 10.284 mmol) at room temperature. The reaction mixture was heated to 50° C. for 5 h. The reaction mixture was cooled to room temperature, water (60 mL) was added, the precipitated product was collected by filtration, washed with water and dried to afford 2.2 g (78%) of ethyl 4-(5-chloropyrazin-2-yl)-2-[(3S,4R)-4-{[(3,4-dichloro-5-methyl-1H-pyrrol-2-yl)carbonyl]amino}-3-methylpiperidin-1-yl]-1,3-thiazole-5-carboxylate.

$^1$H NMR (400 MHz, CDCl$_3$): δ 0.93 (m, 3H), 1.11 (t, 3H), 1.82 (m, 2H), 2.07 (s, 4H), 3.60 (m, 4H), 4.09 (q, 2H), 4.25 (m, 1H), 7.21 (d, 1H), 8.76 (d, 1H), 8.86 (d, 1H), 12.03 (s, 1H);

LC-MS: m/z 557(M+H).

Examples 144-163

The following Examples were prepared according to the procedure described for Example 60 from the starting materials indicated.

| Ex | Compound | Data | SM |
|---|---|---|---|
| 144 | Ethyl 2-[(3S,4R)-4-{[(3,4-dichloro-5-methyl-1H-pyrrol-2-yl)carbonyl]amino}-3-methylpiperidin-1-yl]-4-[5-(4-ethylpiperazin-1-yl)pyrazin-2-yl]-1,3-thiazole-5-carboxylate | ¹H NMR (400 MHz, DMSO-d₆): δ 1.58 (m, 6H), 1.76 (s, 2H), 1.87 (s, 2H), 2.18 (s, 3H), 3.37 (m, 4H), 3.54 (s, 1H), 3.66 (s, 3H), 4.25 (d, 2H), 7.25 (d, 1H), 8.33 (d, 1H), 8.80 (br s, 1H), 12.32 (br s, 1H). LC-MS: m/z 594.3 (M + H) | Example 143 and ethylpiperidine |
| 145 | Ethyl 2-[(3S,4R)-4-{[(3,4-dichloro-5-methyl-1H-pyrrol-2-yl)carbonyl]amino}-3-methylpiperidin-1-yl]-4-[5-(piperidin-1-yl)pyrazin-2-yl]-1,3-thiazole-5-carboxylate | ¹H NMR (400 MHz, DMSO-d₆): δ 0.92 (d, 3H), 1.14 (t, 3H), 1.56 (m, 6H), 1.81 (m, 2H), 2.19 (s, 4H), 3.61 (m, 8H), 4.08 (m, 2H), 4.25 (s, 1H), 7.20, (d, 1H), 8.30 (s, 2H), 12.04 (s, H), LC-MS: m/z 606 (M + H) | Example 143 and piperidine |

-continued

| Ex | Compound | Data | SM |
|---|---|---|---|
| 146 | Ethyl 2-[(3S,4R)-4-{[(3,4-dichloro-5-methyl-1H-pyrrol-2-yl)carbonyl]amino}-3-methylpiperidin-1-yl]-4-[5-(morpholin-4-yl)pyrazin-2-yl]-1,3-thiazole-5-carboxylate | $^1$H NMR (400 MHz, DMSO-$d_6$): δ 0.92 (d, 3H), 1.14 (t, 3H), 1.82 (m, 2H), 2.18 (s, 4H), 3.56 (m, 7H), 3.72 (m, 5H), 4.09 (m, 2H), 4.25 (m, 1H), 7.20 (d, 1H), 8.32 (d, 1H), 8.34 (d, 1H), 12.03 (s, 1H). LC-MS: m/z 608 (M + H) | Example 143 and morpholine |
| 147 | Ethyl 2-[(3S,4R)-4-{[(3,4-dichloro-5-methyl-1H-pyrrol-2-yl)carbonyl]amino}-3-methylpiperidin-1-yl]-4-[5-(4-methylpiperazin-1-yl)pyrazin-2-yl]-1,3-thiazole-5-carboxylate | $^1$H NMR (400 MHz, DMSO-$d_6$): δ 0.91 (d, 3H), 1.14 (t, 3H), 1.79 (m, 2H), 2.19 (m, 7H), 2.39 (s, 4H), 3.53 (m, 8H), 4.08 (m, 2H), 4.23 (m, 1H), 7.22 (d, 1H), 8.30 (s, 2H), 12.08 (s, 1H). LC-MS: m/z 621.3 (M + H) | Example 143 and methylpiperazine |
| 148 | Ethyl 2-[(3S,4R)-4-{[(3,4-dichloro-5-methyl-1H- | $^1$H NMR (400 MHz, DMSO-$d_6$): δ 0.92 (d, 3H), 1.13 (t, | Example 143 and piperazine |

-continued

| Ex | Compound | | Data | SM |
|---|---|---|---|---|
| | pyrrol-2-yl)carbonyl]amino}-3-methylpiperidin-1-yl]-4-[5-(piperazin-1-yl)pyrazin-2-yl]-1,3-thiazole-5-carboxylate | 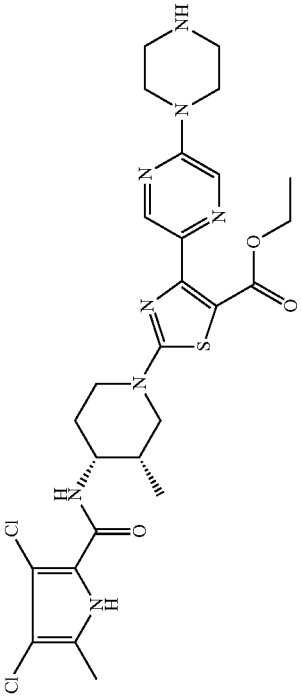 | 3H), 1.81 (m, 2H), 2.19 (s, 4H), 3.85 (t, 3H), 3.40 (m, 4H), 3.63 (m, 6H), 4.10 (m, 2H) 4.25 (m, 1H), 7.23 (d, 1H), 8.30 (s, 1H), 8.32 (s, 1H), 12.12 (s, 1H). LC-MS: m/z 607 (M + H) | |
| 149 | Ethyl 2-{(3S,4R)-4-{[(3,4-dichloro-5-methyl-1H-pyrrol-2-yl)carbonyl]amino}-3-methylpiperidin-1-yl]-4-(5-{[2-(2-oxopyrrolidin-1-yl)ethyl]amino}pyrazin-2-yl)-1,3-thiazole-5-carboxylate | 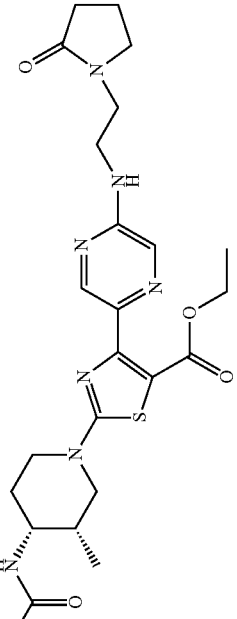 | ¹H NMR (400 MHz, DMSO-d₆): δ 0.92 (d, 3H), 1.15 (t, 3H), 1.86 (m, 4H), 2.15 (m, 5H), 3.40 (m, 7H), 3.62 (m, 4H), 4.09 (m, 2H), 4.24 (s, 1H), 7.20 (d, 1H), 7.40 (t, 1H), 7.90 (d, 1H), 8.21 (d, 1H), 12.04 (s, 1 H). LC-MS: m/z 649.3 (M + H) | Example 143 and 1-(2-aminoethyl)imido-2-one |
| 150 | Ethyl 2-{(3S,4R)-4-{[(3,4-dichloro-5-methyl-1H-pyrrol-2-yl)carbonyl]amino}-3- | | ¹H NMR (400 MHz, DMSO-d₆): δ 0.92 (t, 3H), 1.15 (m, 3H), 1.81 (m, 2H), 2.19 (s, 4H), 3.28 (s, 3H), 3.52 (m, | Example 143 and 2-methoxyethylamine |

| Ex | Compound | Data | SM |
|---|---|---|---|
|  | methylpiperidin-1-yl]-4-{5-[(2-methoxyethyl)amino]pyrazin-2-yl}-1,3-thiazole-5-carboxylate | 5H), 3.69 (m, 3H), 4.08 (m, 2H), 4.25 (s, 1H), 7.20 (d, 1H), 7.43 (s, 1H), 7.96 (s, 1H), 8.19 (s, 1H), 12.03 (s, 1H). LC-MS: m/z 596.2 (M + H) |  |
| 151 | Ethyl 2-{(3S,4R)-4-[[(3,4-dichloro-5-methyl-1H-pyrrol-2-yl)carbonyl]amino]-3-methylpiperidin-1-yl]-4-{5-{[2-(morpholin-4-yl)ethyl]amino}pyrazin-2-yl}-1,3-thiazole-5-carboxylate | $^1$H NMR (400 MHz, DMSO-d$_6$): δ 0.93 (d, 3H), 1.16 (t, 3H), 1.81 (m, 2H), 2.19 (s, 4H), 2.42 (s, 4H), 3.44 (m, 4H), 3.60 (m, 8H), 4.10 (m, 2H), 4.26 (s, 1H), 7.19 (d, 1H), 7.25 (m, 1H), 7.96 (d, 1H), 8.20 (s, 1H), 12.02 (s, 1H) LC-MS: m/z 651.13 (M + H) | Example 143 and morpholin-4-ethylamine |
| 152 | Ethyl 2-{(3S,4R)-4-[[(3,4-dichloro-5-methyl-1H-pyrrol-2-yl)carbonyl]amino]-3-methylpiperidin-1-yl]-4-{5- | $^1$H NMR (400 MHz, CDCl$_3$): δ 1.02 (m, 3H), 1.93 (m, 2H), 2.24 (s, 3H), 2.25 (m, 2H), 3.33 (s, 6H), 3.49 (m, 6H), 3.75 (m, 2H), 3.77 (m, 1H), | Example 143 and 1,3-dimethoxypropan-2-amine |

| Ex | Compound | Data | SM |
|---|---|---|---|
| | [(1,3-dimethoxypropan-2-yl)amino]pyrazin-2-yl]-1,3-thiazole-5-carboxylate | 4.24 (m, 2H), 4.31 (m, 1H), 4.40 (m, 1H), 5.12 (d, 1H), 6.77 (d, 1H), 7.97 (s, 1H), 8.43 (s, 1H), 9.27 (s, 1H). LC-MS: m/z 640.44 (M + H) | |
| 153 | Ethyl 2-[(3S,4R)-4-{[(3,4-dichloro-5-methyl-1H-pyrrol-2-yl)carbonyl]amino}-3-methylpiperidin-1-yl]-4-(5-{[2-(2-oxoimidazolidin-1-yl)ethyl]amino}pyrazin-2-yl)-1,3-thiazole-5-carboxylate | $^1$H NMR (400 MHz, DMSO-d$_6$): δ 0.92 (m, 3H), 1.23 (t, 3H), 1.81 (m, 2H), 2.19 (s, 4H), 3.19 (m, 4H), 3.42 (m, 5H), 3.62 (m, 3H), 4.09 (q, 2H), 4.25 (s, 1H), 6.31 (s, 1H), 7.20 (d, 1H), 7.41 (t, 1H), 7.93 (s, 1H), 8.21 (s, 1H), 12.04 (s, 1H). LC-MS: m/z 650 (M + H) | Example 143 and 2-oxoimidazolindin-1-ethylamie |
| 154 | Ethyl 2-[(3S,4R)-4-{[(3,4-dichloro-5-methyl-1H-pyrrol-2-yl)carbonyl]amino}-3-methylpiperidin-1-yl]-4-(5-{[2-(dimethylamino)ethyl]amino} | $^1$H NMR (400 MHz, DMSO-d$_6$): δ 0.91 (t, 3H), 1.15 (m, 3H), 1.80 (m, 2H), 2.19 (d, 9H), 2.49 (m, 2H), 3.42 (m, 2H), 3.55 (m, 4H), 4.08 (m, 2H), 4.25 (s, 1H), 7.21 (d, 1H), 7.27 (t, 1H), 7.96 (d, 1H), 8.20 | Example 143 and N,N-dimethylaminoethyl-amine |

| Ex | Compound | Data | SM |
|---|---|---|---|
|  | pyrazin-2-yl)-1,3-thiazole-5-carboxylate | (d, 1H), 12.05 (s, 1H). LC-MS: m/z 609.3 (M + H) |  |
| 155 | Ethyl 2-{(3S,4R)-4-{[(3,4-dichloro-5-methyl-1H-pyrrol-2-yl)carbonyl]amino}-3-methylpiperidin-1-yl]-4-(5-{[2-(4-methylpiperazin-1-yl)ethyl]amino}pyrazin-2-yl)-1,3-thiazole-5-carboxylate | ¹H NMR (400 MHz, CDCl₃): δ 1.04 (m, 3H), 1.29 (m, 6H), 2.02 (m, 2H), 2.33 (m, 6H), 2.64 (m, 8H), 3.35 (m, 1H), 3.48 (m, 2H), 3.62 (m, 1H), 3.76 (m, 2H), 4.22 (m, 2H), 4.41 (brs, 1H), 5.44 (m, 1H), 6.81 (d, 1H), 7.97 (s, 1H), 8.43 (s, 1H), 9.78 (brs, 1H). LC-MS: m/z 664.50 (M + H) | Example 143 and 4-methylpiperazine-1-ethylamine |
| 156 | Ethyl 2-{(3S,4R)-4-{[(3,4-dichloro-5-methyl-1H-pyrrol-2-yl)carbonyl]amino}-3-methylpiperidin-1-yl]-4-{5-[4-(2-methylpropyl)piperazin-1- | ¹H NMR (400 MHz, DMSO-d₆): δ 0.89 (m, 9H), 1.12 (m, 3H), 1.80 (m, 3H), 2.08 (d, 2H), 2.18 (s, 4H), 2.44 (m, 4H), 3.56 (m, 8H), 4.09 (m, 2H), 4.25 (s, 1H), 7.20 (d, 1H), 8.31 (d, 2H), 12.03 (s, 1H), | Example 143 and 2-methylpropylpiperazine |

| Ex | Compound | Data | SM |
|---|---|---|---|
| | yl]pyrazin-2-yl}-1,3-thiazole-5-carboxylate | LC-MS: m/z 663.3 (M + H) | |
| 157 | Ethyl 2-{(3S,4R)-4-{[(3,4-dichloro-5-methyl-1H-pyrrol-2-yl)carbonyl]amino}-3-methylpiperidin-1-yl]-4-(5-{4-[(1-methylpiperidin-3-yl)methyl]piperazin-1-yl}pyrazin-2-yl)-1,3-thiazole-5-carboxylate 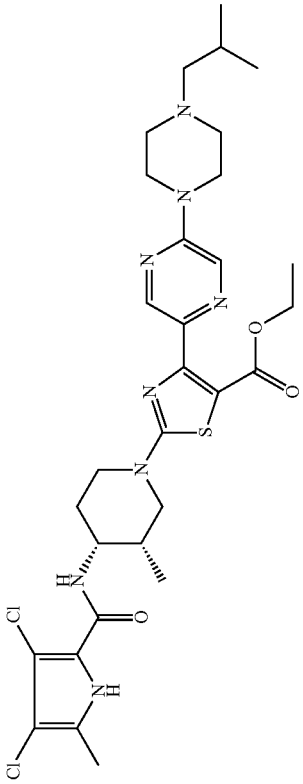 | 1H NMR (400 MHz, CDCl3): δ 1.04 (m, 3H), 1.27 (m, 10H), 1.41 (m, 4H), 1.88 (m, 4H), 2.02 (m, 7H), 2.44(m, 4H), 3.31 (m, 1H), 3.61 (m, 6H), 4.18 (m, 2H), 4.40 (brs, 1H), 6.76 (d, 1H), 8.17 (s, 1H), 8.49 (s, 1H), 9.34 (s, 1H). LC-MS: m/z 718.53 (M + H) | Example 143 and 1-methylpiperidin-3-methylpiperazine |
| 158 | Ethyl 4-{5-[4-(cyclohexylmethyl)piperazin-1-yl]pyrazin-2-yl}-2-[(3S,4R)-4-{[(3,4-dichloro-5-methyl-1H-pyrrol-2-yl)carbonyl]amino}-3- 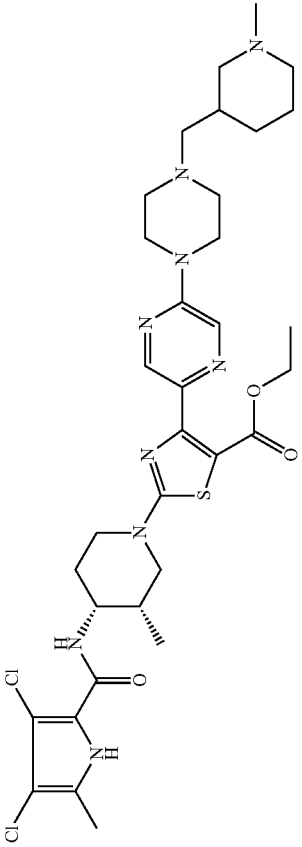 | 1H NMR (400 MHz, DMSO-d6): δ 0.83 (m, 3H), 0.91 (t, 3H), 1.14 (m, 4H), 1.51 (m, 9H), 2.10 (d, 2H), 2.17 (s, 4H), 2.41 (t, 4H), 3.55 (m, 8H), 4.07 (m, 2H), 4.23 (m, 1H), 7.18 (d, | Example 143 and cyclohexylmethyl-piperazine |

| Ex | Compound | Data | SM |
|---|---|---|---|
| | methylpiperidin-1-yl]-1,3-thiazole-5-carboxylate | 1H), 8.29 (s, 1H), 8.30 (s, 1H), 12.01 (s, 1H). LC-MS: m/z 703.4 (M + H) | |
| 159 | Ethyl 2-[(3S,4R)-4-{[(3,4-dichloro-5-methyl-1H-pyrrol-2-yl)carbonyl]amino}-3-methylpiperidin-1-yl]-4-{5-[4-(pentan-3-yl)piperazin-1-yl]pyrazin-2-yl}-1,3-thiazole-5-carboxylate 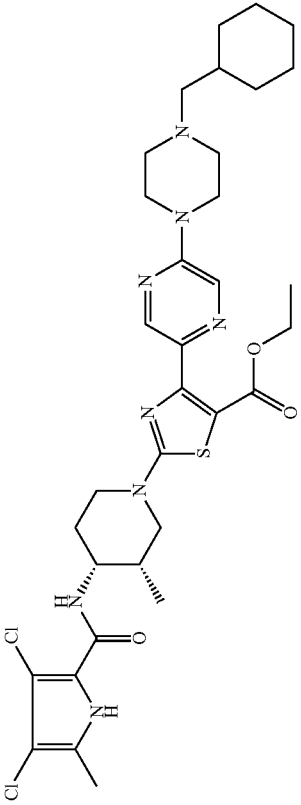 | ¹H NMR (400 MHz, DMSO-d₆): δ 0.90 (m, 9H), 1.14 (t, 3H), 1.28 (m, 2H), 1.47 (m, 2H), 1.81 (m, 2H), 2.21 (m, 5H), 2.56 (m, 4H), 3.55 (m, 8H), 4.09 (m, 2H), 4.25 (s, 1H), 7.20 (d, 1H), 8.30 (s, 1H), 8.31 (s, 1H), 12.04 (s, 1H). LC-MS: m/z 677.4 (M + H) | Example 143 and 4-pentan-3-piperazine |
| 160 | Ethyl 2-[(3S,4R)-4-{[(3,4-dichloro-5-methyl-1H-pyrrol-2-yl)carbonyl]amino}-3-methylpiperidin-1-yl]-4-(5-{4-[2-(diethylamino)ethyl]piperazin- 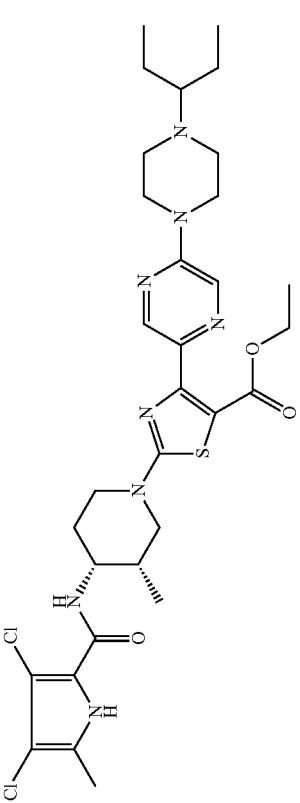 | ¹H NMR (400 MHz, CDCl₃): δ 1.02 (m, 7H), 1.28 (m, 10H), 1.94 (m, 2H), 2.25 (m, 4H), 2.60 (m, 4H), 3.30 (m, 1H),3.60 (m, 6H), 4.18 (m, 2H), 4.40 (brs, 1H), 6.79 (d, 1H), 8.18 (s, 1H), 8.50 (s, | Example 143 and 2-diethylaminoethyl-piperazine |

| Ex | Compound | | Data | SM |
|---|---|---|---|---|
| | 1-yl]pyrazin-2-yl)-1,3-thiazole-5-carboxylate | | 1H), 9.71 (brs, 1H). LC-MS: m/z 706.76 (M + H) | |
| 161 | Ethyl 2-[(3S,4R)-4-{[(3,4-dichloro-5-methyl-1H-pyrrol-2-yl)carbonyl]amino}-3-methylpiperidin-1-yl]-4-{5-[(3R)-3-methylpiperazin-1-yl]pyrazin-2-yl}-1,3-thiazole-5-carboxylate | 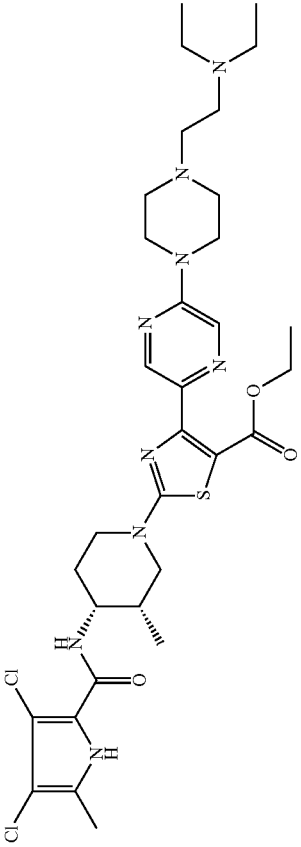 | ¹H NMR (400 MHz, DMSO-d₆): δ 0.92 (d, 3H), 1.03 (d, 3H), 1.14 (t, 3H), 1.81 (m, 2H), 2.18 (s, 4H), 2.72 (m, 2H), 2.82 (m, 1H), 2.96 (d, 1H), 3.55 (m, 6H), 4.08 (q, 2H), 4.23 (m, 3H), 7.21 (d, 1H), 8.30 (s, 2H), 12.04 (s, 1H), LC-MS: m/z 621.4 (M + H) | Example 143 and (3R)-3-methylpiperazine |
| 162 | Ethyl 2-[(3S,4R)-4-{[(3,4-dichloro-5-methyl-1H-pyrrol-2-yl)carbonyl]amino}-3-methylpiperidin-1-yl]-4-{5-[4-(2-hydroxyethyl)piperazin-1- | 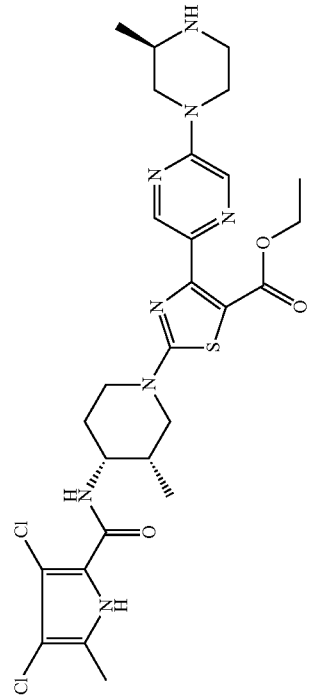 | ¹H NMR (400 MHz, DMSO-d₆): δ 0.92 (d, 3H), 1.14 (t, 3H), 1.81 (m, 2H), 2.18 (s, 4H), 2.43 (t, 2H), 2.51 (m, 4H), 3.55 (m, 9H), 3.71 (m, 1H), 4.11 (q, 2H), 4.25 (m, 1H), 4.47 (t, 1H), 7.21 (d, 1H), | Example 143 and 2-hydroxyethylamine |

| Ex | Compound | Data | SM |
|---|---|---|---|
| | y]]pyrazin-2-yl]-1,3-thiazole-5-carboxylate 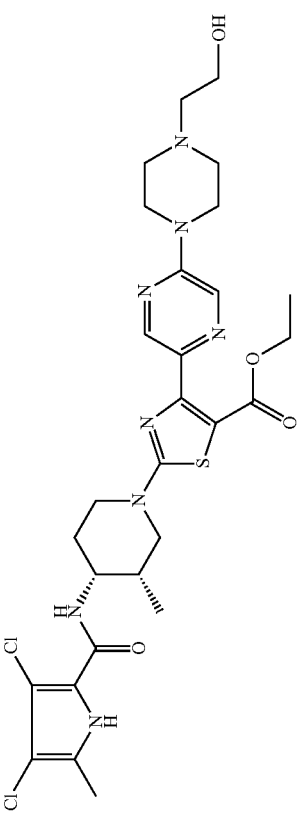 | 8.32 (s, 2H), 12.05 (s, 1H). LC-MS: m/z 651.5 (M + H) | |
| 163 | Ethyl 2-[(3S,4R)-4-{[(3,4-dichloro-5-methyl-1H-pyrrol-2-yl)carbonyl]amino}-3-methylpiperidin-1-yl]-4-{5-[4-(tetrahydrofuran-2-ylmethyl)piperazin-1-yl]pyrazin-2-yl]}-1,3-thiazole-5-carboxylate 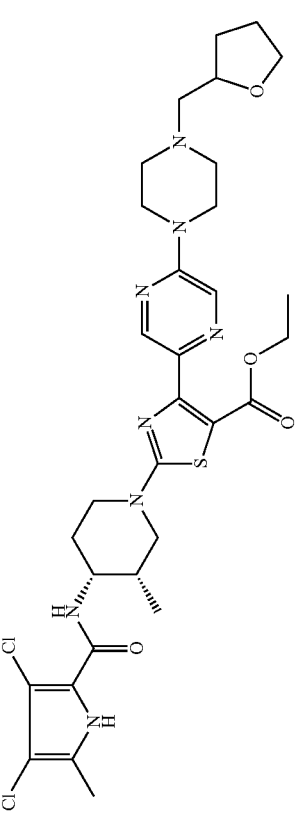 | ¹H NMR (¹H NMR (400 MHz, DMSO-d₆): δ 0.91 (d, 3H), 1.21 (t, 3H), 1.46 (m, 2H), 1.78 (m, 4H), 1.91 (m, 2H), 2.17 (s, 4H), 2.47 (m, 2H), 2.50 (m, 1H), 2.60 (m, 2H), 3.44 (m, 1H), 3.61 (m, 6H), 3.72 (m, 2H), 3.94 (m, 1H), 4.09 (q, 2H), 4.24 (m, 1H), 7.20 (d, 1H), 8.30 (d, 2H), 12.03 (s, 1H). LC-MS: m/z 691.4 (M + H) | Example 143 and 4-tetrahydrofuran-2methylpiperazine |

Examples 164-183

The following Examples were prepared according to the procedure described for Example 61 from the starting materials in the table.

| Ex | Compound | Data | SM |
|---|---|---|---|
| 164 | 2-[(3S,4R)-4-{[(3,4-dichloro-5-methyl-1H-pyrrol-2-yl)carbonyl]amino}-3-methylpiperidin-1-yl]-4-[5-(4-ethylpiperazin-1-yl)pyrazin-2-yl]-1,3-thiazole-5-carboxylic acid | $^1$H NMR (400 MHz, DMSO-$d_6$): δ 0.92 (d, 3H), 1.22 (m, 5H), 1.81 (m, 2H), 2.15 (m, 4H), 3.03 (m, 4H), 3.80 (m, 6H), 4.12 (d, 1H), 4.28 (m, 1H), 4.42 (m, 2H), 7.59 (s, 1H), 8.52 (s, 1H), 9.03 (s, 1H), 11.42 (s, 1H), 12.60 (m, 1H). LC-MS: m/z 607.5 (M + H) | Example 144 |
| 165 | 2-[(3S,4R)-4-{[(3,4-dichloro-5-methyl-1H-pyrrol-2-yl)carbonyl]amino}-3-methylpiperidin-1-yl]-4-[5-(piperidin-1-yl)pyrazin-2-yl]-1,3-thiazole-5-carboxylic acid | $^1$H NMR (400 MHz, DMSO-$d_6$): δ 0.94 (d, 3H), 1.64 (m, 6H), 1.82 (m, 2H), 2.19 (s, 3H), 3.63 (m, 10H), 4.26 (m, 1H), 7.20 (d, 1H), 8.41 (s, 1H), 8.99 (s, 1H), 12.04 (s, 1H). LC-MS: m/z 578 (M + H) | Example 145 |
| 166 | 2-[(3S,4R)-4-{[(3,4-dichloro-5-methyl-1H- | $^1$H NMR (400 MHz, DMSO-$d_6$): δ 0.94 (d, 3H), 1.84 (t, | Example 146 |

| Ex | Compound | Data | SM |
|---|---|---|---|
| | pyrrol-2-yl)carbonyl]amino}-3-methylpiperidin-1-yl]-4-[5-(morpholin-4-yl)pyrazin-2-yl]-1,3-thiazole-5-carboxylic acid | 2H), 2.19 (s, 4H), 3.54 (m, 3H), 3.72 (m, 10H), 4.26 (t, 1H), 7.20 (d, 1H), 8.43 (s, 1H), 9.02 (s, 1H), 12.04 (s, 1H). LC-MS: m/z 580.2 (M + H) | |
| 167 | 2-[(3S,4R)-4-{[(3,4-dichloro-5-methyl-1H-pyrrol-2-yl)carbonyl]amino}-3-methylpiperidin-1-yl]-4-[5-(4-methylpiperazin-1-yl)pyrazin-2-yl]-1,3-thiazole-5-carboxylic acid | ¹H NMR (400 MHz, DMSO-d₆): δ 0.94 (d, 3H), 1.82 (m, 2H), 2.19 (s, 4H), 2.70 (s, 3H), 3.10 (s, 3H), 3.60 (m, 7H), 4.24 (s, 1H), 4.37 (m, 2H), 7.27 (d, 1H), 8.52 (s, 1H), 9.03 (s, 1H), 10.35 (s, 1H), 12.15 (s, 1H), LC-MS: m/z 593.3 (M + H) | Example 147 |
| 168 | 2-[(3S,4R)-4-{[(3,4-dichloro-5-methyl-1H-pyrrol-2-yl)carbonyl]amino}-3-methylpiperidin-1-yl]-4-[5- | ¹H NMR (400 MHz, DMSO-d₆): δ 0.93 (d, 3H), 1.82 (m, 2H), 2.19 (s, 4H), 3.17 (m, 4H), 3.62 (m, 5H), 3.78 (s, 1H), 3.9 (s, 4H), 4.27 (s, 1H), | Example 148 |

| Ex | Compound | Data | SM |
|---|---|---|---|
| | (piperazin-1-yl)pyrazin-2-yl]-1,3-thiazole-5-carboxylic acid | 7.37 (d, 1H), 8.49 (s, 1H), 9.02 (s, 1H), 12.28 (s, 1H) LC-MS: m/z 579.3 (M + H) | |
| 169 | 2-[(3S,4R)-4-{[(3,4-dichloro-5-methyl-1H-pyrrol-2-yl)carbonyl]amino}-3-methylpiperidin-1-yl]-4-(5-{[2-(2-oxopyrrolidin-1-yl)ethyl]amino}pyrazin-2-yl)-1,3-thiazole-5-carboxylic acid | ¹H NMR (400 MHz, DMSO-d₆): δ 0.94 (d, 3H), 1.88 (m, 5H), 2.16 (m, 6H), 3.41 (m, 5H), 3.56 (m, 6H), 4.26 (s, 1H), 7.26 (d, 1H), 8.03 (s, 1H), 8.95 (s, 1H), 12.12 (s, 1H). LC-MS: m/z 621.3 (M + H) | Example 149 |
| 170 | 2-[(3S,4R)-4-{[(3,4-dichloro-5-methyl-1H-pyrrol-2-yl)carbonyl]amino}-3-methylpiperidin-1-yl]-4-{5-[(2-methoxyethyl)amino]pyrazin- | ¹H NMR (400 MHz, DMSO-d₆): δ 0.93 (d, 3H), 1.81 (m, 2H), 2.07 (s, 3H), 2.19 (s, 4H), 3.28 (s, 3H) 3.68 (m, 6H), 4.26 (s, 1H), 7.27 (d, 1H), 7.99 (s, 1H), 8.04 (s, 1H), 8.92 (s, 1H), 12.14 (s, 1H) | Example 150 |

| Ex | Compound | Data | SM |
|---|---|---|---|
| | 2-yl}-1,3-thiazole-5-carboxylic acid | LC-MS: m/z 568.4 (M + H) | |
| 171 | 2-[(3S,4R)-4-{[(3,4-dichloro-5-methyl-1H-pyrrol-2-yl)carbonyl]amino}-3-methylpiperidin-1-yl]-4-(5-{[2-(morpholin-4-yl)ethyl]amino}pyrazin-2-yl)-1,3-thiazole-5-carboxylic acid | $^1$H NMR (400 MHz, DMSO-d$_6$): δ 0.94 (d, 3H), 1.82 (m, 2H), 2.19 (s, 4H), 3.13 (m, 4H), 3.64 (m, 11H), 3.97 (s, 2H) 4.27 (s, 1H), 8.06 (s, 1H), 8.20 (s, 1H), 8.96 (s, 1H), 12.17 (s, 1H). LC-MS: m/z 623.5 (M + H) | Example 151 |
| 172 | 2-[(3S,4R)-4-{[(3,4-dichloro-5-methyl-1H-pyrrol-2-yl)carbonyl]amino}-3-methylpiperidin-1-yl]-4-{5-[(1,3-dimethoxypropan-2-yl)amino]pyrazin-2-yl}-1,3-thiazole-5-carboxylic acid | $^1$H NMR (400 MHz, DMSO-d$_6$): δ 0.93 (d, 3H), 1.82 (m, 2H), 2.19 (m, 4H), 3.32 (m, 6H), 3.65 (m, 8H), 4.34 (m, 2H), 7.21 (d, 1H), 7.96 (d, 1H), 8.02 (s, 1H), 8.95 (s, 1H), 12.04 (s, 1H). LC-MS: m/z 612.48 (M + H) | Example 152 |

| Ex | Compound | Data | SM |
|---|---|---|---|
| 173 | 2-[(3S,4R)-4-{[(3,4-dichloro-5-methyl-1H-pyrrol-2-yl)carbonyl]amino}-3-methylpiperidin-1-yl]-4-(5-{[2-(2-oxoimidazolidin-1-yl)ethyl]amino}pyrazin-2-yl)-1,3-thiazole-5-carboxylic acid 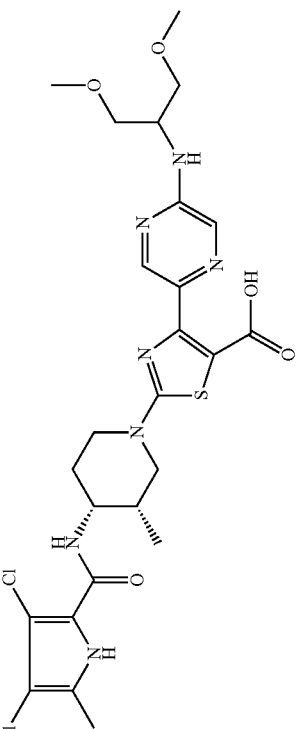 | $^1$H NMR (400 MHz, DMSO-d$_6$): δ 0.94 (m, 3H), 1.82 (s, 2H), 2.19 (s, 4H), 3.23 (m, 4H), 3.49 (m, 2H), 3.53 (m, 6H), 4.26 (s, 1H), 6.30 (s, 1H), 7.31 (d, 1H), 7.97 (s, 1H), 8.02 (s, 1H), 8.94 (s, 1H), 12.19 (s, 1H) LC-MS: m/z 622.3 (M + H) | Example 153 |
| 174 | 2-[(3S,4R)-4-{[(3,4-dichloro-5-methyl-1H-pyrrol-2-yl)carbonyl]amino}-3-methylpiperidin-1-yl]-4-(5-{[2-(dimethylamino)ethyl]amino}pyrazin-2-yl)-1,3-thiazole-5-carboxylic acid 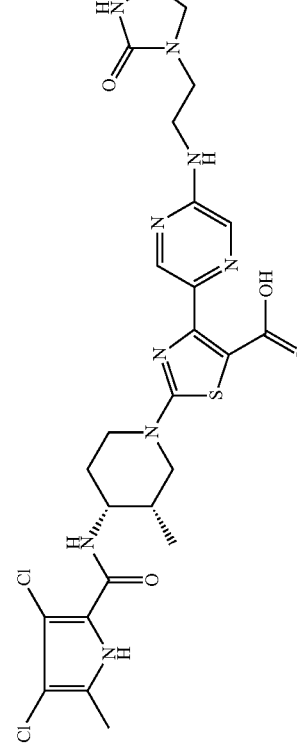 | $^1$H NMR (400 MHz, DMSO-d$_6$): δ 0.93 (d, 3H), 1.81 (m, 2H), 2.07 (s, 3H), 2.19 (s, 6H), 2.79 (s, 4H), 3.26 (m, 2H), 3.66 (m, 3H), 4.27 (s, 1H), 7.44 (d, 1H), 8.06 (s, 1H), 8.27 (s, 1H), 8.96 (s, 1H), 12.37 (s, 1H), 16.49 (s, 1H) LC-MS: m/z 581.2 (M + H) | Example 154 |

| Ex | Compound | | Data | SM |
|---|---|---|---|---|
| 175 | 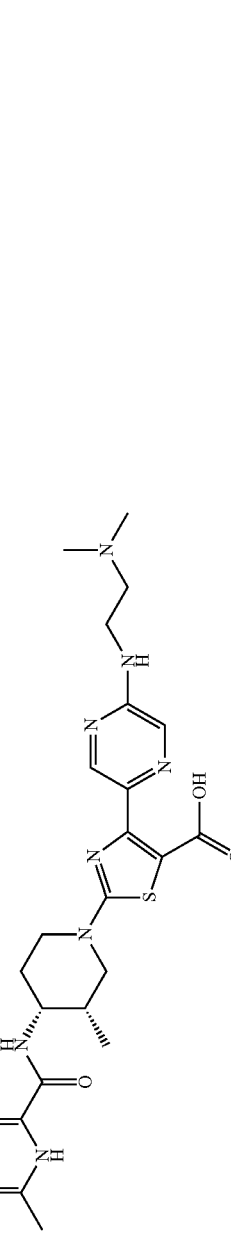 2-[(3S,4R)-4-{[(3,4-dichloro-5-methyl-1H-pyrrol-2-yl)carbonyl]amino}-3-methylpiperidin-1-yl]-4-(5-{[2-(4-methylpiperazin-1-yl)ethyl]amino}pyrazin-2-yl)-1,3-thiazole-5-carboxylic acid | | $^1$H NMR (400 MHz, DMSO-d$_6$): δ 0.93 (d, 3H), 1.82 (m, 2H), 2.19 (m, 4H), 2.41-2.98 (m, 13H), 3.58 (m, 7H), 4.27 (m, 1H), 7.38 (br s, 1H), 7.96 (br s, 1H), 8.01 (s, 1H), 8.94 (s, 1H), 12.28 (br s, 1H). LC-MS: m/z 636.47 (M + H) | Example 155 |
| 176 | 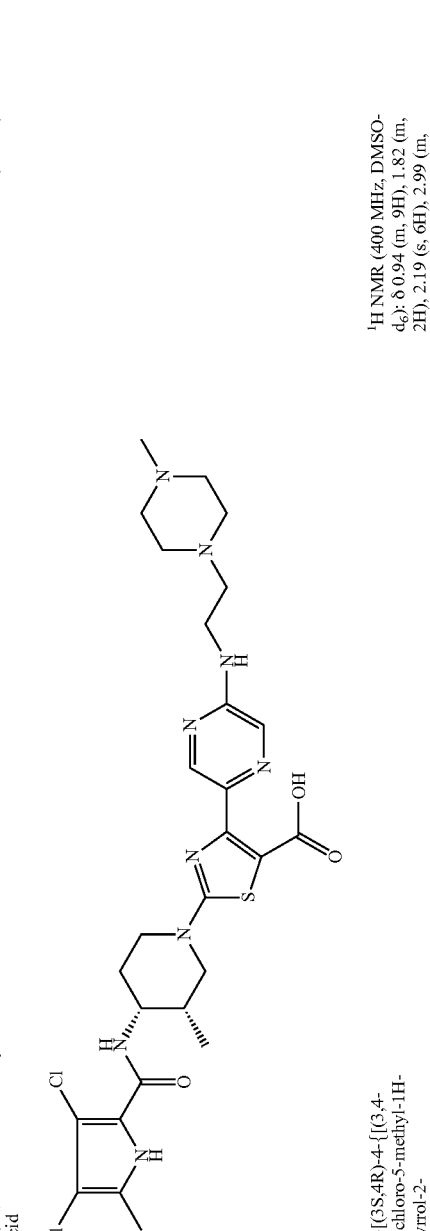 2-[(3S,4R)-4-{[(3,4-dichloro-5-methyl-1H-pyrrol-2-yl)carbonyl]amino}-3-methylpiperidin-1-yl]-4-{5-[4-(2-methylpropyl)piperazin-1-yl]pyrazin-2-yl}-1,3-thiazole-5-carboxylic acid | | $^1$H NMR (400 MHz, DMSO-d$_6$): δ 0.94 (m, 9H), 1.82 (m, 2H), 2.19 (s, 6H), 2.99 (m, 4H), 3.65 (m, 8H), 4.27 (s, 1H), 4.52 (s, 1H), 7.34 (s, 1H), 8.51 (s, 1H), 9.02 (s, 1H), 10.18 (s, 1H), 12.24 (s, 1H). LC-MS: m/z 637.4 (M + H) | Example 156 |

| Ex | Compound | Data | SM |
|---|---|---|---|
| 177 | 2-[(3S,4R)-4-{[(3,4-dichloro-5-methyl-1H-pyrrol-2-yl)carbonyl]amino}-3-methylpiperidin-1-yl]-4-(5-{4-[(1-methylpiperidin-3-yl)methyl]piperazin-1-yl}pyrazin-2-yl)-1,3-thiazole-5-carboxylic acid 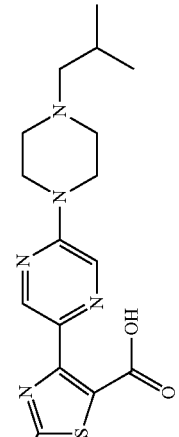 | ¹H NMR (400 MHz, DMSO-d₆): δ 0.93 (d, 3H), 1.10 (m, 2H), 1.76 (m, 5H), 2.19 (m, 4H), 2.73 (m, 5H), 3.14 (m, 5H), 3.63 (m, 9H), 4.28 (brs, 1H), 4.57 (brs, 1H), 7.38 (d, 1H), 8.56 (s, 1H), 9.05 (s, 1H), 10.27 (brs, 1H), 11.09 (brs, 1H), 12.27 (s, 1H).<br><br>LC-MS: m/z 691.70 (M + H) | Example 157 |
| 178 | 4-{5-[4-(cyclohexylmethyl)piperazin-1-yl]pyrazin-2-yl}-2-[(3S,4R)-4-{[(3,4-dichloro-5-methyl-1H-pyrrol-2-yl)carbonyl]amino}-3-methylpiperidin-1-yl]-1,3-thiazole-5-carboxylic acid 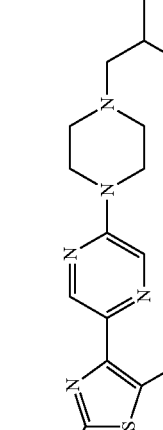 | ¹H NMR (400 MHz, DMSO-d₆): δ 0.94 (m, 5H), 1.19 (m, 4H), 1.68 (m, 7H), 1.81 (s, 4H), 2.19 (s, 4H), 2.97 (m, 2H), 3.10 (m, 2H), 3.61 (m, 4H), 4.27 (s, 1H), 4.53 (d, 2H), 7.33 (s, 1H), 8.55 (s, 1H), 9.04 (s, 1H), 12.21 (s, 1H), 16.42 (s, | Example 158 |

| Ex | Compound | Data | SM |
|---|---|---|---|
| 179 | 2-[(3S,4R)-4-{[(3,4-dichloro-5-methyl-1H-pyrrol-2-yl)carbonyl]amino}-3-methylpiperidin-1-yl]-4-{5-[4-(pentan-3-yl)piperazin-1-yl]pyrazin-2-yl}-1,3-thiazole-5-carboxylic acid 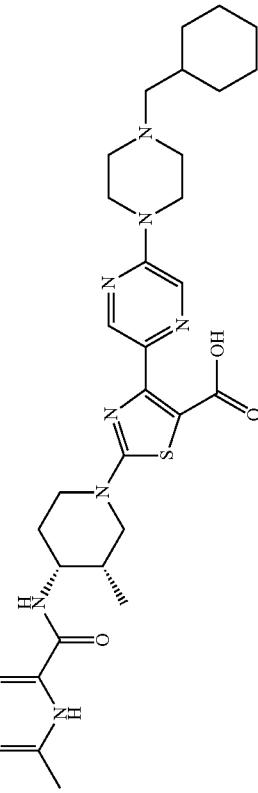 | 1H). LC-MS: m/z 675.5 (M + H) ¹H NMR (400 MHz, DMSO-d₆): δ 0.88 (m, 9H), 1.27 (d, 2H), 1.43 (d, 2H), 1.81 (m, 2H), 2.17 (s, 5H), 2.56 (s, 3H), 3.29 (s, 3H), 3.58 (m, 7H), 4.24 (s, 1H), 7.18 (d, 1H), 8.39 (s, 1H), 8.98 (s, 1H) 12.03 (s, 1H). LC-MS: m/z 649.5 (M + H) | Example 159 |
| 180 | 2-[(3S,4R)-4-{[(3,4-dichloro-5-methyl-1H-pyrrol-2-yl)carbonyl]amino}-3-methylpiperidin-1-yl]-4-(5-{4-[2-(diethylamino)ethyl]piperazin-1-yl}pyrazin-2-yl)-1,3-thiazole-5-carboxylic acid 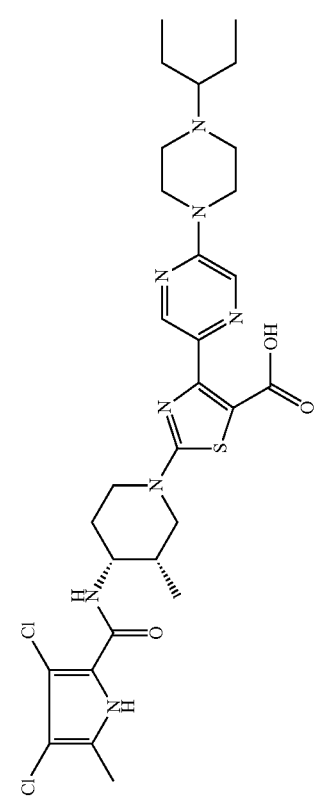 | ¹H NMR (400 MHz, DMSO-d₆): δ 0.94 (d, 3H), 1.18 (m, 6H), 1.81 (m, 2H), 2.19 (m, 4H), 2.50 (m, 6H), 3.01 (m, 6H), 3.73 (m, 8H), 4.28 (brs, 1H), 7.50 (brs, 1H), 8.53 (s, 1H), 9.01 (s, 1H), 12.45 (s, 1H). LC-MS: m/z 706.76 (M + H) | Example 160 |

| Ex | Compound | Data | SM |
|---|---|---|---|
| 181 | 2-[(3S,4R)-4-{[(3,4-dichloro-5-methyl-1H-pyrrol-2-yl)carbonyl]amino}-3-methylpiperidin-1-yl]-4-{5-[(3R)-3-methylpiperazin-1-yl]pyrazin-2-yl}-1,3-thiazole-5-carboxylic acid 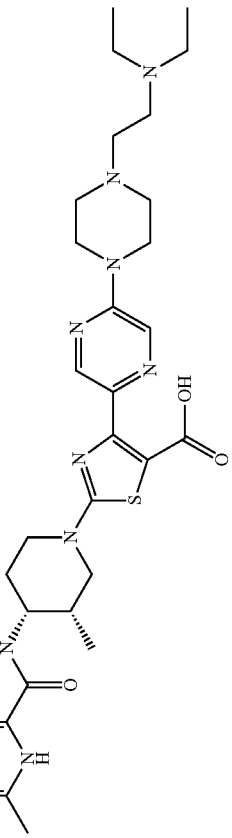 | $^{1}$H NMR (400 MHz, DMSO-d$_6$): δ 0.91 (d, 3H), 1.29 (d, 3H), 1.80 (m, 2H), 2.17 (s, 4H), 3.17 (m, 5H), 3.59 (m, 3H), 3.77 (m, 1H), 4.26 (s, 1H), 4.48 (d, 2H), 7.43 (d, 1H), 8.52 (s, 1H), 9.01 (s, 1H), 9.43 (s, 1H), 9.54 (s, 1H), 12.37 (s, 1H). LC-MS: m/z 593.4 (M + H) | Example 161 |
| 182 | 2-[(3S,4R)-4-{[(3,4-dichloro-5-methyl-1H-pyrrol-2-yl)carbonyl]amino}-3-methylpiperazin-1-yl]-4-{5-[4-(2-hydroxyethyl)piperazin-1-yl]pyrazin-2-yl}-1,3-thiazole-5-carboxylic acid 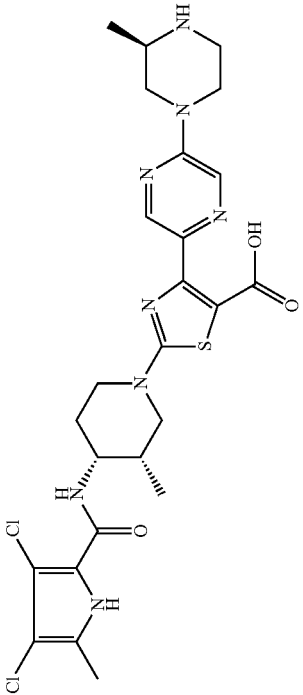 | $^{1}$H NMR (400 MHz, DMSO-d$_6$): δ 0.93 (d, 3H), 1.82 (m, 2H), 2.19 (s, 4H), 3.21 (m, 4H), 3.62 (m, 10H), 4.27 (s, 1H), 4.56 (brs, 2H), 5.39 (s, 1H), 7.33 (d, 1H) 8.53 (s, 1H), 9.04 (s, 1H), 10.29 (s, 1H), 12.22 (s, 1H). LC-MS: m/z 623.26 (M + H) | Example 162 |

| Ex | Compound | Data | SM |
|---|---|---|---|
| 183 | 2-[(3S,4R)-4-{[(3,4-dichloro-5-methyl-1H-pyrrol-2-yl)carbonyl]amino}-3-methylpiperidin-1-yl]-4-{5-[4-(tetrahydrofuran-2-ylmethyl)piperazin-1-yl]pyrazin-2-yl}-1,3-thiazole-5-carboxylic acid | $^1$H NMR (400 MHz, DMSO-$d_6$): δ 0.94 (d, 3H) 1.23 (m, 2H), 1.50 (m, 2H), 1.82 (m, 5H), 1.99 (m, 12H), 2.18 (s, 4H), 2.93 (m, 5H), 3.76 (m, 7H), 4.12 (s, 1H), 4.27 (s, 1H), 7.28 (d, 1H), 8.47 (s, 1H), 9.02 (s, 1H), 12.17 (s, 1H). LC-MS: m/z 663.3 (M + H) | Example 163 |

Example 184

Methyl 2-[(3S,4R)-4-{[(3,4-dichloro-5-methyl-1H-pyrrol-2-yl)carbonyl]amino}-3-methoxypiperidin-1-yl]-4-[4-(piperidin-1-yl)pyrimidin-2-yl]-1,3-thiazole-5-carboxylate

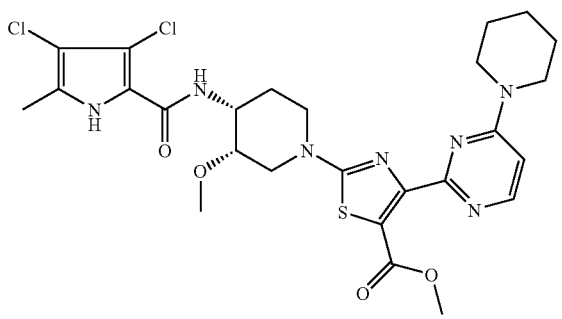

To a stirred solution of methyl 2-chloro-4-[4-(piperidin-1-yl)pyrimidin-2-yl]-1,3-thiazole-5-carboxylate (Intermediate 67, 30 mg, 0.08 mmol) in N-methylpyrrolidinone (0.5 mL), N,N-diisopropyl ethylamine (23 mg, 0.18 mmol) and 3,4-dichloro-N-[(3S,4R)-3-methoxypiperidin-4-yl]-5-methyl-1H-pyrrole-2-carboxamide (WO2006087543, 27 mg, 0.09 mol) were added at room temperature. The above reaction mixture was heated at 90° C. for 3 h. The reaction mixture was cooled to room temperature, diluted with water (5 mL) and stirred for 1 h. The solid obtained was collected by filtration and dried to obtain methyl 2-[(3S,4R)-4-{[(3,4-dichloro-5-methyl-1H-pyrrol-2-yl)carbonyl]amino}-3-methoxypiperidin-1-yl]-4-[4-(piperidin-1-yl)pyrimidin-2-yl]-1,3-thiazole-5-carboxylate 35 mg (66%).

$^1$H NMR (400 MHz, DMSO-$d_6$): δ 1.51 (bs, 4H), 1.63 (s, 2H), 2.18 (s, 3H), 2.41 (m, 2H), 2.96 (m, 1H), 3.38 (s, 3H), 3.57 (m, 2H), 3.95 (m, 1H), 4.28 (m, 2H), 6.79 (d, 1H), 7.16 (d, 1H), 8.18 (d, 1H), 12.12 (br s, 1H).
LC-MS: m/z 608.45 (M+H).

Examples 185-188

The following Examples were prepared according to the procedure described for Example 184 from the starting materials indicated in the table.

| Ex | Compound | Data | SM |
|---|---|---|---|
| 185 | Methyl 2-[(3S,4R)-4-{[(3,4-dichloro-5-methyl-1H-pyrrol-2-yl)carbonyl]amino}-3-methoxypiperidin-1-yl]-4-[4-(morpholin-4-yl)pyrimidin-2-yl]-1,3-thiazole-5-carboxylate | $^1$H NMR (400 MHz, DMSO-$d_6$): δ 0.93 (d, 2H), 1.75 (bs, 2H), 2.18 (s, 3H), 3.37 (s, 3H), 3.57 (m, 9H), 4.01 (m, 2H), 4.27 (m, 2H), 6.83 (d, 1H), 7.17 (d, 1H), 8.25 (d, 1H), 12.16 (bs, 1H) LC-MS: m/z 610.3 (M + H) | Intermediate 68 |
| 186 | methyl 2-[(3S,4R)-4-{[(3,4-dichloro-5-methyl-1H-pyrrol-2-yl)carbonyl]amino}-3-methoxypiperidin-1-yl]-4-[4-(4-methylpiperazin-1-yl)pyrimidin-2-yl]-1,3-thiazole-5-carboxylate | $^1$H NMR (400 MHz, DMSO-$d_6$): δ 1.09 (t, 2H), 1.75 (m, 2H), 2.18 (m, 6H), 2.34 (m, 4H), 3.38 (m, 4H), 3.57 (m, 7H), 4.10 (m, 1H), 4.27 (m, 2H), 6.81 (d, 1H), 7.15 (d, 1H), 8.21 (d, 1H), 12.10 (bs, 1H). LC-MS: m/z 623.44 (M + H) | Intermediate 69 |

| Ex | Compound | Data | SM |
|---|---|---|---|
| 187 | Methyl 2-[(3S,4R)-4-{[(3,4-dichloro-5-methyl-1H-pyrrol-2-yl)carbonyl]amino}-3-methoxypiperidin-1-yl]-4-{4-[4-(2-methylpropyl)piperazin-1-yl]pyrimidin-2-yl}-1,3-thiazole-5-carboxylate | $^1$H NMR (400 MHz, DMSO-$d_6$): δ 0.86 (d, 6H), 0.97 (m, 1H), 1.23 (m, 3H), 1.77 (m, 3H), 2.05 (d, 2H), 2.18 (s, 3H), 2.37 (m, 4H), 3.38 (s, 3H), 3.57 (m, 6H), 4.01 (m, 2H), 4.25 (m, 1H), 6.79 (d, 1H), 7.17 (d, 1H), 8.20 (d, 1H), 12.18 (bs, 2H)<br><br>LC-MS: m/z 665.44 (M + H) | Intermediate 70 |
| 188 | Methyl 2-[(3S,4R)-4-{[(3,4-dichloro-5-methyl-1H-pyrrol-2-yl)carbonyl]amino}-3-methoxypiperidin-1-yl]-4-[4-(4-ethylpiperazin-1-yl)pyrimidin-2-yl]-1,3-thiazole-5-carboxylate | $^1$H NMR (400 MHz, DMSO-$d_6$): δ 0.93 (d, 3H), 1.02 (t, 3H), 1.75 (m, 2H), 2.18 (s, 3H), 2.40 (m, 6H), 3.38 (s, 3H), 3.57 (m, 7H), 4.01 (m, 1H), 4.25 (m, 2H), 6.82 (d, 1H), 7.15 (d, 1H), 8.21 (d, 1H), 12.15 (bs, 1H).<br><br>LC-MS: m/z 637.4 (M + H). | Intermediate 71 |

Example 189

2-[(3S,4R)-4-{[(3,4-dichloro-5-methyl-1H-pyrrol-2-yl)carbonyl]amino}-3-methoxy piperidin-1-yl]-4-[4-(piperidin-1-yl)pyrimidin-2-yl]-1,3-thiazole-5-carboxylic acid

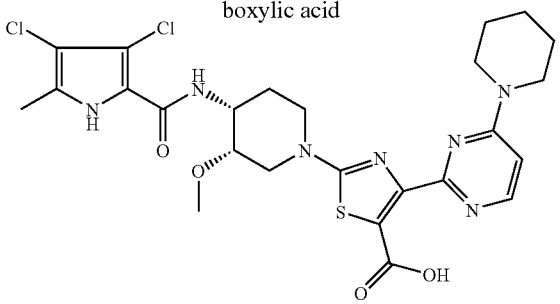

To a stirred solution of methyl 2-[(3S,4R)-4-{[(3,4-dichloro-5-methyl-1H-pyrrol-2-yl)carbonyl]amino}-3-methoxypiperidin-1-yl]-4-[4-(piperidin-1-yl)pyrimidin-2-yl]-1,3-thiazole-5-carboxylate (Example 184, 35 mg. 0.06 mmol) in tetrahydrofuran (5 mL) was added a solution of lithium hydroxide (9.6 mg, 0.23 mmol) in water (1 mL). The reaction mixture was stirred at room temperature for 18 h. The reaction mixture was concentrated to dryness. The resulting residue was diluted with water (2 mL) and the aqueous layer was extracted with diethyl ether (2×10 mL). The aqueous layer was acidified to pH 4-5 with 2N HCl solution, solid obtained was filtered and dried to yield 2-[(3S,4R)-4-{[(3,4-dichloro-5-methyl-1H-pyrrol-2-yl)carbonyl]amino}-3-methoxypiperidin-1-yl]-4-[4-(piperidin-1-yl)pyrimidin-2-yl]-1,3-thiazole-5-carboxylic acid 27 mg (79%).

$^1$H NMR (400 MHz, DMSO-$d_6$): δ 1.51-1.82 (m, 7H), 2.18 (s, 3H), 3.18-3.84 (m, 12H), 4.25 (m, 1H), 4.55 (m, 1H), 6.99 (d, 1H), 7.16 (d, 1H), 8.31 (d, 1H), 12.15 (bs, 1H).

$D_2O$: 1.66 (m, 7H), 2.18 (s, 3H), 3.41 (m, 4H), 3.59 (m, 4H), 3.85 (m, 5H), 4.42 (m, 1H), 4.52 (m, 1H), 6.95 (d, 1H), 8.28 (d, 1H)

LC-MS: m/z 594.40 (M+H).

Examples 190-193

The following Examples were prepared according to the procedure described for Example 189 from the starting material indicated in the table.

| Ex | Compound | Data | SM |
|---|---|---|---|
| 190 | 2-[(3S,4R)-4-{[(3,4-dichloro-5-methyl-1H-pyrrol-2-yl)carbonyl]amino}-3-methoxy piperidin-1-yl]-4-[4-(morpholin-4-yl)pyrimidin-2-yl]-1,3-thiazole-5-carboxylic acid | $^1$H NMR (400 MHz, DMSO-$d_6$): δ 1.76 (m, 2H), 2.18 (s, 3H), 3.37 (m, 5H), 3.56 (m, 1H), 3.81 (m, 9H), 4.26 (m, 1H), 4.41 (m, 1H), 7.05 (d, 1H), 7.20 (d, 1H), 8.40 (d, 1H), 12.20 (s, 1H). LC-MS: m/z 596.4 (M + H) | Example 185 |
| 191 | 2-[(3S,4R)-4-{[(3,4-dichloro-5-methyl-1H-pyrrol-2-yl)carbonyl]amino}-3-methoxy piperidin-1-yl]-4-[4-(4-methylpiperazin-1-yl)pyrimidin-2-yl]-1,3-thiazole-5-carboxylic acid | $^1$H NMR (400 MHz, DMSO-$d_6$): δ 1.77(m, 2H), 2.19 (s, 3H), 2.84 (s, 3H), 3.22 (m, 2H), 3.41 (m, 7H), 3.91 (m, 2H), 4.24 (m, 2H), 4.68 (m, 4H), 7.07 (d, 1H), 8.44 (d, 1H), LC-MS: m/z 609.40 (M + H). | Example 186 |
| 192 | 2-[(3S,4R)-4-{[(3,4-dichloro-5-methyl-1H-pyrrol-2-yl)carbonyl]amino}-3-methoxy piperidin-1-yl]-4-{4-[4-(2-methylpropyl)piperazin-1-yl]pyrimidin-2-yl}-1,3-thiazole-5-carboxylic acid | $^1$H NMR (400 MHz, DMSO-$d_6$): δ 1.00 (d, 6H), 2.12 (m, 1H), 2.18 (s, 3H), 3.08 (m, 5H), 3.34 (m, 4H), 3.59 (m, 7H), 3.95 (m, 1H), 4.29 (m, 1H), 4.50 (m, 1H).7.10 (d, 1H), 7.21 (d, 1H), 8.49 (d, 1H), 10.38 (bs, 1H), 12.22 (s, 1H) LC-MS: m/z 651.46 (M + H). | Example 187 |

| Ex | Compound | Data | SM |
|---|---|---|---|
| 193 | 2-[(3S,4R)-4-{[(3,4-dichloro-5-methyl-1H-pyrrol-2-yl)carbonyl]amino}-3-methoxy piperidin-1-yl]-4-[4-(4-ethylpiperazin-1-yl)pyrimidin-2-yl]-1,3-thiazole-5-carboxylic acid | $^1$H NMR (400 MHz, DMSO-$d_6$): δ 1.28 (t, 3H), 1.77 (m, 2H), 2.18 (s, 3H), 3.08 (m, 4H), 3.21-3.62 (m, 10H), 3.92 (m, 1H), 4.27 (m, 1H), 4.51 (m, 3H), 7.11 (m, 2H), 8.49 (d, 1H), 10.63 (bs, 1H), 12.20 (s, 1H).<br><br>LC-MS: m/z 623.35(M + H). | Example 188 |

Example 194

Ethyl 4-{5-[(1,4-diazabicyclo[2.2.2]oct-2-ylmethyl)amino]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylate

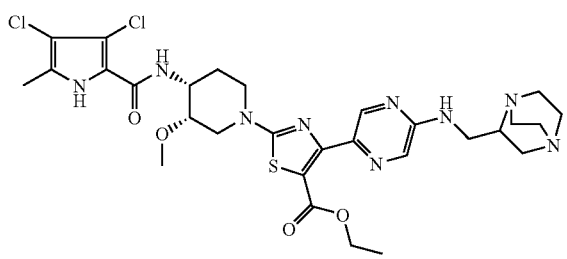

Ethyl 4-(5-chloropyrazin-2-yl)-2-[(3S,4R)-4-{[(3,4-dichloro-5-methyl-1H-pyrrol-2-yl)carbonyl]amino}-3-methoxypiperidin-1-yl]-1,3-thiazole-5-carboxylate (Example 59, 330 mg, 0.57 mmol) was added to a solution of 1-(1,4-diazabicyclo[2.2.2]oct-2-yl)methanamine (EP748807, 407 mg, 2.88 mmol) and N,N-Diisopropylethylamine (0.38 mL, 2.88 mmol) in N-methyl 2-pyrrolidinone (5 mL) and the resulting reaction mixture was stirred for 20 h at 80° C. The reaction mixture was cooled to room temperature, poured into water (40 mL) and extracted with ethyl acetate (3×50 mL). The combined organic layer was washed with brine, dried over anhydrous sodium sulphate and concentrated under reduce pressure to yield crude product which was purified by flash column chromatography over silica gel (0-30% methanol in chloroform) to afford 80 mg (20.5%) of ethyl 4-{5-[(1,4-diazabicyclo[2.2.2]oct-2-ylmethyl)amino]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylate as an off-white solid.

$^1$H NMR (400 MHz, DMSO-$d_6$): δ 1.09 (t, 3H), 1.76 (m, 2H), 2.09-2.20 (m, 7H), 2.44 (m, 4H), 2.81-2.93 (m, 5H), 2.98-3.01 (m, 4H), 4.25 (m, 2H), 4.30 (m, 4H), 7.29 (m, 3H), 7.17 (d, 1H), 8.33 (d, 2H)

LC-MS: m/z 678.48 (M+H).

Example 195

4-{5-[(1,4-diazabicyclo[2.2.2]oct-2-ylmethyl)amino]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylic acid

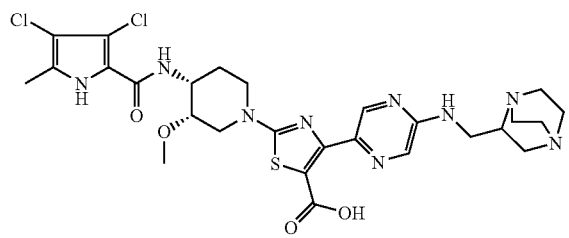

Ethyl 4-{5-[(1,4-diazabicyclo[2.2.2]oct-2-ylmethyl)amino]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylate (Example 194, 100 mg, 0.14 mmol) was dissolved in methanol (3 mL) and water (1 mL). Lithium hydroxide monohydrate (18 mg, 0.44 mmol) was added and the reaction mixture was stirred at room temperature for 16 h. The methanol was completely evaporated. The resulting crude product was taken in water (20 mL) and acidified to pH 6 with 2N hydrochloric acid (1.0 mL). The aqueous layer was concentrated to a residue, which was purified by preparative thin layer chromatography to afford 64 mg (66.8%) of 4-{5-[(1,4-diazabicyclo[2.2.2]oct-2-ylmethyl)amino]pyrazin-2-yl}-2-[(3S,4R)-4-{[(3,4-dichloro-5-methyl-1H-pyrrol-2-yl)carbonyl]amino}-3-methoxypiperidin-1-yl]-1,3-thiazole-5-carboxylic acid as a light yellow solid.

$^1$H NMR (400 MHz, DMSO-$d_6$): δ 1.16-1.23 (m, 3H), 1.77 (m, 2H), 2.09-2.19 (m, 5H), 2.19-2.43 (m, 3H), 2.50-2.89 (m, 5H), 3.06 (m, 1H), 3.56 (m, 1H), 3.87 (s, 3H), 4.25-4.39 (m, 3H), 7.18 (d, 1H), 8.41 (s, 1H), 8.94 (s, 1H)

LC-MS: m/z 650.51 (M+H).

Example 196

Methyl 2-[(3S,4R)-4-{[(4-chloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylate

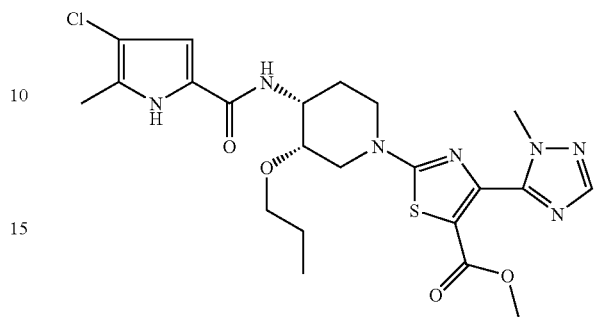

Methyl 2-chloro-4-(1-methyl-1H-1,2,4-triazol-5-yl)-1,3-thiazole-5-carboxylate (Intermediate 2, 68 mg, 0.267 mmol) was added to a solution of 4-chloro-5-methyl-N-[(3R,4S)-3-propoxypiperidin-4-yl]-1H-pyrrole-2-carboxamide (Intermediate 74, 80 mg, 0.267 mmol) and DIPEA (0.04 mL, 0.8025 mmol) in N-methyl 2-pyrrolidinone (1.0 mL) and the resulting reaction mixture was stirred overnight at 80° C. The reaction mixture was cooled to room temperature and poured into water (30 mL). The solid that formed was collected by filtration, washed well with diethyl ether (30 mL) and dried to afford methyl 2-[(3S,4R)-4-{[(4-chloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylate 80 mg (57.1%) as solid.

$^1$H NMR (400 MHz, CDCl$_3$): δ 0.85 (t, 3H), 1.60 (m, 2H), 2.01 (m, 2H), 2.28 (s, 3H), 3.31 (m, 4H), 3.68 (m, 2H), 3.74 (s, 3H), 3.85 (s, 3H), 4.08 (m, 1H), 4.31 (m, 1H), 6.17 (d, 1H), 7.98 (s, 1H), 9.15 (s, 1H).

LCMS: m/z 522.3 (M+H).

Examples 197-199

The following Examples were prepared according to the procedure described for Example 196 from the starting materials described in the table.

| Ex | Compound | Data | SM |
|---|---|---|---|
| 197 | Methyl 2-[(3S,4R)-4-{[(4-chloro-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylate | $^1$H NMR (400 MHz, CDCl$_3$): δ 0.91 (t, 3H), 160 (m, 2H), 2.01 (m, 2H), 2.25 (s, 3H), 3.20 (m, 2H), 3.37 (m, 4H), 3.63 (m, 4H), 3.71 (s, 3H), 4.09 (s, 3H), 4.28 (m, 1H), 4.34 (m, 1H), 6.19 (d, 1H), 7.15 (2d, 2H), 9.27 (s, 1H). LCMS: m/z 565.2 (M + H). | Intermediate 74 and Intermediate 1 |

| Ex | Compound | Data | SM |
|---|---|---|---|
| 198 | Ethyl 2-[(3S,4R)-4-{[(4-chloro-5-methyl-1H-pyrrol-2-yl)carbonyl]amino}-3-propoxypiperidin-1-yl]-4-(3-fluoropyridin-2-yl)-1,3-thiazole-5-carboxylate | $^1$H NMR (400 MHz, CDCl$_3$): δ 0.86 (t, 3H), 1.16 (t, 3H), 1.59 (m, 2H), 2.02 (m, 2H), 2.25 (s, 3H), 3.28 (m, 4H), 4.16 (m, 4H), 4.28 (m, 1H), 4.44 (m, 1H), 6.21 (d, 1H), 7.37 (m, 1H), 7.48 (d, 1H), 8.50 (d, 1H), 9.29 (s, 1H).<br>LCMS: m/z 550.3 (M + H). | Intermediate 74 and Intermediate 4 |
| 199 | Ethyl 2-[(3S,4R)-4-{[(4-chloro-5-methyl-1H-pyrrol-2-yl)carbonyl]amino}-3-propoxypiperidin-1-yl]-4-(pyrazin-2-yl)-1,3-thiazole-5-carboxylate | $^1$H NMR (400 MHz, CDCl$_3$): δ 0.85 (t, 3H), 1.02 (m, 2H), 1.22 (t, 3H), 2.02 (m, 2H), 2.28 (s, 3H), 3.32 (m, 4H), 3.71 (m, 1H), 4.19 (m, 4H), 4.45 (m, 1H), 6.19 (d, 1H), 8.57 (s, 1H), 8.66 (s, 1H), 8.88 (s, 1H), 9.08 (s, 1H). | Intermediate 74 and Intermediate 3 |

Example 200

2-[(3S,4R)-4-{[(4-chloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylic acid

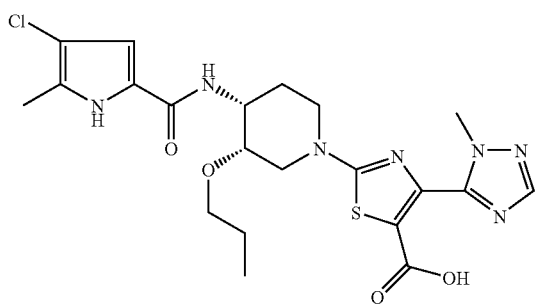

Methyl 2-[(3S,4R)-4-{[(4-chloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylate (Example 196, 80 mg, 0.153 mmol) was dissolved in methanol (30 mL), and 2N sodium hydroxide (6 mL) was added and stirred at room temperature for 4 h. The methanol was completely evaporated and water (20 mL) was added. The aqueous layer was washed with diethyl ether (2×20 mL) and the aqueous layer was acidified to pH 3 with 2N hydrochloric acid (2.0 mL). The obtained solid was filtered and dried to afford 2-[(3R,4S)-4-{[(4-chloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylic acid 60 mg (75%) as solid.

$^1$H NMR (400 MHz, DMSO-d$_6$): δ 0.73 (t, 3H), 1.39 (m, 2H), 1.97 (m, 2H), 2.18 (s, 3H), 3.30 (m, 4H), 3.69 (m, 1H), 4.00 (m, 2H), 4.02 (s, 3H), 4.06 (m, 2H), 6.87 (s, 1H), 7.63 (d, 1H), 8.25 (s, 1H), 11.63 (s, 1H).

LCMS: m/z 508.2 (M+H).

Example 201-203

The following Examples were prepared according to the procedure described for Example 200 from the starting materials indicated in the table.

| Ex | Compound | Data | SM |
|---|---|---|---|
| 201 | 2-[(3S,4R)-4-{[(4-chloro-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylic acid | ¹H NMR (400 MHz, DMSO-d₆): δ 0.72 (t, 3H), 1.41 (m, 2H), 1.97 (m, 2H), 2.13 (s, 3H), 3.23 (s, 3H), 3.37 (m, 2H), 3.43 (m, 2H), 3.55 (m, 2H), 3.74 (m, 4H), 4.21 (m, 1H), 4.82 (m, 2H), 6.86 (s, 1H), 7.33 (s, 1H), 7.50 (s, 1H), 7.65 (d, 1H), 11.64 (s, 1H). LCMS: m/z 551.2 (M + H) | Example 197 |
| 202 | 2-[(3S,4R)-4-{[(4-chloro-5-methyl-1H-pyrrol-2-yl)carbonyl]amino}-3-propoxypiperidin-1-yl]-4-(3-fluoropyridin-2-yl)-1,3-thiazole-5-carboxylic acid | ¹H NMR (400 MHz, DMSO-d₆): δ 0.80 (t, 3H), 1.38 (m, 2H), 1.99 (m, 2H), 2.18 (s, 3H), 3.29 (m, 2H), 3.45 (m, 2H), 3.65 (m, 1H), 4.03 (m, 1H), 4.16 (m, 2H), 6.87 (s, 1H), 7.54 (m, 1H), 7.62 (m, 1H), 7.77 (m, 1H), 8.45 (m, 1H), 11.63 (s, 1H), 12.80 (s, 1H). LCMS: m/z 522.2 (M + H) | Example 198 |
| 203 | 2-[(3S,4R)-4-{[(4-chloro-5-methyl-1H-pyrrol-2-yl)carbonyl]amino}-3-propoxypiperidin-1-yl]-4-(pyrazin-2-yl)-1,3-thiazole-5-carboxylic acid | ¹H NMR (400 MHz, DMSO-d₆): δ 0.72 (t, 3H), 1.37 (m, 2H), 2.00 (m, 2H), 2.13 (s, 3H), 3.33 (m, 2H), 3.49 (m, 2H), 3.67 (m, 1H), 4.01 (m, 1H), 4.19 (m, 2H), 6.86 (s, 1H), 7.62 (d, 1H), 8.78 (m, 1H), 8.83 (m, 1H), 9.33 (s, 1H), 11.63 (s, 1H) LCMS: m/z 505.2 (M + H) | Example 199 |

Examples 204-207

The following Examples were prepared according to the procedure described for Example 196 from the starting materials described in the table.

| Ex | Compound | Data | SM |
|---|---|---|---|
| 204 | Methyl 2-[(3S,4R)-4-{[(4-chloro-3-cyano-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylate | $^1$H NMR (400 MHz, DMSO-$d_6$): δ 0.76 (t, 3H), 1.45 (m, 2H), 1.88 (m, 2H), 2.17 (s, 3H), 3.48 (m, 4H), 3.45 (m, 1H), 3.65 (s, 3H), 3.72 (s, 3H), 4.25 (m, 3H), 7.54 (d, 1H), 8.01 (s, 1H). LC-MS: m/z 547.3 (M + H) | Intermediate 76 and Intermediate 2 |
| 205 | Methyl 2-[(3S,4R)-4-{[(4-chloro-3-cyano-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylate | $^1$H NMR (400 MHz, DMSO-$d_6$): δ 0.76 (t, 3H), 1.45 (m, 2H), 1.88 (m, 2H), 2.17 (s, 3H), 3.17 (s, 3H), 3.38 ((m, 6H), 3.50 (m, 2H), 3.61 (s, 3H), 3.67 (m, 1H), 4.00 (m, 2H), 4.23 (m, 1H), 6.94 (s, 1H), 7.25 (s, 1H), 7.56 (d, 1H). LC-MS: m/z 590.4 (M + H) | Intermediate 76 and Intermediate 1 |
| 206 | Ethyl 2-[3S,4R)-4-{[4-chloro-3-cyano-5-methyl-1H-pyrrol-2-yl)carbonyl]amino}-3-propoxypiperidin-1-yl]-4-(3-fluoropyridin-2-yl)-1,3-thiazole-5-carboxylate | $^1$H NMR (400 MHz, DMSO-$d_6$): δ 0.73 (t, 3H), 1.03 (t, 3H), 1.44 (m, 2H), 1.92 (m, 2H), 2.17 (s, 3H), 3.33 (m, 4H), 3.66 (m, 1H), 3.95 (m, 1H), 4.05 (m, 2H), 4.22 (m, 2H), 7.55 (m, 2H), 7.81 (m, 1H), 8.47 (d, 1H), 12.69 (s, 1H). LC-MS: m/z 575.4 (M + H) | Intermediate 76 and Intermediate 4 |
| 207 | Ethyl 2-[(3S,4R)-4-{[(4-chloro-3-cyano-5-methyl- | $^1$H NMR (400 MHz, DMSO-$d_6$): δ 0.76 (t, 3H), 1.08 (t, 3H), | Intermediate 76 and Intermediate 3 |

-continued

| Ex | Compound | Data | SM |
|---|---|---|---|
| | 1H-pyrrol-2-yl)carbonyl]amino}-3-propoxypiperidin-1-yl]-4-(pyrazin-2-yl)-1,3-thiazole-5-carboxylate | 1.45 (m, 2H), 1.90 (m, 2H), 2.19 (s, 3H), 3.30 (m, 4H), 3.67 (m, 1H), 3.98 (m, 1H), 4.10 (m, 2H), 4.23 (m, 2H), 7.56 (d, 1H), 8.67 (s, 1H), 8.70 (s, 1H), 8.82 (s, 1H), 12.72 (s, 1H). LC-MS: m/z 558.4 (M + H) | |

Example 208-211

The following Examples were prepared according to the procedure described for Example 200 from the starting materials indicated in the table.

| Ex | Compound | Data | SM |
|---|---|---|---|
| 208 | 2-[(3S,4R)-4-{[(4-chloro-3-cyano-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylic acid | $^1$H NMR (400 MHz, DMSO-$d_6$): δ 0.72 (t, 3H), 1.41 (m, 2H), 1.97 (m, 2H), 2.13 (s, 3H), 3.23 (s, 3H), 3.37 (m, 2H), 3.43 (m, 2H), 3.55 (m, 2H), 3.74 (m, 4H), 4.21 (m, 1H), 4.82 (m, 2H), 6.86 (s, 1H), 7.33 (s, 1H), 7.50 (s, 1H), 7.65 (d, 1H), 11.64 (s, 1H). LCMS: m/z 551.2 (M + H) | Example 204 |
| 209 | 2-[(3S,4R)-4-{[(4-chloro-3-cyano-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylic acid | $^1$H NMR (400 MHz, DMSO-$d_6$): δ 0.71 (t, 3H), 1.45 (m, 2H), 1.91 (m, 2h), 1.92 (s, 3H), 3.23 (s, 3H), 3.42 (m, 4H), 3.71 (m, 2H), 3.72 (m, 1H), 3.95 (m, 1H), 4.27 (m, 2H), 4.82 (m, 2H), 7.34 (s, 1H), 7.51 (s, 1H), 7.60 (d, 1H), 12.70 (s, 1H). LC-MS: m/z 576.3 (M + H). | Example 205 |

-continued

| Ex | Compound | Data | SM |
|---|---|---|---|
| 210 | 2-[(3S,4R)-4-{[(4-chloro-3-cyano-5-methyl-1H-pyrrol-2-yl)carbonyl]amino}-3-propoxypiperidin-1-yl]-4-(3-fluoropyridin-2-yl)-1,3-thiazole-5-carboxylic acid | $^1$H NMR (400 MHz, DMSO-d$_6$): δ 0.70 (t, 3H), 1.41 (m, 2H), 1.90 (m, 2H), 2.20 (s, 3H), 3.38 (m, 4H), 3.70 (m, 1H), 4.02 (m, 1H), 4.29 (m, 2H), 7.70 (d, 1H), 8.78 (s, 1H), 8.84 (s, 1H), 9.35 (s, 1H), 12.90 (s, 1H), 15.30 (s, 1H). (LC-MS: m/z 547.3 (M + H) | Example 206 |
| 211 | 2-[(3S,4R)-4-{[(4-chloro-3-cyano-5-methyl-1H-pyrrol-2-yl)carbonyl]amino}-3-propoxypiperidin-1-yl]-4-(pyrazin-2-yl)-1,3-thiazole-5-carboxylic acid | $^1$H NMR (400 MHz, DMSO-d$_6$): δ 0.72 (t, 3H), 1.43 (m, 2H), 1.90 (m, 2H), 2.20 (s, 3H), 3.37 (m, 2H), 3.47 (m, 2H), 3.67 (m, 1H), 3.95 (m, 1H), 4.24 (m, 2H), 7.54 (m, 1H), 7.61 (d, 1H), 7.77 (m, 1H), 8.45 (s, 1H), 12.75 (s, 1H) (LC-MS: m/z 530.3 (M + H). | Example 207 |

Examples 212-214

The following Examples were prepared according to the procedure described for Example 196 from the starting materials indicated in the table.

| Ex | Compound | Data | SM |
|---|---|---|---|
| 212 | Methyl 2-[(3S,4R)-4-{[(3,4-dichloro-5-methyl-1H-pyrrol-yl)carbonyl]amino}-3-propoxypiperidin-1-yl]-4-(1-methyl-1H-1,2,4-triazol-5-yl)-thiazole-5-carboxylate | $^1$H NMR (400 MHz, CDCl$_3$): δ 0.86 (t, 3H), 1.55 (m, 2H), 2.06 (m, 2H), 2.27 (s, 3H), 3.34 (m, 4H), 3.73 (s, 3H), 3.84 (t, 3H), 4.05 (m, 1H), 4.29 (m, 1H) 4.31 (m, 2H), 7.26 (d, 1H), 7.97 (s, 1H), 9.45 (s, 1H). LCMS: m/z 556.3 (M + H) | Intermediate 78 and Intermediate 2 |

| Ex | Compound | Data | SM |
|---|---|---|---|
| 213 | Ethyl 2-[(3S,4R)-4-{[(3,4-dichloro-5-methyl-1H-pyrrol-2-yl)carbonyl]amino}-3-propoxypiperidin-1-yl]-4-(3-fluoropyridin-2-yl)-1,3-thiazole-5-carboxylate | $^1$H NMR (400 MHz, CDCl$_3$): δ 0.84 (t, 3H), 1.02 (m, 2H), 1.16 (t, 3H), 2.09 (m, 2H), 2.27 (s, 3H), 3.33 (m, 4H), 3.70 (m, 2H), 4.16 (m, 3H), 4.33 (m, 1H), 7.26 (d, 1H), 7.46 (m, 1H), 8.51 (d, 1H), 9.44 (s, 1H). LCMS: m/z 584.3 (M + H) | Intermediate 78 and Intermediate 4 |
| 214 | Methyl 2-[(3S,4R)-4-{[(3,4-dichloro-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylate | $^1$H NMR (400 MHz, CDCl$_3$): δ 0.95 (t, 3H), 1.58 (m, 2H), 1.89 (m, 2H) 2.03 (m, 2H), 2.27 (s, 3H), 3.22 (m, 2H), 3.35 (m, 4H), 3.63 (m 4H), 3.71 (s, 3H), 4.10 (m, 2H), 4.38 (m, 1H), 7.19 (d, 1H), 7.21 (d, 1H), 7.26 (s, 1H), 9.35 (s, 1H). LCMS: m/z 599.3 (M + H) | Intermediate 78 and Intermediate 1 |

Examples 215-217

The following Examples were prepared according to the procedure described for Example 200 from the starting materials indicated in the table.

| Ex | Compound | Data | SM |
|---|---|---|---|
| 215 | 2-[3S,4R)-4-{[3,4-dichloro-5-methyl-1H-pyrrol-2-yl)carbonyl]amino}-3-propoxypiperidin-1-yl]-4-(1-methyl-1H-1,2,4-triazol-5-yl)-1,3-thiazole-5-carboxylic acid | $^1$H NMR (400 MHz, DMSO-d$_6$): δ 0.75 (t, 3H), 1.46 (m, 2H), 1.80 (m, 2H), 2.18 (s, 3H), 3.29 (s, 3H), 3.39 (m, 2H), 3.67 (m, 1H), 4.05 (m, 1H), 4.08 (m, 2H), 4.30 (m, 2H), 7.10 (d, 1H), 8.24 (s, 1H), 12.14 (s, 1H)) | Example 212 |

| Ex | Compound | Data | SM |
|---|---|---|---|
| | 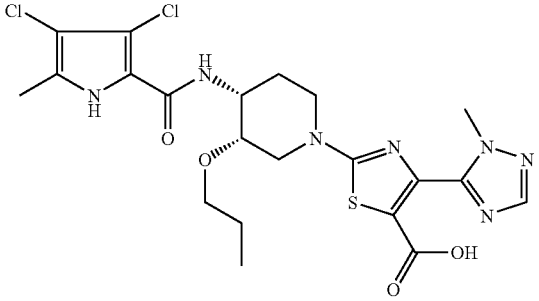 | LCMS: m/z 542.0 (M + H) | |
| 216 | 2-[(3S,4R)-4-{[(3,4-dichloro-5-methyl-1H-pyrrol-2-yl)carbonyl]amino}-3-propoxypiperidin-1-yl]-4-[1-(2-methoxyethyl)-1H-imidazol-2-yl]-1,3-thiazole-5-carboxylic acid<br><br>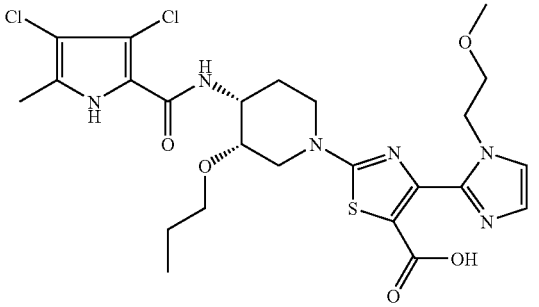 | $^1$H NMR (400 MHz, DMSO-d$_6$): δ 0.77 (t, 3H), 1.47 (m, 2H), 1.81 (m, 2H), 2.18 (s, 3H), 3.30 (s, 3H), 3.35 (m, 2H), 3.39 (m, 1H), 3.61 (m, 2H), 3.72 (m, 2H), 3.96 (m, 1H), 4.28 (m, 2H), 4.82 (m, 2H), 7.10 (d, 1H), 7.33 (s, 1H), 7.50 (s, 1H), 12.15 (s, 1H)<br>LCMS: m/z 585.3 (M + H). | Example 214 |
| 217 | 2-[(3S,4R)-4-{[(3,4-dichloro-5-methyl-1H-pyrrol-2-yl)carbonyl]amino}-3-propoxypiperidin-1-yl]-4-(3-fluoropyridin-2-yl)-1,3-thiazole-5-carboxylic acid | $^1$H NMR (400 MHz, DMSO-d$_6$): δ 0.77 (t, 3H), 1.47 (m, 2H), 1.78 (m, 2H), 3.18 (s, 3H), 3.33 (m, 4H), 3.62 (m, 1H), 3.93 (m, 1H), 4.26 (m, 2H), 7.09 (d, 1H), 7.52 (m, 1H), 7.76 (t, 1H), 8.44 (m, 1H), 12.14 (s, 1H), 12.85 (s, 1H).<br>LCMS: m/z 556.0 (M + H). | Example 213 |

Intermediate 1

Methyl 2-chloro-4-[1-(2-methoxyethyl)-1H-imidazol-2-yl]-1,3-thiazole-5-carboxylate

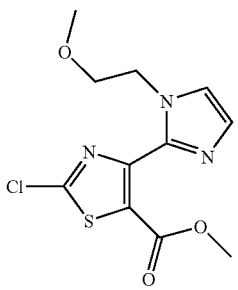

Methyl 2-amino-4-[1-(2-methoxyethyl)-1H-imidazol-2-yl]-1,3-thiazole-5-carboxylate (Intermediate 5; 0.55 g, 2.2 mmol) was suspended in glacial acetic acid (20 ml) and concentrated HCl (30 ml). The solution was cooled to 0° C. and to this a solution of sodium nitrite in water (15 ml) was added dropwise. After stirring at 0° C. for 10 mins, the reaction was slowly warmed to room temperature and stirred for 1 hour. Once complete by LCMS, a solution of urea (0.25 g) in water (10 ml) was added dropwise. After stirring at room temperature for 30 mins, solvent was removed under reduced pressure. The residue was partitioned with sat. NaHCO$_3$ (aq) and EtOAc. Extraction with EtOAc (×3), drying with MgSO$_4$ and concentrating yielded an orange oil which was used without purification (0.20 g). MS (ES) (M+H)$^+$: 302 for C$_{11}$H$_{12}$ClN$_3$O$_3$S; NMR: 3.34 (s, 3H), 3.62 (m, 2H), 3.81 (s, 3H), 4.22 (m, 2H), 7.24 (s, 2H).

Intermediates 2-4

The following Intermediates were synthesized by an analogous method to Intermediate WW from the starting materials (SM) given in the table below.

| Int | Compound | Data | SM |
| --- | --- | --- | --- |
| 2 | Methyl 2-chloro-4-(1-methyl-1H-1,2,4-triazol-5-yl)-1,3-thiazole-5-carboxylate | MS (ES) (M + H)$^+$: 259 for C$_8$H$_8$ClN$_4$O$_2$S NMR: 3.92 (s, 6H), 8.04 (s, 1H). | Intermediate 6 |
| 3 | Ethyl 2-chloro-4-pyrazin-2-yl-1,3-thiazole-5-carboxylate | MS (ES) (M + H)$^+$: 270 for C$_{10}$H$_8$ClN$_3$O$_2$S NMR: 1.16 (t, 3H), 4.22 (q, 2H), 8.76 (m, 2H), 9.03 (s, 1H) | Intermediate 7 |
| 4 | Ethyl 2-chloro-4-(3-fluoropyridin-2-yl)-1,3-thiazole-5-carboxylate | MS (ES): 287 (MH$^+$) for C$_{11}$H$_8$ClFN$_2$O$_2$S $^1$H-NMR (CDCl$_3$) δ: 1.25 (t, 3H); 4.28 (q, 2H); 7.55 (dd, 1H); 7.62 (t, 1H); 8.62 (d, 1H). | Intermediate 8 |

Intermediate 5

Methyl 2-amino-4-[1-(2-methoxyethyl)-1H-imidazol-2-yl]-1,3-thiazole-5-carboxylate

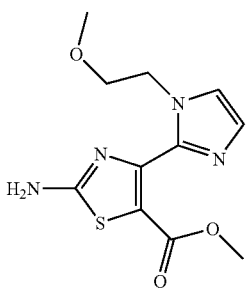

N-Iodosuccinimide (9.3 g, 41 mmol) was added to a mixture of 7.52 g (41 mmol) methyl 3-(1-methyl-1H-imidazol-2-yl)-3-oxopropanoate (Intermediate 10) and 7.5 g Amberlyst-15 resin in 400 ml EtOAc followed by stirring for 1 hour at room temperature. The resin was filtered off and rinsed with EtOAc. Solvent was removed from the filtrate and the residue was taken up in diethyl ether. Insoluble material was filtered off and rinsed with additional ether. Solvent was removed from the filtrate and the residue was dissolved in 200 ml MeOH before added 4.7 g (62 mmol) thiourea. The mixture was heated at reflux for 1 hour. Solvent was removed and the residue was taken up in aqueous $Na_2CO_3$. Insoluble material was collected by filtration and rinsed well with water. The solids were dried in vacuo affording 4.51 g of product: MS (ES) (M+H)$^+$: 283 for $C_{11}H_{14}N_4O_3S$ NMR: 3.22 (s, 3H), 3.61 (m, 2H), 3.69 (s, 3H), 4.32 (m, 2H), 7.91 (s, 2H), 8.41 (s, 2H).

Intermediates 6-8

The following Intermediates were synthesized by an analogous method to Intermediate 5 from the starting materials (SM) given in the table below.

| Int | Compound | | Data | SM |
|---|---|---|---|---|
| 6 | Methyl 2-amino-4-(1-methyl-1H-1,2,4-triazol-5-yl)-1,3-thiazole-5-carboxylate | | MS (ES) (M + H)$^+$: 240 for $C_8H_9N_5O_2S$ NMR: 3.61 (s, 3H), 3.71 (s, 3H), 7.96 (s, 1H), 8.10 (s, 2H). | Intermediate 9 |
| 7 | Ethyl 2-amino-4-pyrazin-2-yl-1,3-thiazole-5-carboxylate | | MS (ES) (M + H)$^+$: 251 for $C_{10}H_{10}N_4O_2S$ NMR: 1.07 (t, 3H), 4.04 (q, 2H), 7.99 (s, 2H), 8.65 (d, 1H), 8.69 (d, 1H), 8.81 (s, 1H) | Intermediate 11 |
| 8 | Ethyl 2-amino-4-(3-fluoropyridin-2-yl)-1,3-thiazole-5-carboxylate | | MS (ES): 268 (MH$^+$) for $C_{11}H_{10}FN_3O_2S$ $^1$H-NMR (DMSO-D6) δ: 1.01 (t, 3H); 3.99 (q, 2H); 7.53 (dd, 1H); 7.77 (t, 1H); 7.95 (s, 2H); 8.44 (d, 1H). | Intermediate 12 |

Intermediate 9

Methyl 3-(1-methyl-1H-1,2,4-triazol-5-yl)-3-oxopropanoate

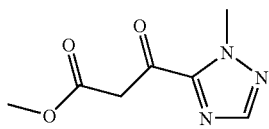

NaH (7.84 g, 196 mmol of a 60% dispersion in oil) was added portion-wise to a solution of 6.18 g (34.5 mmol) of 1-(1-methyl-1H-1,2,4-triazol-5-yl)ethanone (Ohta, S.; Kawasaki, I.; Fukuno, A.; Yamashita, M.; Tada, T.; Kawabata, T. *Chem. Pharm. Bull.* (1993), 41(7), 1226-31) in 100 ml dimethylcarbonate. The mixture was heated to 90° C. for 2 hour forming a thick slurry. After cooling to room temperature, the mixture was slowly transferred to 1N HCl over ice. The pH of the mixture was brought to about 7 with NaHCO₃ before being saturated with NaCl and extracted 4 times with EtOAc. The EtOAc was dried (MgSO₄) and concentrated to give an oil that was chromatographed on silica gel (100% DCM followed by gradient elution to 50% EtOAc in DCM). Product (5.3 g) was obtained as an oil. NMR: 3.78 (s, 3H), 4.11 (s, 2H), 4.22 (s, 3H), 7.94 (s, 1H).

Intermediates 10-12

The following Intermediates were synthesized by an analogous method to Intermediate 9 from the starting materials (SM) given in the table below.

| Int | Compound | Data | SM |
|---|---|---|---|
| 10 | Methyl 3-[1-(2-methoxyethyl)-1H-imidazol-2-yl]-3-oxopropanoate | MS (ES) (M + H)⁺: 227 for $C_{10}H_{14}N_2O_4$ NMR: 3.18 (s, 3H), 3.61 (m, 5H), 4.07 (s, 2H), 4.52 (m, 2H), 7.24 (s, 1H), 7.61 (s, 1H) | Intermediate 13 |
| 11 | Ethyl 3-oxo-3-pyrazin-2-ylpropanoate | MS (ES) (M + H)⁺: 195 for $C_9H_{10}N_2O_3$ NMR: 1.15 (t, 3H), 4.11 (q, 2H), 4.18 (s, 2H), 8.82 (s, 1H), 8.94 (s, 1H), 9.17 (s, 1H) | pyrazine-2-carboxylic acid |
| 12 | Ethyl 3-(3-fluoropyridin-2-yl)-3-oxopropanoate | MS (ES): 212 (MH⁺) for $C_{10}H_{10}FNO_3$ ¹H-NMR (DMSO-D6) δ: 1.15 (t, 3H); 3.99 (q, 2H); 4.10 (s, 2H); 7.45 (dd, 1H); 8.36 (t, 1H); 8.56 (d, 1H). | 3-fluoropyridine carboxylic acid |

Intermediate 13

1-[1-(2-Methoxyethyl)-1H-imidazol-2-yl]ethanone

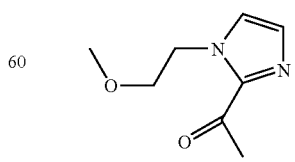

A solution of 30 ml (75 mmol) of 2.5 M n-butyllithium in hexanes was added slowly to a solution of 8.48 g (61.3 mmol) 1-(2-Methoxyethyl)-1H-imidazole (WO 2003055876 A1 in 200 ml THF cooled in a dry ice-acetone bath. After stirring 1 hour, 8 ml (75 mmol) of N-methoxy-N-methylacetamide was added quickly, and the solution was allowed to warm to room temperature over 30 min. After quenching with aqueous NH$_4$Cl, the mixture was diluted with water and extracted twice with EtOAc, which was washed with brine, dried (MgSO$_4$) and concentrated to give an oil that was chromatographed on silica gel (100% DCM followed by gradient elution to 50% EtOAc in DCM). Product (8.5 g) was obtained as a mobile oil. MS (ES) (M+H)$^+$: 169 for C$_8$H$_{12}$CN$_2$O$_2$ NMR: 2.69 (s, 3H), 3.34 (s, 3H), 3.71 (m, 2H), 4.61 (m, 2H), 7.12 (s, 1H), 7.26 (s, 1H).

Intermediate 14

Ethyl 3-bromo-4-chloro-5-methyl-1H-pyrrole-2-carboxylate

Bromine (0.56 ml, 11 mmol) was added to a solution of 1 g (5.3 mmol) of ethyl 4-chloro-5-methyl-1H-pyrrole-2-carboxylate (WO2006087543) and 0.8 ml (5.7 mmol) Et$_3$N in CH$_2$Cl$_2$. After stirring at room temperature for 2 h, aqueous NaHSO$_3$ was added and the CH$_2$Cl$_2$ was removed and the aqueous residue was partitioned between water and EtOAc. The EtOAc layer was separated and washed with brine. The EtOAc layer was dried over anhydrous MgSO$_4$, and the solvent was removed to give 1.5 g of the product as a solid. MS (ES) (MH$^+$): 240 for C$_8$H$_9$BrClNO$_2$; NMR (d$_6$-DMSO): 1.3 (t, 3H), 2.2 (s, 3H), 4.2 (q, 2H), 12.3 (s, 1H).

Intermediate 15

Ethyl 4-chloro-3-cyano-5-methyl-1H-pyrrole-2-carboxylate

Nitrogen gas was bubbled through a mixture of 1.4 g (5.25 mmol) of ethyl 3-bromo-4-chloro-5-methyl-1H-pyrrole-2-carboxylate (Intermediate 14), 470 g (4 mol) Zn(CN)$_2$, 250 mg (0.26 mmol) Pd$_2$(dba)$_3$ and 302 mg (0.26 mmol) dppf in 15 ml DMF for 15 min. The mixture was heated at 130° C. for 1 h. Additional Zn(CN)$_2$ (1 g), Pd$_2$(dba)$_3$ (500 mg) and dppf (604 mg) were added. After bubbling through N$_2$ for 15 min and heating at 130° C. for 2 h, additional Zn(CN)$_2$ (0.5 g), Pd$_2$(dba)$_3$ (250 mg) and dppf (302 mg) were added. Heating was continued at 130° C. for 2 h. Solvent was removed and the residue was partitioned between EtOAc and water. The EtOAc was separated and washed with brine. Combined aqueous layers were extracted again with EtOAc, which was washed with brine. Combined EtOAc extracts were dried (MgSO$_4$) and concentrated. The residue was purified by silica gel chromatography (100% CH$_2$Cl$_2$ followed by gradient elution to 5% MeOH in CH$_2$Cl$_2$) to afford 750 mg of product as a solid. MS (ES) (MH$^+$): 213 for C$_9$H$_9$ClN$_2$O$_2$; NMR (d$_6$-DMSO): 1.3 (t, 3H), 2.2 (s, 3H), 4.3 (q, 2H), 13.1 (s, 1H).

Intermediate 16

4-Chloro-3-cyano-5-methyl-1H-pyrrole-2-carboxylic acid

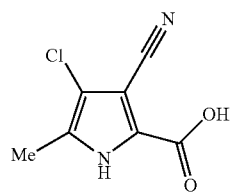

A solution of 670 mg (3.2 mmol) of ethyl 4-chloro-3-cyano-5-methyl-1H-pyrrole-2-carboxylate (Intermediate 15) and 3.2 ml (3.2 mmol) 1N NaOH in 20 ml MeOH was heated at 100° C. in a microwave reactor for 2 h. The mixture was diluted with water and extracted with EtOAc. The EtOAc was washed with 1N NaOH. The combined aqueous layers were acidified with concentrated HCl and extracted 2 times with EtOAc, each extract being washed with brine. The combined EtOAc layers were dried over anhydrous MgSO$_4$, filtered and the solvent was removed to give 535 mg of product as a solid. MS (ES) (M−H$^-$): 183 for C$_7$H$_5$ClN$_2$O$_2$; NMR (d$_6$-DMSO): 2.2 (s, 3H), 12.9 (s, 1H), 13.3 (s, 1H).

Intermediate 17

Ethyl (3S,4R)-4-[(tert-butoxycarbonyl)amino]-3-(prop-2-en-1-yloxy)piperidine-1-carboxylate

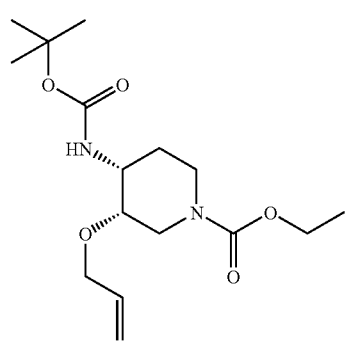

Chiral HPLC purification on Cis(±)ethyl-4-[(tert-butoxycarbonyl)amino]-3-(prop-2-en-1-yloxy)piperidine-1-carboxylate (15 g) (WO2006087543) was performed using a Chiralpak AD column and methanol as the eluent to provide 6.3 g of the title compound.

MS (ES) (M+H): 329, for C$_{16}$H$_{28}$N$_2$O$_5$; NMR: 1.28 (t, 3H), 1.47 (s, 9H), 1.68 (m, 2H), 2.88 (brt, 2H), 3.50 (m, 1H), 3.68 (m, 1H), 3.90 (m, 1H), 4.00-4.45 (m, 3H), 4.10 (q, 2H), 4.92 (brs, 1H), 5.20 (m, 2H), 5.86 (m, 1H).

Intermediate 18

Ethyl (3S,4R)-4-amino-3-(prop-2-en-1-yloxy)piperidine-1-carboxylate

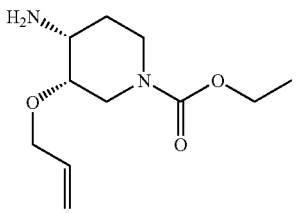

Ethyl (3S,4R)-4-[(tert-butoxycarbonyl)amino}-3-(prop-2-en-1-yloxy)piperidine-1-carboxylate (Intermediate 17, 5 g, 12.7 mmol) was dissolved in dichloromethane (200 mL) and trifluoroacetic acid (9.79 mL, 127 mmol) was added. The reaction mixture was allowed to stir for 3 h at room temperature. The reaction mixture was basified with saturated sodium bicarbonate solution (pH ~8) and the layers were separated. The aqueous layer was extracted with dichloromethane; organic layer was dried over anhydrous sodium sulphate and concentrated under reduced pressure to afford 2.7 g (93.24%). MS (ES) (M+H): 228. for $C_{11}H_{20}N_2O_3$.

Intermediate 19

Ethyl (3S,4R)-4-{[(3,4-dichloro-5-methyl-1H-pyrrol-2-yl)carbonyl]amino}-3-(prop-2-en-1-yloxy)piperidine-1-carboxylate

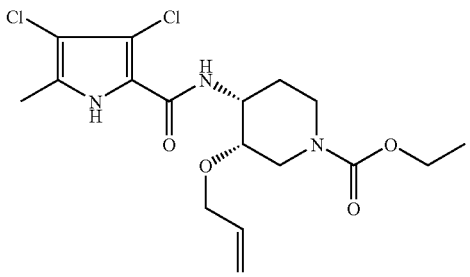

To a solution of 3,4-dichloro-5-methyl-1H-pyrrole-2-carboxylic acid (WO200687543, 2.27 g, 11.8 mmol) and Ethyl (3S,4R)-4-amino-3-(prop-2-en-1-yloxy)piperidine-1-carboxylate (Intermediate 18, 2.7 g, 11.8 mmol) in dichloromethane (180 mL) was added HOBt (1.85 g, 11.8 mM) and N-methylmorpholine (3.8 mL, 35.43 mmol). The reaction mixture was stirred for 1 h at room temperature and EDC HCl (4.07 g, 21.3 mmol) was added. The resulting reaction mixture was stirred for room temperature overnight, treated by the addition of 2 N HCl (120 mL) and the resulting layers were evaporated. The organic layer was washed with sodium bicarbonate (150 mL), water (150 mL) and brine, dried over anhydrous sodium sulphate, filtered, concentrated under vacuum. Purification by column chromatography (silica gel, 35% ethylacetate in pet ether) to afforded 3.5 g (73.6%) as brown solid. NMR (400 MHz, DMSO-d$_6$): δ 1.24 (t, 3H), 1.62 (m, 2H), 2.16 (s, 3H), 2.97 (m, 2H), 3.53 (m, 2H), 3.97 (m, 4H), 4.15 (q, 2H), 4.21 (m, 1H), 5.13 (d, 1H), 5.23 (d, 1H), 5.87 (m, 1H), 7.10 (d, 1H), 12.10 (s, 1H).

Intermediate 20

3,4-Dichloro-5-methyl-N-[(3S,4R)-3-(prop-2-en-1-yloxy)piperidin-4-yl]-1H-pyrrole-2-carboxamide

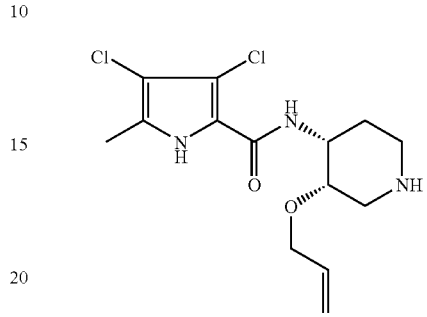

To as solution of Ethyl (3S,4R)-4-{[(3,4-dichloro-5-methyl-1H-pyrrol-2-yl)carbonyl]amino}-3-(prop-2-en-1-yloxy)piperidine-1-carboxylate (Intermediate 19, 2.5 g, 6.20 mmol) in toluene (450 mL) was added iodine (6.31 g, 24.8 mmol) followed by hexamethyldisilane (10.34 mL, 49.62 mmol and the reaction mixture was refluxed for 30 h. The reaction mixture was treated with 10% sodium thiosulphate (300 mL) and layers were separated. The aqueous layer was extracted with toluene and the organic layer was dried over anhydrous sodium sulphate and concentrated under reduced pressure. Purification by column chromatography (silica, 4% methanol in dichloromethane) afforded 750 mg (36.54%) of 3,4-dichloro-5-methyl-N-[(3S,4R)-3-(prop-2-en-1-yloxy)piperidin-4-yl]-1H-pyrrole-2-carboxamide.

LC-MS: m/z 331 (M+H)
$^1$H NMR (400 MHz, DMSO-d$_6$): δ 1.57 (m, 2H), 2.16 (s, 3H), 2.56 (s, 1H), 2.81 (d, 1H), 3.07 (d, 1H), 3.40 (m, 1H), 3.90 (m, 1H), 4.14 (m, 2H), 5.14 (d, 1H), 5.27 (d, 1H), 5.92 (m, 1H), 7.12 (d, 1H).

Intermediate 21

Ethyl (3S,4R)-4-{[(4-chloro-3-cyano-5-methyl-1H-pyrrol-2-yl)carbonyl]amino}-3-(prop-2-en-1-yloxy)piperidine-1-carboxylate

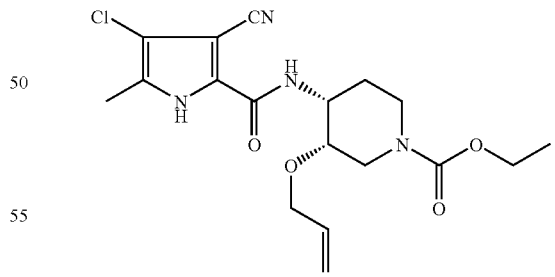

To a solution of 4-chloro-3-cyano-5-methyl-1H-pyrrole-2-carboxylic acid (Intermediate 16, 562 mg, 3.07 mmol) and ethyl (3S,4R)-4-amino-3-(prop-2-en-1-yloxy)piperidine-1-carboxylate (Intermediate 18, 700 mg, 3.07 mmol) in dichloromethane (150 mL) were added HOBt (470 mg, 3.07 mmol) and N-methyl morpholine (1.01 mL, 9.21 mmol). The reaction mixture was stirred for 1 h at room temperature and EDC HCl (1.05 g, 5.52 mmol) was added. The resulting reaction mixture, stirred at room temperature overnight. The reaction mixture was quenched with the addition of 2 N HCl (100 mL). The organic layer was washed with sodium bicarbonate (150 mL), water (150 mL) and brine, and dried over anhydrous sodium sulphate, filtered, and concentrated under vacuum. Purification by column chromatography (silica, 35% ethyl acetate in pet ether) afforded Ethyl (3S,4R)-4-{[(4-chloro-3-cyano-5-methyl-1H-pyrrol-2-yl)carbonyl]amino}-3-(prop-2-en-1-yloxy)piperidine-1-carboxylate 1.1 g (90%) as brown solid.

LC-MS: m/z 395 (M+H).

Intermediate 22

4-Chloro-3-cyano-5-methyl-N-[(3S,4R)-3-(prop-2-en-1-yloxy)piperidin-4-yl]-1H-pyrrole-2-carboxamide

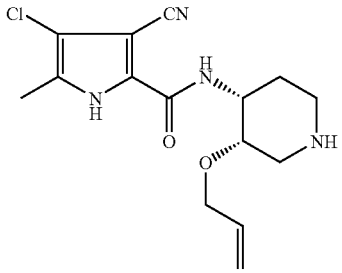

To as solution of ethyl (3S,4R)-4-{[(4-chloro-3-cyano-5-methyl-1H-pyrrol-2-yl)carbonyl]amino}-3-(prop-2-en-1-yloxy)piperidine-1-carboxylate (Intermediate 21, 1.1 g, 2.79 mmol) in toluene (190 mL) was added iodine (2.9 g, 11.16 mmol) followed by hexamethyldisilane (4.65 mL, 22.33 mmol). The reaction mixture was heated to reflux for 30 h and then cooled to room temperature. The reaction mixture was treated 10% sodium thiosulphate (150 mL) and the layers were separated. The aqueous layer was extracted with toluene and the organic layer was dried over anhydrous sodium sulphate and concentrated under reduced pressure. Purification by column chromatography (silica, 4% methanol in dichloromethane) afforded 300 mg (33%) of 4-chloro-3-cyano-5-methyl-N-[(3S,4R)-3-(prop-2-en-1-yloxy)piperidin-4-yl]-1H-pyrrole-2-carboxamide LC-MS: m/z 323 (M+H).

$^1$H NMR (400 MHz, DMSO-d$_6$): δ 1.58 (m, 1H), 1.70 (m, 1H), 2.18 (s, 3H), 2.69 (m, 3H), 2.93 (d, 1H), 3.17 (d, 1H), 3.33 (m, 1H), 3.52 (br s, 1H), 3.97 (m, 1H), 4.10 (m, 2H), 5.11 (d, 1H), 5.31 (d, 1H), 5.90 (m, 1H), 7.50 (d, 1H).

Intermediate 23

Ethyl (3S,4R)-4-benzylamino-3-ethoxypiperidine-1-carboxylate

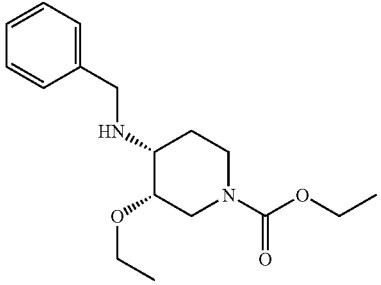

Cis(±)-Ethyl (4-(benzylamino)-3-ethoxypiperidine-1-carboxylate

Chiral HPLC purification on Cis(±)ethyl 4-[benzylamino]-3-ethoxypiperidine-1-carboxylate (21 g) (WO2006087543) was performed using a Chiralpak AD column and methanol as the eluent to provide 11 g of the title compound.

MS (ES) MH$^+$: 307 for C$_{17}$H$_{26}$N$_2$O$_3$; NMR: 1.08 (t, 3H); 1.15 (t, 3H); 1.50 (m, 2H); 1.75 (br s, 1H); 2.65 (br s, 1H); 2.92 (m, 2H); 3.47 (br s, 1H); 3.55 (m, 1H); 3.71 (m, 3H); 3.88 (br s, 1H); 3.98-4.05 (m, 2H); 7.18-7.34 (m 5H)

Intermediate 24

Ethyl (3S,4R)-4-amino-3-ethoxypiperidine-1-carboxylate

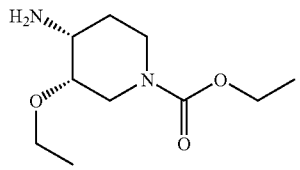

Ethyl (3S,4R)-4-{[(benzyloxy)carbonyl]amino}-3-ethoxypiperidine-1-carboxylate (Intermediate 23, 2.4 g, 6.87 mmol) was dissolved in methanol (150 mL) and hydrogenated over 10% palladium on carbon (1.5 g) under 50 psi of hydrogen pressure for 2 h at room temperature. The reaction mixture was then filtered through a celite bed and the filtrate was concentrated under reduced pressure to yield 1.33 g (89.62%) of Ethyl (3S,4R)-4-amino-3-ethoxypiperidine-1-carboxylate as liquid.

MASS (ES+v): m/z 217 (M+H).

Intermediate 25

Ethyl (3S,4R)-4-{[(3,4-dichloro-5-methyl-1H-pyrrol-2-yl)carbonyl]amino}-3-ethoxypiperidine-1-carboxylate

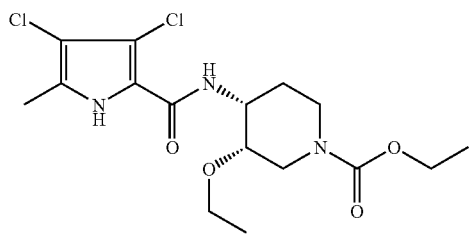

To a solution of 3,4-dichloro-5-methyl-1H-pyrrole-2-carboxylic acid (WO200687543, 1.18 g, 6.15 mmol) and ethyl (3S,4R)-4-amino-3-ethoxypiperidine-1-carboxylate (Intermediate 24, 1.33 g, 6.15 mmol) in dichloromethane (170 mL) were added HOBT (941 mg, 6.15 mmol) and N-methyl morpholine (2.02 mL, 18.45 mmol). The reaction mixture was stirred for 1 h at room temperature and EDC HCl (2.11 g, 11.07 mmol) was added. The resulting reaction mixture was stirred for room temperature overnight. The reaction was quenched with the addition of 2N HCl (120 mL). The organic layer was washed with sodium bicarbonate (150 mL), water (150 mL), and brine, and dried over anhydrous sodium sulphate, filtered, concentrated under vacuum. Purification by flash column chromatography (silica, 35% ethylacetate in pet ether) afforded ethyl (3S,4R)-4-{[(3,4-dichloro-5-methyl-1H-pyrrol-2-yl)carbonyl]amino}-3-ethoxypiperidine-1-carboxylate 1.9 g (49%) as solid.

$^1$H NMR (400 MHz, DMSO-d$_6$): δ 1.15 (t, 3H), 1.17 (t, 3H), 1.59 (m, 2H), 2.15 (s, 3H), 2.94 (m, 2H), 3.37 (t, 1H), 3.46 (m, 1H), 3.97 (m, 1H), 6.64 (m, 1H), 4.03 (q, 2H), 4.10 (q, 2H), 7.07 (d, 1H), 12.10 (s, 1H).
LC-MS: m/z 391 (M+H).

Intermediate 26

3,4-Dichloro-N-[(3S,4R)-3-ethoxypiperidin-4-yl]-5-methyl-1H-pyrrole-2-carboxamide

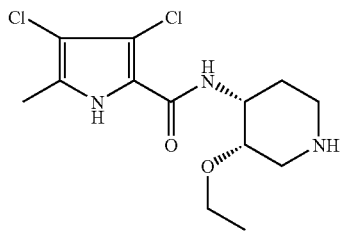

A solution of ethyl (3S,4R)-4-{[(3,4-dichloro-5-methyl-1H-pyrrol-2-yl)carbonyl]amino}-3-ethoxypiperidine-1-carboxylate (Intermediate 25, 1.9 g, 4.85 mmol), potassium hydroxide (1.9 g, 34.01 mmol), and hydrazine hydrate (1.71 mL, 34.01 mmol) in ethylene glycol (150 mL) was stirred for 40 h at 120° C. The reaction mixture was poured in to water (120 mL) and extracted with ethyl acetate (2×150 mL). The combined organic extracts were dried over anhydrous sodium sulphate, filtered, concentrated in vacuo to yield the crude product, which was triturated with water (30 mL) to afford 3,4-dichloro-N-[(3S,4R)-3-ethoxypiperidin-4-yl]-5-methyl-1H-pyrrole-2-carboxamide 1.0 g (65%) as solid.
LC-MS: m/z 320.11 (M+H).
$^1$H NMR (400 MHz, DMSO-d$_6$): δ 1.16 (t, 3H), 1.58 (m, 2H), 2.18 (s, 3H), 2.55 (s, 1H), 2.84 (d, 1H), 3.06 (d, 1H), 3.39 (m, 4H), 3.63 (m, 1H), 4.02 (m, 1H), 4.42 (s, 1H), 7.10 (d, 1H).

Intermediate 27

4-Chloro-5-methyl-1H-pyrrole-2-carboxylic acid

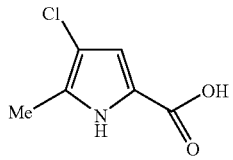

Aqueous lithium hydroxide (2 M, 4 ml) was warmed to 50° C. and a solution of ethyl 4-chloro-5-methyl-1H-pyrrole-2-carboxylate (Intermediate 28, 0.30 g, 1.60 mmol) in MeOH was added to it. The reaction was heated to 80° C. and stirred for two hours. The MeOH was removed and the aqueous solution was cooled to 0° C. and acidified with 30% HCl. The precipitated product (0.23 g, 92%) was filtered and dried. MS (ES): 160 (M+1) for C$_6$H$_6$ClNO$_2$; NMR (CDCl$_3$): 2.25 (s, 3H), 6.85 (s, 1H), 8.98 (brs, 1H).

Intermediate 28

Ethyl 4-chloro-5-methyl-1H-pyrrole-2-carboxylate

N-Chlorosuccinimide (0.67 g, 5.08 mmol) was added to a solution of ethyl 5-methyl-1H-pyrrole-2-carboxylate (Intermediate 29, 0.65 g, 4.23 mmol) in chloroform (20 ml). The reaction was warmed to 40° C. and stirred for 4 h, then poured to a beaker containing 2 N NaOH (20 ml) at 0° C. The layers were separated and the aqueous layer was extracted with chloroform 3 times. The combined organic extracts were dried over magnesium sulfate and concentrated. The resultant off-white solid was purified by flash chromatography (hexanes/EtOAc, 16:1) to give the title product as a white solid (0.3 g, 38%). MS (ES): 188 (M+1) for C$_8$H$_{10}$ClNO$_2$; NMR (CDCl$_3$): 1.34 (t, 3H), 2.27 (s, 3H), 4.30 (q, 2H), 6.76 (s, 1H), 9.07 (brs, 1H).

Intermediate 29

Ethyl 5-methyl-1H-pyrrole-2-carboxylate

Sodium (2.79 g, 0.121 mmol) was dissolved in anhydrous EtOH (100 ml), then 2,2,2-trichloro-1-(5-methyl-1H-pyrrol-2-yl)ethanone (Intermediate 30, 22.5 g, 0.099 mmol) was added in small portions. The dark brown solution was stirred at room temperature for 30 min then concentrated under vacuum to a small volume. The mixture was cooled in an ice bath and 3 N HCl was added slowly, then the mixture was extracted with diethyl ether (3×100 ml). The ether extracts were washed with 10% NaHCO$_3$, water and brine, dried over Na$_2$SO$_4$ and concentrated in vacuo to give the title compound as a brown solid. (15.04 g). NMR: 1.32 (t, 3H), 2.1 (s, 3H), 4.371 (q, 2H), 5.96 (dd, 1H), 6.78 (dd, 1H), 11.67 (s, 1H).

Intermediate 30

2,2,2-Trichloro-1-(5-methyl-1H-pyrrol-2-yl)ethanone

2-Methyl-1H-pyrrole (Intermediate 31, 10 g, 0.123 mmol) in anhydrous diethyl ether (30 ml) was added dropwise over 1 h to a stirred solution of trichloroacetyl chloride (29 g, 0.16 mmol) in anhydrous Et$_2$O (100 ml). The mixture was stirred for a further 1 h then K$_2$CO$_3$ (10 g/30 ml) was added slowly through a dropping funnel. The organic phase was dried over Na$_2$SO$_4$ and treated with decolorizing charcoal (3 g) for 30 min at room temperature. The resulting purple solution was concentrated and triturated with n-hexanes to give the title compound as a purple solid. (16.72 g). NMR (CDCl$_3$): 2.36 (s, 3H), 6.04 (dd, 1H), 7.45 (dd, 1H), 10.344 (s, 1H).

Intermediate 31

2-Methyl-1H-pyrrole

Potassium hydroxide (50 g, 0.89 mmol) was added to a solution of ethylene glycol (750 ml) and 1H-pyrrole-2-carbaldehyde (50 g, 0.53 mmol). Hydrazine hydrate (37 ml, 0.745 mmol) was added slowly over 15 min. The reaction mixture was refluxed at 90° C. for 90 min. The mixture was cooled to room temperature and cold water (250 ml) was added. The aqueous mixture was extracted with DCM (250 ml). The organic phase was washed with water (250 ml), dried over Na$_2$SO$_4$ and concentrated in vacuo. Kugelrohr distillation gave the title compound as a clear colorless liquid (29.75 g). NMR: 2.1 (s, 3H), 5.77 (s, 1H), 5.9 (dd, 1H), 6.25 (dd, 1H), 10.54 (s, 1H).

Intermediate 32

Ethyl (3S,4R)-4-{[(4-chloro-3-cyano-5-methyl-1H-pyrrol-2-yl)carbonyl]amino}-3-ethoxypiperidine-1-carboxylate

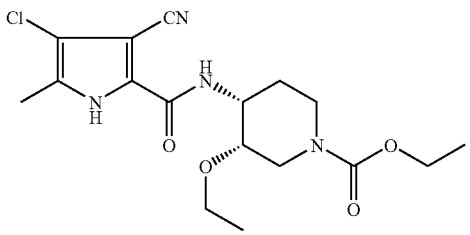

To a solution of 4-chloro-3-cyano-5-methyl-1H-pyrrole-2-carboxylic acid (Intermediate 16, 1.01 g, 5.55 mmol) and ethyl (3S,4R)-4-amino-3-ethoxypiperidine-1-carboxylate (Intermediate 24, 1.2 g, 5.55 mmol) in dichloromethane (480 mL) were added HOBt (850 mg, 5.55 mmol) and N-methyl morpholine (1.82 mL, 16.66 mmol). The reaction mixture was stirred for 1 h at room temperature and EDC HCl (1.9 g, 9.99 mmol) was added. The resulting reaction mixture was stirred at room temperature overnight. The reaction mixture was quenched with 2N hydrochloric acid (120 mL). The organic layer was washed with sodium bicarbonate (150 mL), water (150 mL) and brine, dried over anhydrous sodium sulphate, filtered, concentrated under vacuum. Purification by flash column chromatography (silica, 35% ethylacetate in pet ether) afforded ethyl (3S,4R)-4-{[(4-chloro-3-cyano-5-methyl-1H-pyrrol-2-yl)carbonyl]amino}-3-ethoxypiperidine-1-carboxylate 1.5 g (71%) as solid.

$^1$H NMR (400 MHz, DMSO-d$_6$): δ 1.15 (m, 6H), 1.59 (m, 2H), 2.20 (s, 3H), 3.01 (m, 2H), 3.42 (m, 1H), 3.50 (m, 1H), 3.61 (m, 1H), 4.06 (m, 4H), 7.46 (d, 1H), 12.69 (s, 1H)
LCMS: m/z 383 (M+H).

Intermediate 33

4-Chloro-3-cyano-N-[(3S,4R)-3-ethoxypiperidin-4-yl]-5-methyl-1H-pyrrole-2-carboxamide

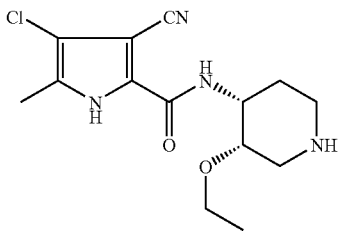

A solution of ethyl (3S,4R)-4-{[(4-chloro-3-cyano-5-methyl-1H-pyrrol-2-yl)carbonyl]amino}-3-ethoxypiperidine-1-carboxylate (Intermediate 32, 1.5 g, 3.92 mmol), potassium hydroxide (1.54 g, 27.48 mmol), and hydrazine hydrate (1.38 mL, 27.48 mmol) in ethylene glycol (200 mL) was stirred for 60 h at 120° C. The reaction mixture was poured in to water (300 mL) and extracted with ethyl acetate (2×300 mL). The combined organic extracts were dried over anhydrous sodium sulphate, filtered, concentrated under vacuum to yield the crude product which was triturated with water (150 mL) to afford 4-chloro-3-cyano-N-[(3S,4R)-3-ethoxypiperidin-4-yl]-5-methyl-1H-pyrrole-2-carboxamide (670 mg, 55%) as solid.

LCMS: m/z 311 (M+H).

$^1$H NMR (400 MHz, DMSO-d$_6$): δ 1.16 (t, 3H), 1.75 (m, 2H), 2.18 (s, 3H), 2.78 (m, 2H), 3.01 (d, 1H), 3.21 (d, 1H), 3.46 (m, 2H), 3.54 (m, 1H), 3.58 (m, 2H), 4.08 (m, 1H), 7.41 (d, 1H).

Intermediate 34

Ethyl (3S,4R)-4-{[(4-chloro-5-methyl-1H-pyrrol-2-yl)carbonyl]amino}-3-ethoxypiperidine-1-carboxylate

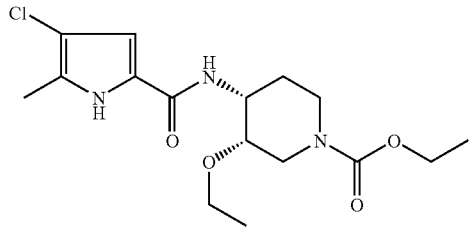

To a solution of 4-chloro-5-methyl-1H-pyrrole-2-carboxylic acid (Intermediate 27, 0.87 g, 5.55 mol) and ethyl (3S,4R)-4-amino-3-ethoxypiperidine-1-carboxylate (Intermediate 24, 1.2 g, 5.55 mmol) in dichloromethane (150 mL) was added HOBT (850 mg, 0.55 mmol) and N-methyl morpholine (1.82 mL, 1.66 mmol). The reaction mixture was stirred for 1 h at room temperature and EDC HCl (1.9 g, 9.99 mmol) was added. The resulting reaction mixture was stirred at room temperature overnight. The reaction mixture was quenched with the addition of 2N HCl (120 mL). The organic layer was washed with sodium bicarbonate (150 mL), water (150 mL) and brine, dried over anhydrous sodium sulphate, filtered, concentrated under vacuum. Purification by column chromatography (silica, 35% ethyl acetate in pet ether) afforded Ethyl (3S,4R)-4-{[(4-chloro-5-methyl-1H-pyrrol-2-yl)carbonyl]amino}-3-ethoxypiperidine-1-carboxylate 1.6 g (80%) as brown solid.

LCMS: m/z 358 (M+H).

$^1$H NMR (400 MHz, DMSO-d$_6$): δ 1.11 (t, 3H), 1.20 (t, 3H), 1.46 (d, 1H), 1.80 (m, 1H), 2.17 (s, 3H), 2.90 (m, 2H), 3.38 (m, 1H), 3.50 (m, 2H), 4.03 (m, 5H), 6.85 (s, 1H), 7.51 (d, 1H), 11.58 (s, 1H).

Intermediate 35

4-Chloro-N-[(3S,4R)-3-ethoxypiperidin-4-yl]-5-methyl-1H-pyrrole-2-carboxamide

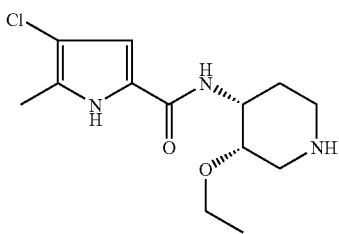

A solution of ethyl (3S,4R)-4-{[(4-chloro-5-methyl-1H-pyrrol-2-yl)carbonyl]amino}-3-ethoxypiperidine-1-carboxylate (Intermediate 34, 1.6 g, 4.48 mmol), potassium hydroxide (1.76 g, 31.37 mmol), and hydrazine hydrate (1.6 mL, 31.37 mmol) in ethylene glycol (180 mL) was stirred for 40 h at 120° C. The reaction mixture was poured in to water (120 mL) and extracted with ethyl acetate (2×150 mL). The combined organic extracts were dried over anhydrous sodium sulphate, filtered, concentrated in vacuo to yield the crude product which was triturated with water (30 mL) to afford 4-chloro-N-[(3S,4R)-3-ethoxypiperidin-4-yl]-5-methyl-1H-pyrrole-2-carboxamide 480 mg (37%) as solid.

LCMS: m/z 285 (M+H).

Intermediate 36

Methyl (3S,4R)-4-benzylamino-3-methylpiperidine-1-carboxylate

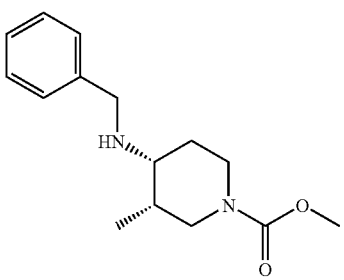

Chiral HPLC purification on Cis(±)methyl-4benzylamino]-3-methylpiperidine-1-carboxylate (*Helvetica Chimica Acta,* 1969, 52, 629-639, 20 g) was performed using a Chiralpak AD column and methanol as the eluent to provide 9 g of the title compound.

$^1$H NMR (400 MHz, CDCl$_3$): δ 0.92 (d, 3H), 1.53 (m, 1H), 1.62 (m, 1H), 1.80 (br s, 1H), 3.04 (m, 1H), 3.40 (m, 2H), 3.48 (m, 1H), 3.68 (s, 3H).

Intermediate 37

Methyl (3S,4R)-4-amino-3-methylpiperidine-1-carboxylate

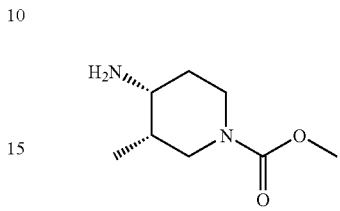

Methyl (3S,4R)-4-(benzylamino)-3-methylpiperidine-1-carboxylate (8.0 g, 0.02 mol) was dissolved in methanol (200 mL) and hydrogenated at room temperature, under 50 psi of hydrogen pressure, in the presence of palladium (2.5 g) on carbon for 2 h. The solution was then filtered and concentrated under reduced pressure to yield 3.5 g (92%) Methyl (3S,4R)-4-amino-3-methylpiperidine-1-carboxylate as liquid.

MASS (APCI): m/z 173.3 (M+H).
$^1$H NMR (400 MHz, CDCl$_3$): δ 0.92 (d, 3H), 1.53 (m, 1H), 1.62 (m, 1H), 1.80 (br s, 1H), 3.04 (m, 1H), 3.40 (m, 2H), 3.48 (m, 1H), 3.68 (s, 3H).

Intermediate 38

Methyl (3S,4R)-4-{[(4-chloro-5-methyl-1H-pyrrol-2-yl)carbonyl]amino}-3-methylpiperidine-1-carboxylate

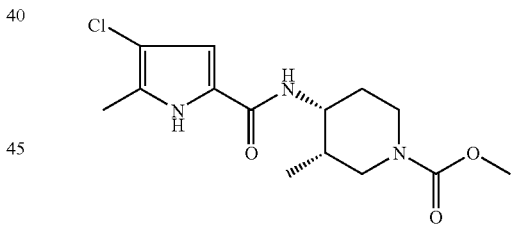

To a solution of 4-chloro-5-methyl-1H-pyrrole-2-carboxylic acid (Intermediate 27, 2.5 g, 15.82 mmol) and methyl (3S,4R)-4-amino-3-methylpiperidine-1-carboxylate (Intermediate 37, 2.72 g, 15.82 mmol) in dichloromethane (200 mL) were added HOBt (2.42 g, 15.82 mmol) and N-methyl morpholine (5.2 mL, 47.46 mmol). The reaction mixture was stirred for 1 h at room temperature and EDC HCl (5.43 g, 28.47 mmol) was added. The resulting reaction mixture was stirred at room temperature overnight. The reaction was quenched with the addition of 2N HCl (120 mL). The organic layer was washed with sodium bicarbonate (150 mL), water (150 mL), and brine, dried over anhydrous sodium sulphate, filtered, concentrated under vacuum. Purification by column chromatography (silica, 35% ethylacetate in petroleum ether) afforded methyl (3S,4R)-4-{[(4-chloro-5-methyl-1H-pyrrol-2-yl)carbonyl]amino}-3-methylpiperidine-1-carboxylate 2.2 g (46%) as brown solid.

Mass (APCI): m/z 314.0 (M+H)

¹H NMR (400 MHz, DMSO-d₆): δ 0.83 (s, 3H), 1.54 (m, 1H), 1.66 (m, 1H), 2.18 (s, 3H), 3.58 (m, 2H), 3.52 (m, 1H), 3.67 (s, 3H), 4.12 (m, 1H), 6.90 (s, 1H), 7.54 (d, 1H), 11.56 (s, 1H).

Intermediate 39

4-Chloro-5-methyl-N-[(3S,4R)-3-methylpiperidin-4-yl]-1H-pyrrole-2-carboxamide

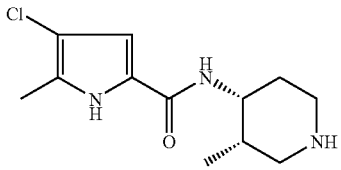

A solution of methyl (3S,4R)-4-{[(4-chloro-5-methyl-1H-pyrrol-2-yl)carbonyl]amino}-3-methylpiperidine-1-carboxylate (Intermediate 38, 2.2 g, 7.05 mmol), potassium hydroxide (2.76 g, 49.35 mmol), and hydrazine hydrate (2.5 mL, 49.35 mmol) in ethylene glycol (150 mL) was stirred for 40 h at 120° C. The reaction mixture was poured in to water (120 mL) and extracted with ethyl acetate (2×150 mL). The combined organic extracts were dried over anhydrous sodium sulphate, filtered, concentrated in vacuo to yield the crude product which was triturated with water (30 mL) to afford 4-chloro-5-methyl-N-[(3S,4R)-3-methylpiperidin-4-yl]-1H-pyrrole-2-carboxamide 950 mg (52%) as brown solid.

MASS (APCI): m/z 256.0 (M+H)

¹H NMR (400 MHz, DMSO-d₆): δ 0.93 (d, 3H), 1.39 (m, 1H), 1.59 (m, 1H), 1.88 (br s, 1H), 2.17 (s, 3H), 2.68 (m, 3H), 2.89 (m, 1H), 4.01 (m, 1H), 6.89 (s, 1H), 7.42 (d, 1H), 11.52 (s, 1H).

Intermediate 40

Methyl (3S,4R)-4-{[(3,4-dichloro-5-methyl-1H-pyrrol-2-yl)carbonyl]amino}-3-methylpiperidine-1-carboxylate

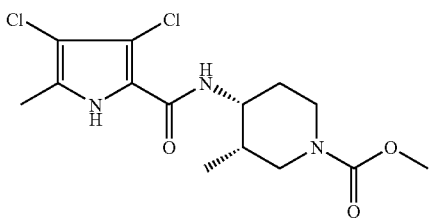

To a solution of 3,4-dichloro-5-methyl-1H-pyrrole-2-carboxylic acid (WO2006087543. 2.8 g, 14.53 mmol) and methyl (3S,4R)-4-amino-3-methylpiperidine-1-carboxylate (Intermediate 37, 2.5 g, 14.53 mmol) in dichloromethane (200 mL) was added HOBT (2.22 g, 14.53 mmol) and N-methyl morpholine (4.82 mL, 43.60 mmol). The reaction mixture was stirred for 1 h at room temperature and EDC HCl (5.12 g, 26.16 mmol) was added. The resulting reaction mixture was stirred at room temperature overnight. The reaction mixture was quenched with 2N hydrochloric acid (120 mL). The organic layer was washed with sodium bicarbonate (150 mL), water (150 mL), and brine, dried over anhydrous sodium sulphate, filtered, concentrated under vacuum. Purification by column chromatography (silica, 35% ethylacetate in pet ether) afforded methyl (3S,4R)-4-{[(3,4-dichloro-5-methyl-1H-pyrrol-2-yl)carbonyl]amino}-3-methylpiperidine-1-carboxylate 3.4 g (67%) as brown solid.

MASS (APCI): m/z 348.0 (M+H).

¹H NMR (400 MHz, DMSO-d₆): δ 0.85 (d, 3H), 2.01 (m, 2H), 2.18 (s, 3H), 3.39 (m, 4H), 3.52 (s, 3H), 4.16 (m, 1H), 7.05 (d, 1H), 12.01 (s, 1H).

Intermediate 41

3,4-Dichloro-5-methyl-N-[(3S,4R)-3-methylpiperidin-4-yl]-1H-pyrrole-2-carboxamide

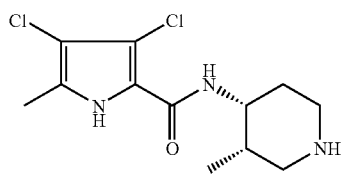

A solution of methyl (3S,4R)-4-{[(3,4-dichloro-5-methyl-1H-pyrrol-2-yl)carbonyl]amino}-3-methylpiperidine-1-carboxylate (Intermediate 40, 3.4 g, 9.79 mmol), potassium hydroxide (3.84 g, 68.58 mmol), and hydrazine hydrate (3.6 mL, 68.58 mmol) in ethylene glycol (180 mL) was stirred for 60 h at 120° C. The reaction mixture was poured in to water (300 mL) and extracted with ethyl acetate (2×300 mL). The combined organic extracts were dried over anhydrous sodium sulphate, filtered, concentrated under vacuum to yield the crude product, which was triturated with water (150 mL) to afford 3,4-dichloro-5-methyl-N-[(3S,4R)-3-methylpiperidin-4-yl]-1H-pyrrole-2-carboxamide 1.8 g, (63%) as solid.

¹H NMR (400 MHz, DMSO-d₆): δ 0.86 (d, 3H), 1.88 (br s, 1H), 2.01 (br s, 1H), 2.18 (s, 3H), 2.69 (m, 4H), 4.11 (br s, 2H), 6.90 (d, 1H).

Intermediate 42

Methyl (3S,4R)-4-{[(4-chloro-3-cyano-5-methyl-1H-pyrrol-2-yl)carbonyl]amino}-3-methylpiperidine-1-carboxylate

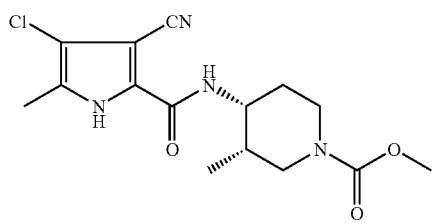

To a solution of 4-chloro-3-cyano-5-methyl-1H-pyrrole-2-carboxylic acid (Intermediate 16, 2.12 g, 0.02 mol) and methyl (3S,4R)-4-amino-3-methylpiperidine-1-carboxylate (Intermediate 37, 2.0 g, 0.02 mol) in dichloromethane (200 mL) was added HOBt (1.77 g, 0.02 mol) and N-methyl morpholine (3.8 mL, 0.03 mol) and then the mixture was stirred for 1 h at room temperature. EDC HCl (3.98 g, 0.0208 mol) was added to the reaction mixture and stirred at room temperature overnight. The reaction mixture was added to 2N hydrochloric acid (200 mL). The organic layer was washed with sodium bicarbonate (200 mL), water (250 mL), and brine. The organic layer was dried over anhydrous sodium sulphate, filtered, concentrated under vacuum to get methyl (3S,4R)-4-{[(4-chloro-3-cyano-5-methyl-1H-pyrrol-2-yl) carbonyl]amino}-3-methylpiperidine-1-carboxylate 3.3 g (72%) as white solid.

$^1$H NMR (400 MHz, DMSO-d$_6$): δ 0.84 (d, 3H), 1.63 (br s, 2H), 2.00 (br s, 1H), 2.21 (s, 3H), 3.30 (s, 3H), 3.59 (s, 9H), 4.13 (br s, 1H), 7.78 (d, 1H), 12.55 (s, 1H).

LC-MS: m/z 338.9 (M+H).

Intermediate 43

4-Chloro-3-cyano-5-methyl-N-[(3S,4R)-3-methylpi-peridin-4-yl]-1H-pyrrole-2-carboxamide

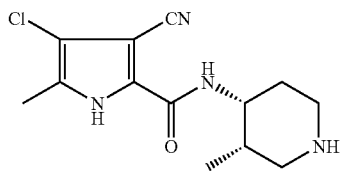

A solution of methyl (3S,4R)-4-{[(4-chloro-3-cyano-5-methyl-1H-pyrrol-2-yl)carbonyl]amino}-3-methylpiperi-dine-1-carboxylate (Intermediate 42, 3.3 g, 8.39 mmol), potassium hydroxide (3.3 g, 58.77 mmol), and hydrazine hydrate (2.97 mL, 58.77 mmol) in ethylene glycol (200 mL) was stirred for 48 h at 120° C. The reaction mixture was poured in to water (200 mL), then extracted with ethyl acetate (2×250 mL). The combined organic layers were dried over anhydrous sodium sulphate, filtered, concentrated under vacuum to yield the crude product, which was triturated with water (100 mL) to afford 4-chloro-3-cyano-5-methyl-N-[(3S, 4R)-3-methylpiperidin-4-yl]-1H-pyrrole-2-carboxamide 1.5 g (63%) as solid.

$^1$H NMR (400 MHz, DMSO-d$_6$): δ 0.88 (d, 3H), 1.67 (br s, 2H), 1.98 (m, 1H), 2.21 (s, 3H), 2.79 (m, 4H), 2.92 (m, 1H), 4.09 (br s, 1H), 7.53 (d, 1H).

MASS (APCI): 281.0 (M+H).

Intermediate 44

5-Chloropyrazine-2-carboxylic acid

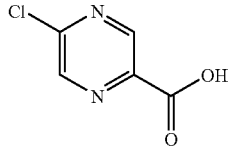

5-Hydroxypyrazine-2-carboxylic acid (1.0 g, 0.007 mol) was taken in thionyl chloride (10 mL), to this solution dim-ethylformamide (0.1 mL) was added which was heated to reflux for 16 h. After this period, excess thionyl chloride was distilled off to get crude compound, which was added to ice (20 g) and extracted with ethyl acetate (2×70 mL). The organic layers were combined and dried over anhydrous sodium sulphate and concentrated under reduced pressure to obtain brown solid which was triturated with diethyl ether (30 mL) to afford 600 mg (75%) of 5-chloropyrazine-2-carboxy-lic acid.

$^1$H NMR (400 MHz, DMSO-d$_6$): δ 8.94 (s, 1H), 9.04 (s, 1H), 13.92 (s, 1H)

Mass (APCI): m/z 157.0 (M−H). .

Intermediate 45

Ethyl 3-(5-chloropyrazin-2-yl)-3-oxopropanoate

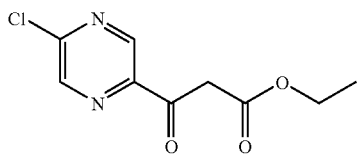

5-Chloropyrazine-2-carboxylic acid (Intermediate 44, 21 g, 0.132 mol) was taken in thionyl chloride (100 mL) which was heated to reflux for 2 h and excess thionyl chloride was distilled off under reduced pressure to obtain a residue, which was dissolved in dry tetrahydrofuran (100 mL). In another round bottom flask ethyl hydrogen malonoate (15.8 g, 0.132 mol) was dissolved in tetrahydrofuran (500 mL) which was cooled to 0° C. To the resulting solution was added methyl magnesium bromide (88 mL, 0.265 M) and stirred the reaction mixture was stirred for 30 min before triethylamine (39.9 g, 0.396 M) was added. To this reaction mixture the above prepared acid chloride mixture was added, stirred for 2 h at room temperature and tetrahydrofuran was evaporated from the reaction mixture and the water (500 mL) was added and extracted with ethyl acetate (2×200 mL). The organic layers were combined and dried over anhydrous sodium sulphate, concentrated under reduced pressure to get obtain crude product which was purified by flash column chromatography (10% ethyl acetate/pet ether) to afford 16.0 g (53.16%) of ethyl 3-(5-chloropyrazin-2-yl)-3-oxopropanoate white solid.

$^1$H NMR (400 MHz, CDCl$_3$): δ 1.26 (t, 3H), 1.28 (t, 3H), 4.18 (s, 2H), 4.20 (q, 2H), 4.30 (q, 2H), 6.28 (s, 1H), 8.57 (s, 1H), 8.61 (s, 1H), 8.89 (s, 1H), 9.04 (s, 1H), 12.35 (s, 1H).

Mass (APCI): m/z 227 (M−H).

Intermediate 46

Ethyl 2-amino-4-(5-chloropyrazin-2-yl)-1,3-thiazole-5-carboxylate

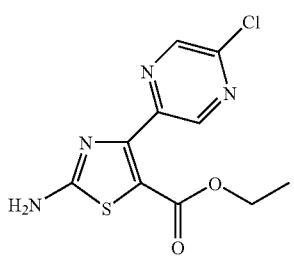

Ethyl 3-(5-chloropyrazin-2-yl)-3-oxopropanoate (Intermediate 45, 2.0 g, 8.77 mM) was dissolved in ethyl acetate (30 mL), to this amberlyst resin (2.0 g) and N-iodosuccina-mide (2.1 g, 9.64 mM) were added and stirred for 1 h at room temperature. The resin was filtered and the filtrate was concentrated under reduced pressure to afford crude compound, which was dissolved in methanol (25 mL). Thiourea (0.99 g, 13.15 mM) was added to the reaction mixture and the reaction mixture was heated to reflux for 2 h. The methanol was concentrated under reduced pressure and the resulting residue was partitioned between sodium bicarbonate solution (50 mL) and extracted with ethyl acetate (50 mL). The organic layers were combined and dried over anhydrous sodium sul-phate, filtered, concentrated under reduced pressure to obtain crude compound which was purified by flash column chromatography (gradient up to 50% of ethyl acetate/pet ether) to afford 500 mg (20.06%) of ethyl 2-amino-4-(5-chloropyrazin-2-yl)-1,3-thiazole-5-carboxylate off-white solid.

$^1$H NMR (400 MHz, DMSO-d$_6$): δ 1.08 (t, 3H), 4.12 (q, 2H), 8.02 (s, 2H), 8.72 (s, 1H), 8.84 (s, 1H).

Mass (APCI): m/z 285.0 (M+H).

Intermediate 47

Ethyl 2-bromo-4-(5-chloropyrazin-2-yl)-1,3-thiazole-5-carboxylate

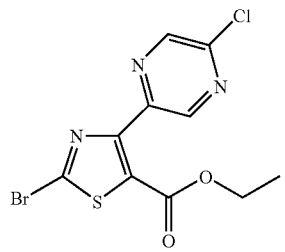

To a 0° C. solution of copper bromide (238 mg, 1.056 mM) in acetonitrile (30 mL) was added tert-butyl nitrite (87 mg, 0.845 mM) and the reaction mixture was stirred 30 min followed by addition of ethyl 2-amino-4-(5-chloropyrazin-2-yl)-1,3-thiazole-5-carboxylate (Intermediate 46, 200 mg, 0.704 mM). The reaction mixture was stirred for 2 h at room temperature. Acetonitrile was removed from the reaction mixture by distillation and then water (50 mL) was added. The reaction mixture was extracted with diethyl ether (2×50 mL). The organic layers were combined and dried over anhydrous sodium sulphate, filtered and concentrated under reduced pressure to obtain crude product which was purified by flash column chromatography (gradient up to 10% of ethyl acetate/pet ether) to afford 50 mg (20.4%) of ethyl 2-bromo-4-(5-chloropyrazin-2-yl)-1,3-thiazole-5-carboxylate as off white solid.

$^1$H NMR (400 MHz, CDCl$_3$): δ 1.34 (t, 3H), 4.38 (q, 2H), 8.68 (s, 1H), 8.84 (s, 1H).

Mass (APCI): m/z 349.9 (M+H).

Intermediate 48

Ethyl 2-hydroxypropanoate

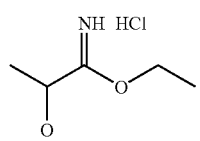

To a stirred solution of 2-hydroxypropanenitrile (50 g, 704 mmol) in diethylether (300 mL) was added dry ethanol (51 mL, 774 mmol). To the above reaction mixture HCl gas was passed at −5° C. for 2 h. and stirred at room temperature for 16 h. The solid that formed was collected by filtration and washed with diethyl ether (200 mL) to obtain ethyl 2-hydroxypropanoate 75 g (90%) as white solid.

1H NMR (400 MHz, DMSO-d6): δ 1.38 (t, 3H), 4.49 (q, 1H), 6.55 (br s, 1H).

MASS (APCI+ve Scan): m/z 117 (M+H).

Intermediate 49

2-Hydroxypropanamide

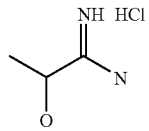

To a stirred solution of ethyl 2-hydroxypropanoate (Intermediate 48, 237 g, 1549 mmol) in dry ethanol (1000 mL) ammonia gas was passed for 90 min at −5° and stirred at room temperature for another 16 h. The solid that formed was collected by filtration and washed with diethyl ether (200 mL) to obtain 2-hydroxypropanamide 145 g (75%) as a white solid.

$^1$H NMR (400 MHz, DMSO-d$_6$): δ 1.35 (d, 3H), 4.49 (q, 1H), 6.25 (br s, 1H), 8.60 (br s, 3H).

MASS (APCI+ve Scan): m/z 89 (M+H).

Intermediate 50

2-(1-Hydroxyethyl)pyrimidin-4(3H)-one

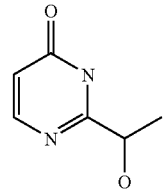

To a stirred solution of ethyl 3-oxopropanoate (Intermediate 49, 3.4 g, 24.18 mmol) in water (4 mL), a solution of 2-hydroxypropanamide (1 g 8.06 mmol) in water (4 mL) was added dropwise at 10° C. and stirred at room temperature for 18 h. The reaction mixture was cooled to 0° C. and the pH was adjusted to 7 using acetic acid (3 mL). The aqueous layer was extracted with n-butanol (2×40 mL). The organic layer was dried and concentrated under reduced pressure to obtain 2-(1-hydroxyethyl)pyrimidin-4(3H)-one 0.75 g (66.9%).

$^1$H NMR (400 MHz, DMSO-d$_6$): δ 1.30 (d, 3H), 4.50 (q, 2H), 6.10 (d, 1H), 7.80 (d, 1H).

Intermediate 51

2-Acetylpyrimidin-4(3H)-one

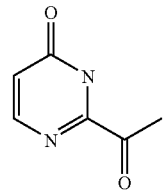

To a stirred solution of 2-(1-hydroxyethyl)pyrimidin-4 (3H)-one (Intermediate 50, 5 g, 35.71 mmol) in dichloroethane (200 mL), manganese dioxide (31 g, 357.1 mmol) was added. The reaction mixture was heated to 90° C. for 5 h. The reaction mixture was filtered through a celite bed and washed with dichloroethane (60 mL). The filtrate was concentrated to dryness to yield 1.6 g (32.6%) 2-acetylpyrimidin-4(3H)-one.
$^1$H NMR (400 MHz, DMSO-d$_6$): δ 2.50 (s, 3H), 6.50 (d, 1H), 8.05 (d, 1H), 12.60 (s, 1H).
LC-MS: m/z 138 (M+H).

Intermediate 52

1-[4-(Piperidin-1-yl)pyrimidin-2-yl]ethanone

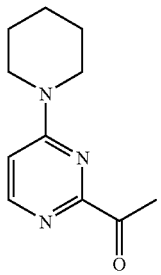

To a stirred solution of 2-acetylpyrimidin-4(3H)-one (Intermediate 51, 500 mg, 3.62 mmol) in dichloromethane (10 mL) cooled to 0° C., pyridine (860 mg, 10.87 mmol) was added and stirred for 10 min at 0° C., followed by the addition of methane sulfonyl chloride (830 mg, 7.23 mmol) at 0° C. The above reaction mixture was stirred at room temperature for overnight. The reaction mixture was washed with water (50 mL), the aqueous layer was extracted with dichloromethane (50 mL). The combined organic layer was washed with brine solution, dried over anhydrous sodium sulphate and concentrated under reduced pressure. The crude residue was dissolved in acetonitrile; piperidine (616 mg, 7.24 mmol) was added and the reaction mixture was stirred for 2 h at room temperature. The reaction mixture was concentrated under reduced pressure; water (50 mL) was added and extracted with ethyl acetate (2×30 mL). The combined organic layer was washed with brine and dried over anhydrous sodium sulphate and concentrated under reduced pressure to yield the crude product, which was purified by column chromatography over silica gel (10-50% ethyl acetate/pet ether) to obtain 1-[4-(piperidin-1-yl)pyrimidin-2-yl]ethanone 200 mg (46.8%).
$^1$H NMR (400 MHz, CDCl$_3$): δ 1.61 (m, 6H), 2.66 (s, 3H), 3.68 (m, 4H), 6.56 (d, 1H), 8.31 (d, 1H).
LC-MS: m/z 204 (M+H).

Intermediate 53-56

The following Intermediates were prepared according to the procedure described for Intermediate 52 from the starting materials indicated in the table.

| Int | Compound | Data | SM |
|---|---|---|---|
| 53 | 1-[4-morpholin-4-yl)pyrimidin-2-yl]]ethanone | $^1$H NMR (400 MHz, CDCl$_3$) δ 2.68 (s, 3H), 3.70 (m, 4H), 3.81 (m, 4H), 6.57 (d, 1H), 8.39 (d, 1H). MASS (APCI +ve Scan): m/z 208 (M + H) | Intermediate 51 and morpholine |
| 54 | 1-[4-(4-methylpiperazin-1-yl)pyrimidin-2-yl]ethanone | $^1$H NMR (400 MHz, CDCl$_3$): δ 2.33 (s, 3H), 2.50 (m, 4H), 2.68 (s, 3H), 3.73 (m, 4H), 6.58 (d, 1H), 8.34 (d, 1H), LC-MS: m/z 221.49 (M + H) | Intermediate 51 and methylpiperazine |

| Int | Compound | Data | SM |
|---|---|---|---|
| 55 | 1-{4-[4-(2-methylpropyl)piperazin-1-yl]pyrimidin-2-yl}ethanone | $^1$H NMR (400 MHz, CDCl$_3$): δ 0.92 (m, 6H), 1.81 (m, 1H), 2.12 (d, 2H), 2.48 (t, 4H), 2.68 (s, 3H), 3.71 (m, 4H), 6.56 (d, 1H), 8.34 (d, 1H) MASS (APCI +ve Scan): m/z 263.1 (M + H). | Intermediate 51 and 2-methylpropylpiperazine |
| 56 | 1-[4-(4-ethylpiperazin-1-yl)pyrimidin-2-yl]ethanone | $^1$H NMR (400 MHz, CDCl$_3$): δ 1.13 (t, 3H), 2.54 (m, 6H), 2.68 (s, 3H), 3.74 (bs, 4H), 6.58 (d, 1H), 8.36 (d, 1H). MASS (APCI +ve Scan): m/z 235 (M + H) | Intermediate 51 and ethylpiperazine |

Intermediate 57

Methyl 3-oxo-3-[4-(piperidin-1-yl)pyrimidin-2-yl]propanoate

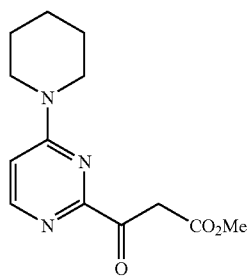

To a stirred solution of 1-[4-(piperidin-1-yl)pyrimidin-2-yl]ethanone (Intermediate 52, 0.6 g, 2.92 mmol) in dimethylcarbonate (10 mL), sodium hydride (0.281 g, 11.7 mmol, 60%) was added portion wise at 0-5° C. over a period of 10 min. The reaction mixture was heated to 90° C. for 4 h. The reaction mixture was quenched by adding ice water. The aqueous layer pH was adjusted to neutral with dilute HCl, the aqueous layer was extracted with ethyl acetate (2×50 mL). The organic layer was dried and concentrated. The crude product was purified by column chromatography (75% ethylacetate & pet ether) to obtain methyl 3-oxo-3-[4-(piperidin-1-yl)pyrimidin-2-yl]propanoate 0.4 g (52%).

$^1$H NMR (400 MHz, CDCl$_3$): δ 1.65 (m, 6H), 3.67 (bs, 4H), 3.71 (s, 3H), 4.06 (s, 3H) 6.57 (d, 1H), 8.31 (d, 1H).

MASS (APCI+ve Scan): m/z 264 (M+H).

Intermediate 58-61

The following Intermediates were prepared according to the procedure described for Intermediate 57 from the starting materials indicated in the table.

| Int | Compound | Data | SM |
|---|---|---|---|
| 58 | Methyl 3-[4-(morpholin-4-yl)pyrimidin-2-yl]-3-oxopropanoate | MASS (APCI +ve Scan): m/z 266 (M + H). | Intermediate 53 |
| 59 | Methyl 3-[4-(4-methylpiperazin-1-yl)pyrimidin-2-yl]-3-oxopropanoate | MASS (APCI +ve Scan): m/z 279 (M + H) | Intermediate 54 |
| 60 | Methyl 3-{4-[4-(2-methylpropyl)piperazin-1-yl]pyrimidin-2-yl}-3-oxopropanoate | MASS (APCI +ve Scan): m/z 320.9 (M + H) | Intermediate 55 |
| 61 | Methyl 3-[4-(4-ethylpiperazin-1-yl)pyrimidin-2-yl]-3-oxopropanoate | MASS (APCI +ve Scan): m/z 293 (M + H) | Intermediate 56 |

Intermediate 62

Methyl 2-amino-4-[4-(piperidin-1-yl)pyrimidin-2-yl]-1,3-thiazole-5-carboxylate

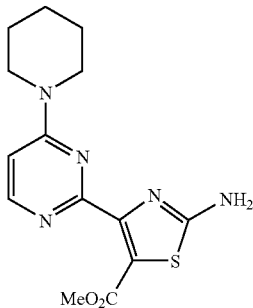

To a stirred solution of methyl 3-oxo-3-[4-(piperidin-1-yl)pyrimidin-2-yl]propanoate (Intermediate 57, 0.4 g, 1.52 mmol) in ethyl acetate (20 mL), N-iodosuccinamide (0.374 g, 1.672 mmol) and Amberlyst resin-15 (0.40 g) were added. The reaction mixture was stirred at room temperature for 30-40 min. The reaction mixture was filtered and the filtrate was concentrated to dryness. The obtained crude (iodo compound) was dissolved in methanol (20 mL) and thiourea (0.138 g, 1.852 mmol) was added. The reaction mixture was stirred at room temperature for 1 h. The reaction mixture was concentrated to dryness. The residue was basified with saturated sodium bicarbonate solution (20 mL). The aqueous layer was extracted with ethyl acetate (2×50 mL). The combined organic layer was dried and concentrated to obtain the crude which was purified by prep HPLC to obtain methyl 2-amino-4-[4-(piperidin-1-yl)pyrimidin-2-yl]-1,3-thiazole-5-carboxylate 0.080 g (16.5%)

$^1$H NMR (400 MHz, DMSO-$d_6$): δ 1.61 (d, 6H), 3.68 (s, 3H), 3.84 (bs, 4H), 7.22 (d, 1H), 8.19 (d, 1H), 8.35 (d, 1H).
LC-MS: m/z 320 (M+H).

Intermediate 63-66

The following Intermediates were prepared according to the procedure described for Intermediate 62 from the starting materials indicated in the table.

| Int | Compound | Data | SM |
|---|---|---|---|
| 63 | Methyl 2-amino-4-[4-(morpholin-4-yl)pyrimidin-2-yl]-1,3-thiazole-5-carboxylate | $^1$H NMR (400 MHz, DMSO-$d_6$): δ 3.67 (s, 3H), 3.73 (t, 4H), 3.85 (t, 4H), 7.19 (d, 1H), 8.16 (bs, 4H), 8.41 (d, 1H). LC-MS: m/z 322.4 (M + H). | Intermediate 58 |
| 64 | Methyl 2-amino-4-[4-(4-methylpiperazin-1-yl)pyrimidin-2-yl]-1,3-thiazole-5-carboxylate | $^1$H NMR (400 MHz, DMSO-$d_6$): δ 2.21 (s, 3H), 2.36 (bs, 4H), 3.30 (s, 3H), 3.58 (bs, 4H), 6.79 (d, 1H), 7.80 (bs, 2H), 8.21 (d, 1H). MASS (APCI +ve Scan: m/z 335 (M + H) | Intermediate 59 |

-continued

| Int | Compound | Data | SM |
|---|---|---|---|
| 65 | methyl 2-amino-4-{4-[4-(2-methylpropyl)piperazin-1-yl]pyrimidin-2-yl{-1,3-thiazole-5-carboxylate | MASS (APCI +ve Scan): m/z 377.1 (M + H) | Intermediate 60 |
| 66 | Methyl 2-amino-4-[4-(4-ethylpiperazin-1-yl)pyrimidin-2-yl]-1,3-thiazole-5-carboxylate | $^1$H NMR (400 MHz, DMSO-d$_6$): δ 1.02 (t, 3H), 2.40 (bs, 4H), 3.32 (s, 3H), 3.55 (bs, 4H), 3.32 (s, 3H), 3.55 (bs, 4H), 6.78 (d, 1H), 7.83 2H), 8.21 (d, 1H), MASS (APCI +ve Scan): m/z 349.41 (M + H) | Intermediate 61 |

Intermediate 67

Methyl 2-chloro-4-[4-(piperidin-1-yl)pyrimidin-2-yl]-1,3-thiazole-5-carboxylate

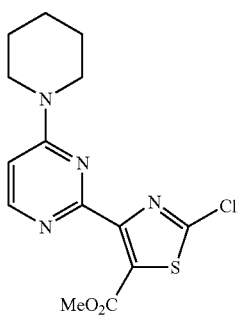

To a stirred solution of methyl 2-amino-4-[4-(piperidin-1-yl)pyrimidin-2-yl]-1,3-thiazole-5-carboxylate (Intermediate 62, 0.070 g, 0.219 mmol) in concentrated HCl (1 mL), sodium nitrite (0.045 g, 0.658 mmol) in water (1 mL) was added drop wise at 0° C. The reaction mixture was stirred at room temperature for 30 min. The reaction mixture was cooled to 5-10° C. and basified with saturated sodium bicarbonate solution (20 mL). The aqueous layer was extracted with ethyl acetate (2×30 mL). The combined organic layer was washed with brine solution, dried and concentrated under reduced pressure to obtain methyl 2-chloro-4-[4-(piperidin-1-yl)pyrimidin-2-yl]-1,3-thiazole-5-carboxylate 0.040 g (54%).
$^1$H NMR (400 MHz, CDCl$_3$): δ 1.60 (d, 6H), 3.62 (bs, 4H), 3.80 (s, 3H), 6.46 (d, 1H), 8.27 (d, 1H).
MASS (APCI+ve Scan): m/z 339 (M+H).

Intermediate 68-71

The following Intermediates were prepared according to the procedure described for Intermediate 67 from the starting materials indicated in the table.

| Int | Compound | Data | SM |
|---|---|---|---|
| 68 | Methyl 2-chloro-4-[4-(morpholin-4-yl)pyrimidin-2-yl]-1,3-thiazole-5-carboxylate | $^1$H NMR (400 MHz, CDCl$_3$): δ 3.66 (t, 3H), 3.77 (t, 4H), 3.81 (s, 3H), 6.51 (d, 1H), 8.35 (d, 1H), MASS (APCI +ve Scan): m/z 341 (M + H) | Intermediate 63 |
| 69 | methyl 2-chloro-4-[4-(4-methylpiperazin-1-yl)pyrimidin-2-yl]-1,3-thiazole-5-carboxylate | $^1$H NMR (400 MHz, CDCl$_3$): δ 2.34 (s, 3H) 2.48 (t, 4H), 3.68 (bs, 4H), 3.81 (s, 3H), 6.51 (d, 1H), 8.33 (d, 1H), MASS (APCI +ve Scan): m/z 354.1 (M + H) | Intermediate 64 |
| 70 | Methyl 2-chloro-4-{4-[4-(2-methylpropyl)piperazin-1-yl]pyrimidin-2-yl}-1,3-thiazole-5-carboxylate | $^1$H NMR (400 MHz, CDCl$_3$): δ 0.92 (m, 6H), 2.10 (d, 3H), 2.45 (t, 4H), 3.65 (bs, 4H), 3.81 (s, 3H), 6.48 (d, 1H), 8.29 (d, 1H) MASS (APCI +ve Scan): m/z 395.8 (M + H) | Intermediate 65 |

| Int | Compound | Data | SM |
|---|---|---|---|
| 71 | Methyl 2-chloro-4-[4-(4-ethylpiperazin-1-yl)pyrimidin-2-yl]-1,3-thiazole-5-carboxylate 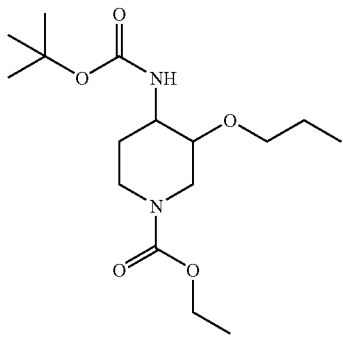 | $^1$H NMR (400 MHz, CDCl$_3$): δ 1.12 (t, 3H), 2.47 (m, 6H), 3.69 (bs, 4H), 3.81 (s, 3H), 6.49 (s, 3H), 6.49 (d, 1H), 8.33 (d, 1H). MASS (APCI +ve Scan): m/z 368 (M + H) | Intermediate 66 |

Intermediate 72

Ethyl-(3S,4R)-4-[(tert-butoxycarbonyl)amino]-3-(propyoxypiperidine-1-carboxylate

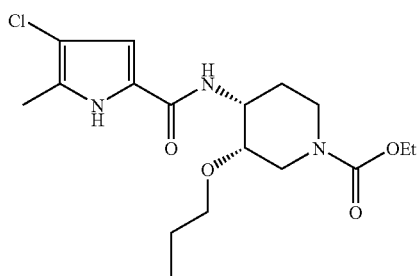

Chiral HPLC purification of Cis(±)ethyl-4-[(tert-butoxycarbonyl)amino]-3-(propyoxypiperidine-1-carboxylate (WO2006087543, Chiralpak AD, 70% hexane/30% 1:1 ethanol:methanol/0.1% diethylamine, flow rate 120 mL/min) provided 2 g of the desired product.

NMR: 0.94 (m, 3H), 1.25 (m, 3H), 1.43 (s, 9H), 1.53 (m, 2H), 1.71 (m, 1H), 3.04 (m, 2H), 3.37 (m, 2H), 3.50 (m, 2H), 3.69 (m, 1H), 3.89 (m, 1H), 4.15 (m, 2H), 6.5 (d, 1H).

Intermediate 73

Ethyl (3S,4R)-4-{[(4-chloro-5-methyl-1H-pyrrol-2-yl)carbonyl]amino}-3-propoxypiperidine-1-carboxylate Ethyl-(3S,4R)-4-[(tert-butoxycarbonyl)amino]-3-(propyoxypiperidine-1-carboxylate (Intermediate 72, 3 g) was treated with TFA (5 mL) for 30 min and the concentrated under reduced pressure. The resulting residue was dissolved in dichloromethane (150 mL) with 4-chloro-5-methyl-1H-pyrrole-2-carboxylic acid (Intermediate 27, 1.45 g, 9.13 mmol), HOBT (1.676 g, 10.95 mmol) and N-methyl morpholine (2.76 g, 27.39 mmol). The reaction mixture was stirred for 1 h at room temperature and 1-Ethyl-3-(3-dimethylaminopropyl)carbodiimide hydrochloride (3.02 g, 16.43 mmol) was added. The resulting reaction mixture was stirred at room temperature overnight. The reaction mixture was quenched with 2N hydrochloric acid (30 mL) and the layers were separated. The organic layer was washed with sodium bicarbonate (40 mL), water (60 mL) and finally with brine successively and dried over anhydrous sodium sulphate, filtered, and concentrated under vacuum to afford ethyl (3S,4R)-4-{[(4-chloro-5-methyl-1H-pyrrol-2-yl)carbonyl]amino}-3-propoxypiperidine-1-carboxylate 2.8 g (84%) as solid.

$^1$H NMR (400 MHz, CDCl$_3$): δ 0.95 (t, 3H), 1.22 (t, 3H), 1.65 (m, 6H), 2.21 (s, 3H), 2.81 (m, 2H), 3.21 (m, 2H), 3.4 (m, 3H), 3.71 (m, 1H), 4.4 (m, 1H), 6.21 (d, 1H), 9.91 (s, 1H)

LC-MS: m/z 372.3 (M+H).

Intermediate 74

4-Chloro-5-methyl-N-[(3S,4R)-3-propoxypiperidin-4-yl]-1H-pyrrole-2-carboxamide

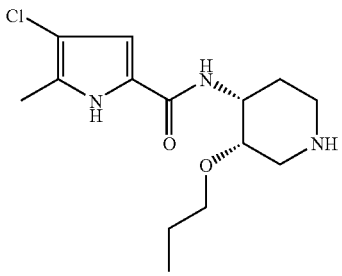

A solution of ethyl (3R,4S)-4-{[(4-chloro-5-methyl-1H-pyrrol-2-yl)carbonyl]amino}-3-propoxypiperidine-1-carboxylate (Intermediate 73, 2.8 g, 7.547 mmol) potassium hydroxide (4.2 g, 75.47 mmol), and Hydrazine hydrate (3.6 mL, 75.47 mmol) in ethylene glycol (100 mL) was stirred for 60 h at 120° C. The reaction mixture was poured into water (300 mL) and extracted with ethyl acetate (2×300 mL). The combined organic extracts were dried over anhydrous sodium sulphate, filtered, and concentrated under vacuum to afford 4-chloro-5-methyl-N-[(3S,4R)-3-propoxypiperidin-4-yl]-1H-pyrrole-2-carboxamide 650 mg, 30% as solid.

$^1$H NMR (400 MHz, CDCl$_3$): δ 0.98 (t, 3H), 1.62 (m, 4H), 2.21 (t, 3H), 2.61 (m, 2H), 3.12 (m, 2H), 3.32 (m, 1H), 3.61 (m, 2H), 4.15 (m, 1H), 6.21 (d, 1H), 6.4 (s, 1H), 9.45 (s, 1H).

LC-MS: m/z 300.2 (M+H).

Intermediate 75

Ethyl (3R,4S)-4-{[(4-chloro-3-cyano-5-methyl-1H-pyrrol-2-yl)carbonyl]amino}-3-propoxypiperidine-1-carboxylate

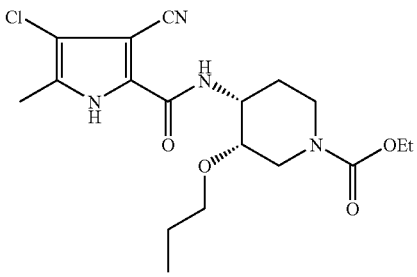

To a solution of 4-chloro-3-cyano-5-methyl-1H-pyrrole-2-carboxylic acid (Intermediate 16, 2 g, 8.69 mmol) and ethyl (3S,4R)-4-amino-3-propoxypiperidine-1-carboxylate (see Intermediate 73, 1.59 g, 8.695 mmol) in dichloromethane (150 mL) was added N-Hydroxybenzotriazole (1.6 g, 10.43 mM) and N-methylmorpholine (2.63 g, 26.08 mmol). The reaction mixture was stirred for 1 h at room temperature and 1-Ethyl-3-(3-dimethyl amino propyl)carbodiimide hydrochloride (2.87 g, 15.6 mM) was added. The resulting reaction mixture was stirred at room temperature overnight. The reaction mixture was quenched with 2N hydrochloric acid (50 mL) and the layers were separated. The organic layer was washed with sodium bicarbonate (40 mL), water (60 mL) and finally with brine successively and dried over anhydrous sodium sulphate, filtered, concentrated under vacuum to afford ethyl (3S,4R)-4-{[(4-chloro-3-cyano-5-methyl-1H-pyrrol-2-yl)carbonyl]amino}-3-propoxypiperidine-1-carboxylate 2.6 g (76%) as solid.

$^1$H NMR (400 MHz, DMSO-d$_6$): δ 0.95 (t, 3H), 1.25 (t, 3H), 1.75 (m, 4H), 2.30 (s, 3H), 2.97 (m, 3H), 3.49 (m, 2H), 4.01 (m, 3H), 4.13 (m, 2H), 7.21 (d, 1H), 11.19 (s, 1H).

MASS: m/z 397.1 (M+H).

Intermediate 76

4-Chloro-3-cyano-5-methyl-N-[(3S,4R)-3-propoxypiperidin-4-yl]-1H-pyrrole-2-carboxamide

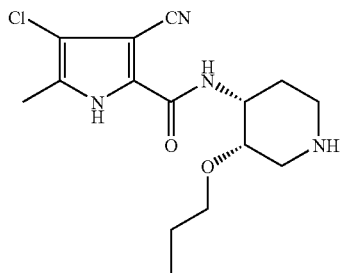

A solution of ethyl (3S,4R)-4-{[(4-chloro-3-cyano-5-methyl-1H-pyrrol-2-yl)carbonyl]amino}-3-propoxypiperidine-1-carboxylate (Intermediate 75, 2.6 g, 6.56 mmol), potassium hydroxide (3.67 g, 65.6. mmol), and hydrazine hydrate (3.28 g, 65.6 mmol) in ethylene glycol (100 mL) was stirred for 60 h at 120° C. The reaction mixture was cooled to room temperature and poured into water (75 mL) and extracted with ethyl acetate (2×100 mL). The combined organic extracts were dried over anhydrous sodium sulphate, filtered, concentrated under vacuum to afford 4-chloro-3-cyano-5-methyl-N-[(3S,4R)-3-propoxypiperidin-4-yl]-1H-pyrrole-2-carboxamide 1.5 g, 71% as solid.

$^1$H NMR (400 MHz, DMSO-d$_6$): δ 0.95 (t, 3H), 1.75 (m, 4H), 2.30 (m, 1H), 2.62 (m, 2H), 3.12 (m, 2H), 3.30 (m, 3H), 3.42 (m, 2H), 3.55 (m, 1H), 4.19 (m, 1H), 7.19 (m, 1H).

LC-MS: m/z 325.2 (M+H).

Intermediate 77

Ethyl (3S,4R)-4-{[(3,4-dichloro-5-methyl-1H-pyrrol-2-yl)carbonyl]amino}-3-propoxypiperidine-1-carboxylate

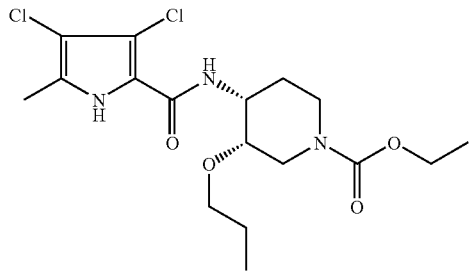

To a solution of 3,4-dichloro-5-methyl-1H-pyrrole-2-carboxylic acid (WO2006087543, 1.77 g, 9.13 mmol) and ethyl (3S,4R)-4-amino-3-propoxypiperidine-1-carboxylate (see Intermediate 73, 2.1 g, 9.13 mmol) in dichloromethane (150 mL) was added N-Hydroxybenzotriazole (1.67 g, 10.95 mmol) and N-methylmorpholine (2.76 g, 27.39 mmol). The reaction mixture was stirred for 1 h at room temperature and 1-Ethyl-3-(3-dimethylaminopropyl)carbodiimide hydrochloride (3.023 g, 16.43 mmol) was added. The resulting reaction mixture was stirred at room temperature overnight. The reaction mixture was quenched with 2N hydrochloric acid (30 mL) and the layers were separated. The organic layer was washed with sodium bicarbonate (40 mL), water (60 mL) and finally with brine successively, and dried over anhydrous sodium sulphate, filtered, and concentrated under vacuum to afford ethyl (3S,4R)-4-{[(3,4-dichloro-5-methyl-1H-pyrrol-2-yl)carbonyl]amino}-3-propoxypiperidine-1-carboxylate 3.3 g (89.1%) as solid.

$^1$H NMR (400 MHz, CDCl$_3$): δ 0.95 (t, 3H), 1.30 (t, 3H), 1.60 (m, 2H), 1.80 (m, 2H), 2.22 (s, 3H), 3.90 (m, 2H), 3.25 (m, 1H), 3.42 (m, 1H), 3.65 (m, 1H), 4.22 (m, 4H), 4.41 (m, 1H). 7.21 (d, 1H), 9.91 (m, 1H)

LCMS: m/z 407.3 (M+H). .

Intermediate 78

3,4-Dichloro-5-methyl-N-[(3S,4R)-3-propoxypiperidin-4-yl]-1H-pyrrole-2-carboxamide

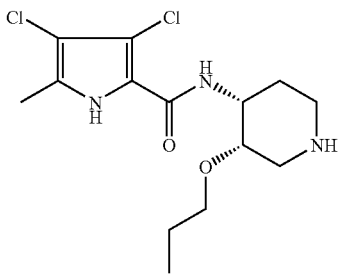

A solution of ethyl (3S,4R)-4-{[(3,4-dichloro-5-methyl-1H-pyrrol-2-yl)carbonyl]amino}-3-propoxypiperidine-1-carboxylate (Intermediate 77, 3.3 g, 8.12 mmol) potassium hydroxide (4.55 g, 81.2 mmol), and hydrazine hydrate (4.06 g, 81.2 mmol) in ethylene glycol (100 mL) was stirred for 60 h at 120° C. The reaction mixture was cooled to room temperature and poured into water (300 mL) and extracted with ethyl acetate (2×300 mL). The combined organic extracts were dried over anhydrous sodium sulphate, filtered, and concentrated under vacuum to afford 3,4-dichloro-5-methyl-N-[(3S,4R)-3-propoxypiperidin-4-yl]-1H-pyrrole-2-carboxamide 1.5 mg, (62.5%) as solid.

$^1$H NMR (400 MHz, DMSO-$d_6$): δ 0.95 (t, 3H), 1.59 (m, 4H), 2.20 (s, 3H), 2.51 (m, 4H), 2.80 (m, 2H), 3.25 (m, 1H), 3.51 (m, 1H), 4.01 (m, 1H), 7.05 (d, 1H).

LC-MS: m/z 334.2 (M+H).

The invention claimed is:

1. The compound 2-[(3S,4R)-4-{[(3,4-dichloro-5-methyl-1H-pyrrol-2-yl)carbonyl]amino}-3-methoxypiperidin-1-yl]-4-{5-[2-(dimethylamino)ethoxy]pyrazin-2-yl}-1,3-thiazole-5-carboxylic acid.

2. A pharmaceutically acceptable salt of the compound 2-[(3S,4R)-4-{[(3,4-dichloro-5-methyl-1H-pyrrol-2-yl)carbonyl]amino}-3-methoxypiperidin-1-yl]-4-{5-[2-(dimethylamino)ethoxy]pyrazin-2-yl}-1,3-thiazole-5-carboxylic acid.

3. A mixture of the compound 2-[(3S,4R)-4-{[(3,4-dichloro-5-methyl-1H-pyrrol-2-yl)carbonyl]amino}-3-methoxypiperidin-1-yl]-4-{5-[2-(dimethylamino)ethoxy]pyrazin-2-yl}-1,3-thiazole-5-carboxylic acid and a pharmaceutically acceptable salt thereof.

4. A pharmaceutical composition comprising a compound of claim 1 or 2, and a pharmaceutically acceptable excipient or carrier.

5. A pharmaceutical composition comprising the mixture of claim 3, and a pharmaceutically acceptable excipient or carrier.

* * * * *